(12) United States Patent
Hammons et al.

(10) Patent No.: US 9,550,970 B2
(45) Date of Patent: Jan. 24, 2017

(54) CULTURE SYSTEMS, APPARATUS, AND RELATED METHODS AND ARTICLES

(75) Inventors: Aaron Hammons, Huntsville, AL (US); Micah B. Harvey, Madison, AL (US); David W. Langford, Madison, AL (US); Joseph McGinty, Madison, AL (US); Steven M. Faes, Canisteo, NY (US); Christopher D. Pittman, Huntsville, AL (US)

(73) Assignee: INQ BIOSCIENCES CORPORATION, Huntsville, AL (US)

( * ) Notice: Subject to any disclaimer, the term of this patent is extended or adjusted under 35 U.S.C. 154(b) by 809 days.

(21) Appl. No.: 13/030,039

(22) Filed: Feb. 17, 2011

(65) Prior Publication Data
US 2011/0207209 A1    Aug. 25, 2011

Related U.S. Application Data

(60) Provisional application No. 61/305,458, filed on Feb. 17, 2010, provisional application No. 61/422,083, filed on Dec. 10, 2010.

(51) Int. Cl.
C12M 3/00    (2006.01)
C12M 1/00    (2006.01)
C12M 1/32    (2006.01)

(52) U.S. Cl.
CPC .............. C12M 23/42 (2013.01); C12M 23/12 (2013.01); C12M 23/40 (2013.01)

(58) Field of Classification Search
CPC ....... C12M 23/42; C12M 24/12; C12M 24/40; C12M 24/403
(Continued)

(56) References Cited

U.S. PATENT DOCUMENTS 3,922,203 A * 11/1975 Aldridge et al. ............... 435/34
5,010,014 A *  4/1991 Gebhardt ................... 435/297.2
(Continued)

FOREIGN PATENT DOCUMENTS

| WO | 2006/005808 | 1/2006 |
| WO | 2007/047581 | 4/2007 |
| WO | 2009/108953 | 9/2009 |

OTHER PUBLICATIONS

International Search Report for corresponding International Application No. PCT/US2011/025334, mailed Feb. 8, 2012, 4 pages.
(Continued)

*Primary Examiner* — William H Beisner
(74) *Attorney, Agent, or Firm* — Seed IP Law Group LLP

(57) ABSTRACT

Culture systems, devices and related methods and articles may automate the culturing or incubation process according to defined culturing protocols. Such may employ removable multi-well growth cassette. Wells may be subdivided into subwells. Such may employ removable media and waste cartridges and/or gas canisters to supply consumables, which may be supplied in kits, for example with processor executable culturing protocols. Direct fluidic coupling between growth cassettes and the removable cartridges or canisters may be employed. Operational and/or environmental conditions may be sensed or monitored, and may be used to adjust or alter operation. A microscopy subsystem may capture images which may be stored and/or analyzed. Analysis may be used to adjust or alter operation.

29 Claims, 105 Drawing Sheets

(58) Field of Classification Search
USPC .............................. 435/297.2, 303.1, 293.1
See application file for complete search history.

(56) References Cited

U.S. PATENT DOCUMENTS

| | | | |
|---|---|---|---|
| 5,565,353 A | 10/1996 | Klebe et al. | |
| 5,985,653 A * | 11/1999 | Armstrong et al. | 435/303.1 |
| 5,994,129 A | 11/1999 | Armstrong et al. | |
| 6,653,124 B1 * | 11/2003 | Freeman | 435/297.1 |
| 7,919,307 B2 * | 4/2011 | Klaus et al. | 435/289.1 |
| 2006/0275896 A1 | 12/2006 | Anderson et al. | 435/303.1 |
| 2007/0148762 A1 | 6/2007 | Miyake et al. | |
| 2007/0275455 A1 | 11/2007 | Hung et al. | |
| 2008/0032396 A1 * | 2/2008 | Chokshi | 435/294.1 |
| 2008/0064088 A1 | 3/2008 | Shuler et al. | |
| 2009/0047260 A1 | 2/2009 | Van Dyke | 424/93.7 |
| 2009/0221059 A1 * | 9/2009 | Williams et al. | 435/287.2 |

OTHER PUBLICATIONS

Written Opinion of the International Searching Authority for corresponding International Application No. PCT/US2011/025334, mailed Feb. 8, 2012, 7 pages.
Cohen et al., "Dynamic Proteomics of Individual Cancer Cells in Response to a Drug," Science 322:1511-1516, Dec. 5, 2008.
Jones et al., "Scoring Diverse Cellular Morphologies in Image-Based Screens with Iterative Feedback and Machine Learning," PNAS 106(6):1826-1831, Feb. 10, 2009.
ATCC: Feeder Layer Cells and Attachment Factors, URL=http://www.atcc.org/CulturesandProducts/CellBiology/MediaSeraandReagents/FeederLayerCelsAttachmentFactors/tabid/530/Default.aspx, download date May 9, 2011, 1 page.
Chip-Man Tech, "Home,"URL=http://www.chipmantech.com/, download date Dec. 3, 2010, 1 page.
Chip-Man Tech, "Technology," URL= http://www.chipmantech.com/Technology.asp?ID=9&Level1ID=10, download date Dec. 3, 2010, 2 pages.
Chip-Man Tech, "Products,"URL=http://www.chipmantech.com/Cell_IQ.asp?ID=17&Level1ID=13, download date Dec. 3, 2010, 1 page.
Chip-Man Tech, "Applications," URL=http://www.chipmantech.com/Applications.asp?ID=15&Level1ID=9, download date Dec. 3, 2010, 1 page.
Chip-Man Tech, "Angiogenesis," URL=http://www.chipmantech.com/Angiogenesis.asp?ID=10&Level1ID=9&Level2ID=9, download date Dec. 3, 2010, 1 page.
Chip-Man Tech, "Stem Cells," URL=http://www.chipmantech.com/Stem_Cells.asp?ID=14&Level1ID=9&Level2ID=10, download date Dec. 3, 2010, 2 pages.
Chip-Man Tech, "Neurite Outgrowth," URL=http://www.chipmantech.com/Neurite_Outgrowth.asp?ID=12&Level1ID=9&Level2ID=12, download date Dec. 3, 2010, 1 page.
WaferGen Biosystems, "SmartSlide 50," URL=http://www.wafergen.com/wp-content/uploads/2010/09/FILE6_SmartSlide-50.pdf, download date May 9, 2011, 1 page.
WaferGen Biosystems, "Home," URL=http://www.wafergen.com, download date Dec. 3, 2010, 1 page.
WaferGen Biosystems, "SmartSlide," URL=http://www.wafergen.com/system/smartslide/, download date Dec. 3, 2010, 1 page.
WaferGen Biosystems, "SmartChip Real-time PCR System," URL=http://www.wafergen.com/system/smartchip-realtime-per-system/, download date Dec. 3, 2010, 1 page.
WaferGen Biosystems, "SmartChip Cycler," URL=http://www.wafergen.com/system/smartchip-realtime-per-system/smartchip-cycler/, download date Dec. 3, 2010, 1 page.
WaferGen Biosystems, "SmartChip Panels," URL= http://www.wafergen.com/system/smartchip-panels/, download date Dec. 3, 2010, 1 page.
LabHut.com, "Glass Coated Microtiter Plates (Microplates)," URL=http://www.labhut.com/products/microplates/glass_coated.php, download date Nov. 29, 2010, 1 page.

* cited by examiner

Create New Protocol | Experimental Protocol Table | Add Event

Parameters: [°C] [Gas 1] [Gas 2] [Gas 3] [Gas 4] [Gas psi] [Media 1] [Media 2] [Media Volume] [Circulation Rate] [Collection Rate] [Notifications] [Imaging]

| Event | Temp | Gas 1 | Gas 2 | Gas 3 | Gas 4 Filler | Gas Pressure | Media 1 | Media 2 Filler | Media Volume |
|---|---|---|---|---|---|---|---|---|---|
| DD:HH:MM | °C | % | % | % | % | psi | % | % | ml |
| Initial | 40 | 2.5 | 7.5 | 15 | 75 | 8 | 90 | 10 | 3 |
| Enter DD:HH:MM | 40 | 2.5 | 7.5 | 15 | 75 | 8 | 90 | 10 | 3 |

[Add Event]

---

Parameters: [°C] [Gas 1] [Gas 2] [Gas 3] [Gas 4] [Gas psi] [Media 1] [Media 2] [Media Volume] [Circulation Rate] [Collection Rate] [Notifications] [Imaging]

| Event | Temp | Gas 1 | Gas 2 | Gas 3 | Gas 4 Filler | Gas Pressure | Media 1 | Media 2 Filler | Media Volume |
|---|---|---|---|---|---|---|---|---|---|
| DD:HH:MM | °C | % | % | % | % | psi | % | % | ml |
| Initial | 40 | 2.5 | 7.5 | 15 | 75 | 8 – 15 (15 Hz) | 90 | 10 | |
| 00:01:30 | | | | | | | 75 | 25 | |
| Enter DD:HH:MM | 40 | 2.5 | 7.5 | 15 | 75 | 8 | 90 | 10 | 3 |

[Add Event]

Results Home | Find Results

Enter project or experiment name... [ Find Results ]

(continued from last page)

Showing results 1 - 20 of 53 matching "[Entered Keywords]"

[ Explore Results ] [ Create Report ] [ Custom Report ] [ Compare Results ] [ Export... ]

Sort By: [ Most Recent ▼ ]

☐ Group Results By Project

<< 1 2 3 >>

☐ Experiment Name [Ended date, time]
Project: Project Name
This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

☐ Experiment Name [Ended date, time]
Project: Project Name
This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

☐ Experiment Name [Ended date, time]
Project: Project Name
This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

☐ Experiment Name [Ended date, time]
Project: Project Name
This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

☐ Experiment Name [Ended date, time]
Project: Project Name
This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

[ Explore Results ] [ Create Report ] [ Custom Report ] [ Compare Results ] [ Export... ]

Results Home | Find Results | Grouped By Project     (continued from last page)

Enter project or experiment name...   [Find Results]

Showing results 1 - 20 of 53 matching "[Entered Keywords]"    ☐ Group Results By Project

[Explore Results] [Create Report] [Custom Report] [Compare Results] [Export...]

Sort By: [Most Recent ▼]                                          << 1 2 3 >>

Project Name
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

Project Name
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

Project Name
☐ <u>Experiment Name</u> [Ended date, time]
   This is the experiment description. Lorem ipsum dolor sit amet, consectetur adipiscing elit. Praesent pulvinar euismod augue, eu sagittis enim dolor tristique nec. Nulla egestas vehicula dui, eget facilisis tortor tempor non.

[Explore Results] [Create Report] [Custom Report] [Compare Results] [Export...]

CULTURE SYSTEMS, APPARATUS, AND RELATED METHODS AND ARTICLES

CROSS REFERENCE TO RELATED APPLICATIONS

This application claims benefit under 35 U.S.C. 119(e) to U.S. provisional patent application Ser. No. 61/305,458 filed Feb. 17, 2010 and U.S. provisional patent application Ser. No. 61/422,083 filed Dec. 10, 2010, both of which are incorporated by reference herein in their entireties.

BACKGROUND

Technical Field

The present disclosure generally relates to the field of culturing or incubation, for example culturing or incubating biological materials such as cells, for scientific research, performing assays, or bulk (e.g., commercial) production of cells, cell lines or tissue.

Description of the Related Art

There are many applications which employ culturing or incubation of biological materials, for example cells. Some applications may be directed to scientific research. Some applications may be directed to assaying or analyzing samples or specimens, for instance in diagnostics or forensics. Still other applications may be directed to production or manufacture of cells, tissue or other biological materials, for example cells, cell lines or tissue. The biological materials may be used for a variety of purposes, for example for transplants (e.g., stem cells), grafts (e.g., skin graft) or for other therapeutic purposes.

Various types of biological materials may be cultured. For instance, various cells or cell lines may be cultured. Culturing typically involves providing growth medium to which a biological material to be cultured or incubated is added. Culturing typically also involves controlling one or more environmental conditions, for instance temperature, for a period of time.

Culturing is a fundamental component of much scientific research, as well as performing assays for diagnostic and/or forensic purposes. While there has been some automation, culturing is still typically a manual, tedious process. Culturing may take place in Petri dishes, plates, culture bottles, flasks, submerged cultures (e.g., chemostats), etc. A growth medium is typically placed in the Petri dishes or wells of the plates. The biological material to be cultured is then added to the Petri dishes or wells of the plates, often using a pipette or other tool. The Petri dishes or plates may be heated to some desire or defined temperature by a heater.

From time-to-time, the Petri dishes or plates are removed from the incubator for examination of the biological material. Examination may be visual, using the unaided eye or using a microscope. Examination may include the use of reagents and/or stains. In some instances, examination may require the withdrawal of biological material from the Petri dishes or wells of the plates. Withdrawal may be accomplished using a pipette or other tool.

The culturing or incubation may continue over a relatively long period of time, and may require frequent adjustments in environmental conditions and/or frequent examination, which may be required throughout a 24 hour daily cycle. Such can be a daunting task for any researcher, particular individuals or those with a small group of assistants.

New, more automated, approaches to culturing are desirable.

BRIEF SUMMARY

The present disclosure relates to a culture system that automates various aspects of culturing or growth of biological materials such as cells, and/or analysis of such biological materials. In particular, the culture system removably receives a multi-well growth cassette or cartridge which holds biological material to be cultured and/or analyzed. The culture system may removably receive one or more media cartridges and/or waste cartridges. The culture system provides fluid communicative paths between the media cartridges and/or waste cartridges and wells of the growth cassette. Thus, media can be introduced to the wells of the growth cassette or cartridge and waste can be removed therefrom. In addition, the culture system may include a gas subsystem selectively operable to produce an atmosphere of a desired or defined composition at least proximate to the wells of the growth cassette. Such may automate or at least simplify what is otherwise a cumbersome process, and may allow dynamically changing atmosphere, for example in response to certain sensed, measured or otherwise determined conditions. Additionally, or alternatively, the culture system may include a microscopy subsystem, selectively operable to capture digital images or digital image data of the wells of the growth cassette including the contents thereof.

Notably, the culture system comprises at least one control subsystem including at least one processor and at least one non-transitory storage medium to store processor-executable instructions. The control subsystem controls operation of the various other components of the culture system. The control subsystem may be communicatively coupled to one or more external computing devices. The external computing devices include at least one processor and at least one non-transitory storage medium to store processor-executable instructions. The external computing device may be used to control operation of the culture system and/or receive, display or analyze digital image information of a culture within one or more wells of the growth cassette captured by the microscopy subsystem.

The various systems, apparatus, devices, methods, articles and kits described herein may provide a number of advantages over other approaches. For example, the approach taught herein may make the end user more efficient saving time, reducing workload, and allowing remote operation. The approach taught in here may enable the growth of stem cells in a more controlled fashion than current manual approaches. The approach taught herein may allow end users to purchase or obtain kits, with all the required materials. Such may be more efficient than obtaining materials in a piecemeal fashion, and may reduce waste. The approach taught herein may reduce the amount of materials required. The approach taught herein may provide a less expensive than other approaches, for example supplying only the required amount of materials. The approach taught herein may even be more energy efficient then other approaches, although such has not yet been ascertained.

A culture system may be summarized as including a housing having a growth cassette receiver sized and dimensioned to removably receive respective ones of a number of multi-well growth cassettes therein, which multi-well growth cassette has a plurality of wells; a media subsystem that includes at least one actuator responsive to at least one control signal to selectively control delivery of media to at least one well of the multi-well growth cassette when the at least one multi-well growth cassette is received in the growth cassette receiver, and at least one actuator responsive to at least one control signal to change a flow path of media between at least one media inlet and respective ones of the wells of the multi-well growth cassette; a waste subsystem that includes at least one actuator responsive to at least one control signal to control extraction of waste from at least one well of the multi-well growth cassette when the at least one multi-well growth cassette is received in the growth cassette receiver, and at least one actuator responsive to at least one control signal to selectively change a flow path of waste between delivery to at least one waste outlet and delivery to at least one of the wells of the multi-well growth cassette; an environmental subsystem that includes an atmosphere control subsystem having an atmosphere supply subsystem including at least one actuator responsive to at least one control signal to selectively supply a selected gas to an atmosphere to which the content of at least one well of the multi-well growth cassette is exposed when the at least one multi-well growth cassette is received in the growth cassette receiver; and a control subsystem including at least one processor and at least one non-transitory storage medium to store instructions executable by the at least one processor, the control subsystem communicatively coupled to provide at least one control signal to control the actuators of the media subsystem, the actuators of the waste subsystem and the actuators of the atmosphere supply subsystem as part of executing at least one defined culturing protocol. The environmental subsystem may further include a well contents temperature control subsystem including at least one selectively controllable current source operable to provide current to at least one heater element as part of executing the at least one defined culturing protocol and at least one signal indicative of a sensed temperature of at least one of the wells of the multi-well growth cassette or the content thereof. The environmental subsystem may further include a well contents temperature control subsystem including at least one selectively controllable current source electrically coupleable to a least one heater element carried by the multi-well growth cassette when the at least one multi-well growth cassette is received in the growth cassette receiver. The atmosphere control subsystem may further include at least one atmosphere heater positioned to heat the atmosphere to which the content of at least one well of the multi-well growth cassette is exposed when the at least one multi-well growth cassette is received in the growth cassette receiver, the at least one atmosphere heater selectively controllable in response to at least one control signal provided by the control subsystem as part of executing the least one defined culturing protocol. The atmosphere control subsystem may further include a relative humidity control subsystem including at least one of humidification actuator coupled to control at least one of a humidifier or a dehumidifier to adjust a relative humidity of the atmosphere to which the content of at least one well of the multi-well growth cassette is exposed when the at least one multi-well growth cassette is received in the growth cassette receiver, the at least one humidification actuator selectively controllable in responsive to at least one control signal provided by the control subsystem as part of executing the least one defined culturing protocol. The atmosphere control subsystem may further include at least one fan actuator coupled to control a fan to circulate the atmosphere to which the content of at least one well of the multi-well growth cassette is exposed when the at least one multi-well growth cassette is received in the growth cassette receiver, the at least one fan actuator selectively controllable in response to at least one control signal provided by the control subsystem as part of executing the least one defined culturing protocol.

The culture system may further include an evacuation pump actuator coupled to drive an evacuation pump to evacuate a volume at least proximate at least one well of the multi-well growth cassette when the at least one multi-well growth cassette is received in the growth cassette receiver, the evacuation pump actuator selectively responsive to at least one control signal provided by the control subsystem as part of executing the at least one defined culturing protocol.

The culture system may further include a microscopy subsystem including at least one image transducer, each of the at least one image transducer having a respective field-of-view and operable to produce digital image information, and a number of optical components that form at least one optical path between the at least one image transducer and at least one well of the multi-well growth cassette when the multi-well growth cassette is received in the growth cassette receiver. The at least one image transducer may be communicatively coupled to provide image information to the at least one processor in response to at least one control signal provided by the control subsystem as part of executing the at least one defined culturing protocol. The control subsystem may include a microprocessor and a digital signal processor, the digital signal processor, and the at least one image transducer may be communicatively coupled to provide image information to the digital signal processor. The at least one imager may be responsive to at least control signal provided by the control subsystem to capture digital images as specified by the at least one defined protocol. The microscopy subsystem may further include a microscopy illumination subsystem including at least one source of electromagnetic radiation positioned to selectively illuminate the content of at least one well of the multi-well growth cassette when the at least one multi-well growth cassette is received in the growth cassette receiver, such that illumination which passes through or is reflected by the content of the at least one well of the multi-well growth cassette passes along the at least one optical path to the at least one image transducer.

The culture system may further include an illumination subsystem including at least one source of electromagnetic radiation positioned to selectively illuminate the content of at least one well of the multi-well growth cassette when the at least one multi-well growth cassette is received in the growth cassette receiver, such that illumination which ]passes through or is reflected by the content of the at least one well of the multi-well growth cassette passes along the at least one optical path to the at least one image transducer, the illumination subsystem operable to selectively regulate at least a time of exposure to electromagnetic radiation to which the content of at least one well of the multi-well growth cassette is selectively exposed in response to the at least one defined protocol. The environmental control subsystem may further include an illumination exposure control subsystem include at least one current source, the at least one current source electrically coupled to at least one source of electromagnetic radiation positioned to selectively expose the content of at a portion of at least one well of the multi-well growth cassette when the at least one multi-well growth cassette is received in the growth cassette receiver, the at least one current source of the illumination exposure control subsystem responsive to at least one control signal provided by the control subsystem to selectively regulate at least a time of exposure to electromagnetic radiation to which the content of at least one well of the multi-well growth cassette is selectively exposed in response to the at least one defined protocol. The illumination exposure control subsystem may be further operable to selectively regulate at least one of a wavelength of electromagnetic radiation, an intensity of electromagnetic radiation, or an amount of electromagnetic radiation, to which the content of at least one well of the multi-well growth cassette is selectively exposed as specified by the at least one defined protocol. The environmental control subsystem may further include that at least one source of electromagnetic radiation, that at least one source of electromagnetic radiation including a number of light emitting diodes.

The culture system may further include a stimulus subsystem including at least one stimulus actuator coupled to cause a stimulus to be applied at least one of the wells of the multi-well growth cassette or the contents thereof when the at least one multi-well growth cassette is received in the growth cassette receiver, the at least one stimulus actuator responsive to at least one control signal provided by the control subsystem in response to the at least one defined culturing protocol. The stimulus subsystem may further include at least one stimulus transducer selected from the group consisting of at least one of an electric motor and a linkage coupled thereto to produce mechanical oscillations, an ultrasound piezoelectric transducer coupled to produce ultrasonic pressure wave oscillations, a Helmholtz coil coupled to produce a magnetic field, or a pulsed jet coupled to produce pulsate fluid flow. The housing may include at least two media cartridge receivers sized and dimensioned to removable receive respective media cartridges and at least one gas canister receivers sized and dimensioned to removably receive respective gas canisters. The media cartridges may be fluidly coupled directly to the at least one media inlet of the growth cassette without any intervening conduit of the culture system. The gas canisters may be fluidly coupled directly to a gas permeable membrane of the growth cassette without any intervening conduit of the culture system. The housing may further include at least two waste cartridge receivers sized and dimensioned to removably receive respective waste cartridges. At least one size or dimension of the media cartridge receivers may be different from at least one size or dimension of the waste cartridge receivers to prevent insert of the media or waste cartridges in an incorrect one of the media or waste cartridge receivers. The waste cartridges may be fluidly coupled directly to the at least one waste outlet of the growth cassette without any intervening conduit of the culture system. The media cartridges may be fluidly coupled directly to the at least one media inlet of the growth cassette without any intervening conduit of the culture system. The gas canisters may be fluidly coupled directly to a gas permeable membrane of the growth cassette without any intervening conduit of the culture system.

The culture system may further include at least one automatic data collection device operable to read at least one data carriers carried by at least one of the growth cassettes, the media cartridges or the gas canisters, the automatic data collection device communicatively coupled to the control subsystem to provide data collection information read from the data carriers to the at least one processor. The data carriers may include at least one of a machine-readable symbol, a radio frequency identification transponder, a magnetic stripe, or a touch memory device, and the automatic data collection device is at least one of a machine-readable symbol reader, a radio frequency identification transponder reader, a magnetic stripe reader, or a touch memory reader. The control subsystem may determine if any media cartridge is incorrectly inserted in a waste cartridge receiver or if any waste cartridge is incorrectly inserted in a media cartridge receiver, and at least one of prevents operation of the culture system or may produce an alert in response to the determination. The at least one actuator of the media subsystem that selectively controls delivery of media to at least one well of the multi-well growth cassette may include at least a first media inlet valve actuator and a second media inlet valve actuator, the first and the second media inlet valve actuators selectively drivingly coupled to respective media inlet valves on the growth cassette when the growth cassette is positioned in the culture system. The at least one actuator of the media subsystem that selectively changes the flow path of media between the at least one media inlet and respective ones of the wells of the multi-well growth cassette may include at least one diverter valve actuator selectively drivingly coupled to a diverter valve on the growth cassette when the growth cassette is positioned in the culture system. The at least one actuator of the waste subsystem that controls extraction of waste from at least one well of the multi-well growth cassette may include at least a first waste pump actuator and a second waste pump actuator, the first and second waste pump actuators selectively drivingly coupled to respective conduits on the growth cassette when the growth cassette is positioned in the culture system. The at least one actuator of the waste subsystem that selectively changes the flow path of waste between delivery to the at least one waste outlet and delivery to the at least one of the wells of the multi-well growth cassette may include at least a first waste outlet valve actuator and a second waste outlet actuator, the first and the second waste outlet valve actuators selectively drivingly coupled to respective waste outlet valves on the growth cassette when the growth cassette is positioned in the culture system. The at least one actuator of the atmosphere supply subsystem that selectively supplies the selected gas to the atmosphere to which the content of the at least one well of the multi-well growth cassette is exposed may include at least a first gas inlet valve actuator and a second gas inlet valve actuator, the first and the second gas inlet valve actuators selectively drivingly coupled to respective gas inlet valves on the growth cassette when the growth cassette is positioned in the culture system.

The culture system may further include the growth cassette, which includes a number of interchangeable covers, selectively securable to cover the wells, at least one of the interchangeable covers being a vented cover, and at least one of the covers being a non-vented cover.

The culture system may further include a plurality of the growth cassette, at least a first one of the growth cassettes having wells of a first volume and at least a second one of the growth cassettes having wells of a second volume, different than the first volume. The growth cassette may include a number of interchangeable covers, selectively securable to cover the wells, at least one of the interchangeable covers being a vented cover, and at least one of the covers being a non-vented cover.

The culture system as above described in any combination.

A method of operating a culture system having a housing, a growth cassette receiver, a media subsystem including a number of media cartridge receivers, a waste subsystem including a number of waste cartridge receivers, an environmental subsystem including a number of gas canister receivers, and a control subsystem may be summarized as including removably receiving respective ones of a number of multi-well growth cassettes having a plurality of wells by the growth cassette receiver; controlling delivery of media to at least one well of the multi-well growth cassette when the at least one multi-well growth cassette is received in the growth cassette receiver by the media subsystem; changing a flow path of the media between at least one media inlet and respective ones of the wells of the multi-well growth cassette by the media subsystem; extracting waste from at least one well of the multi-well growth cassette when the at least one multi-well growth cassette is received in the growth cassette receiver by the waste subsystem, selectively changing a flow path of waste between delivery to at least one waste outlet and delivery to at least one of the wells of the multi-well growth cassette by the waste subsystem; and selectively supplying a selected gas to an atmosphere to which the content of at least one well of the multi-well growth cassette is exposed when the at least one multi-well growth cassette is received in the growth cassette receiver by an atmosphere control subsystem of the environmental subsystem.

The method may further include executing at least one defined culturing protocol stored in at least one non-transitory storage medium by at least one processor of the control subsystem; and producing a plurality of control signals to control a number of actuators of the media subsystem, a number of actuators of the waste subsystem and a number of actuators of the atmosphere supply subsystem as part of executing the at least one defined culturing protocol.

The method may further include selectively controlling at least one selectively controllable current source to provide current to at least one growth cassette heater element in response to the at least one the defined culturing protocol; and receiving at least one signal indicative of a sensed temperature of at least one of the wells of the multi-well growth cassette or the content thereof by the control subsystem. Selectively controlling at least one selectively controllable current source to provide current to at least one growth cassette heater element in response to the at least one the defined culturing protocol may include selectively controlling the at least one selectively controllable current source to provide current to at least one growth cassette heater element carried by the multi-well growth cassette.

The method may further include selectively controlling at least one atmosphere heater of the environmental control subsystem in response to the least the defined protocol, the at least one atmosphere heater positioned to heat the atmosphere to which the content of at least one well of the multi-well growth cassette is exposed when the at least one multi-well growth cassette is received in the growth cassette receiver.

The method may further include selectively controlling at least one of a humidifier or a dehumidifier of a relative humidity control subsystem of the environmental control subsystem to adjust a relative humidity of the atmosphere to which the content of at least one well of the multi-well growth cassette is exposed when the at least one multi-well growth cassette is received in the growth cassette receiver in response to the least the defined culturing protocol.

The method may further include selectively operating at least one fan actuator of an atmosphere control subsystem of the environmental control subsystem, the fan actuator coupled to control a fan to circulate the atmosphere to which the content of at least one well of the multi-well growth cassette is exposed when the at least one multi-well growth cassette is received in the growth cassette receiver, in response to at least one control signal provided by the control subsystem as part of executing the at least one defined culturing protocol.

The method may further include selectively operating an evacuation pump actuator of the environmental control subsystem to evacuate a volume at least proximate at least one well of the multi-well growth cassette when the at least one multi-well growth cassette is received in the growth cassette receiver, in response to at least one control signal provided by the control subsystem as part of executing the at least one defined culturing protocol.

The method may further include a microscopy subsystem, which may further include producing digital image information by at least one image transducer of the microscopy subsystem, the microscopy subsystem having a number of optical components that form at least one optical path between the at least one image transducer and at least one well of the multi-well growth cassette when the multi-well growth cassette is received in the growth cassette receiver.

The method may further include communicatively coupling the image information to at least one processor of the control subsystem in response to at least one control signal provided by the control subsystem as part of executing the at least one defined culturing protocol.

The method may further include communicatively coupling the image information to at least one digital signal processor of the control subsystem in response to at least one control signal provided by the control subsystem as part of executing the at least one defined culturing protocol.

The method may further include providing to at least control signal by the control subsystem to cause the at least one image transducer to capture digital images as specified by the at least one defined culturing protocol.

The microscopy subsystem may further include a microscopy illumination subsystem including at least one source of electromagnetic radiation positioned to selectively illuminate the content of at least one well of the multi-well growth cassette when the at least one multi-well growth cassette is received in the growth cassette receiver, which may further include providing to at least control signal by the control subsystem to cause the at least one source of electromagnetic radiation to illuminate the content of at least one well of the multi-well growth cassette as specified by the at least one defined culturing protocol.

The method wherein the environmental control subsystem may further include an illumination exposure control subsystem including at least one current source, the at least one current source electrically coupled to at least one source of electromagnetic radiation positioned to selectively expose the content of at a portion of at least one well of the multi-well growth cassette when the at least one multi-well growth cassette is received in the growth cassette receiver, may further include providing at least control signal by the control subsystem to cause the at least one source of electromagnetic radiation to illuminate the content of at least one well of the multi-well growth cassette as specified by the at least one defined culturing protocol to selectively regulate at least a time of exposure to electromagnetic radiation to which the content of at least one well of the multi-well growth cassette is selectively exposed in response to the at least one defined protocol. Providing at least control signal by the control subsystem to cause the at least one source of electromagnetic radiation to illuminate the content of at least one well of the multi-well growth cassette may further include providing at least control signal to selectively regulate at least one of a wavelength of electromagnetic radiation, an intensity of electromagnetic radiation, or an amount of electromagnetic radiation, to which the content of at least one well of the multi-well growth cassette is selectively exposed as specified by the at least one defined protocol.

The method wherein the culture system may further include a stimulus subsystem including at least one stimulus actuator coupled to cause a stimulus to be applied at least one of the wells of the multi-well growth cassette or the contents thereof when the at least one multi-well growth cassette is received in the growth cassette receiver, may further include providing to at least control signal by the control subsystem to the at least one stimulus actuator as part of executing the at least one defined culturing protocol.

The method wherein the housing may include at least two media cartridge receivers sized and dimensioned to removable receive respective media cartridges and at least one gas canister receivers sized and dimensioned to removably receive respective gas canisters may further include removably receiving a number of media cartridges by respective ones of the media cartridge receivers; and removably receiving a number of gas canisters by respective ones of the gas canister receivers. Removably receiving a number of media cartridges by respective ones of the media cartridge receivers may include fluidly coupling a respective media outlet of the media cartridges directly to at least one media inlet of the growth cassette without any intervening conduit of the culture system and wherein removably receiving a number of gas canisters by respective ones of the gas canister receivers includes fluidly coupling a respective gas output of the gas canisters directly to a gas permeable membrane of the growth cassette without any intervening conduit of the culture system. The method wherein the housing may further include at least two waste cartridge receivers sized and dimensioned to removably receive respective waste cartridges may further include removably receiving a number of waste cartridges by respective ones of the waste cartridge receivers. Removably receiving a number of waste cartridges by respective ones of the waste cartridge receivers may includes fluidly coupling a respective waste inlet of the waste cartridges directly to a respective waste outlet of the growth cassette without any intervening conduit of the culture system.

The method may further include at least one automatic data collection device operable to automatically read at least one data carrier carried by at least one of the growth cassettes, a number of removable media cartridges, a number of removable waste cartridges and a number of removable gas canisters, the automatic data collection device communicatively coupled to the control subsystem to provide data collection information read from the data carriers to the at least one processor.

The method may further include determining if any media cartridge is incorrectly inserted in a waste cartridge receivers or if any waste cartridge is incorrectly inserted in a media cartridge receiver by the control subsystem, and at least one of: preventing operation of the culture system in response to the determination; or producing an alert in response to the determination.

The method as described above in any combination.

A culture system may be summarized as including a housing having at least one growth chamber non-removably located in the housing; a media subsystem that includes at least one actuator responsive to at least one control signal to selectively control delivery of media to the at least one growth chamber, and at least one actuator responsive to at least one control signal to change a flow path of media between at least one media inlet and the at least one growth chamber; a waste subsystem that includes at least one actuator responsive to at least one control signal to control extraction of waste from the at least one growth chamber, and at least one actuator responsive to at least one control signal to selectively change a flow path of waste between delivery to at least one waste outlet and delivery to the at least one growth chamber; an environmental subsystem that includes an atmosphere control subsystem having an atmosphere supply subsystem including at least one actuator responsive to at least one control signal to selectively supply a selected gas to an atmosphere to which the content of the at least one growth chamber; and a control subsystem including at least one processor and at least one non-transitory storage medium to store instructions executable by the at least one processor, the control subsystem communicatively coupled to provide at least one control signal to control the actuators of the media subsystem, the actuators of the waste subsystem and the actuators of the atmosphere supply subsystem as part of executing at least one defined culturing protocol.

A method of operating a culture system having a housing at least one growth chamber, a media subsystem including a number of media cartridge receivers, a waste subsystem including a number of waste cartridge receivers, an environmental subsystem including a number of gas canister receivers, and a control subsystem may be summarized as including controlling delivery of media to the at least one growth chamber by the media subsystem; changing a flow path of the media between at least one media inlet and the at least one growth chamber by the media subsystem; extracting waste from the at least one growth chamber by the waste subsystem, selectively changing a flow path of waste between delivery to at least one waste outlet and delivery to the at least one growth chamber by the waste subsystem; and selectively supplying a selected gas to an atmosphere to which the content of the at least one growth chamber is exposed when the at least one multi-well growth cassette is received in the growth cassette receiver by an atmosphere control subsystem of the environmental subsystem.

A culture system may be summarized as including a housing having a growth cassette receiver sized and dimensioned to removably receive respective ones of a number of multi-well growth cassettes therein, which multi-well growth cassette has a plurality of wells; a control subsystem including at least one processor and at least one non-transitory storage medium to store instructions executable by the at least one processor to execute at least one defined culturing protocol and produce a corresponding set of control signals in response to execution of the at least one defined culturing protocol; and an environmental subsystem that includes an atmosphere control subsystem, comprising: atmosphere supply subsystem including at least one actuator responsive to at least one control signal from the control subsystem to selectively supply a selected gas to an atmosphere to which the content of at least one well of the multi-well growth cassette is exposed when the at least one multi-well growth cassette is received in the growth cassette receiver as specified by the at least one culturing protocol; and at least one atmosphere heater current source responsive to at least one control signal from the control subsystem to supply current to at least one atmosphere heater element which is positioned to heat the atmosphere to which the content of at least one well of the multi-well growth cassette is exposed when the at least one multi-well growth cassette is received in the growth cassette receiver, as specified by the at least one culturing protocol. The atmosphere control subsystem may further include a relative humidity control subsystem including at least one of humidification actuator coupled to control at least one of a humidifier or a dehumidifier to adjust a relative humidity of the atmosphere to which the content of at least one well of the multi-well growth cassette is exposed when the at least one multi-well growth cassette is received in the growth cassette receiver, the at least one humidification actuator selectively controllable in responsive to at least one control signal provided by the control subsystem as part of the least the defined culturing protocol. The atmosphere control subsystem may further include at least one fan actuator coupled to control a fan to circulate the atmosphere to which the content of at least one well of the multi-well growth cassette is exposed when the at least one multi-well growth cassette is received in the growth cassette receiver, the at least one fan actuator selectively controllable in responsive to at least one control signal provided by the control subsystem as part of the least the defined culturing protocol. The housing may include at least two gas canister receivers sized and dimensioned to removably receive respective gas canisters. The gas canisters may be fluidly coupled directly to a gas permeable membrane of the growth cassette without any intervening conduit of the culture system. The gas canisters may be fluidly coupled directly to a gas mixing chamber of the growth cassette without any intervening conduit of the culture system. The atmosphere control subsystem may further include a manifold that fluidly communicatively couple a plurality of the gas canisters to the at least one well of the multi-well growth cassette. The atmosphere control subsystem may further include at least one vent actuator responsive to at least one control signal from the control subsystem to selective vent the atmosphere externally from the culture system. The environmental control subsystem may further include an illumination exposure control subsystem include at least one current source, the at least one current source electrically coupled to at least one source of electromagnetic radiation positioned to selectively expose the content of at a portion of at least one well of the multi-well growth cassette when the at least one multi-well growth cassette is received in the growth cassette receiver, the at least one current source of the illumination exposure control subsystem responsive to at least one control signal provided by the control subsystem to selectively regulate at least a time of exposure to electromagnetic radiation to which the content of at least one well of the multi-well growth cassette is selectively exposed in response to the at least one defined culturing protocol. The illumination exposure control subsystem may be further operable to selectively regulate at least one of a wavelength of electromagnetic radiation, an intensity of electromagnetic radiation, or an amount of electromagnetic radiation, to which the content of at least one well of the multi-well growth cassette is selectively exposed as specified d by the at least one defined culturing protocol. The environmental control subsystem mat further include that at least one source of electromagnetic radiation, that at least one source of electromagnetic radiation including a number of light emitting diodes.

The culture system may further include a number of sensors positioned to sense at least one environmental condition of the culture system, and wherein the control subsystem is communicatively coupled to control the environmental subsystem based at least in part in response to the environmental conditions sensed the number of sensors as specified by the at least one culturing protocol.

The culture system may further include at least one image transducer having a field-of-view that encompasses at least a portion of at least one of the wells of the multi-well growth cassette, and wherein the control subsystem is communicatively coupled to control the environmental subsystem based at least in part in response to image data acquired by the at least one image transducer.

The culture system as described above in any combination.

A method of operating a culture system having a housing, a growth cassette receiver, a media subsystem including a number of media cartridge receivers, a waste subsystem including a number of waste cartridge receivers, an environmental subsystem including a number of gas canister receivers, and a control subsystem may be summarized as including removably receiving respective ones of a number of multi-well growth cassettes having a plurality of wells by the growth cassette receiver; selectively supplying a selected gas to an atmosphere to which the content of at least one well of the multi-well growth cassette is exposed when the at least one multi-well growth cassette is received in the growth cassette receiver as specified by the at least one culturing protocol by an atmosphere supply subsystem of the environmental subsystem in response to at least one control signal from the control subsystem as part of executing at least one defined culturing protocol; and responsive to at least one control signal from the control subsystem to supplying current to at least one atmosphere heater element which is positioned to heat the atmosphere to which the content of at least one well of the multi-well growth cassette is exposed when the at least one multi-well growth cassette is received in the growth cassette receiver, as specified by the at least one culturing protocol by at least one atmosphere heater current source of the environmental subsystem in response to at least one control signal from the control subsystem as part of executing the at least one defined culturing protocol.

The method wherein the atmosphere control subsystem may further include a relative humidity control subsystem including at least one of humidification actuator coupled to control at least one of a humidifier or a dehumidifier to adjust a relative humidity of the atmosphere to which the content of at least one well of the multi-well growth cassette is exposed when the at least one multi-well growth cassette is received in the growth cassette receiver may further include selectively controlling the at least one humidification actuator in responsive to at least one control signal provided by the control subsystem as part of executing the least the defined culturing protocol.

The method wherein the atmosphere control subsystem may further include at least one fan actuator coupled to control a fan to circulate the atmosphere to which the content of at least one well of the multi-well growth cassette is exposed when the at least one multi-well growth cassette is received in the growth cassette receiver may further include selectively controlling the at least one fan actuator in responsive to at least one control signal provided by the control subsystem as part of executing the least the defined protocol.

The method wherein the housing may include at least two gas canister receivers sized and dimensioned to removable receive respective gas canisters may further include removably receiving a number of gas canisters by respective ones of the gas canister receivers. Removably receiving a number of gas canisters by respective ones of the gas canister receivers may include fluidly coupling a respective gas output of the gas canisters directly to a gas permeable membrane of the growth cassette without any intervening conduit of the culture system.

The method wherein the atmosphere control subsystem may further include at least one vent actuator responsive to at least one control signal from the control subsystem may further include selectively operating the vent actuator to vent the atmosphere externally from the culture system.

The method wherein the environmental control subsystem may further include an illumination exposure control subsystem that includes at least one current source, the at least one current source electrically coupled to at least one source of electromagnetic radiation positioned to selectively expose the content of at a portion of at least one well of the multi-well growth cassette when the at least one multi-well growth cassette is received in the growth cassette receiver may further include operating the at least one current source of the illumination exposure control subsystem in responsive to at least one control signal provided by the control subsystem to selectively regulate at least a time of exposure to electromagnetic radiation to which the content of at least one well of the multi-well growth cassette is selectively exposed as part of executing the at least one defined culturing protocol. The at least one current source of the illumination exposure control subsystem may further include operating the at least one current source of the illumination exposure control subsystem to selectively regulate at least one of a wavelength of electromagnetic radiation, an intensity of electromagnetic radiation, or an amount of electromagnetic radiation, to which the content of at least one well of the multi-well growth cassette is selectively exposed as specified d by the at least one defined protocol.

The method wherein the environmental control subsystem may include a number of sensors positioned to sense at least one environmental condition of the culture system, the sensors communicatively coupled to the control subsystem, may further include adjusting operation of the environmental control system based least in part in response to the environmental conditions sensed the number of sensors as specified by the at least one culturing protocol.

The method wherein the culture system may further include at least one image transducer having a field-of-view that encompasses at least a portion of at least one of the wells of the multi-well growth cassette may further include adjusting operation of the environmental subsystem based at least in part in response to image data acquired by the at least one image transducer.

The method as described above in any combination.

A culture system may be summarized as including a housing having at least one growth chamber non-removably located therein; a control subsystem including at least one processor and at least one non-transitory storage medium to store instructions executable by the at least one processor to execute at least one defined culturing protocol and produce a corresponding set of control signals in response to execution of the at least one defined culturing protocol; and an environmental subsystem that includes an atmosphere control subsystem, including atmosphere supply subsystem including at least one actuator responsive to at least one control signal from the control subsystem to selectively supply a selected gas to an atmosphere to which the content of the least one growth chamber as specified by the at least one culturing protocol; and at least one atmosphere heater current source responsive to at least one control signal from the control subsystem to supply current to at least one atmosphere heater element which is positioned to heat the atmosphere to which the content of the least one growth chamber, as specified by the at least one culturing protocol.

A method of operating a culture system having a housing, at least one growth chamber, a media subsystem including a number of media cartridge receivers, a waste subsystem including a number of waste cartridge receivers, an environmental subsystem including a number of gas canister receivers, and a control subsystem may be summarized as including selectively supplying a selected gas to an atmosphere to which the content of the at least one growth chamber as specified by the at least one culturing protocol by an atmosphere supply subsystem of the environmental subsystem in response to at least one control signal from the control subsystem as part of executing at least one defined culturing protocol; and responsive to at least one control signal from the control subsystem to supplying current to at least one atmosphere heater element which is positioned to heat the atmosphere to which the content of the at least one growth chamber, as specified by the at least one culturing protocol by at least one atmosphere heater current source of the environmental subsystem in response to at least one control signal from the control subsystem as part of executing the at least one defined culturing protocol.

A culture system may be summarized as including a housing having a growth cassette receiver sized and dimensioned to removably receive respective ones of a number of multi-well growth cassettes therein, which multi-well growth cassette has a plurality of wells; a microscopy subsystem that includes at least one optical component and at least one image sensor configured to produce a number of digital images of the content of at least a portion of at least one of the wells of the multi-well growth cassette; and a control subsystem including at least one processor and at least one non-transitory storage medium to store instructions executable by the at least one processor, the control subsystem communicatively coupled to receive digital image information from the microscopy subsystem and communicatively coupled to control at least one culturing operation in response to the digital image information.

The culture system may further include a media subsystem that includes at least one actuator responsive to at least one control signal to selectively control delivery of media to at least one well of the multi-well growth cassette when the at least one multi-well growth cassette is received in the growth cassette receiver, and at least one actuator responsive to at least one control signal to change a flow path of media between at least one media inlet and respective ones of the wells of the multi-well growth cassette, and wherein the at least one culturing operation controlled by the control subsystem in response to the digital image information includes delivery of media to at least one well of the multi-well growth cassette.

The culture system may further include a waste subsystem that includes at least one actuator responsive to at least one control signal to control extraction of waste from at least one well of the multi-well growth cassette when the at least one multi-well growth cassette is received in the growth cassette receiver, and at least one actuator responsive to at least one control signal to selectively change a flow path of waste between delivery to at least one waste outlet and delivery to at least one of the wells of the multi-well growth cassette, and wherein the at least one culturing operation controlled by the control subsystem in response to the digital image information includes extraction of waste from at least one well of the multi-well growth cassette.

The culture system may further include an environmental subsystem that includes an atmosphere control subsystem having an atmosphere supply subsystem including at least one actuator responsive to at least one control signal to selectively supply a selected gas to an atmosphere to which the content of at least one well of the multi-well growth cassette is exposed when the at least one multi-well growth cassette is received in the growth cassette receiver, and wherein the at least one culturing operation controlled by the control subsystem in response to the digital image information includes supply of the selected gas to at least one well of the multi-well growth cassette. The instructions may configure the control subsystem to analyze a number of physical registration features of the growth cassette. The instructions may configure the control subsystem to analyze a number of optical registration indicia carried by the growth cassette.

The culture system as described above in any combination.

A method of operating a culture system having a housing, a growth cassette receiver, a microscopy system that includes at least one optical component and at least one image sensor configured to produce a number of digital images, and a control subsystem including at least one processor and at least one non-transitory storage medium to store instructions executable by the at least one processor may be summarized as including removably receiving respective ones of a number of multi-well growth cassettes having a plurality of wells by the growth cassette receiver; producing a number of digital images of the content of at least a portion of at least one of the wells of the multi-well growth cassette in response to at least one control signal from the control subsystem as part of executing at least one defined culturing protocol; and adjusting at least one culturing operation based at least in part on the digital image information in response to at least one control signal from the control subsystem as part of executing the at least one defined culturing protocol.

The culture system may further include a media subsystem that includes at least one actuator responsive to at least one control signal to selectively control delivery of media to at least one well of the multi-well growth cassette when the at least one multi-well growth cassette is received in the growth cassette receiver, and at least one actuator responsive to at least one control signal to change a flow path of media between at least one media inlet and respective ones of the wells of the multi-well growth cassette, and wherein adjusting at least one culturing operation based at least in part on the digital image information includes adjusting a delivery of media to at least one well of the multi-well growth cassette. The culture system may further include a waste subsystem that includes at least one actuator responsive to at least one control signal to control extraction of waste from at least one well of the multi-well growth cassette when the at least one multi-well growth cassette is received in the growth cassette receiver, and at least one actuator responsive to at least one control signal to selectively change a flow path of waste between delivery to at least one waste outlet and delivery to at least one of the wells of the multi-well growth cassette, and wherein adjusting at least one culturing operation based at least in part on the digital image information includes adjusting an extraction of waste from at least one well of the multi-well growth cassette. The culture system may further include an environmental subsystem that includes an atmosphere control subsystem having an atmosphere supply subsystem including at least one actuator responsive to at least one control signal to selectively supply a selected gas to an atmosphere to which the content of at least one well of the multi-well growth cassette is exposed when the at least one multi-well growth cassette is received in the growth cassette receiver, and wherein adjusting at least one culturing operation based at least in part on the digital image information includes adjusting a supply of the selected gas to at least one well of the multi-well growth cassette.

The method may further include analyzing a number of physical registration features of the growth cassette.

The method may further include analyzing a number of optical registration indicia carried by the cassette.

The method as described above in any combination.

A culture system may be summarized as including a housing having a growth cassette receiver sized and dimensioned to removably receive respective ones of a number of multi-well growth cassettes therein, which multi-well growth cassette has a plurality of wells; a user interface subsystem; and a control subsystem including at least one processor and at least one non-transitory storage medium to store instructions executable by the at least one processor, the control subsystem communicatively coupled to the user interface to receive user input indicative of at least one culturing protocol specified by an end user and operable to provide at least one control signal to control at least one actuator of the culturing system to automatically perform the at least one defined culturing protocol specified by the user input.

The culture system may further include a media subsystem that includes at least one actuator responsive to at least one control signal to selectively control delivery of media to at least one well of the multi-well growth cassette when the at least one multi-well growth cassette is received in the growth cassette receiver, and at least one actuator responsive to at least one control signal to change a flow path of media between at least one media inlet and respective ones of the wells of the multi-well growth cassette, and the control subsystem provides the control signal to at least one of the actuators of the media subsystem to automatically perform the at least one defined culturing protocol specified by the user input.

The culture system may further include a waste subsystem that includes at least one actuator responsive to at least one control signal to control extraction of waste from at least one well of the multi-well growth cassette when the at least one multi-well growth cassette is received in the growth cassette receiver, and at least one actuator responsive to at least one control signal to selectively change a flow path of waste between delivery to at least one waste outlet and delivery to at least one of the wells of the multi-well growth cassette, and the control subsystem provides the control signal to at least one of the actuators of the waste subsystem to automatically perform the at least one defined culturing protocol specified by the user input.

The culture system may further include an environmental subsystem that includes an atmosphere control subsystem having an atmosphere supply subsystem including at least one actuator responsive to at least one control signal to selectively supply a selected gas to an atmosphere to which the content of at least one well of the multi-well growth cassette is exposed when the at least one multi-well growth cassette is received in the growth cassette receiver, and the control subsystem provides the control signal to at least one of the actuators of the atmosphere supply subsystem to automatically perform the at least one defined culturing protocol specified by the user input. The user interface may provide a number of user selectable controls that allow a user to select a predefined culturing protocol as the defined protocol culturing to automatically be executed by the culture system. The user interface may provide a number of user selectable controls that allow a user to select a plurality of culturing operations to define the defined culturing protocol to automatically be executed by the culture system. The user selectable controls may allow the user to specify a number of media delivery operations. The user selectable controls may allow the user to specify a number of environmental control operations. The user selectable controls may allow the user to specify a number of atmosphere supply operations. The user selectable controls may allow the user to specify a number of waste extraction operations.

The user selectable controls may allow the user to specify a number of digital image capture operations.

The culture system may further include at least one imager positioned and operable to capture digital images of at least a portion of at least one well of the growth cassette, and wherein the user selectable controls allow the user to specify a number of digital image analysis and feedback operations which specific operations responsive to automatic analysis of captured digital images.

The culture system may further include at least one sensor positioned to sense at least one of an operational condition or an environmental condition of the culture system and wherein the user selectable controls allow the user to specify a number of feedback operations which specific operations responsive to automatic analysis of at least one condition sensed by at least one sensor. The user selectable controls may allow the user to specify at least one recording operation to record at least one of an operational condition or an environmental condition of the culture system, a digital image or an analysis of a digital image. The user interface may include at least one display and the user interface provides a number of the user selectable controls displayed on the display that allow a user to select the defined culturing protocol from a plurality of predefined culturing protocols. The user selectable controls may include at least one pull-down menu including a number of user selectable icon displayed on the display. The user interface may include at least one display and the user interface provides a number of the user selectable controls displayed on the display that allow a user to define the defined culturing protocol. The user selectable controls may include at least one pull-down menu including a number of user selectable icon displayed on the display.

The culture system as described above in any combination.

A method of operating a culture system having a housing, a growth cassette receiver, a user interface subsystem, and a control subsystem including at least one processor and at least one non-transitory storage medium to store instructions executable by the at least one processor may be summarized as including removably receiving respective ones of a number of multi-well growth cassettes having a plurality of wells by the growth cassette receiver; receiving at least one user indication via the user interface that specifies a defined culturing protocol to be executed on the contents of the multi-well growth cassette; and providing by the control subsystem at least one control signal to control at least one actuator of the culturing system to automatically perform the at least one defined culturing protocol specified by the user input. The culture system may further include a media subsystem that includes at least one actuator responsive to at least one control signal to selectively control delivery of media to at least one well of the multi-well growth cassette when the at least one multi-well growth cassette is received in the growth cassette receiver, and at least one actuator responsive to at least one control signal to change a flow path of media between at least one media inlet and respective ones of the wells of the multi-well growth cassette, and wherein providing by the control subsystem at least one control signal to control at least one actuator of the culturing system includes providing the control signal to at least one of the actuators of the media subsystem to automatically perform the at least one defined culturing protocol specified by the user input. The culture system may further include a waste subsystem that includes at least one actuator responsive to at least one control signal to control extraction of waste from at least one well of the multi-well growth cassette when the at least one multi-well growth cassette is received in the growth cassette receiver, and at least one actuator responsive to at least one control signal to selectively change a flow path of waste between delivery to at least one waste outlet and delivery to at least one of the wells of the multi-well growth cassette, and wherein providing by the control subsystem at least one control signal to control at least one actuator of the culturing system includes providing the control signal to at least one of the actuators of the waste subsystem to automatically perform the at least one defined culturing protocol specified by the user input. The culture system may further include an environmental subsystem that includes an atmosphere control subsystem having an atmosphere supply subsystem including at least one actuator responsive to at least one control signal to selectively supply a selected gas to an atmosphere to which the content of at least one well of the multi-well growth cassette is exposed when the at least one multi-well growth cassette is received in the growth cassette receiver, and wherein providing by the control subsystem at least one control signal to control at least one actuator of the culturing system includes providing the control signal to at least one of the actuators of the atmosphere supply subsystem to automatically perform the at least one defined culturing protocol specified by the user input.

The method wherein at least part of the user interface may be a graphical user interface may further include providing a number of user selectable controls as part of the user interface that allow a user to select a predefined culturing protocol as the defined protocol culturing to automatically be executed by the culture system.

The method wherein at least part of the user interface may be a graphical user interface may further include providing a number of user selectable controls that allow a user to select a plurality of culturing operations to define the defined culturing protocol to automatically be executed by the culture system.

The method wherein at least part of the user interface may be a graphical user interface may further include providing a number of user selectable controls that allow the user to specify a number of media delivery operations.

The method wherein at least part of the user interface may be a graphical user interface may further include providing a number of user selectable controls that allow the user to specify a number of environmental control operations.

The method wherein at least part of the user interface may be a graphical user interface may further include providing a number of user selectable controls that allow the user to specify a number of atmosphere supply operations.

The method wherein at least part of the user interface may be a graphical user interface may further include providing a number of user selectable controls that allow the user to specify a number of waste extraction operations.

The method wherein at least part of the user interface may be a graphical user interface may further include providing a number of user selectable controls that allow the user to specify a number of digital image capture operations.

The method wherein the culture system may further include at least one sensor positioned to sense at least one of an operational condition or an environmental condition of the culture system, and wherein at least part of the user interface is a graphical user interface may further include providing a number of user selectable controls that allow the user to specify a number of feedback operations which specific operations responsive to automatic analysis of at least one condition sensed by at least one sensor.

The method wherein at least part of the user interface may be a graphical user interface may further include providing a number of user selectable controls that allow the user to specify at least one recording operation to record at least one of an operational condition or an environmental condition of the culture system, a digital image or an analysis of a digital image.

The method wherein at least part of the user interface may be a graphical user interface may further include providing a number of user selectable controls displayed on a touch screen display that allow a user to select the defined culturing protocol from a plurality of predefined culturing protocols. The method wherein providing a number of user selectable controls displayed on a touch screen display may include providing at least one pull-down menu including a number of user selectable icon displayed on the display, each of the user selectable icons corresponding to a respective one of a number of previously defined culturing protocols.

The method wherein at least part of the user interface may be a graphical user interface may further include providing a number of the user selectable controls displayed on a touch screen display that allow a user to define the defined culturing protocol. Providing a number of the user selectable controls displayed on a touch screen display that allow a user to define the defined culturing protocol may include providing at least one user selectable control that allows a user to select a previously defined culturing protocol as a template to defined a new culturing protocol. Receiving at least one user indication via the user interface that specifies a defined culturing protocol to be executed on the contents of the multi-well growth cassette may include receiving the at least one user indication from a computing device that is separate and distinct from the culture system. Receiving at least one user indication via the user interface that specifies a defined culturing protocol to be executed on the contents of the multi-well growth cassette may include receiving the at least one user indication via a network connection with a remote computing device on which the user interface is present. Receiving at least one user indication via the user interface that specifies a defined culturing protocol to be executed on the contents of the multi-well growth cassette may include receiving the at least one user indication via a network connection with a remote handheld communications device on which the user interface is present.

The method as described above in any combination.

A growth cassette for use with culture systems may be summarized as including a housing having an exterior and an interior, the interior including a plurality of distinct wells, the housing sized and dimensioned to be removably received by a growth cassette receiver of a culture system; a first media inlet accessible from the exterior of the housing; a first media inlet valve selectively operable to control a media flow via the first media inlet; a second media inlet accessible from the exterior of the housing; a second media inlet valve selectively operable to control a media flow via the second media inlet; and a number of channels in the interior of the housing that provide fluid communication between the wells and the first and the second media inlets. The first and the second media inlets may be sized and dimensioned to respectively directly couple to a media outlet of each of a respective one of a number of media cartridges received by the culture system. Such coupling may be without any intervening conduit of the culture system. The first and the second media inlet valves may be selectively coupleable to be driven from an exterior of the housing by a number of respective actuators of the culture system.

The growth cassette may further include at least one diverter valve operable to provide passage from the first and the second media inlets selectively to a first one of the channels which provides fluid communication to a first one of the wells and a second one of the channels which provides fluid communication to a second one of the wells.

The growth cassette may further include a first filter and flow straightening structure located in a fluid path between the at least one diverter valve and the first one of the wells; and a second filter and flow straightening structure located in a fluid path between the at least one diverter valve and the second one of the wells.

The growth cassette may further include a first rupturable membrane covering the first media inlet; and a second rupturable membrane covering the second media inlet. At least a portion of a first one of the channels which provides fluid communication to a first one of the wells may be a tortuous fluid path and at least a portion of a second one of the channels which provides fluid communication to a second one of the wells may be a tortuous fluid path.

The growth cassette may further include at least one heater element positioned along at least a portion of the tortuous fluid path of at least one of the first or the second one of the channels and in intimate contact therewith.

The growth cassette may further include at least one septum that selectively provides access via a removable conduit to at least one of the wells from an exterior of the housing to provide a biological material thereto.

The growth cassette may further include a first waste outlet accessible from the exterior of the housing; a first waste outlet valve selectively operable to control a waste flow via the first waste outlet; a second waste outlet accessible from the exterior of the housing; a second waste outlet valve selectively operable to control a waste flow via the second waste outlet; and wherein at least some of the number of channels in the interior of the housing provide fluid communication between the wells and the first and the second waste outlets. The first and the second waste outlet valves may be sized and dimensioned to respectively directly couple to a waste inlet of each of a respective one or a number of waste cartridges received by the culture system. The first waste outlet valve may provide passage from a first one of the channels which provides fluid communication from a first one of the wells selectively to the first waste outlet or a one of the channels that provides fluid communication to at least one of the wells.

The growth cassette may further include at least one diverter valve operable to provide passage from the first and the second media inlets selectively to a first one of the channels which provides fluid communication to a first one of the wells and a second one of the channels which provides fluid communication to a second one of the wells, and wherein the first waste outlet valve is operable to provides passage from one of the channels which provides fluid communication from a first one of the wells, selectively to the first waste outlet or to the diverter valve; and the second waste outlet valve is operable to provide passage from one of the channels which provides fluid communication from a second one of the wells, selectively to the second waste outlet or to the diverter valve. The first and the second waste outlet values may be selectively coupleable to be driven from an exterior of the housing by a number of respective actuators of the culture system.

The growth cassette may further include at least one pump coupled in a waste flow path between at least one of the wells and at least one of the first or the second waste outlet valves.

The growth cassette may further include a first pump coupled in a first waste flow path between a first one of the wells and the first waste outlet valve; and a second pump coupled in a second waste flow path between a second one of the wells and the second waste outlet valve. The first and the second pump may be selectively coupleable to be driven from an exterior of the housing by a number of respective actuators of the culture system.

The growth cassette may further include a first rupturable membrane covering the first waste outlet; and a second rupturable membrane covering the second waste outlet.

The growth cassette may further include a gas permeable membrane that provides gas communication into at least one of the conduits from an exterior of the housing and that substantially inhibits communication of water vapor therethrough. The culture system wherein the gas permeable membrane may be unidirectional allowing diffusion.

The growth cassette may further include at least one exhaust port that provides fluid communication between at least one of the channels and the exterior of the housing.

The growth cassette may further include at least a first exhaust port that provides fluid communication between a first one of the channels fluidly communicatively coupled to a first one of the wells and the exterior of the housing; and at least a second exhaust port that provides fluid communication between a second one of the channels fluidly communicatively coupled to a second one of the wells and the exterior of the housing. The flow through the first and the second exhaust ports may be unidirectional allowing only exhaustion of gas from the interior of the housing. At least one of the wells may be subdivide into a plurality of sub-wells. The growth cassette may have a floor that includes a number of boundary portions having a first characteristic and a number of sub-well portions having a second characteristic, respective ones of at least some of the boundary portions intermediate pairs of the sub-well portions to form the plurality of sub-wells. The first characteristic may be at least one of a physical or a chemical characteristic that provides a relatively low adhesion of cells to the boundary portions and the second characteristic is at least one of a physical, a chemical or an electrical characteristic that provides a relatively high adhesion of cells to the sub-well portions. The growth cassette may have a floor that includes a number of sub-well portions and a number of raised boundary portions, at least some of the raised boundary portions intermediate pairs of the sub-well portions to form the plurality of sub-wells. The sub-wells may be arranged as a two-dimensional array. At least some of the wells may include a hydrophilic surface therein.

The growth cassette may further include at least one protein located at least some of the wells or sub-wells prior to a sale of the growth cassette. The at least one protein may include at least a first protein and a second protein different than the first protein, the first protein located in at least a first one of the wells or sub-wells and the second protein in a second one of the wells or sub-wells, different than the first one of the wells or sub-wells. At least some of the wells or sub-wells may include a hydrogel coating. At least some of the wells or sub-wells may include silicon dioxide coating.

The growth cassette may further include at least one data carrier coupled to the substrate and bearing identifying information indicative of at least one of an identity of the growth cassette, an identity of a user of the growth cassette, a date and/or time of use of the growth cassette, an environmental condition to which a content of at least one of the wells of the growth cassette was subjected, or an identity of a protocol preformed using the growth cassette. The data carrier may include at least one of a machine-readable symbol, a radio frequency identification transponder, a magnetic stripe, or a touch memory device.

The growth cassette may further include a number of optical registration indicia which provides registration in at least two planar dimensions and about at least one rotational axis. The growth cassette may further include a number of mechanical registration features which provides registration in at least two planar dimensions and about at least one rotational axis. The growth cassette may include a number of hinged covers selectively securable to cover respective ones of the wells of the growth cassette. The growth cassette may include one or more pumps or portions thereof in fluid communication at least one of the wells of the growth cassette. For example, a portion of a flow conduit of the growth cassette may include flexible tubing which may be manipulate to create a pumping action selectively causing a flow to move in a desired direction, or stopping a flow of liquid and/or gas. The flexible tubing may be manipulated via a mechanism (e.g., gears, rollers, electric motor, other actuator) which is separate from the growth cassette. For example, the flexible tubing may be physically or otherwise (e.g., magnetically) accessible from an exterior of a housing of the growth cassette to cause pinching, flexing or other manipulation to create the pumping action.

The growth cassette as described above in any combination.

A removable cartridge for use with culture systems having at least one growth cassette receiver that removably receives growth cassettes may be summarized as including a holder having an interior and an exterior, the exterior sized and dimensioned to be securely removably received in the at least one cartridge receiver of a culture system, the holder having at least one port that provides fluid communication with the interior from the exterior, the at least one port sized and dimensioned to directly couple with a port of a growth cassette without any intervening conduit of the culture system. The removable cartridge may further include a cartridge valve that selectively closes the fluid communication when the removable cartridge is not received in the cartridge receiver of the culture system and that selectively opens the fluid communications in response the removable cartridge being received in the cartridge receiver of the culture system when operable to at least one of open or close the port to control fluid communication between the interior of the bladder and the exterior thereof via the port.

The removable cartridge may further include at least one bladder received in the interior of the holder, the at least one bladder having a bladder interior to releasably contain a fluid therein, the at least one bladder in fluid communications with the at least one port.

The removable cartridge may further include at least one bladder received in the interior of the holder, the at least one bladder having a bladder interior to releasably contain a fluid therein, the at least one bladder in fluid communications with the at least one port; and at least one conduit coupled between the at least one bladder and the port to provide the fluid communications therebetween.

The removable cartridge may further include at least one bladder received in the interior of the holder, the at least one bladder having a bladder interior to releasably contain a fluid therein, the at least one bladder in fluid communications with the at least one port; at least one conduit coupled between the at least one bladder and the port to provide the fluid communications therebetween; and at least one male conduit extending from a distal end of the port and in fluid communications with the at least one bladder via the at least one conduit. The at least one male conduit may be a needle.

The removable cartridge may further include at least one bladder received in the interior of the holder, the at least one bladder having a bladder interior to releasably contain a fluid therein, the at least one bladder in fluid communications with the at least one port; at least one conduit coupled between the at least one bladder and the port to provide the fluid communications therebetween; at least one male conduit extending from a distal end of the port and in fluid communications with the at least one bladder via the at least one conduit; and a bellows positioned at least proximate the distal end of the port and which covers the male conduit.

The removable cartridge may further include at least one bladder received in the interior of the holder, the at least one bladder having a bladder interior to releasably contain a fluid therein, the at least one bladder in fluid communications with the at least one port; and at least one conduit coupled between the at least one bladder and the port to provide the fluid communications therebetween, at least a portion of the at least one conduit forming a pump. The pump may be selectively coupleable to be driven from the exterior of the holder by a respective actuator of the culture system. The portion of the conduit may be physically accessible from the exterior of the holder by the respective actuator of the culture system.

The removable cartridge may further include at least one data carrier coupled to the holder and bearing identifying information indicative of at least one of an identity of the removable cartridge, a least one physical characteristic of the removable cartridge, or a content of removable cartridge. The at least one data carrier may include at least one of a machine-readable symbol, a radio frequency identification transponder, a magnetic stripe, or a touch memory device.

The removable cartridge may further include a fluid contained in the interior of the holder prior to use of the removable cartridge, the fluid taking the form of a cell growth medium.

The removable cartridge may further include a fluid contained in the interior of the holder after use of the removable cartridge, the fluid taking the form of a collected waste after use. The interior of the removable cartridge may be substantially empty prior to use, and may further include a fluid in the form of collected waste after use of the removable cartridge.

The removable cartridge may further include a fluid contained in the interior of the holder prior to use of the removable cartridge, the fluid taking the form of a gas. The gas may be at least one of a quantity of carbon dioxide, a quantity of nitrogen or a quantity of air. The removable cartridge may be disposable. The removable cartridge may be reusable. The removable cartridge may be bladderless, the walls forming a cavity to hold the media or waste.

The culture system as described above in any combination.

A kit packaged for use with an culture system may be summarized as including a multi-well growth cassette having an interior and an exterior, a plurality of wells in the interior and a number of ports providing fluid communication between the exterior and the interior, the exterior of the multi-well growth cassette having an external size and dimension to be removably received by a growth cassette receiver of the culture system; and a number of media cartridges having an interior and an exterior, and at least one port providing fluid communication between the interior and the exterior, the interior containing a respective amount of media of at least one media type, the exterior of the media cartridges each having at least one portion sized and dimensioned to be removably received by at least one media cartridge receiver of the culture system. The at least one port of the media cartridges may be sized and dimensioned to coupled with at least one of the ports of the multi-well growth cassette to provide a direct fluid communication between the interiors thereof. The media cartridges may each include at least one non-transitory automatically readable data carrier that includes information that is indicative of at least the first media type, a cumulative amount of media of each of the media types in the number of media cartridges selected based on a first defined protocol to be performed over a first period of time by the culture system. The wells of the multi-well growth cassettes may each have a respective coating of at least one coating type, the coating selected based on the first defined protocol to be performed by the culture system. At least a first one of the wells of the multi-well growth cassette may have a coating of a first coating type and at least a second one of the wells of the multi-well growth cassette may have a coating of a second coating type, different than the first type of coating, the first and the second coatings selected based on the first defined protocol to be performed over the first period of time by the culture system. The at least one media cartridge may include a first media cartridge containing a first defined amount of a media of a first media type, and at least a second media cartridge containing an second defined amount of a media of a second media type, different from the first media type.

The kit may further include a non-transitory processor-readable storage medium that stores processor executable instructions that define a first protocol completely executable by the incubator system using the growth cassette and the media cartridges that are part of the kit without any additional growth cassettes or media cartridges.

The kit may further include at least one gas canister having an interior and an exterior, and at least one port providing fluid communication between the interior and the exterior, each of the at least one gas canister containing a respective amount of a gas of at least one gas type, the exterior sized and dimensioned to be removably received by a gas canister receiver of the culture system. The at least one port of the gas canister may be sized and dimensioned to coupled with at least one of the ports of the multi-well growth cassette to provide a direct fluid communication between the interiors thereof. The at least one gas canister may include a first gas canister containing a first defined amount of a gas of a first gas type and at least a second gas canister containing a second defined amount of a gas of a second gas type, different from the first type of gas, the quantities of gas of the first and the second types sufficient to perform a first defined protocol by the culture system. The at least one gas canisters may have at least one non-transitory automatically readable data carrier that includes information that is indicative of at least the respective gas type, and wherein a cumulative amount of gas of each of the gas types in the number of gas canisters is selected based on the first defined protocol to be performed over the first period of time by the culture system.

The kit of claim 210 may further include a non-transitory processor-readable storage medium that stores processor executable instructions that define a first protocol completely executable by the culture system using the growth cassette, the media cartridges and the gas canisters that are part of the kit without any additional growth cassettes, media cartridges or gas canisters.

The kit may further include a defined amount of number of dye of at least one dye type, a cumulative amount of dye of each of the dye types selected based on the first defined protocol to be performed over the first period of time by the culture system.

The kit may further include a non-transitory processor-readable storage medium that stores processor executable instructions that define a first protocol executable by the incubator system using the growth cassette and the media cartridges that are part of the kit without any additional growth cassettes, media cartridges or amounts of dyes.

The kit may further include a defined amount of number of reagent of at least one reagent type, a cumulative amount of reagent of each of the reagent types selected based on the first defined protocol to be performed over the first period of time by the culture system.

The kit may further include a non-transitory processor-readable storage medium that stores processor executable instructions that define a first protocol executable by the incubator system using the growth cassette and the media cartridges that are part of the kit without any additional growth cassettes, media cartridges or amounts of reagents.

The kit may further include a number of waste cartridge having an interior and an exterior, and at least one port providing fluid communication between the interior and the exterior, the exterior of each of the waste cartridges sized and dimensioned to be removably received by a waster cartridge receiver of the culture system, the number of waste cartridges selected to hold an amount of waste estimated to be generated over the first period of time in performing a defined protocol. The at least one port of the waste cartridge may be sized and dimensioned to coupled with at least one of the ports of the multi-well growth cassette to provide a direct fluid communication between the interiors thereof.

The kit may further include a non-transitory processor-readable storage medium that stores processor executable instructions that define a first protocol executable by the incubator system using the growth cassette, the media cartridges and the waste cartridges that are part of the kit without any additional growth cassettes, media cartridges or waste cartridges.

The kit as described above in any combination.

DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIGS. 48-60 are screenshots of a protocol definition portion of a user interface used to interact with a culture system, according to one illustrated embodiment.

FIGS. 73-81 are screenshots of a results portion of a user interface used to interact with a culture system, according to one illustrated embodiment.

FIGS. 84-85 are screenshots of a project portion of a user interface used to interact with a culture system, according to one illustrated embodiment.

FIGS. 86-88 are screenshots of an administration portion of a user interface used to interact with a culture system, according to one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, transceivers, networks, servers, and/or microscopes and imaging systems have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
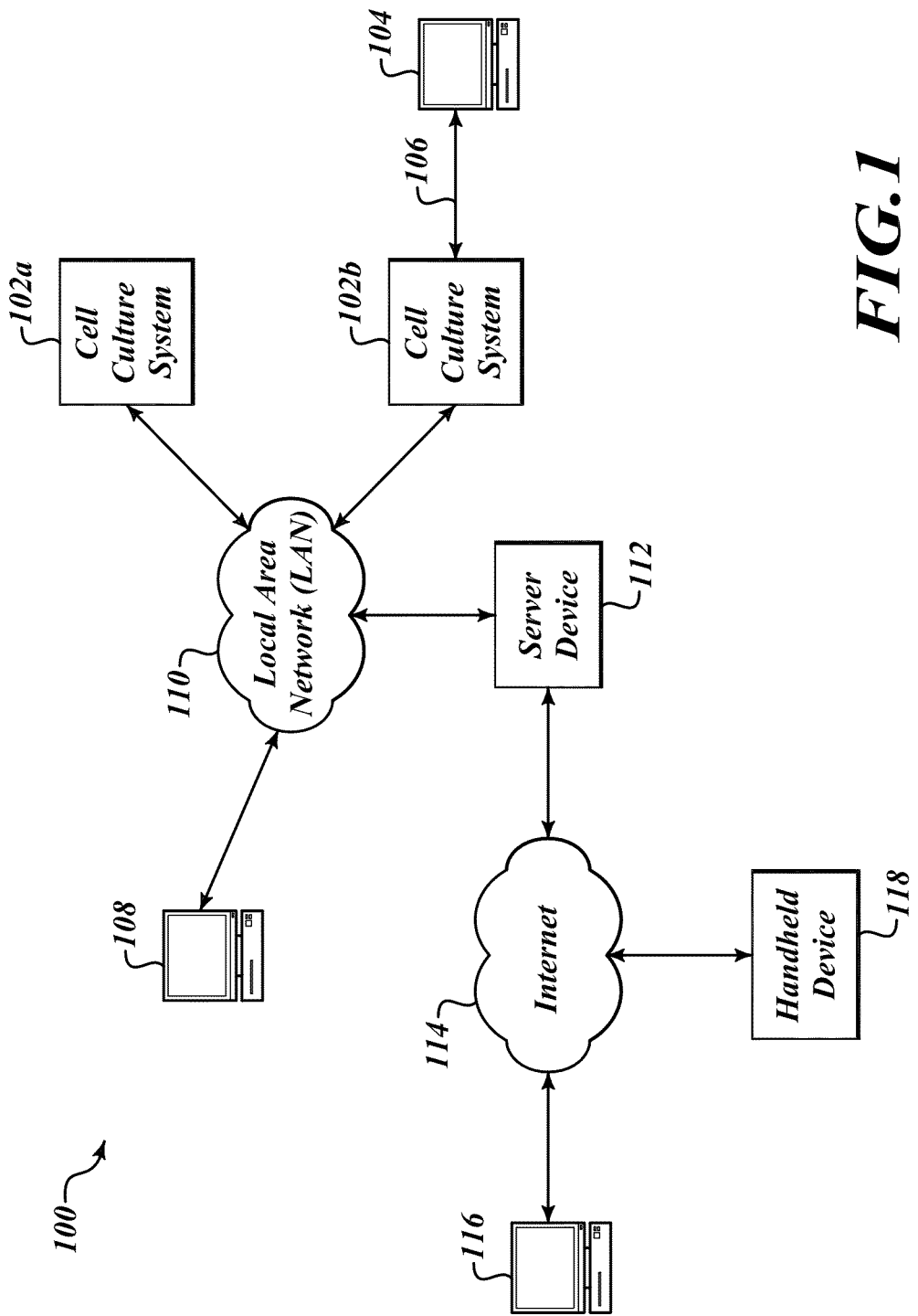
FIG. 1 is a block diagram of a networked environment according to one illustrated embodiment, including a number of cell culture systems communicatively couple to a number of stationary and mobile computing devices.

FIG. 1 shows a networked environment 100, according to one illustrated embodiment.

The networked environment 100 includes a number of culture system 102a, 102b (two illustrated, collectively 102). The culture systems 102 may be communicatively coupled to a first computing system 104, for example via a non-networked channel such as a Universal Serial Bus (USB) 106. The culture systems 102 may additionally, or alternatively, be coupled to a second computing system 108, for example via a networked channel such as a local area network (LAN) 110. The LAN 110 may communicatively couple the culture systems 102 to a server computing system 112. The server computing system 112 may communicatively couple the culture systems 102 via a wide area network (WAN) 114 such as the Internet 114 and/or Worldwide Web portion of the Internet 114 to one or more remote computing devices, for example one or more stationary computing devices 116 such as a desktop computer or workstation and/or one or more mobile computing devices 118 such as a laptop computer, tablet computer, personal digital assistant.

The communicative coupling allows the culture systems 102 to provide information sensed or otherwise collected by the culture systems 102 to the various computing devices 104, 108, 116, 118. Additionally, or alternatively, the communicative coupling allows the culture systems 102 to be controlled by one or more end users via the various computing devices 104, 108, 116, 118. Thus, the culture systems 102 may be controlled using an on-board computer system, non-networked computer system, a networked computer system, an Internet application or an Internet enabled device. The communicatively coupling may allow two or more of the culture systems to be operated as a single collected culture system. Such may facilitate large scale research and testing, or alternatively large scale production.

Figure 2:
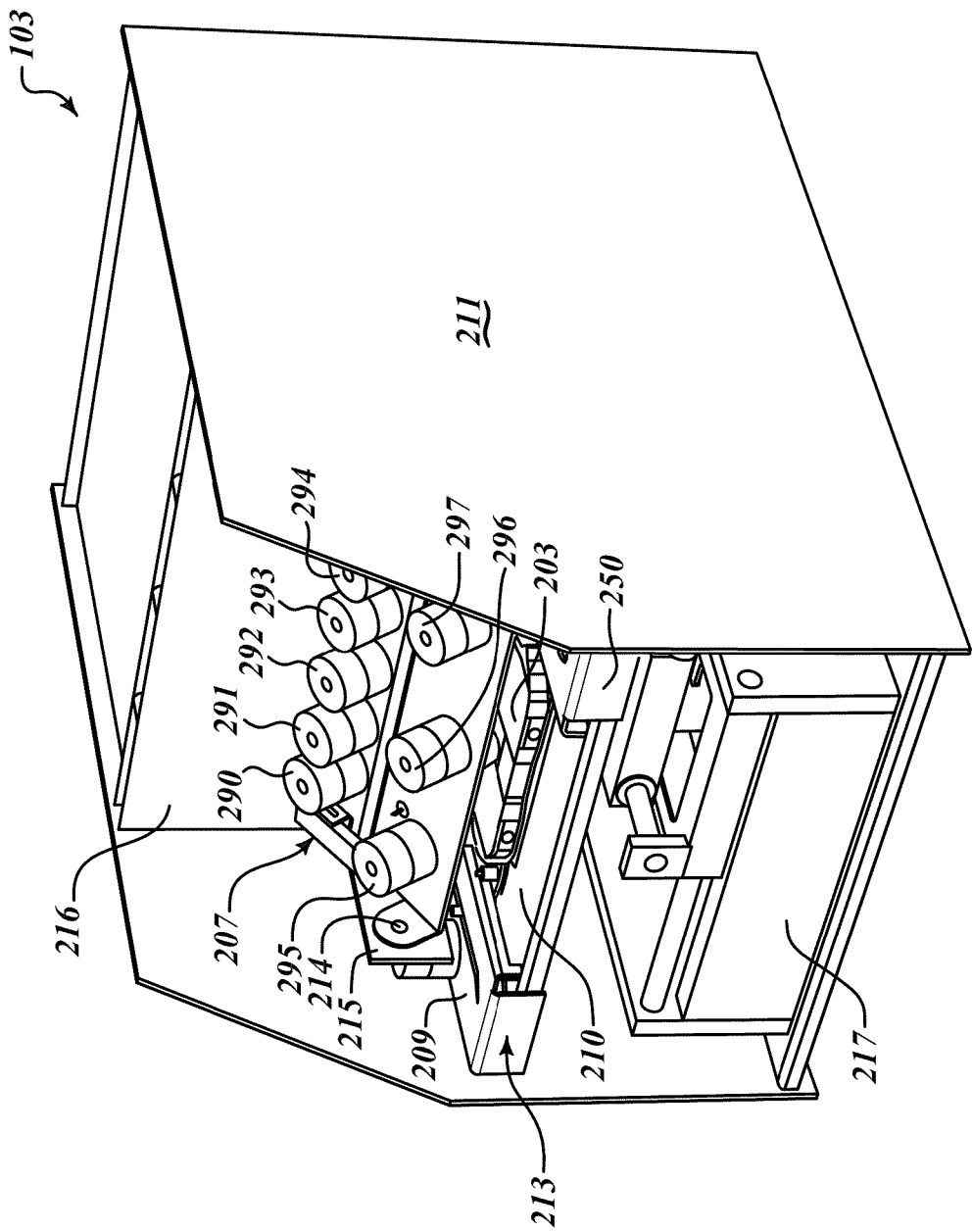
FIG. 2 is an isometric view of an interior of the culture system of FIG. 1, according to one illustrated embodiment.

FIG. 2 shows an interior of the culture system 102, according to one illustrated embodiment.

The culture system 102 includes a frame 211, which may include opposed side walls, a back wall and floor or base. The various other components of the culture system 102 may be physically coupled to the frame 211.

The culture system 102 may include a growth cassette ejector/puller module 213. The growth cassette ejector/puller module 213 is operable to selectively pull or retract a multi-well growth cassette 203 into a growth cassette receiver from an exterior of the culture system 102 and to eject the growth cassette 203 from the growth cassette receiver. The growth cassette ejector/puller module 213 includes a table component 210 and side components 209, 250. The side components 209, 250 comprise motors 251 (visible in FIG. 2), 252 (motor 252 visible in FIG. 3, not visible in FIG. 2) for controlling the ejecting and pulling of the growth cassette 203.

In addition, the cell culture system 102 comprises a pump and valve driving platen 207. The pump and valve driving platen 207 comprises a plurality of drive motors 290-297, which interface with pumps (not shown in FIG. 2) and valves (not shown in FIG. 2) that are located on the growth cassette 203. The pumps and valves are described further herein. FIG. 2 illustrates the pump and valve driving platen 207 in a disengaged (e.g., up) position. Notably, the pump and valve driving platen 207 is movably (e.g., hingedly) coupled at a point 214 to an arm 215 of the frame 211. During operation, the pump and valve driving platen 207 is placed in an engaged position such that the motors 290-297 engage various pumps and valves located on the growth cassette 203.

An internal or interior wall 216 separates the growth cassette 203 from other components (not shown) that are located in the culture system 102. In particular, the wall 216 acts as a thermal barrier that protects cultures (not shown) that may be in the growth cassette 203 from heat that generated from the other components of the culture system 102. The wall 216 may include pockets or cavities to trap air, for example the wall 216 may have a corrugated or matrix structure. Alternatively, the wall 216 may include thermal insulation (e.g., thermally insulative blanket, for example a fiberglass blanket).

The cell culture system 103 may include a microscopy subsystem which may include an X-Y-Z table 217. The X-Y-Z table 217 can be controlled to translate in three-dimensions, along an X-axis or direction, along a Y-axis or direction and along a Z-axis or direction. As will be described further herein, a microscopy device (not shown in FIG. 2) can be installed on the X-Y-Z table 217 for viewing and/or capturing digital images of biological material (e.g., cells) within the wells of the growth cassette 203.

Figure 3:
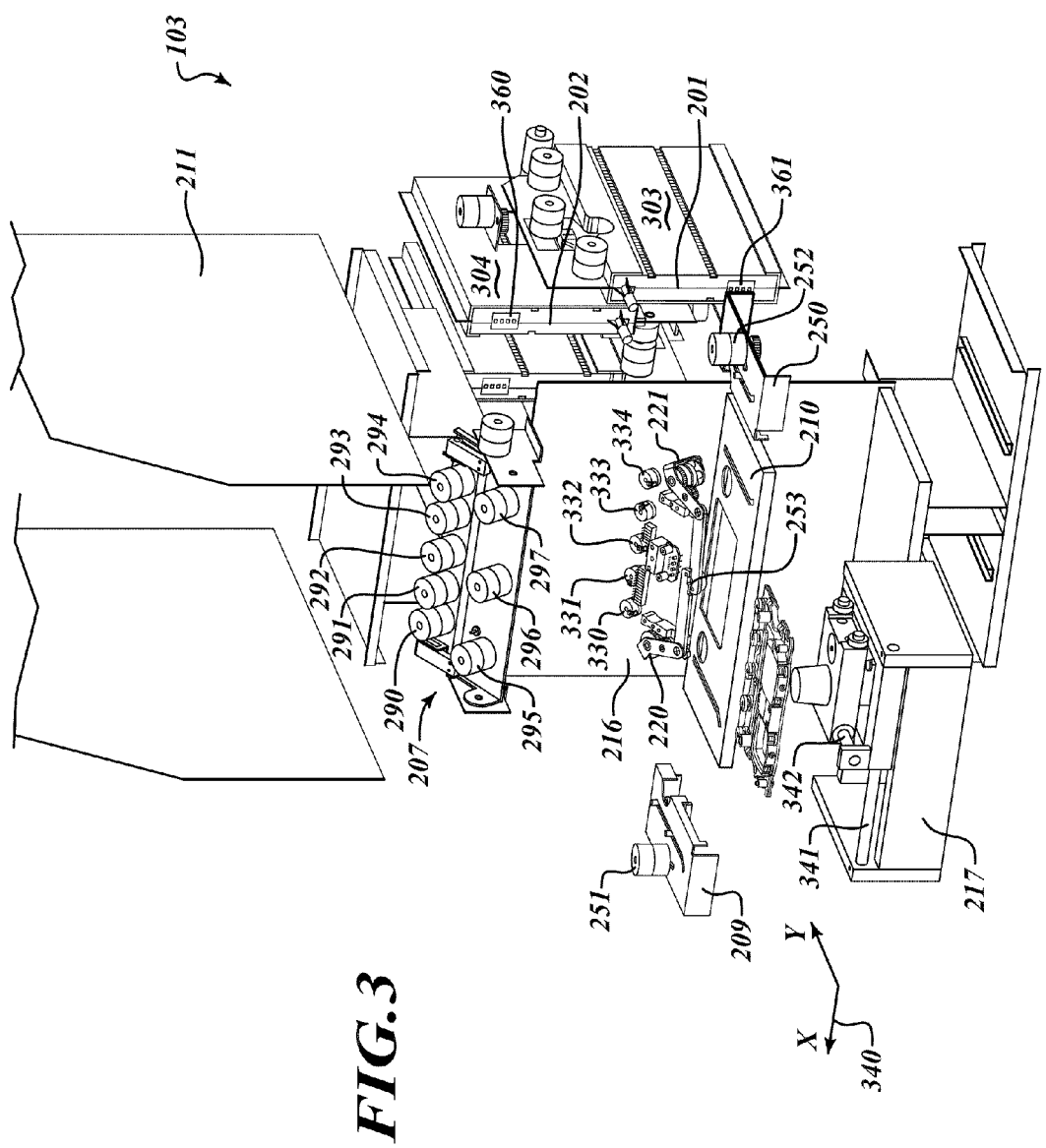
FIG. 3 is an exploded isometric view of the interior of the culture system of FIG. 2.

FIG. 3 depicts an exploded view of the cell culture system 103. As described hereinabove, the cell culture system 103 comprises the X-Y-Z table 217. The X-Y-Z table moves in the X and the Y directions indicated by reference arrow 340. The X-Y-Z table 217 moves in the X-direction along guide 341, and the X-Y-Z table 217 moves in the Y-direction along guide 342. In one embodiment, as indicated hereinabove, a microscopy device (not shown) is attached to the X-Y-Z table 217 so that one can observe or capture digital images of cell cultures contained within the growth cartridge 203. The microscopy device is described further herein.

FIG. 3 further shows an exploded view of the ejector/puller module 213 (FIG. 2). As described, the ejector puller module 213 is made up of the table 210 and the two side components 209, 250. On each side component 209, 250 there is mounted thereto motors 251, 252, respectively. The motors 251, 252 control the ejection and the pulling of the growth cartridge 203.

In addition, each of the motors 290-294 on the valve and pump motor driver platen 207 interfaces with drives 330-334 for controlling valves on the growth cartridge 203. Such valves control media input to the growth cartridge 203 and control waste output from the growth cartridge 203, which is described further herein. In addition, two of the motors 295 and 297 on the valve and pump motor drive platen 207 control the peristaltic pumps 220, 221 that control waste removal from the growth cartridge 203. Additionally, one of the motors 296 controls the actuator arm 253 that controls movement of the peristaltic pumps 220, 221, so that the peristaltic pumps 220, 221 can interface with tubes 813, 814 (FIG. 6) in the growth cartridge 203.

FIG. 3 further shows a waste module 303 and a media module 304. Note that only two modules 303 and 304 are shown in the view of FIG. 3. However, in one exemplary embodiment of the unit 103 there are four modules, including two waste modules and two media modules, which are shown in the back view of FIG. 4.

The waste module 303 comprises a waste cartridge 201 when the waste cartridge 201 is loaded and ready for operation. During operation, waste material (not shown) from the growth cartridge 203 is pumped out of the growth cartridge 203 and into the waste cartridge 201, where it is stored. Such waste material may be analyzed, if desired, to determine what type, if any, waste materials were produced by the cell culture (not shown) during experimentation, e.g., as media is introduced to the cell culture contained within the growth cartridge 203 certain waste products may be produced. Furthermore, the waste cartridge 201 comprises a printed circuit board (PCB) 361. The non-transitory storage medium carried by the PCB 361 can be used to store information related to the waste cartridge 201, such as, for example, a unique identifier identifying the waste cartridge 201.

In addition, the media module 304 comprises a media cartridge 202. Any desired media (not shown) that is to be introduced to the cell culture (not shown) within the growth cartridge 203 is stored in the media cartridge 202 and pumped into the growth cartridge 203, as desired. Exemplary media may include, but is not limited to, Dulbecco's Modified Eagle Medium, fetal bovine serum, or antibiotics. Furthermore, the media cartridge 202 comprises a printed circuit board (PCB) 360. The non-transitory storage medium carried by the PCB 360 can be used to store information related to the media cartridge 202, such as, for example, a unique identifier identifying the media cartridge 201 or any data indicative of the type of media or the amount of media that is stored in the media cartridge 202.

Note that the media cartridge 202 and the waste cartridge 201 are substantially similar to one another in structure and are described further herein.

Figure 4:
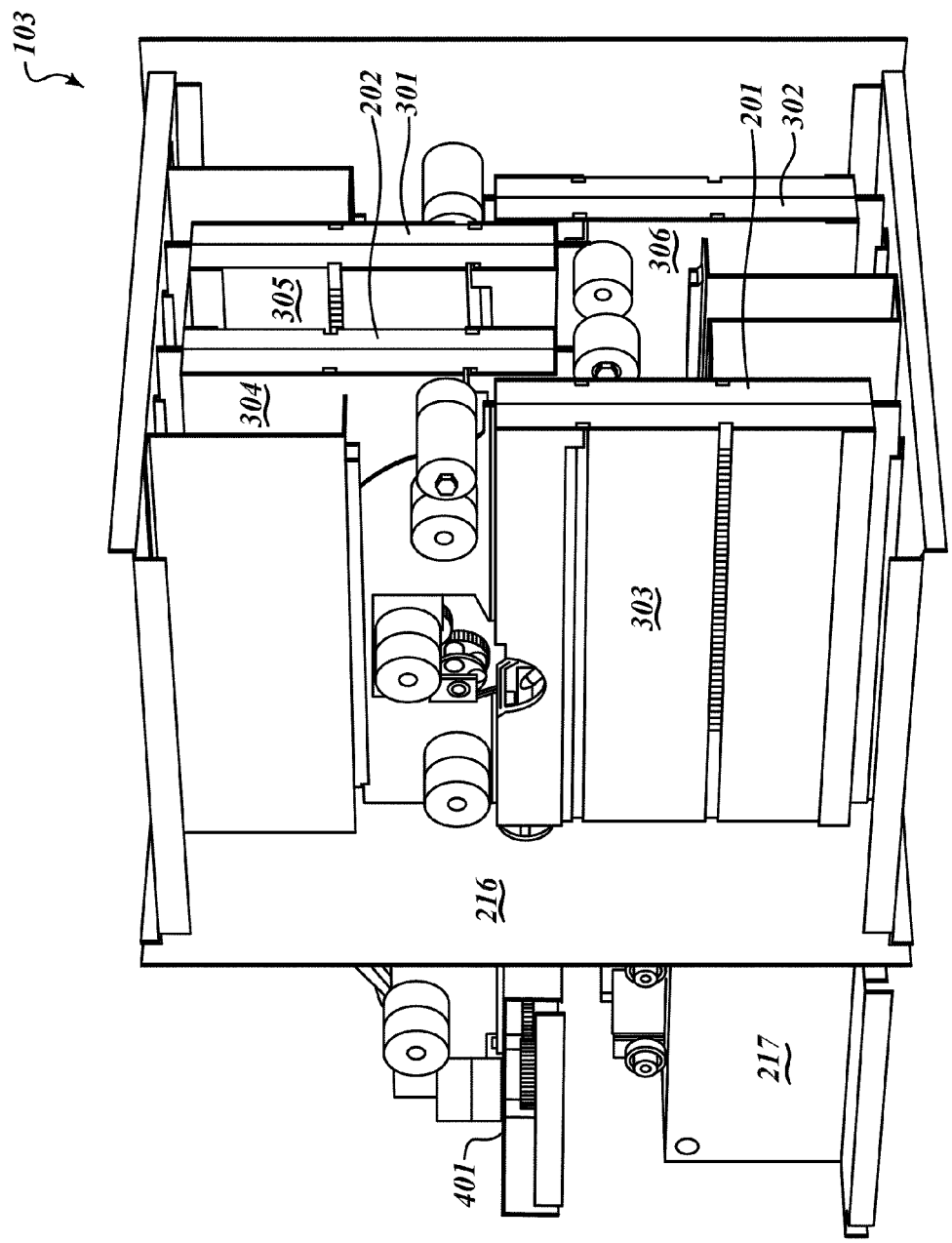
FIG. 4 is a back perspective view of the cell culture system depicted in FIG. 2.

FIG. 4 is a back view of the cell culture system 103. FIG. 4 depicts four modules 303-306. There are two waste modules 303 and 306 and two media modules 304 and 305. Each module comprises a cartridge, 201, 202, 301, and 302. In this regard, waste module 303 comprises waste cartridge 201, media module 304 comprises media cartridge 202, media module 305 comprises media cartridge 301, and waste module 306 comprises the waste cartridge 302. As described hereinabove, the media cartridges 202, 301 contain media that is to be injected into, delivered or otherwise introduced into the growth cartridge 203 (FIG. 3). Whereas the waste cartridges 201, 302 are for receiving and storing any waste that is produced during the cell culture growth within the growth chamber 203. The interface of the cartridges 201, 202, 301, and 302 with the growth cartridge 203 is described further herein.

Notably, some components of the cell culture system 103, such as, for example the growth cassette 203 (FIG. 3) are separated from the waste modules 303, 306 and the media modules 304, 305 by the wall 216. Such separation ensures that the temperature of those separated components are unaffected by the waste modules 303, 306 and the media modules 304, 305.

FIG. 4 also shows a pump drive 401, for example a peristaltic pump drive. The pump drive 401 may drivingly couple or engage a pump integral with the growth cartridge, from an exterior of a housing of the growth cartridge.

Figure 5:
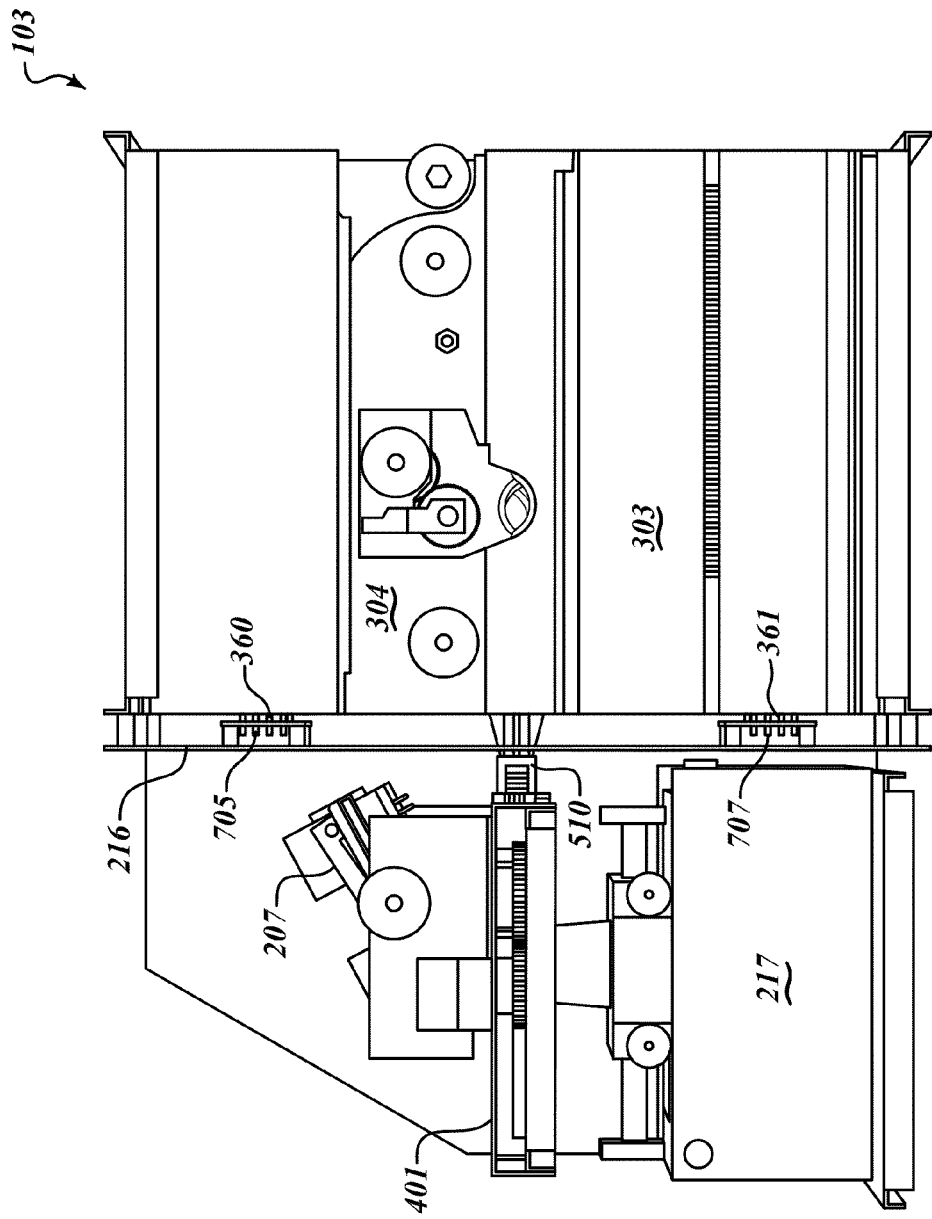
FIG. 5 is a side view of the cell culture system depicted in FIG. 2.

FIG. 5 is a side view of the unit 103 with the frame 211 (FIG. 2) removed. Specifically, FIG. 5 shows the waste module 303 and the media module 304. As described herein, within the waste module 303 is a waste cartridge 201 (FIG. 4). The waste cartridge 201 comprises a protrusion 510 that is inserted through an opening (not shown in FIG. 5) in the wall 216. The protrusion 510 comprises a piercing device (not shown in FIG. 5) that is inserted into the growth cartridge 203, when the growth cartridge 203 is inserted into the cell culture system 103 and the waste cartridge 201 is inserted into the waste cartridge module 303 of the cell culture system 103. Notably, each of the other cartridges 202, 301, and 302 (FIG. 4) has a protrusion (not shown in FIG. 5) that is inserted through the wall 216 and into the growth cartridge 203, which is described further herein.

FIG. 5 further shows contacts 705, 707 coupled to the wall 216, and each contact 706, 707 comprises a plurality of contacts, leads or pins. The pins contact the PCBs 360, 361, and can be used to retrieve any information stored on the PCBs 360, 361. Note that each of the cartridges 201, 202, 301, and 302 comprise PCBs that carry non-transitory computer- or processor-readable storage media (e.g., memories) which store information related to the cartridges 201, 202, 301, and 302. Furthermore, there are contacts for each of the other cartridges not shown in the side view of FIG. 6. As indicated hereinabove, the media cartridges 202, 301 (FIG. 4) and the waste cartridges 201, 302 (FIG. 4) are substantially structurally similar in some respects, except that the media cartridges 202, 301 start out filled with media and introduce the media into the growth cartridge 203 during execution of a culturing protocol. Whereas, the waste cartridges 201, 302 typically start out empty, and are filled with waste extracted from the growth cartridge 203 during execution of the culturing protocol.

FIG. 5 shows the pump and valve driving platen 207 in a disengaged position.

Figure 6:
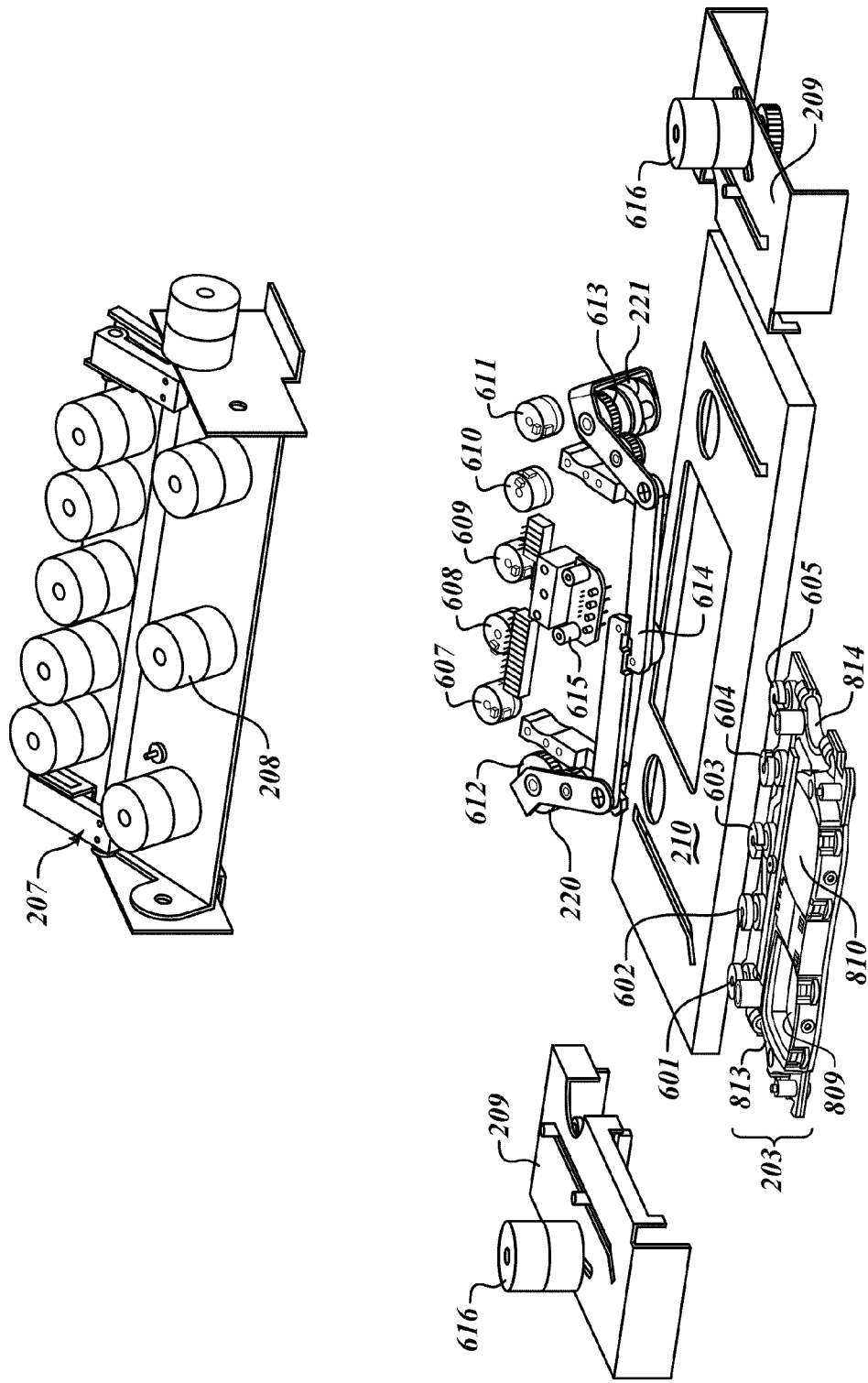
FIG. 6 is a close up view of the exploded view of the cell culture system depicted in FIG. 3.

FIG. 6 is an exploded close up view of the growth cartridge 203. The growth cartridge 203 comprises the two chambers 809 and 810 in which a cell culture (not shown) is housed. In addition, the growth cartridge comprises the plurality of valves 601-605. Further, the growth cartridge 203 comprises tubing 813, 814 that interfaces with the peristaltic pumps 220, 221, respectively.

Each of the valves 601-605 interface with the actuators 330-334. Notably, the motors 290-294 drive the actuators 330-334, which in turn control the valves 601-605. In this regard, the actuators 330-334 open and close the valves 601-605 accordingly.

In addition, FIG. 6 depicts the actuators 612 and 613 that actuate the pumps 220, 221, respectively. In this regard, the motors 295 and 297 drive the actuators 612 and 613, which in turn control the peristaltic pumps 220, 221 that interface with the growth cartridge 203.

Furthermore, an actuator 614 controls movement of the actuator arm 253. The motor 296 drives the actuator 614. As the actuator 614 moves, the actuator arm 253 moves the peristaltic pumps 220, 221 inward toward the growth cartridge 203 so as to interface the pumps with tubing 813, 814, respectively, on the growth chamber 203. Thus, the drive mechanism is part of the cell culture system 103, while the body of the pump is integral with the growth cassette.

With respect to the valves 601-605, valves 601 and 605 control the removal of waste to the waste cartridges 201, 302 (FIG. 4). That is, when the valves 601 and 605 are open, waste (not shown) can move from the chambers 809, 810 to the waste cartridges 301 (FIGS. 4) and 202 (FIG. 4), respectively. In order for waste to be pumped out of the chambers 809, 810, the peristaltic pumps 220, 221 that interface with the tubing 813, 814, respectively, rotate, thereby retrieving waste from the chambers 809, 810 and forwarding waste (not shown) through the valves 601 and 605, when the valves 601 and 605 are opened.

Valves 602 and 604 control the introduction of media (not shown) into the growth cartridge 203. That is, when the valves 602 and 604 are open, media moves from the media cartridges 202 (FIGS. 4) and 301 (FIG. 4) into the growth cartridge 203. Furthermore, the valve 603 controls the mixing of the media from the two separate cartridges 202, 301 and introduction of the media into the growth chambers 809 and 810. In this regard, when valve 609 is opened, the media moving through valves 602 and 604 are mixed together and introduced to the chambers 809 and 810.

A communications interface 615 to provide communications with the growth cassette is visible in FIG. 6. The communications interface 615 may take a variety of forms. For example, the communications interface 615 may take the form illustrated in FIG. 6 including a printed circuit board with pins or other conductive structures suitable to make electrical contacts with terminals on the growth cassette. Also visible in FIG. 6 are cartridge ejector drives and cams 616 (two visible in FIG. 6).

Figure 7:
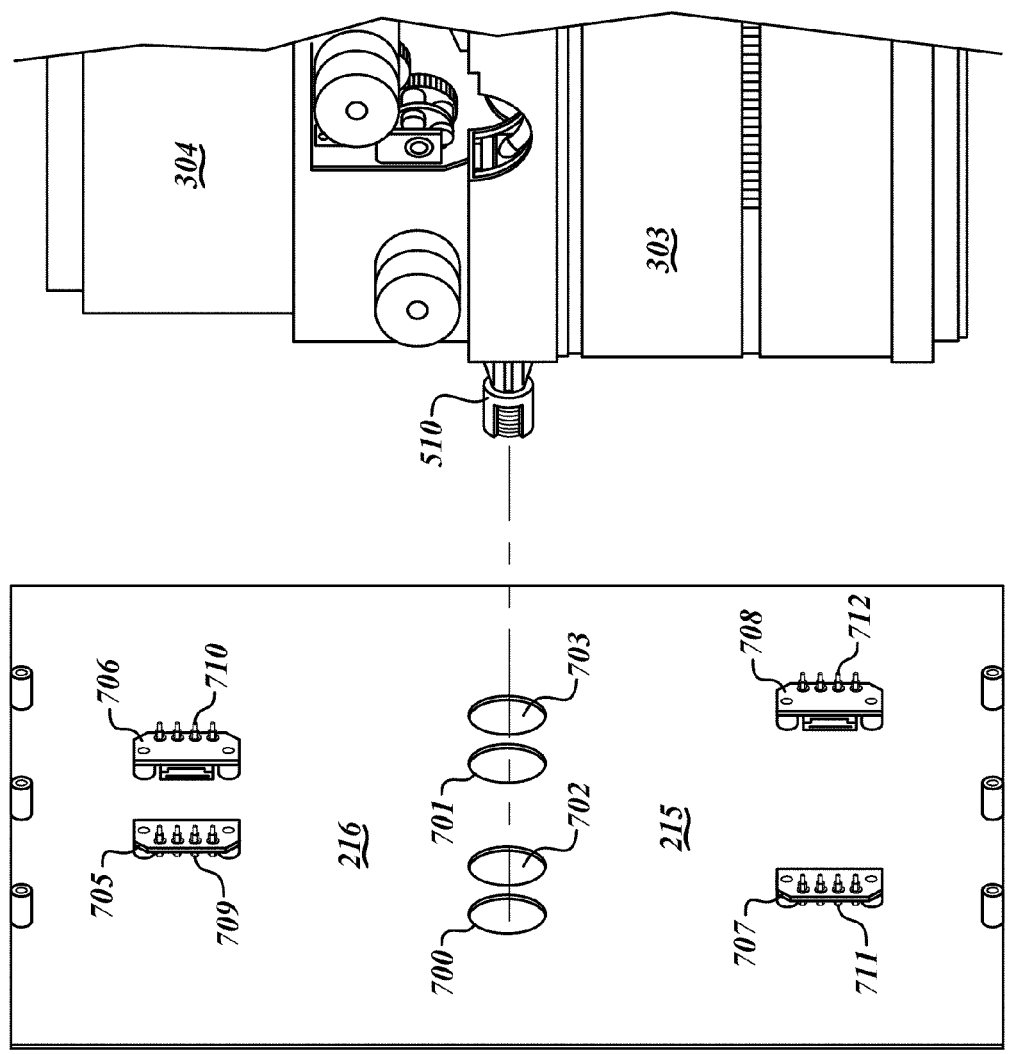
FIG. 7 is a back view of the heat barrier of the cell culture system depicted in FIG. 2.

FIG. 7 depicts a back view of the wall 216 that serves as a heat isolator to protect the cell cultures (not shown) present in the growth cartridge 203 (FIG. 6). As indicated hereinabove, the wall 216 comprises a plurality of contacts 705-708. Such contacts 705-708 each comprise a plurality of pins 709-712, respectively. The contacts 705-708 and respective pins 709-712 line up with and contact with respective sockets, pads or pins of the PCBs located on the cartridges 202, 301, 201, and 302 (FIG. 4), respectively.

In addition, the wall 216 comprises a plurality of openings 700-703 that receive the protrusions from the waste and media cartridges. As described hereinabove, each of the cartridges 201, 202, 301, and 302 (FIGS. 3 and 4) comprise protrusions. As an example, the protrusion 510 on the waste cartridge 201 (FIG. 4) of the waste module 303 will utilize opening 700. The protrusions are inserted through the openings 700-703 so that piercing devices (not shown) within the protrusions can be inserted into the growth cartridge 203 and waste can be extracted from and media can be delivered to the growth cartridge 203.

Figure 8:
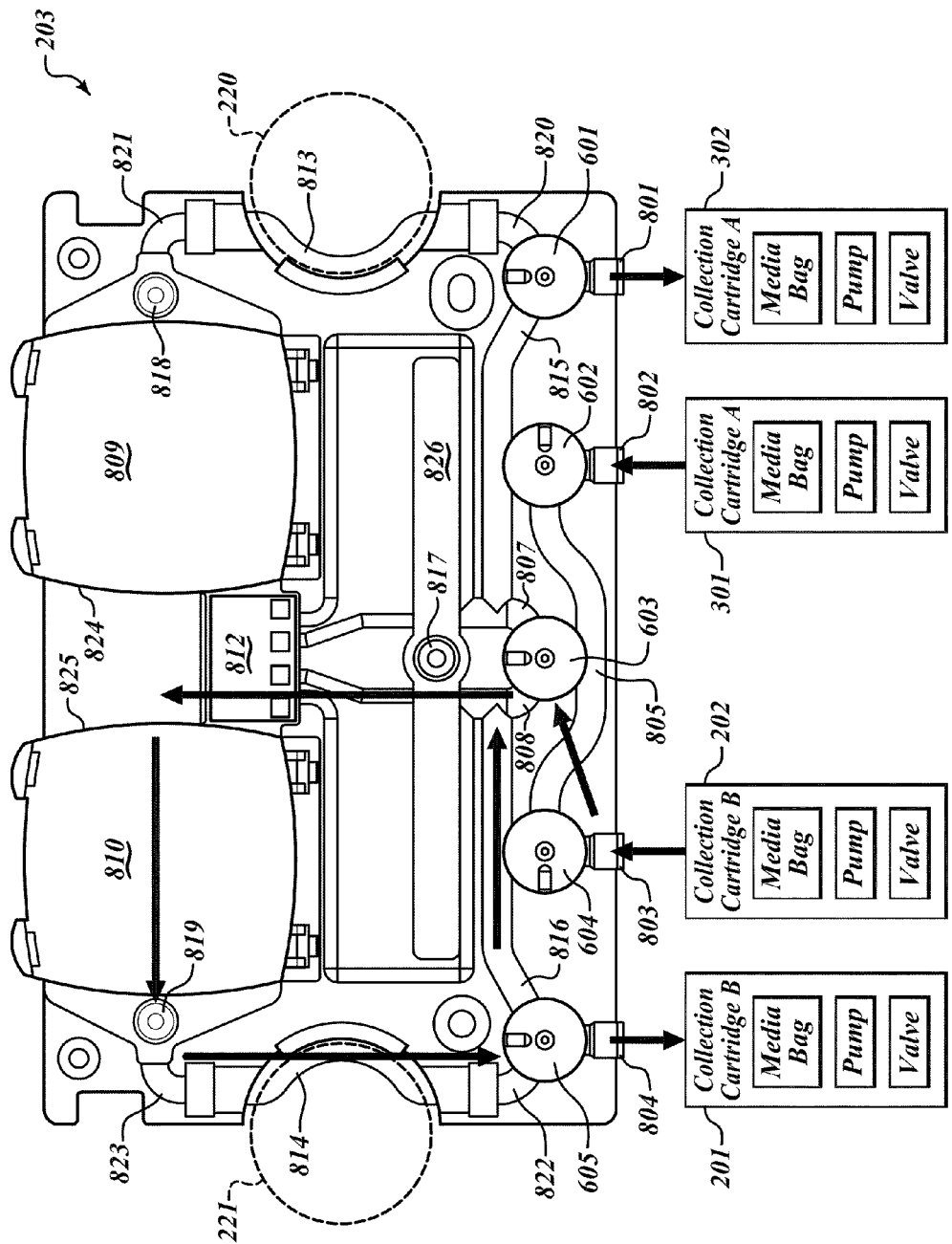
FIG. 8 is a top plan view of an exemplary growth cassette or cartridge that is used in the cell culture system depicted in FIG. 2 in accordance with an embodiment of the present disclosure.

FIG. 8 depicts an exemplary growth cartridge 203 in accordance with an embodiment of the present disclosure. The exemplary growth cartridge 203 comprises two wells or growth chambers 809 and 810, which as illustrated may have substantially square perimeters. Note that two growth chambers are shown but the growth cartridge 203 may comprise more or fewer growth chambers in other embodiments of the present disclosure. A cell culture is placed within one or both of the growth chambers 809 and 810, which is described further herein.

During culturing of a cell culture waste is typically produced within the growth chamber 809. Such waste is moved from the growth chamber 809 to the waste cartridge 302 or is re-circulated through the growth chamber 809. In this regard, the growth chamber 809 is fluidly communicatively coupled to a channel 821, which is fluidly communicatively coupled to the tubing 813. As described hereinabove, the tubing 813 interfaces with a pump 220 (e.g., peristaltic pump, gear pump with magnetically coupled gear head instead of tubing, lobe pump, screw pump, progressive cavity pump), which, when actuated, moves waste through the tubing 813. The tubing 813 is also fluidly communicatively coupled to the channel 820. The valve 601 is a three-way valve, which can be actuated into a position such that waste that is moving through channel 821, the tubing 813, and the channel 820 is directed to the waste cartridge 302 through a piercing device (e.g., .needle or cannula, not shown in FIG. 8) that is connected to the waste cartridge 302 and that is inserted within a septa 801. In another position, the valve 601 can direct waste that is moving through channel 821, the tubing 813 and the channel 820 to another channel 815 so that the waste can be re-circulated through the growth chamber 809 via a channel 807, which is described further herein.

Waste is typically produced during experimentation with respect to a cell culture within the growth chamber 810. Such waste or used media is moved from the growth chamber 810 to the waste cartridge 201 or is re-circulated through the growth chamber 810. In this regard, the growth chamber 810 is coupled to a channel 823, which is coupled to the tubing 814. As described hereinabove, the tubing 814 interfaces with a pump 221 (e.g., peristaltic pump, gear pump), which, when actuated, moves waste through the tubing 814. The tubing 814 is also fluidly communicatively coupled to the channel 822. The valve 605 may advantageously be a three-way valve, which can be actuated into a position such that waste that is moving through channel 823, the tubing 814, and the channel 822 is directed to the waste cartridge 201 through a piercing device (not shown in FIG. 8) that is connected to the waste cartridge 201 and that is inserted within a septa 804. In another position, the valve 605 can direct waste that is moving through channel 823, the tubing 814 and the channel 822 to another channel 816 so that the waste can be re-circulated through the growth chamber 810 via a channel 808, which is described herein.

Additionally, media cartridges 202 and 301 contain media (not shown) that is introduced to the growth chambers 809 and 810 during operation. In this regard, media cartridge 301 comprises a piercing device (e.g., needle or cannula, not shown in FIG. 8) that is inserted through a septa 802. The valve 602 may be a two way valve. In a first position, the valve is closed and no media travels through a channel 805. In an open position, media travels from the media cartridge 301 through the valve 602 to the channel 805. Media cartridge 202 also comprises a piercing device (e.g., needle or cannula, not shown in FIG. 8) that is inserted through a septa 803. The valve 604 is a two way valve. In a first position, the valve is closed and no media travels through the channel 805. In an open position, media travels from the media cartridge 202 through the valve 604 to the channel 805.

Thus, during operation, media can either be introduced to the channel 805 from the media cartridge 301 or the media cartridge 202. In addition, media from both media cartridge 301 and media cartridge 202 can be introduced to the channel 805. In such a scenario, when both valves 602 and 604 are actuated such that media from both media cartridges 301 and 202 are introduced to the channel 805, the media from the media cartridges 301 and 202 are mixed together in the channel 805.

Valve 603 may advantageously be a three way valve. In a closed position, no media flows from the channel 805 to a channel 807 or a channel 808. Note that channels 807 and 808 are tortuous (e.g., convoluted, crenulated, serpentine or snake-like) channels, best illustrated in FIG. 11, that receive media via the valve 603 and direct the media received to the respective growth chambers 809 and 810. In another position, the valve 603 directs media to channel 807, while in another position, the valve 603 directs media to channel 808.

Furthermore, a growth cassette heat in the form of a contact heater (not shown) is located underneath the channels 807 and 808. During operation, as the media traverses the channels 807 and 808, the media is heated to a temperature, for example a nominal temperate specified by a culturing protocol being executed or the particular current time or portion of the culturing protocol. The tortous portion of the channels 807, 808 tends to assure plug flow, where relatively cold media does not mix with relatively hot media, providing good control over media temperature. The tortuous portion of the channels 807, 808 may additionally, or alternatively provide greater surface area over which to conductively transfer heat. The principal heat transfer mechanism of the contact heat is conductive, although some radiant heat transfer may occur.

Additionally, the growth cartridge 203 further comprises a gas bubbler 826. The gas bubbler 826 is substantially rectangular in shape and is hollow. On the bottom side of the gas bubbler 826 is a gas permeable membrane 1200 (FIG. 13, not shown in FIG. 8) that interfaces with the channels 807 and 808. During operation, gas (not shown) is introduced via a septa 817 into the gas bubbler 826. The gas introduced fills the gas bubbler 826 and the gas permeates the gas permeable membrane and is therefore introduced to the media that is traversing the channels 807 and 808. Gas flow may be unidirectional. For example, pressure or head of the gas supply may urge the gas flow towards the conduits leading to the wells of the removable multi-well growth cartridges. Alternatively, the gas permeable membrane may advantageously be unidirectional, that permeable to gas transfer or diffusion away from the gas supply and towards the conduits leading to the wells of the removable multi-well growth cartridges. The gas permeable membrane may block gas flow back toward the supply of gas.

There is also a printed circuit board 812 that carries one or more a temperature sensors 850 (only one called out in FIG. 8) that periodically detects the temperature of the media that is traveling through the channels 807 and 808. Thus, if the temperature varies (e.g., too high or too low) relative to a threshold of a nominal temperature specified by a culturing protocol, adjustments can be made to the growth cassette heater in order to adjust the temperature of the media traveling through the channels 807 and 808.

In addition, the growth cartridge 203 comprises septum 818 and 819. Each septa 818 and 819 is in fluid communication with a valve (not shown), which pumps any excess gas from the growth chambers 809 and 810 to exhaust.

Figure 9:
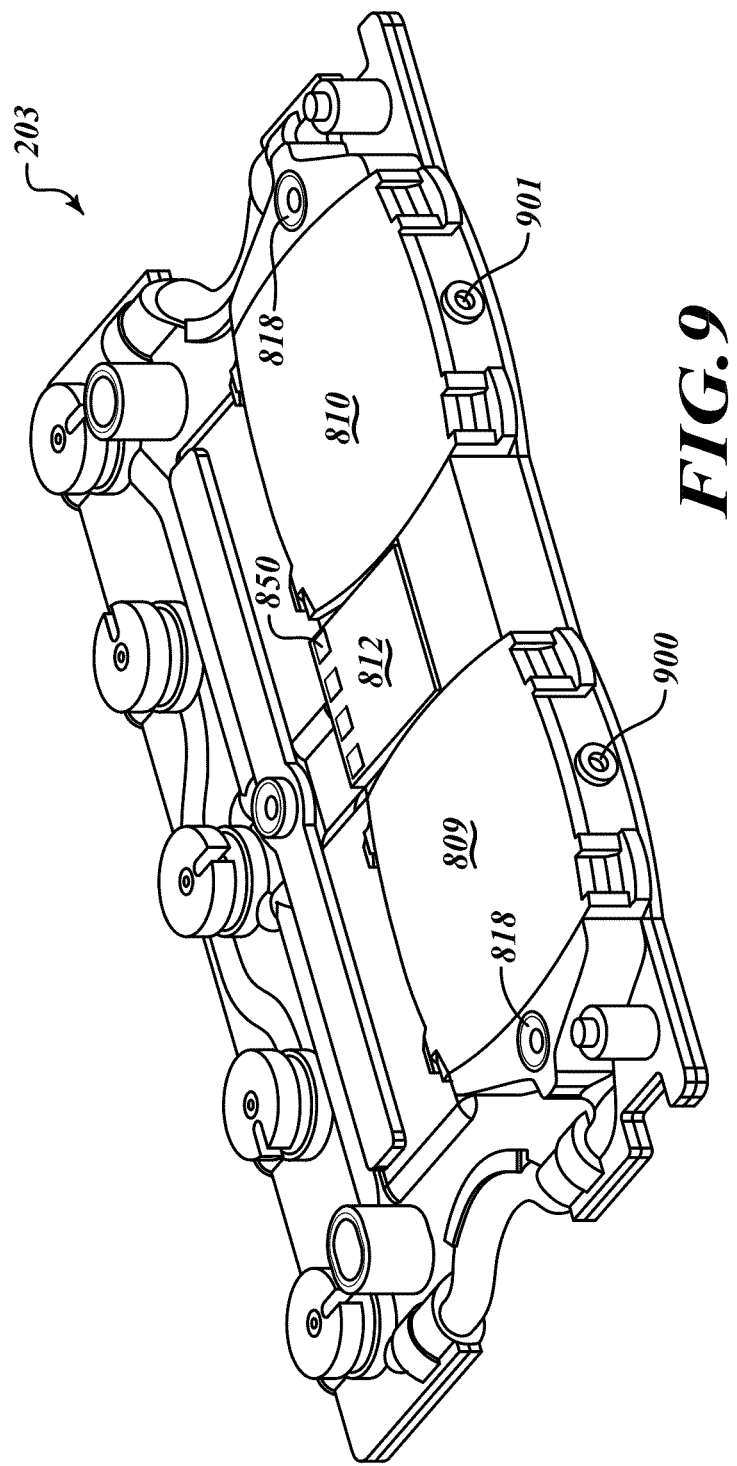
FIG. 9 is a perspective view of the growth cassette or cartridge depicted in FIG. 8.

FIG. 9 is a perspective view of the growth cartridge 203 depicted in FIG. 8. FIG. 9 depicts the growth chambers 809 and 810. On the front of each growth chamber 809 and 810 are septum 900 and 901. During operation, one can insert a syringe comprising cell culture (not shown) into the septum 900 and 901. Upon actuation of the syringe, the cell culture, drug sample, biological or chemical solution is deposited with the growth chambers 809 and 810 for experimentation.

Notably, FIG. 9 further depicts the septum 818 and 819, described hereinabove. Excess gas is pumped from the growth chambers 809 and 810 through the septum 818 and 819.

Figure 10:
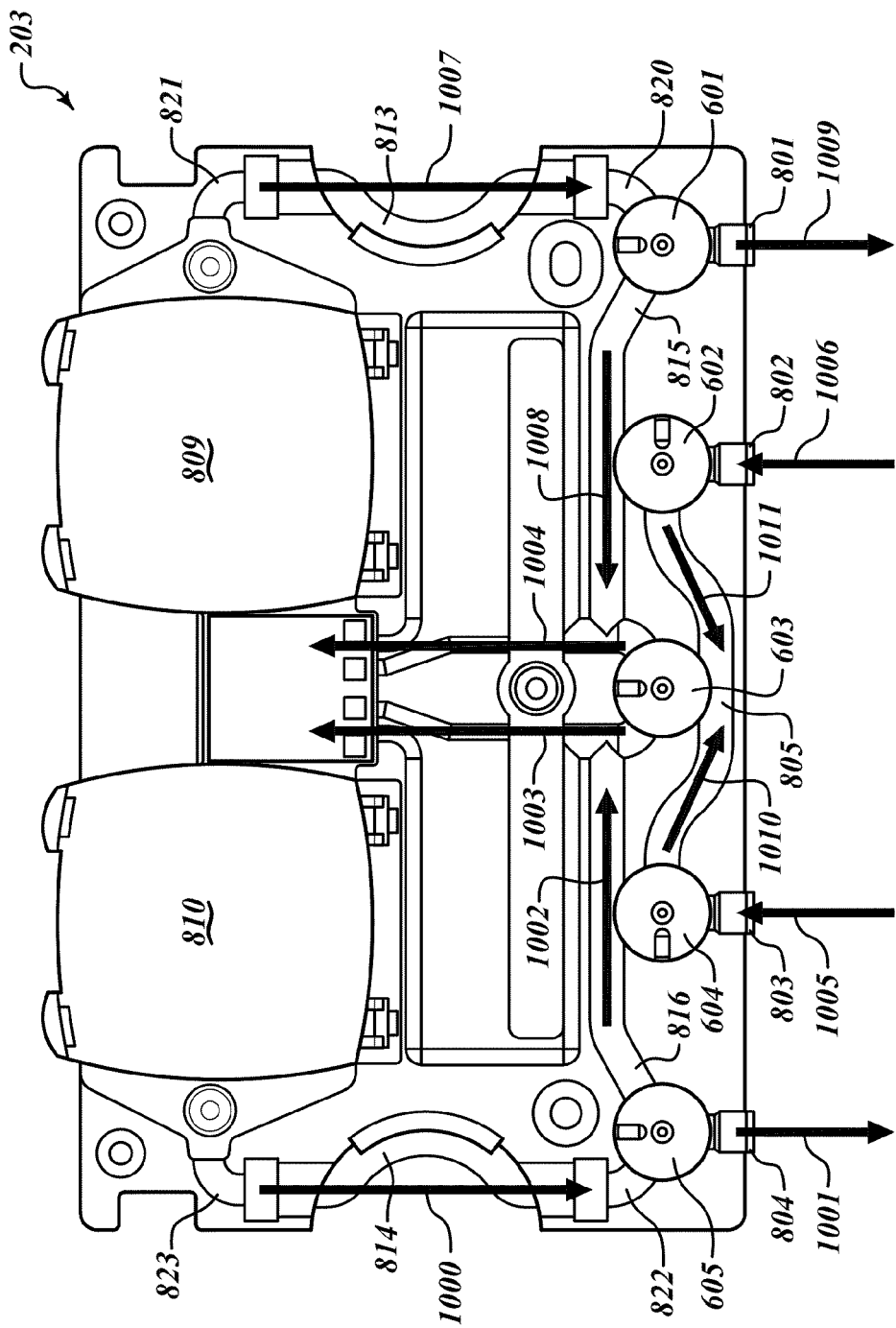
FIG. 10 is a top plan view of the growth cassette or cartridge depicted in FIG. 8.

FIG. 10 depicts movement of the waste and the media through the growth cartridge 203. In this regard, reference arrow 1000 indicates the movement of waste through the channel 822, the tubing 814, and the channel 823. As described hereinabove, based upon the position of the valve 605, the waste can move through the septa 804 and out to a waste cartridge 201 (FIG. 8) as indicated by reference arrow 1001(FIG. 10), or the waste can be re-circulated through the channel 816, as indicated by reference arrow 1002 (FIG. 10) and reference arrow 1003 (FIG. 10). The paths indicated by arrows 1003 and 1004 are come in close or intimate contact with temperature sensors 850 allowing temperature to be sensed.

Reference arrow 1007 indicates the movement of waste through the channel 821, the tubing 813, and the channel 820. As described hereinabove, based upon the position of the valve 601, the waste can move through the septa 801 and out to a waste cartridge 302 (FIG. 8) as indicated by reference arrow 1009, or the waste can be re-circulated through the channel 815, as indicated by reference arrow 1008.

Furthermore, media (not shown) can be introduced to the growth cartridge 203 at septa 803, as indicated by reference arrow 1005. If the valve 604 is in an open position, the media travels into channel 805, as indicated by reference arrow 1010. Media (not shown) can also be introduced to the growth cartridge 203 at septa 802, as indicated by reference arrow 1006. If the valve 602 is in an open position, the media travels into channel 805, as indicated by reference arrow 1011. The media within the channel 805, based upon the position of the valve 603 also travels to the growth chambers 809 and 810, as indicated by reference arrows 1004 and 1003, respectively. As indicated hereinabove, media travels in tortuous channels through the growth cartridge 203, which are not shown in FIG. 10. The reference arrows 1003 and 1004 generally show that the media travels to the growth chambers 809 and 810. The tortuous channels through which the media travels is described in more detail with reference to FIG. 11.

Figure 11:
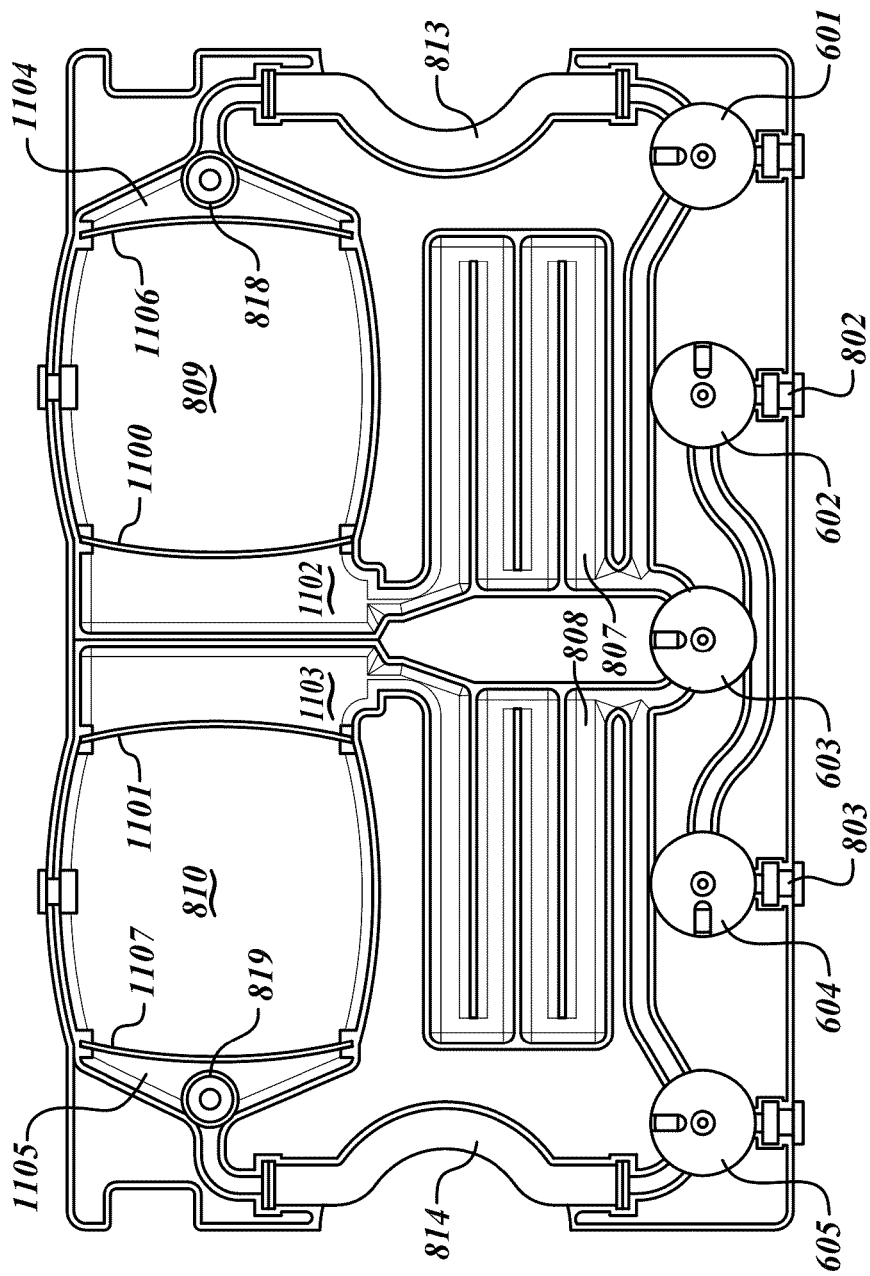
FIG. 11 is a top plan sectional view of the growth cassette or cartridge depicted in FIG. 8.

FIG. 11 depicts a top cut away view of the growth chamber 203. In particular, FIG. 11 shows the tortuous channels 807 and 808 that direct media (not shown) introduced at septum 802 and 803 to the growth chambers 809 and 810. The media flows through the tortuous channels 807 and 808, and the media is heated or otherwise temperature controlled as it flows through the channels 807 and 808 by a growth cassette heater (not shown in FIG. 11) that is underneath the channels 807 and 808.

The media is deposited in chambers 1102 and 1103. The chambers 1102 and 1103 have inside filters 1100 and 1101 that remove stray bacteria and evenly introduce the media to the growth chambers 809 and 810, respectively.

Furthermore, gas and waste move from the growth chambers 809 and 810 into chambers 1104 and 1105 through outside filters 1106 and 1107. As described hereinabove, gas is removed from the chambers 1104 and 1105 via septum 818 and 819, respectively. Further waste is removed as described hereinabove.

An example operation may include one or more of the following. Media A and B may be introduced and mixed via inlets 802, 803. A 3-way valve 603 diverts mixed media flow to channels 807 or 808. Media may be heated as gas is introduced over the tortuous portions of the channels 807, 808. Temperature may be checked via temperature sensors 850. Filters 1102, 1103 remove stray bacteria and evenly flow media to prevent shear (e.g., to obtain approximately laminar flow). Media passes over cells in growth chambers or wells 809, 810. Gas may be exhausted via vents or septum 818, 819 with appropriate filters. Peristatic pumps can move media forward, back or stop the flow. A portion of the peristatic pumps include tubing 813, 814 carried or integral with the growth cassette. Such portion may be drivingly engaged by another portion, the drive mechanism, which is carried by or integral with the cell culturing system 103. Further 3-way valves 601, 605 may be operated to divert flow to waste or collection cartridges, or to re-circulate collected media.

Figure 12:
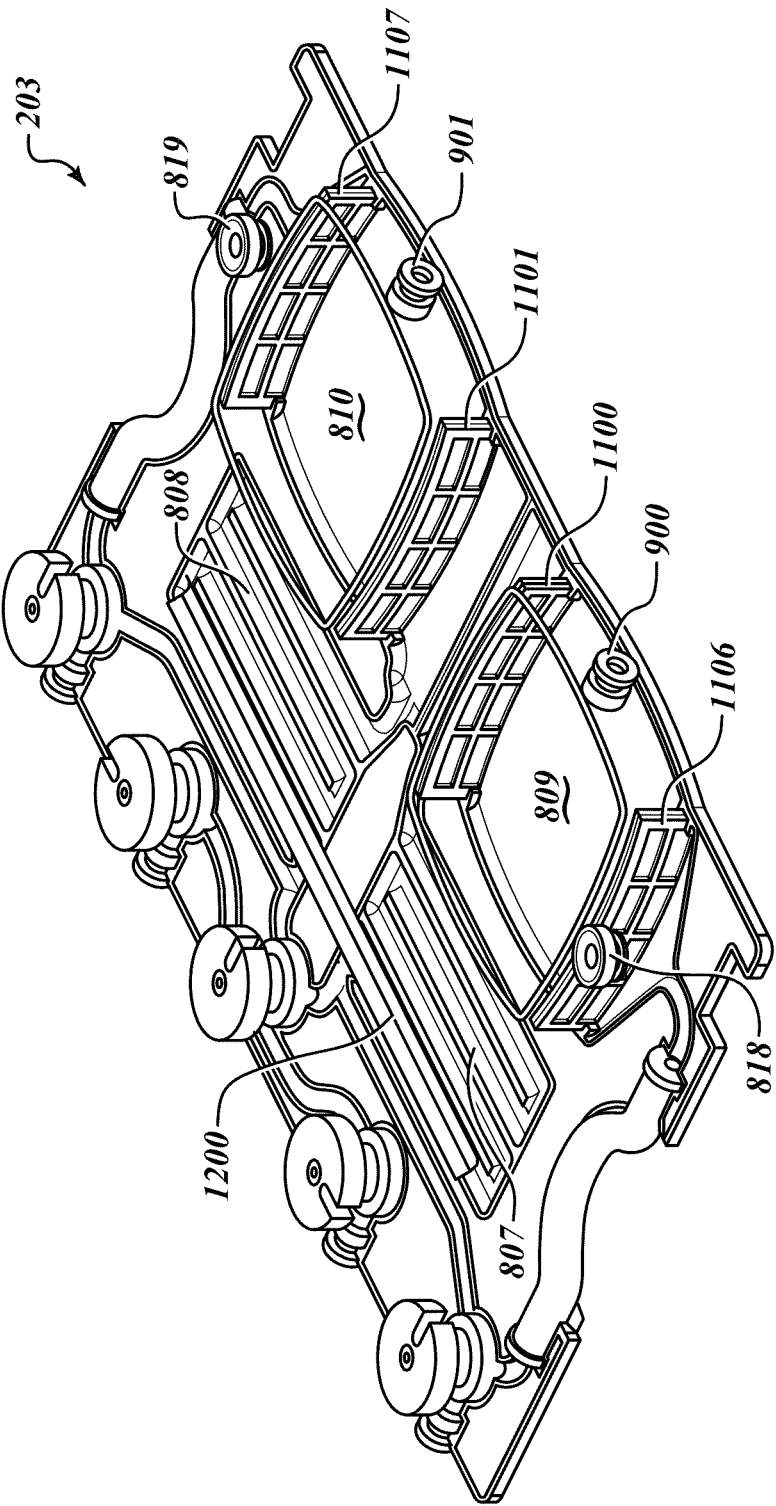
FIG. 12 is a cut away perspective view of the growth cassette or cartridge depicted in FIG. 8.

FIG. 12 depicts a perspective view of the growth cartridge 203 having a top portion removed therefrom. Notably, growth cartridge 203 comprises the substantially square growth chambers 809 and 810. The growth chambers 809 and 810 comprise the septum 900 and 901, respectively, that allow the injection of cell cultures (not shown) into the growth chambers 809 and 810.

Further, FIG. 12 depicts the inside filters 1100 and 1101 that filter out bacteria, reduce shear, and allow for media (not shown) to be evenly distributed into the growth chambers 809 and 810. The media is delivered via the tortuous channels 807 and 808. On top the channels 807 and 808 is the permeable membrane 1200 that is part of the gas bubbler 826 (FIG. 8). The permeable membrane 1200 allows for gas injected into the septa 817 (FIG. 8) to be evenly distributed into media that is flowing through channels 807 and 808.

In addition, FIG. 12 depicts the outside filters 1106 and 1107. The outside filters 1106 and 1107 ensure that the cell culture remains inside the chambers 809 and 810 and also reduces dynamic eddies and shears of media flow.

Gas filters which are part of septum 818, 819 ensure gas sterility. Gas filters may by hydrophobic and only allow gas to pass in one direction, that is into the media.

Figure 13:
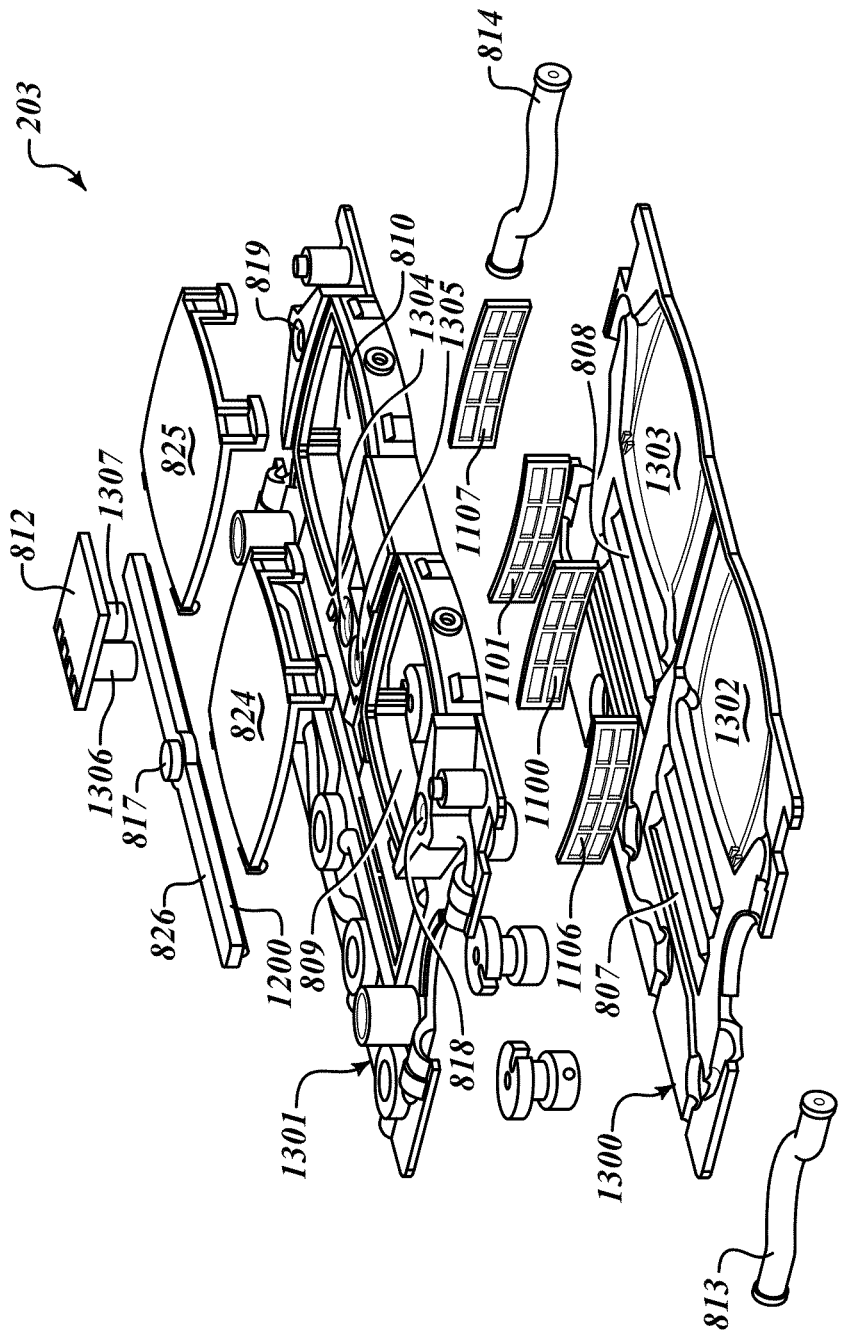
FIG. 13 is an exploded view of the growth cassette or cartridge depicted in FIG. 8.

FIG. 13 is an exploded view of the growth cartridge 203 showing the various components that make up the growth cartridge 203. In this regard, a bottom section 1300 of the growth chamber 203 comprises the floor 1302 and 1303 of the growth chambers 809 and 810, respectively. In addition, the bottom section 1300 shows the tortuous channels 807 and 808 through which media (not shown) flows to the growth chambers 809 and 810. Furthermore, the tubing 813 and 814 is shown broken away from the bottom section 1300.

FIG. 13 further shows the inside filters 1100 and 1101. As described hereinabove, media enters the chambers 1102 (FIGS. 11) and 1103 (FIG. 11) from the tortuous channels 807 and 808, respectively. The media then passes from the chambers 1102 and 1103 into the growth chambers 809 and 810 through the filters 1100 and 1101. The filters 1100 and 1101 remove any bacteria that may be in the media and evenly distributes the media to the growth chambers 809 and 810.

FIG. 13 further shows the outside filters 1106, 1107. As described hereinabove, waste and gas may pass through the filters 1106, 1107 into chambers 1104 (FIGS. 11) and 1105 (FIG. 11). The waste is removed, as described hereinabove, to the waste cartridges 201 (FIGS. 8) and 302 (FIG. 8). Further, gas is pumped from the chambers 1104 and 1105 through the septa or hydrophobic bubbler membranes 818, 819, which are shown on midsection 1301.

In addition, FIG. 13 shows lids or covers 824, 825 that cover the growth chambers 809 and 810, respectively. The lids 824, 825 may be hinged along one edge and may conveniently snap shut or screw on via threads. Different lids 824, 825 may be provided for different purposes, for example lids that seal the wells and other vented lids. Vented lids may come in a variety of forms, and may be selected to achieve desired conditions. For example some vented lids may allow the passage of gases but not liquids. Such vented lids may include a layer of a gas permeable membrane that is not permeable by liquid, such as material sold under the brand GORTEX®. Other vented lids may have apertures with various sizes and/or distributions to achieve different flow rates of gas and/or liquid or vapor. The various lids may be sized and dimensioned to be interchangeably received to cover the wells. Further, some lids 824, 825 may include a coating on the interior thereof. Various suitable coatings are discussed herein in reference to the wells and/or subwells.

Also as shown in FIG. 13, the gas bubbler 826 having the permeable membrane 1200 on its underside, which filters gas into the channels 801, 808 to be introduced to the media that is flowing in the channels 807, 808.

Figure 14:
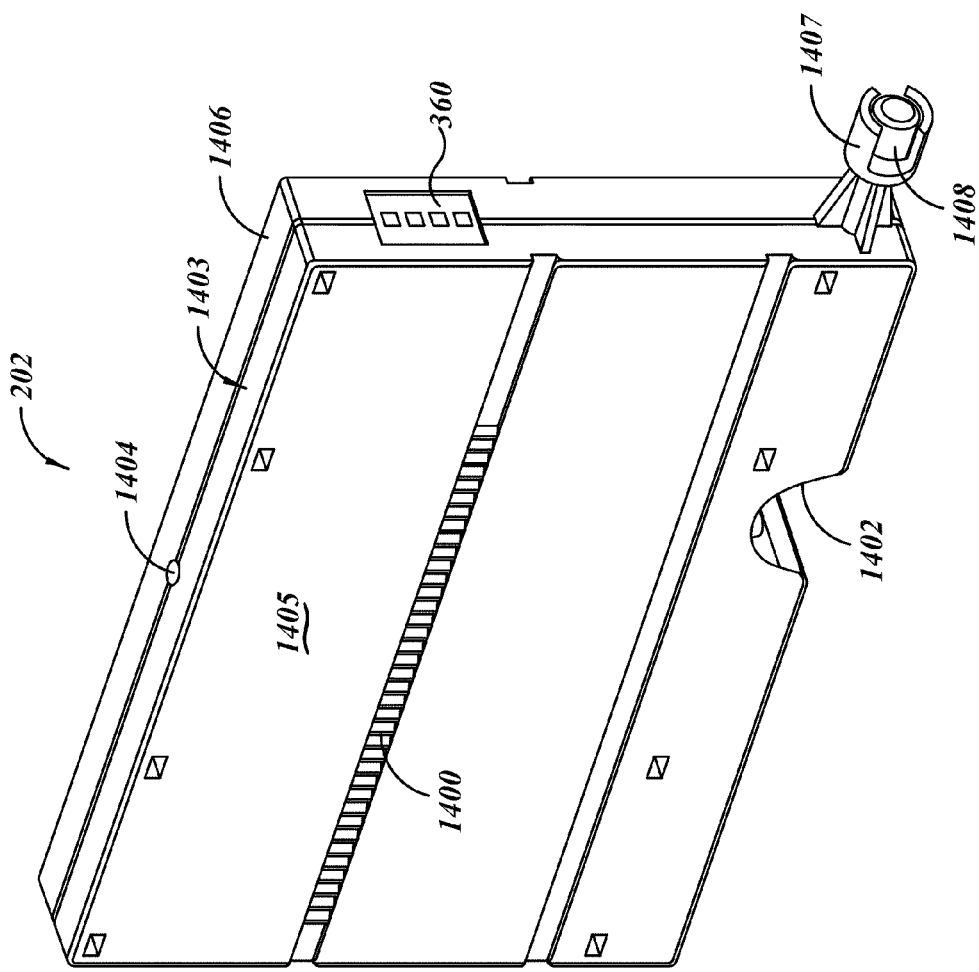
FIG. 14 is a perspective view of a media cartridge used in the cell culture system depicted in FIG. 2 in accordance with an embodiment of the present disclosure.

FIG. 14 depicts the media cartridge 202 in accordance with an embodiment of the present disclosure. Note that the media cartridges 202 and 301 (FIG. 4) are substantially similar. In addition, the media cartridges 202, 301 are structurally substantially similar in some respects to the waste cartridges 201 (FIG. 4) and 302 (FIG. 4). Thus, only one such media cartridge 202 is discussed further herein for brevity. Any differences between the media cartridge 202 and the waste cartridges 201 or 302 are indicated herein in the discussion of the media cartridge 202.

The media cartridge 202 comprises a housing 1403 that is comprised of a side casing 1405 and a side casing 1406. The side casings 1405, 1406 are coupled together to from the housing 1403.

On the side casing 1405, the media cartridge 202 further comprises a gear rack 1400. The rack 1400 interfaces with a gear or pinion driven by an electric motor 1803 (FIG. 18, not shown in FIG. 14) that guides the media cartridge 202 into the media module 304 (FIG. 4). Thus, when a user (not shown) places the media cartridge 202 into the media module 304, a media cartridge sensor (not shown in FIG. 14) detects the initial insert and triggers the motor which pulls or retracts the media cartridge 202 further into the media module or receiver 304 along the rack 1400.

The media cartridge 202 further comprises septa 1404. Septa 1404 enables the introduction of media (not shown) into the media cartridge 202. In addition, if the cartridge is a waste cartridge 201 or 302, the septa 1404 enables withdrawal of waste from the cartridge waste cartridge 201 or 302 for analysis. In this regard, a user would use a syringe and needle to introduce media into the media cartridge 202 or withdraw waste from a waste cartridge 201 or 302.

The media cartridge 202 further comprises the PCB 360, which was described above. The PCB 360 comprises a non-transitory computer- or processor-readable storage medium (e.g., memory, not shown in FIG. 14) that stores data indicative to characteristics about the media cartridge 202. As an example, the storage medium may store data or other information indicative of a unique identifier, type of media that is contained within the media cartridge 202, and/or quantity of media stored in the media cartridge. As explained below, the media cartridge 202 may additionally, or alternatively, include one or more data carriers, for example machine-readable symbols, RFID transponders, magnetic stripes, which store the data and other information. In some embodiments, the PCB 360 may further include a controller (e.g., microprocessor, programmable gate array, application specific integrated circuit) capable of executing instructions, which may also be stored on the storage medium. The instructions may implement a media cartridge program. The media cartridge program may determine the actual contents of the media cartridge 202 at various times during use. Additionally or alternatively, the information stored in the storage medium may include a key, token or other security mechanism, which is required by the culture system to operate. Such may prevent use of unauthorized media cartridges 202, which might damage the culture system. Additionally or alternatively, the media cartridge program interact with the culture system to authenticate the media cartridge. 202

Additionally, the media cartridge 202 comprises an opening 1402. Within the cartridge 202 there is a tubing (not visible in FIG. 14), which is described further herein. A portion of the tubing within the opening 1402 interfaces with a pump 220, 221 (FIG. 3, not shown in FIG. 14). Thus, if media is to be removed from the media cartridge 202 and introduced into the growth cartridge 203 (FIG. 8), the pump would rotate in a direction that pulls media from the media cartridge 202. If the cartridge is a waste cartridge, the peristaltic pump would move in a direction that pulls waste into the waste cartridge from the growth cartridge 203.

The media cartridge 202 further comprises a male coupling port or protrusion 1407. The protrusion 1407 comprises a piercing device 1700 (FIG. 17, not shown in FIG. 14) within bellows 1408 of the protrusion 1407. The bellows 1408 protect a user from being injured by the piercing device and protects the piercing device 1700 from damage when the cartridge 202 is not in use. In operation, the protrusion 1407 is inserted into opening 702 (FIG. 7), and as the piercing device 1700 penetrates the septa 803 (FIG. 8) of the growth cartridge 203, the bellows 1408 are pushed back thereby exposing the piercing device 1700 as the piercing device is inserted into the septa 803.

Figure 18:
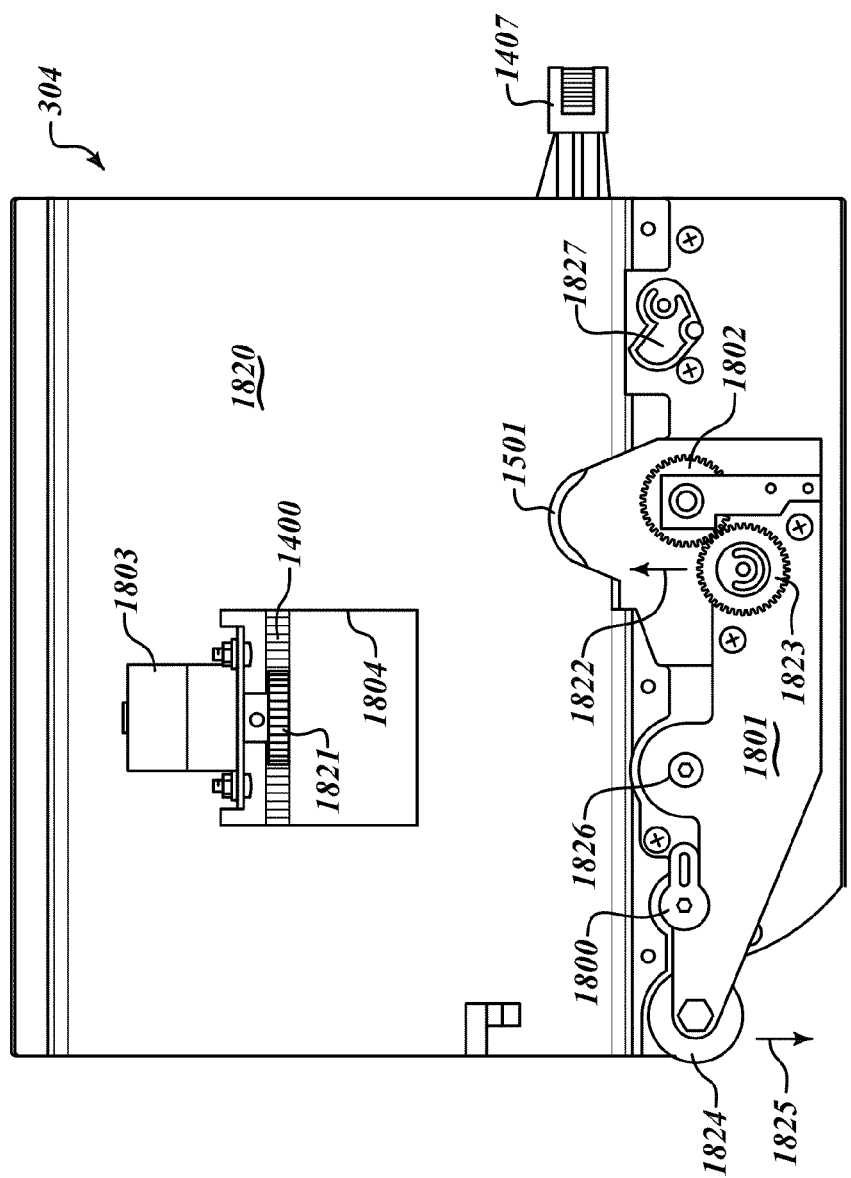
FIG. 18 is a side view of an exemplary media module used in the cell culture system depicted in FIG. 2 in accordance with an embodiment of the present disclosure.

During operation, a pump 220, 221 (FIG. 3), described further with reference to FIG. 18, forces media from the media cartridge 202 through a channel of the protrusion 1407. The media is then injected into the growth cartridge 202 via the piercing device 1700 (e.g., needle or cannula), which is shown and described further herein.

Figure 15A:
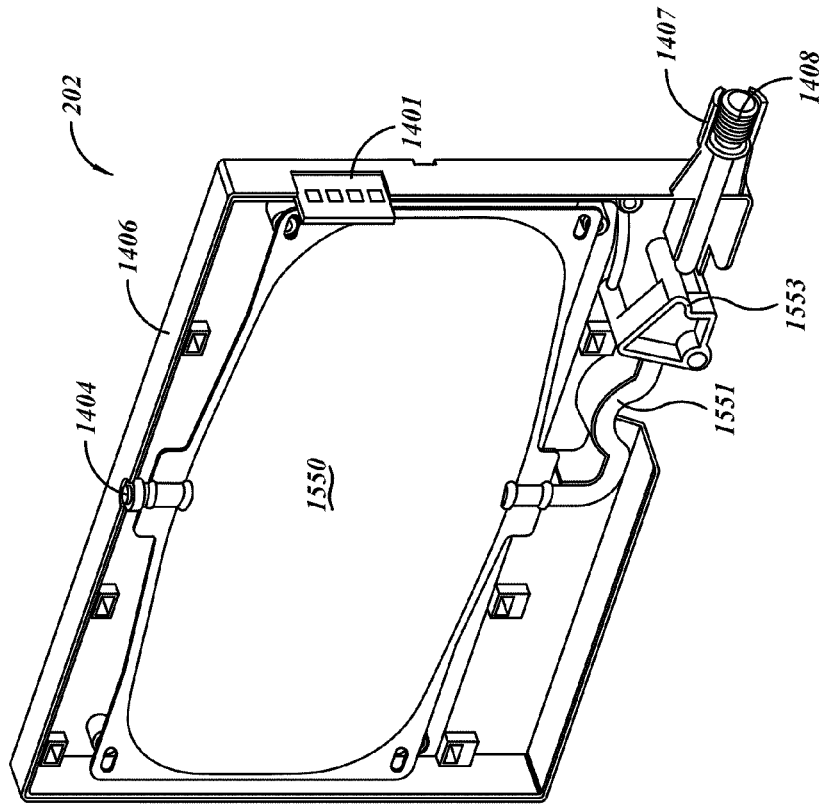
FIG. 15A is a cut away perspective view of the media cartridge depicted in FIG. 14, according to another illustrated embodiment.
Figure 15:
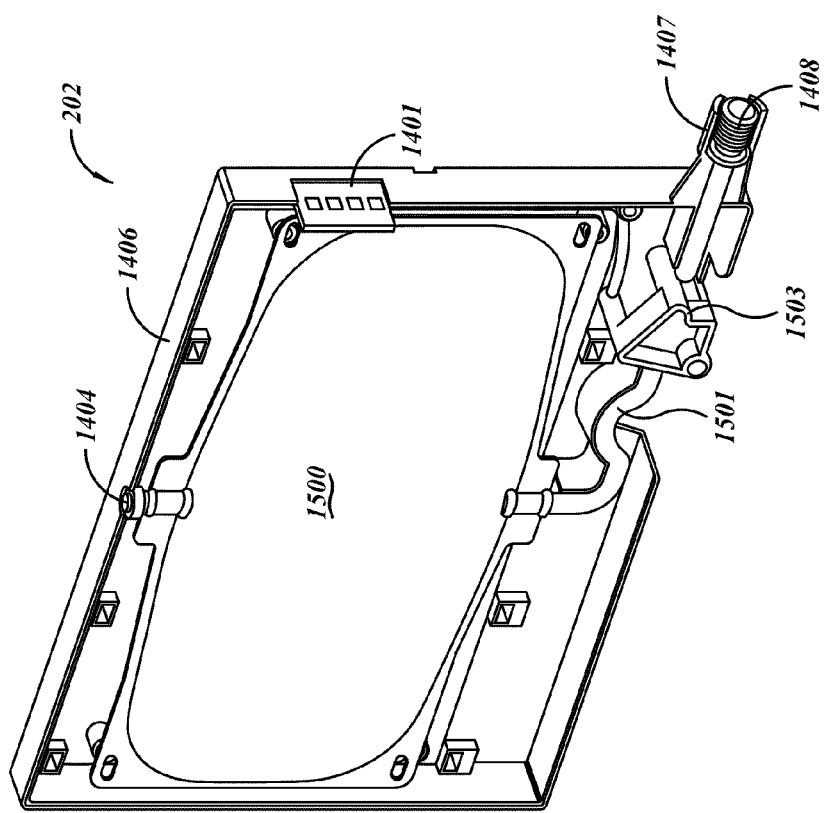
FIG. 15 is a cut away perspective view of the media cartridge depicted in FIG. 14.

FIG. 15 depicts the media cartridge 202 having the side 1405 removed therefrom thereby exposing the inside of the media cartridge 202. The media cartridge 202 comprises a bag 1500 to store media (not shown) that is to be introduced to the growth cartridge 203 (FIG. 8). In one embodiment, the bag 1500 is made of a flexible plastic material. If the cartridge is a waste cartridge 201 (FIG. 4) or 302 (FIG. 4), the bag 1500 stores waste that is retrieved from the growth cartridge 203.

The bag 1500 is connected to the septa 1404 and the tubing 1501. In order to fill the bag 1500 with media (not shown), a user (not shown) inserts a syringe (not shown) that is filled with media into the septa 1404 and actuates the syringe thereby filling the bag 1500 with media.

During operation, the media cartridge 202 is inserted into the module 304 (FIG. 4). When the media cartridge 202 is inserted into the module 304, the piercing device 1700 (FIG. 17) is exposed as the bellows 1408 of the protrusion 1407 compresses, and the piercing device 1700 is inserted into the septa 803 (FIG. 8) of the growth cartridge 203.

The media cartridge 202 further comprises a valve 1503 that pinches the tubing 1501 to keep media from moving from the bag 1500 when the media cartridge 202 is not in use. During use, the valve 1503 is opened via a motor (not shown) and the pump 220, 221 (FIG. 3) is actuated so as to move media contained in the tubing 1501 to the piercing device 1700 (FIG. 17) that is injected in the growth cartridge 203.

FIG. 15A depicts the media cartridge 202 according to an alternative, bladderless embodiment, having the side 1405 removed therefrom thereby exposing the inside of the media cartridge 202. Some structures are identical or similar to structures of the embodiment of FIG. 15, and hence are identified with common reference numbers and discussion of such will not be repeated.

The walls of the media cartridge 202 form a cavity 1550 to store media (not shown) that is to be introduced to the growth cartridge 203 (FIG. 8), omitting the bladder 1500 of the embodiment of FIG. 15. If the cartridge is a waste cartridge 201 (FIG. 4) or 302 (FIG. 4), the cavity 1550 stores waste that is retrieved from the growth cartridge 203.

A septa 1404 and tubing 1551 may provide fluid communication with the cavity 1550. The cavity 1550 may be filled with media (not shown), for example via a syringe (not shown). During operation, the media cartridge 202 is inserted into the module 304 (FIG. 4). On insertion, the piercing device 1700 (FIG. 17) may be exposed as the bellows 1408 of the protrusion 1407 compresses, and the piercing device 1700 is inserted into the septa 803 (FIG. 8) of the growth cartridge 203. The media cartridge 202 may optionally include a valve 1553 that pinches the tubing 1501 to keep media from moving from the cavity 1550 when the media cartridge 202 is not in use. During use, the valve 1553 is opened via a motor (not shown).

Figure 16:
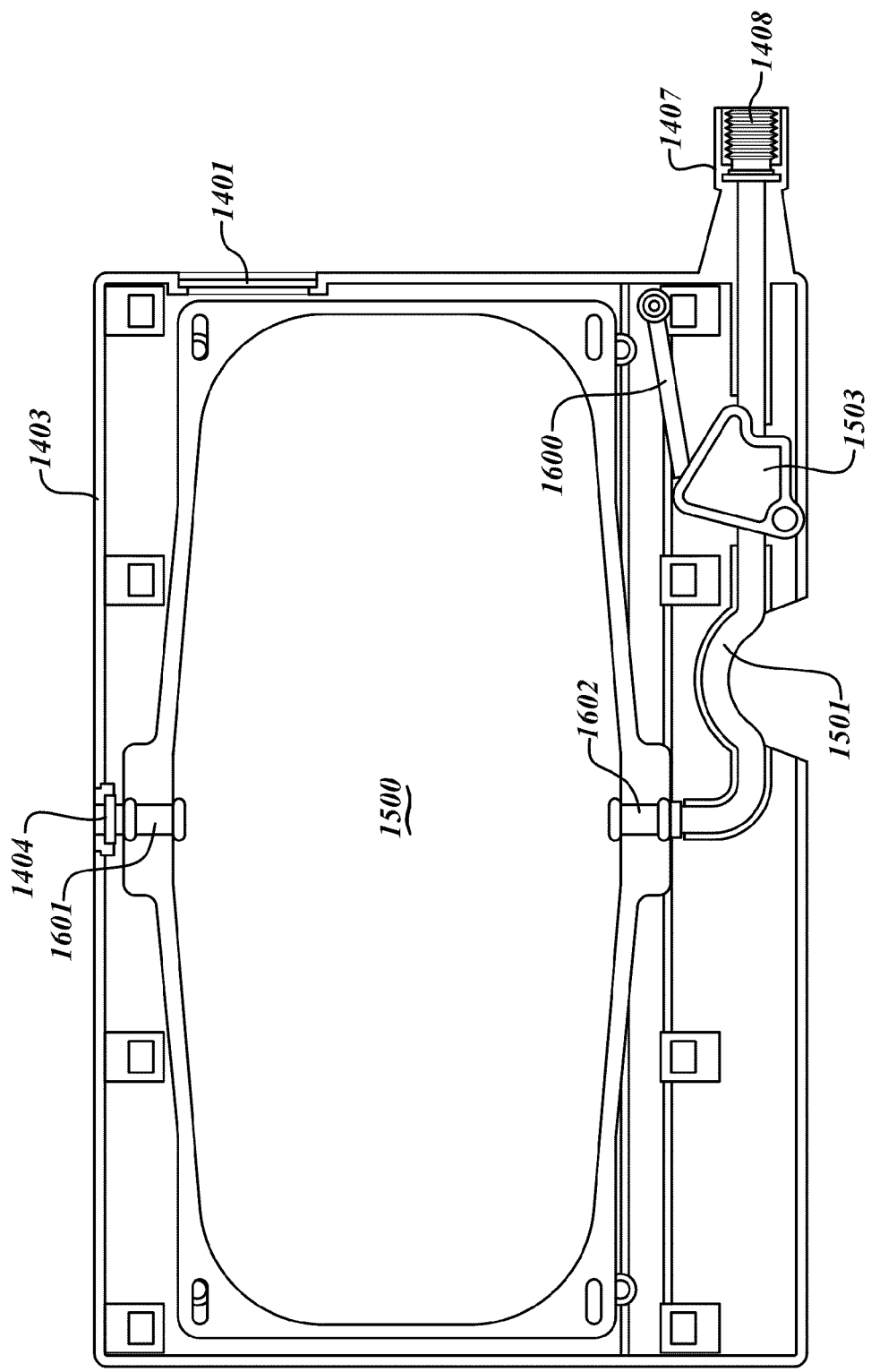
FIG. 16 is a cut away side view of the media cartridge depicted in FIG. 14.

FIG. 16 depicts a side view of the media cartridge 202. FIG. 16 depicts the septa 1404 that is connected to the bag 1500 via a tube 1601. In addition, an interior of the bag or bladder 1500 is fluidly communicatively coupled to the tubing 1501 via a tube 1602. Thus, media (not shown) can be injected into the bag 1500 via a syringe (not shown) that is inserted into the septa 1404 and actuated to empty the contents of the syringe through the tube 1601 and into the bag 1500.

The valve 1503 is shown in its closed position. In this regard, the valve 1503 is spring loaded via the spring 1600 and is kept in a normally closed position. That is, media does not travel to the piercing device (not shown) within the bellows 1408 of the protrusion 1407 when the valve 1503 is closed. During operation, however, the valve 1503 is opened and the pump 220, 221 (FIG. 3) that interfaces with the tubing 1501 forces media through the tubing 1501 and to the channel of the protrusion 1407 and piercing device 1700, which is injected into the septa 803 of the growth cartridge 203.

Figure 17:
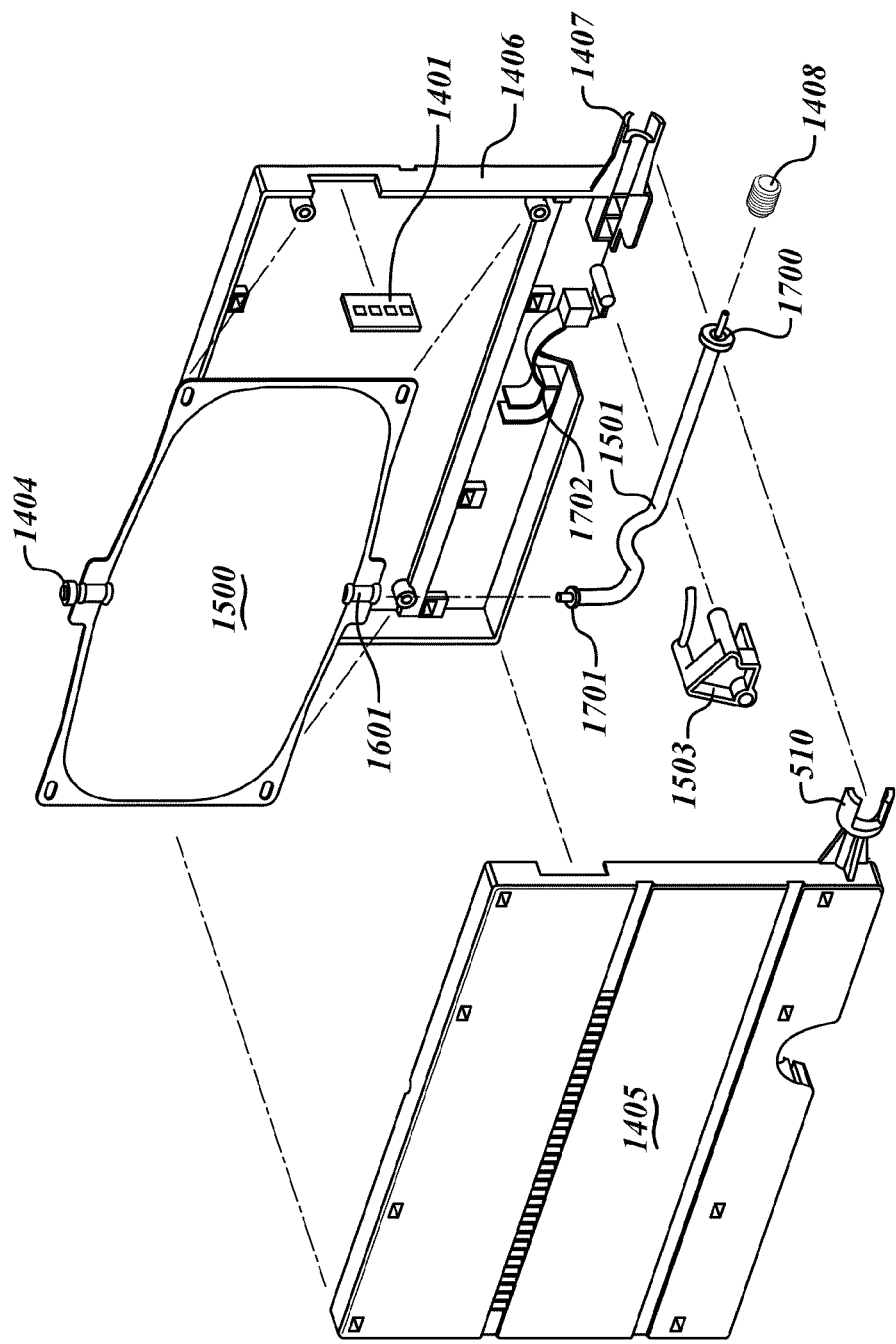
FIG. 17 is an exploded view of the media cartridge depicted in FIG. 14.

FIG. 17 depicts an exploded view of the media cartridge 202. Notably, FIG. 17 depicts the side 1405 and the side 1406 separated one from the other. In addition, FIG. 17 shows the bag 1500 and the septa 1404 that allows for the introduction of media into the bag 1500.

FIG. 17 further depicts the tubing 1501 that is terminated with a piercing device 1700. When the media cartridge 102 is not fully inserted in the media cartridge receiver, the piercing device 1700 is normally covered by the bellows 1408. The tubing 1501 fits within the channel 1702 of the side 1406.

The tubing 1501 further terminates on the other end with a projection (e.g., nipple) 1701. The projection 1701 fits within the tube 1601. Thus, media from the bag 1500 can travel from the bag 1500 to the tubing 1501 via the tube 1601 and the projection 1701.

As described hereinabove, the valve 1503 remains in a closed position when the media cartridge 202 is not in used. However, in operation, the valve 1503 is opened, and the pump 220, 221(FIG. 3) that interfaces with the tubing 1501, pumps media from the bag or bladder 1500 through the piercing device 1700. At least a portion of the piercing device 1700 is injected or extends into the septa 803 (FIG. 8), and media travels out the piercing device 1700 and to the growth cartridge 203 (FIG. 8).

FIG. 18 depicts a side view of the media module 304 having the media cartridge 202 inserted therein. The media module 304 comprises a frame 1820. There is an opening 1804 within the frame 1820 that exposes the rack 1400. Mounted to the frame 1820 is an insertion motor 1803 that actuates a gear 1821 that interfaces with the gear rack 1400. As the gear 1821 rotates it moves the media cartridge 202 in or out of the module 304.

Mounted to the frame 1820 is a pump engagement arm 1801. The engagement arm 1801 is attached to an electric motor 1902 (FIG. 19) that attaches to a transmission or drive 1800 that rotates the arm about pivot 1826 in the direction such that the engagement arm 1810 moves in a counterclockwise direction indicated by reference arrow 1822. As the engagement arm 1801 is rotated by the electric motor 1902 (FIG. 19), the counterweight 1824 aids in the movement of the engagement arm 1801 in the direction indicated by reference arrow 1822. In this regard, the counterweight 1824 applies a force in the direction indicated by reference arrow 1825.

Note that FIG. 18 shows the peristaltic pump engagement arm 1801 disengaged. When engaged, the engagement arm 1801 is rotated up in the direction indicated by reference arrow 1822 such that a pump 220, 221 (FIG. 3, e.g., peristaltic pump) attached to a gear 1802 engages the tubing 1501. Other types of pumps may be employed, for example gear pumps with magnetically coupled gear heads instead of tubing, lobe pumps, screw pumps, progressive cavity pumps, etc.

Attached to the pump engagement arm 1801 are gears 1823 and 1802. The gear 1823 is coupled to electric motor 1901 (FIG. 19) and is coupled to the gear 1082. As the motor 1901 (FIG. 19) rotates the gear 1823, gear 1802 rotates. Gear 1802 is coupled a pump 220, 221 (FIG. 3). Thus, when the engagement arm 1801 is engaged, as the gear 1802 rotates, the pump 220, 221 (FIG. 3) pumps (e.g., rotates) thereby forcing media within the tubing 1501 in a forward direction, if the cartridge is a media cartridge, and in a backward direction if the cartridge is a waste cartridge.

Furthermore, attached to the media module 304 is a valve actuator 1827. The valve actuator 1827 interfaces with the valve 1503 (FIG. 15) to open the valve 1503 (FIG. 15) to allow media to flow to the piercing device 1700 (FIG. 17). In this regard, motor 1900 (FIG. 19) rotates the actuator 1827 so that it moves in an upward direction thereby pushing up on the valve 1503. As the valve 1503 is pushed up, the tubing 1501 (FIG. 15) is unimpeded thereby allowing flow of the media through the tubing 1501.

Figure 19:
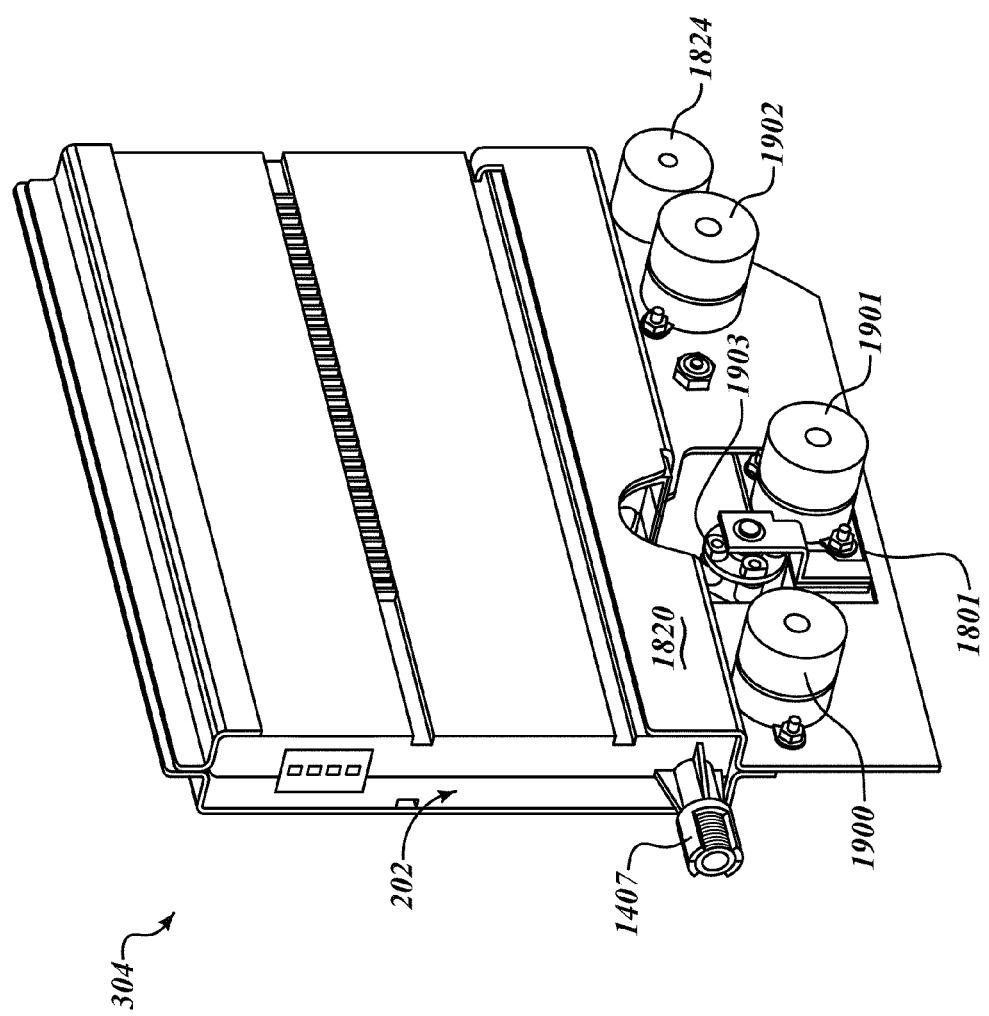
FIG. 19 is a side perspective view of the media module depicted in FIG. 18.

FIG. 19 depicts a side view of the module 304 having the cartridge 202 inserted into the frame 1820. Mounted to the frame 1820 is a plurality of motors. In this regard, a motor 1902 is mounted to the frame 1820, and the motor 1902 is mechanically coupled to the drive 1800 (FIG. 18) that moves the engagement arm 1801 (FIG. 18) upwards in the direction indicated by the reference arrow 1822 (FIG. 18).

In addition a motor 1901 is mounted to the frame 1820. The motor 1901 is mechanically coupled to the gear 1823 (FIG. 18). When the motor 1901 rotates the gear 1823, the gear 1802 (FIG. 18) rotates thereby rotating a peristaltic pump 1903. Note that FIG. 19 shows the engagement arm 1801 is the unengaged position. However, when the engagement arm 1801 is in an engaged position, the pump 1903 interfaces with the tubing 1501 (FIG. 15). As the pump 1903 rotates, media within the tubing 1501 is pushed forward through the piercing device 1700 (FIG. 17). If the cartridge is a waste cartridge, the pump 1903 moves in an opposite direction thereby moving waste into the bag or bladder 1500 (FIG. 15).

Additionally, a motor 1900 is mounted to the frame 1820. The motor 1900 is mechanically attached to the actuator 1827 (FIG. 18). As the motor 1900 rotates, the actuator 1827 rotates thereby pushing upward on the valve 1503 (FIG. 15). When the valve 1503 is pushed upward, the tubing 1501 is unpinched thereby allowing media to flow through the tubing 1501. As described hereinabove, the valve 1503 is normally spring loaded in a closed position thereby pinching the tubing 1501 closed so that media does not escape from the tubing 1501 when the media cartridge 202 is not being used. In addition, if the cartridge is a waste cartridge, the valve 1503 ensures that waste does not escape from the media cartridge 202 when waste is not being pumped into the cartridge.

Figure 20:
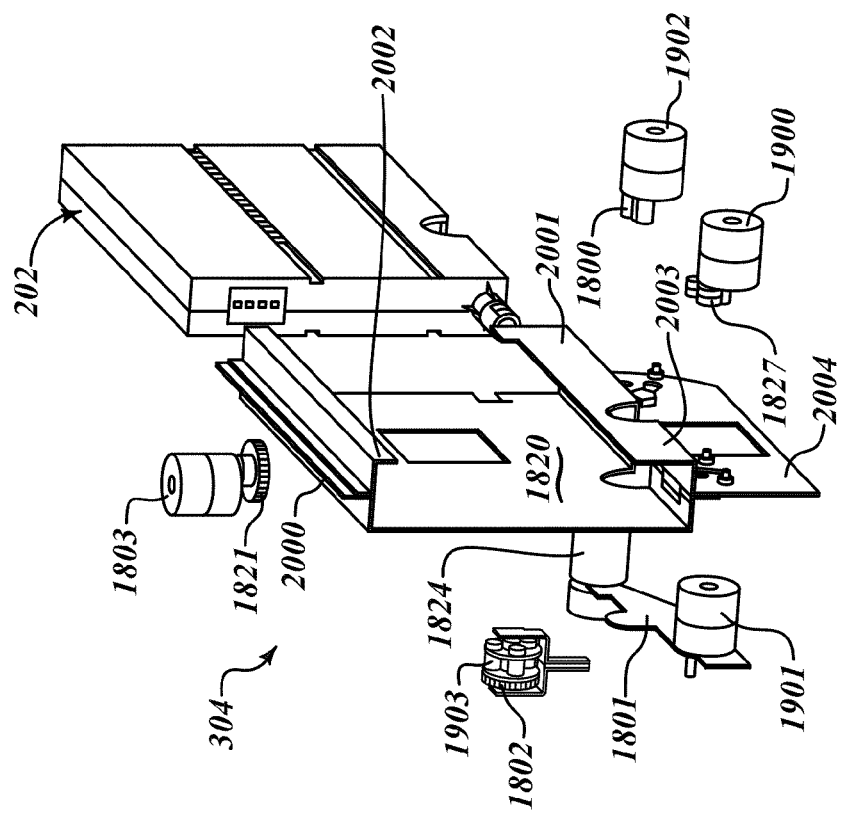
FIG. 20 is a front exploded view of the media module depicted in FIG. 18.

FIG. 20 is an exploded view of the media module 304. In this regard, FIG. 20 depicts the media cartridge 202 removed from the frame 1820. The frame 1820 may, for example, comprise a top L-shaped extension 2000 and a bottom L-shaped extension 2001 that form channels 2002, 2003, respectively, through which the media cartridge 202 slides as it is inserted into the frame 1820.

Notably, as described hereinabove, the rack 1400 (FIG. 14) engages the gear 1821 that is attached to motor 1803. As the cartridge 202 is being inserted into the channels 2002, 2003, a sensor activates the motor 1803 thereby turning the gear 1821, which drivingly couples with the rack 1400 and moves the cartridge 202 into the frame 1820.

In addition, the frame 1820 comprises an extension 2004 that extends downward from the L-shaped extension 2003. The engagement arm 1801 and the various motors 1900 and 1902 are mounted to the extension 2004. Notably, motor 1901 is mounted to the engagement arm 1801.

FIG. 20 further shows the motor 1900 mounted to the actuator 1827. Note that the actuator 1827 pushes up on the valve 1503 (FIG. 15) in order to unpinch the tubing 1501 for fluid flow.

In addition, FIG. 20 depicts the motor 1902 coupled to the drive 1800. The motor 1902 actuates the drive 1800. When actuated, the drive 1800 moves the engagement arm 1801 to the engaged position, i.e., when the pump 1903 engages the tubing 1501.

Furthermore, FIG. 20 depicts the engagement arm 1801. Attached to the engagement arm 1801 are the counterweight 1824 and the motor 1901. As described hereinabove, the motor 1901 is mechanically coupled to the gear 1823 (FIG. 18), which couples to gear 1802. Thus, as the motor 1901 turns gear 1823, gear 1802 rotates thereby rotating the pump 1903. When the engagement arm 1801 is in the engaged position, the pump 1903 interfaces with the tubing 1501 (FIG. 15) of the cartridge 202. Therefore, as the pump 1903 rotates, media contained in the tubing 1501 is moved forward to the piercing device 1700 (FIG. 17).

Figure 21:
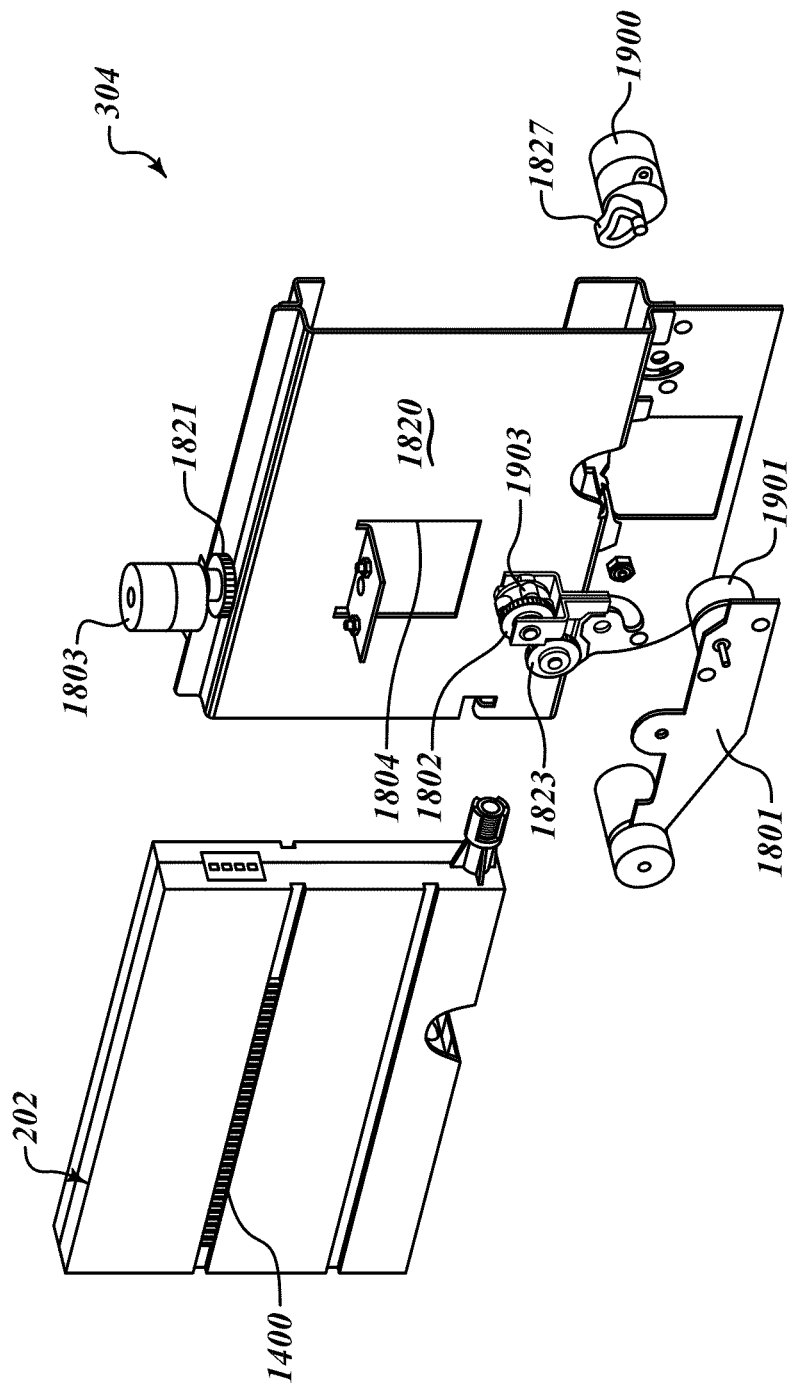
FIG. 21 is a side exploded view of the media module depicted in FIG. 18.

FIG. 21 depicts a side view of the media module 304. Shown in this side view is the opening 1804 through which the gear 1821 contacts the rack 1400 of the cartridge 202. As described hereinabove, as the motor 1803 rotates the gear 1821 that is in contact with the rack 1400, the cartridge 202 is moved in or out of the frame 1820 depending on the direction of rotation of the motor 1803 and gear 1821.

FIG. 21 also depicts the pump 1903. The pump 1903 is coupled to the gear 1802, which is coupled to the gear 1823. The gear 1823 is coupled to the motor 1901, which is mounted to the engagement arm 1801. As the motor 1901 turns the gear 1823, gear 1802 rotates, which in turn rotates the pump 1903, as described in further detail below with reference to FIG. 22.

FIG. 21 further depicts the motor 1900 attached to the actuator 1827. As the motor 1900 turns the actuator 1827, the actuator 1827 pushes up on the valve 1503 (FIG. 15) thereby unpinching the tubing 1501 (FIG. 15). As noted hereinabove, the valve 1503 is in a normally closed position pinching the tubing 1501 closed.

Figure 22:
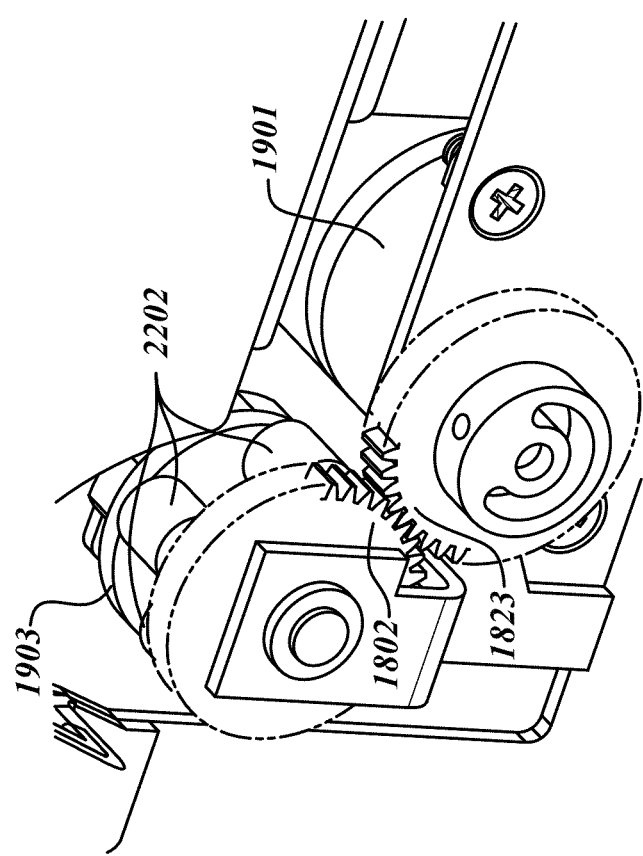
FIG. 22 is a detailed view of a peristaltic pump and corresponding gears used in the media module depicted in FIG. 18.

FIG. 22 is a close up view of the pump 1903. In this regard, the motor 1901 is mechanically coupled to the gear 1823. The gear 1823 couples to the gear 1802, and the gear 1802 is coupled to the pump 1903. The pump 1903 comprises a plurality of rollers 2202. As the motor 1901 turns gear 1823, gear 1802 rotates, which rotates the rollers 2202 in the pump 1903. As the rollers 2202 contact the tubing 1501 (FIG. 15), the rollers 2002 pinch up against the flexible tubing 1501, and forces liquid and gas in the tube to move in a direction that the gear is rotating. The pressure caused by the rollers 2202 on the tubing 1501 by the rotational forces media contained within the tubing 1501 to move through piercing device 1700 (FIG. 17).

If the cartridge were a waste cartridge, the motor 1901 would rotate gear 1823 in an opposite direction, thereby rotating gear 1802 in the opposite direction. Therefore, the rollers 2202 of the pump 1903 would move in a direction to push waste into the bag or bladder 1500 (FIG. 15).

Figure 23:
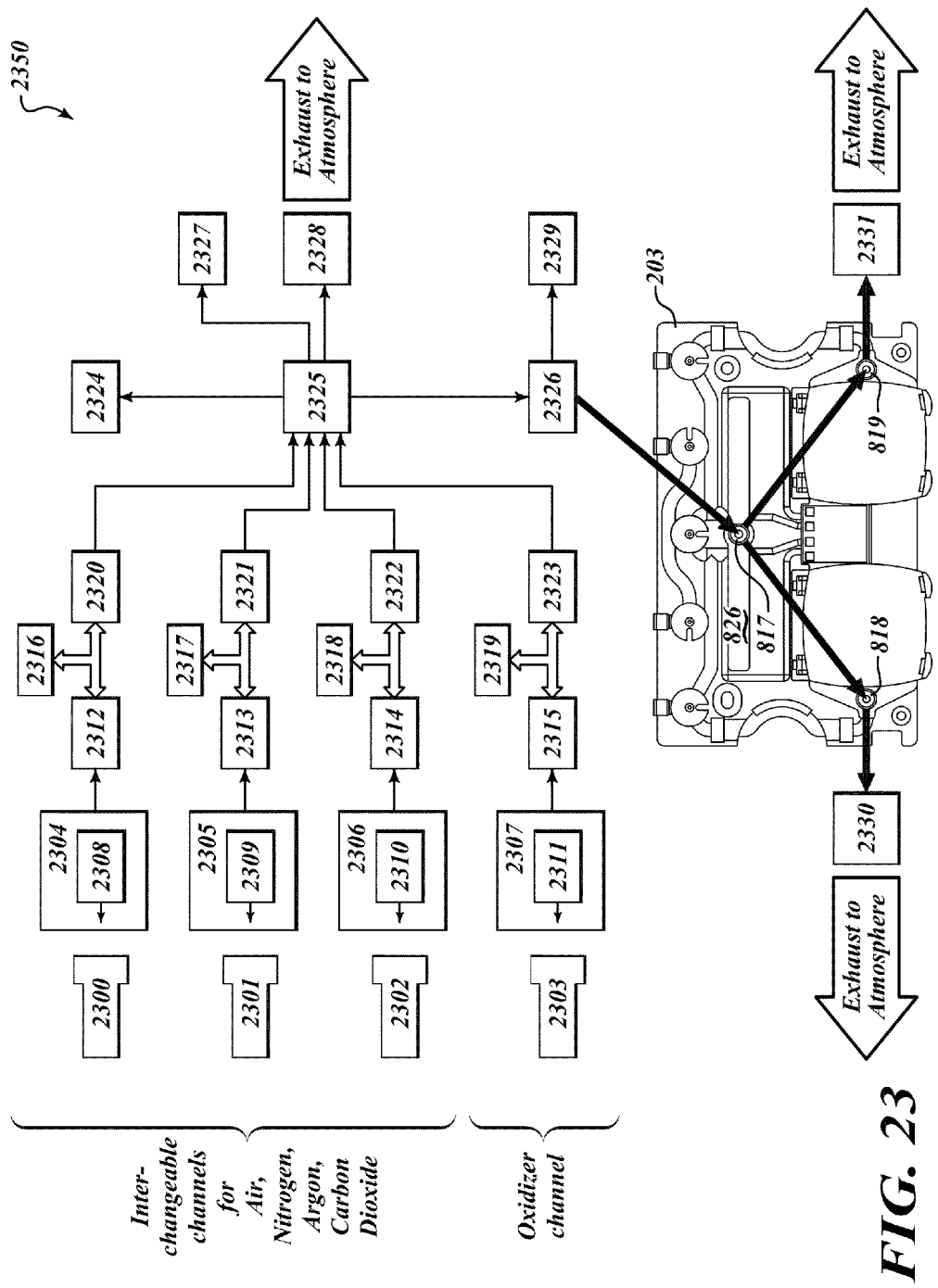
FIG. 23 is a block diagram depicting an exemplary gas subsystem of the cell culture system depicted in FIG. 2 in accordance with an embodiment of the present disclosure.

FIG. 23 is a diagram depicting a gas subsystem 2350 of the cell culture system 103 (FIG. 1) in accordance with an embodiment of the present disclosure. Generally, the gas subsystem 2350 delivers gases to and removes gases from the growth cartridge 203 during experimentation or other operation.

The gas subsystem 2350 comprises a plurality of gas cartridges 2300-2303. Each of the gas cartridges 2300-2303 contains some type of gas or combination of gases. For example, these gases may be oxygen, nitrogen, argon, or carbon dioxide.

The gas subsystem 2350 further comprises a holder assembly 2304-2307 sized, dimensioned or otherwise configured to hold the gas canisters or cartridges 2300-2303, respectively. Each of the holder assemblies 2304-2307 comprises a piercer 2308-2311, respectively. The holder assemblies 2304-2307 hold the gas canisters or cartridges 2300-2303, and the piercers 2308-2311 pierce openings in the gas canisters or cartridges 2300-2303 thereby releasing gas contained within the gas canisters or cartridges 2300-2303.

Note that the gas contained within the gas canisters or cartridges 2300-2303 is contained at a high pressure, such as, for example 200 pounds per square inch (PSI). Therefore, before delivering the gases to the growth cassette or cartridge 203, the pressure of the gases is reduced. Thus, the gas from each of the gas canisters or cartridges 2300-2303 is delivered to regulators 2312-2315, respectively. The regulators 2312-2315 are any type of gas regulator known in the art or future-developed. The gas regulators 2312-1215 reduce the pressure of the gases delivered to 20-25 PSI.

There are sensors 2316-2319 that detect the pressure of the gas before the gas is fed to a mixer 2325. In this regard, the gas pressure detected may indicate that one or more of the gas cartridges 2300-2303 is running low or out of the particular gas. Notably, the pressure should be sensed, measured or otherwise determined upstream (i.e., toward gas canister) of a regulator.

The gas output of the regulators 2312-2315 is fed to the mixer 2325 if two-way valves 2320-2323, respectively, are in open positions. Therefore, one or all of the gases can be delivered to the mixer 2325. Indeed, not all gases from the gas cartridges 2300-2303 have to be delivered to the mixer 2325. A user (not shown) may select, via logic described further herein, which gases and how much of the gas that the user desires to be mixed in mixer 2325 and delivered to the growth cartridge 203.

An atmosphere pressure sensor 2324 and an atmosphere temperature sensor 2327 may be coupled to the mixer 2325 to sense, measure or otherwise determine pressure and temperature of the atmosphere composed by the gas. Thus, during operation, using the formula $$PV=nRT$$

where P represents pressure, V represents volume, n represents the number of molecules, R is the gas constant, and T represents temperature, the system can allow the user to determine which gases and what amounts are being fed into the mixer 2325. Thus during operation, logic (not shown FIG. 23) may be used to control the amount of gas that is in the mixer 2325 based upon the readings from the PSI sensor 2324 and the temperature sensor 2327.

Once the mixer 2325 mixes the gases together in the mixture that the user desires, the gas is delivered to the well or wells via the gas bubbler 826 which is sealed by a gasket 817. As described hereinabove, the gas bubbler 826 delivers the gas to the media (not shown) that is traveling through the channels 807 (FIGS. 8) and 808 (FIG. 8). Delivery of the gas mixture to the gas bubbler 826 is controlled via a two-way valve 2326. Notably, there is an additional pressure sensor 2329 associated with valve 2326 that can measure the pressure of the gas mixture before it is delivered to the growth cartridge 203. Some embodiments will employ a regulator or two-stage valve to control or regulate gas flow. Such may advantageously manage pressure decline in the mixer 2325.

In addition, the gas subsystem 2350 may have a two-way valve 2328. If during the course of an experiment or performing some other culturing protocol or at any time, the mixer 2325 may be emptied via the two-way valve 2328 and the gas mixture may be directed to exhaust externally from the culture system to the atmosphere. As explained below, the culture system 102 may include various sensors to provide feedback of various operational, environmental and/or culture conditions, for example dissolved gas content of the culture medium. Such may be used as feedback to control the operation of the atmosphere or gas supply subsystem.

Furthermore, the gas subsystem 2350 comprises two two-way valves 2330 and 2331 that are in fluid communication with septum 818 and 819. As previously mentioned the septum 181, 819 may include a gas permeable membrane which may form a hydrophobic bubbler membrane. Thus, during the course of an experiment, gas released within the growth cartridge 203 may be exhausted to the atmosphere via the two-way valves 2330 and 2331.

Figure 24:
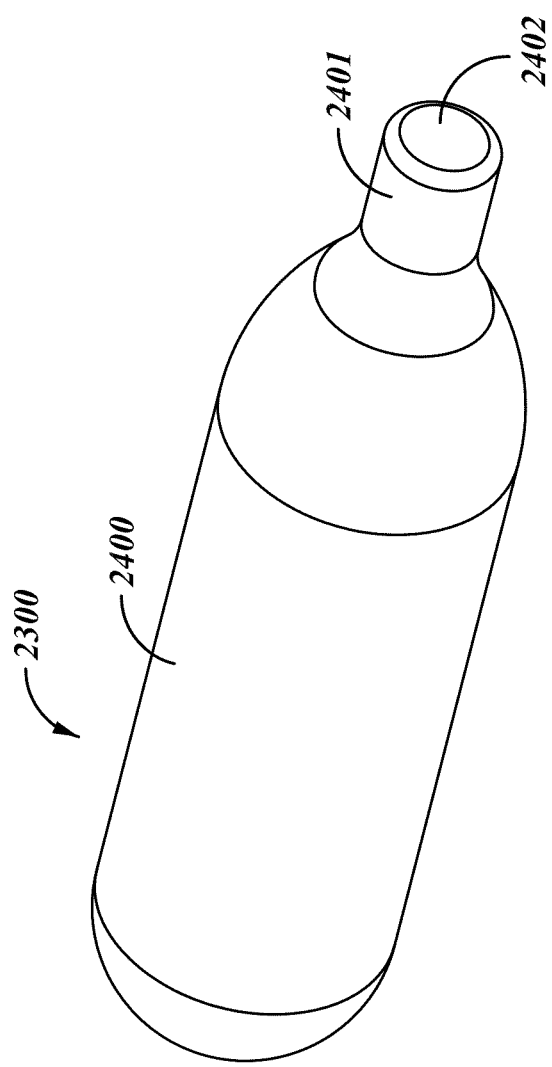
FIG. 24 is a perspective view of an exemplary gas cartridge used in the gas subsystem depicted in FIG. 23 in accordance with an embodiment of the present disclosure.

FIG. 24 depicts an exemplary gas canister or cartridge 2300. Note that only one gas canister or cartridge is described. However, all the other gas canisters or cartridges 2301-2303 are substantially similar to gas cartridge 2300, and only gas canister or cartridge 2300 is described for brevity.

The gas canister or cartridge 2300 comprises a container portion 2400 having an exterior and an interior in which a gas (not shown) is stored. Further, the gas canister or cartridge 2300 comprises a neck 2401 that is sealed with a lid 2402. Note that the gas canister or cartridge 2300 may in one embodiment be an integral piece formed of, for example, a suitable metal.

Figure 25:
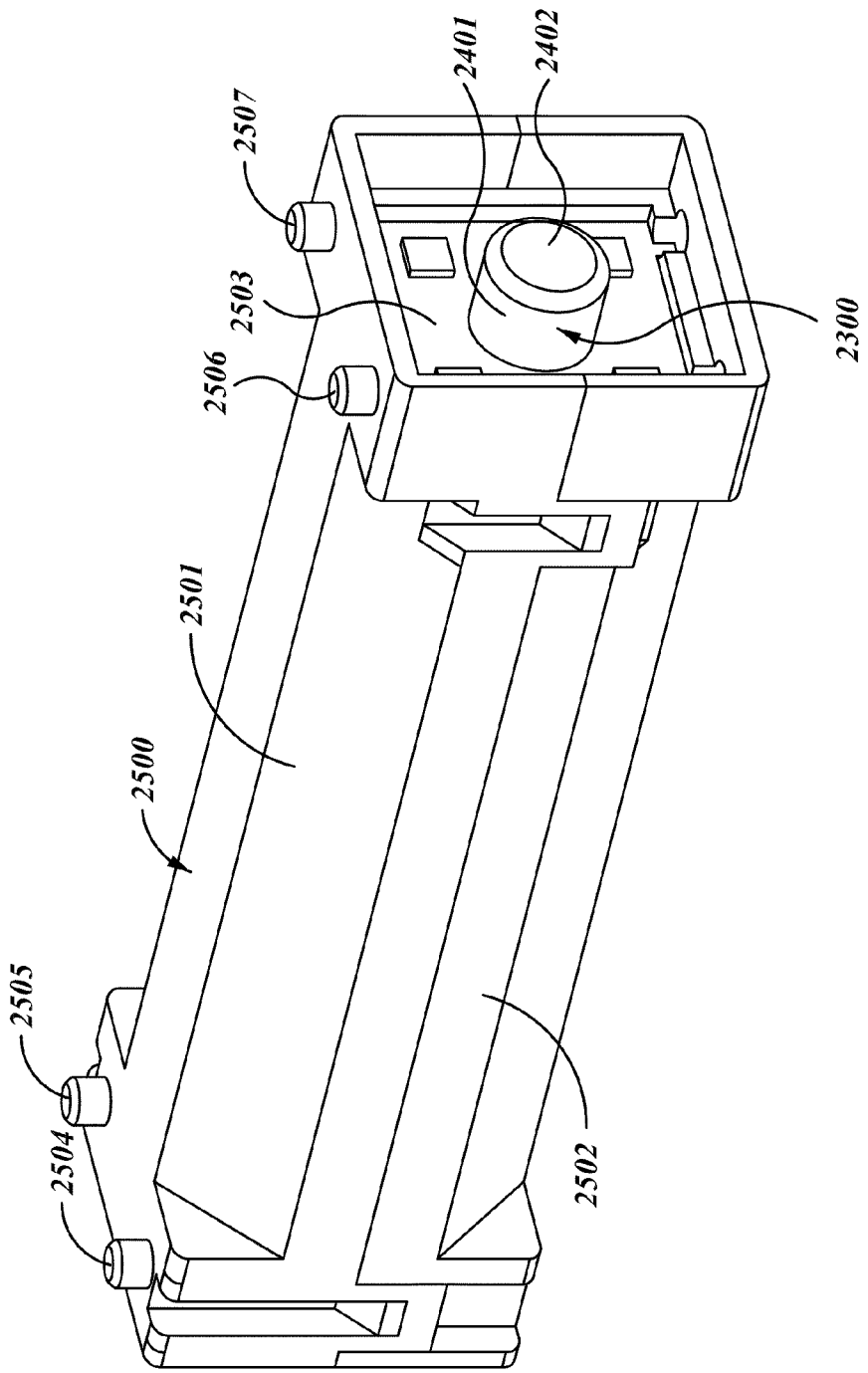
FIG. 25 is a perspective view of an exemplary housing for housing the gas cartridge depicted in FIG. 24 in accordance with an embodiment of the present disclosure.
Figure 26:
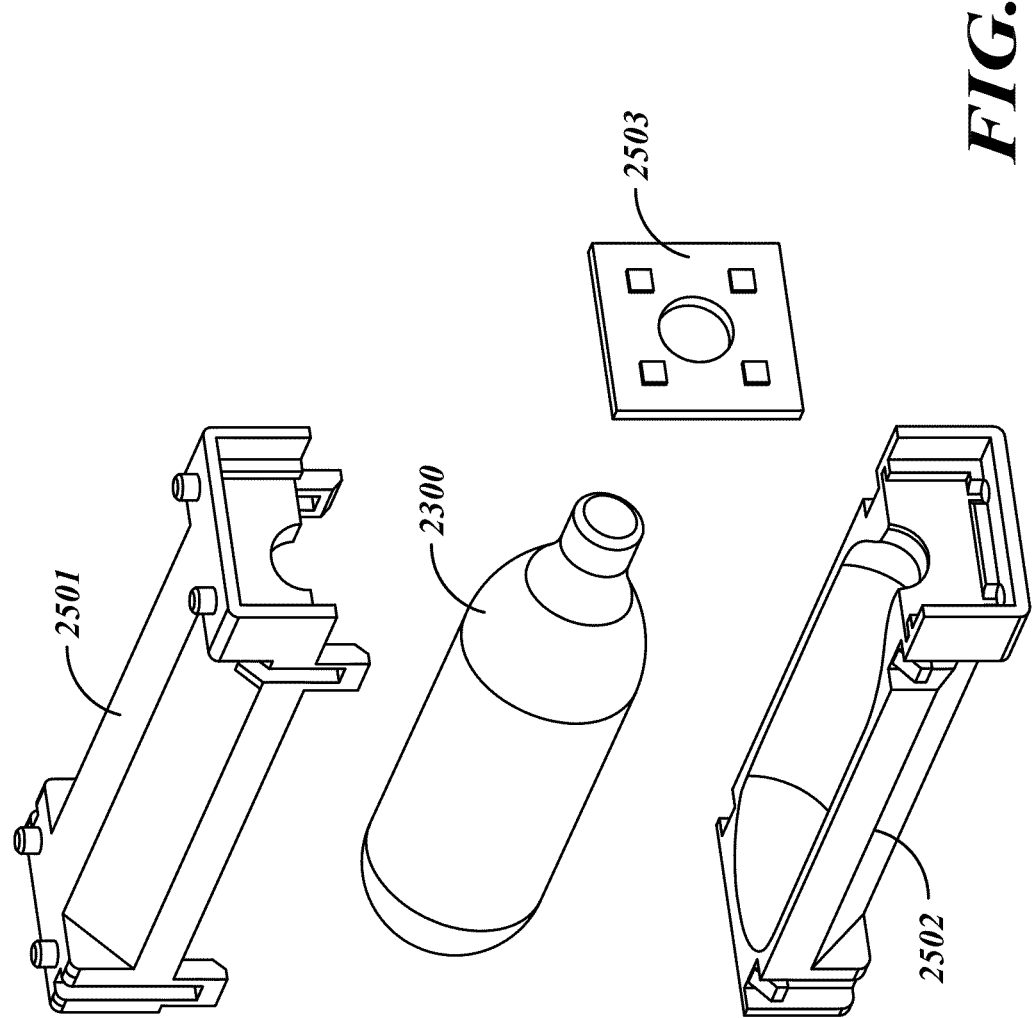
FIG. 26 is an exploded view of the housing depicted in FIG. 25.

FIGS. 25 and 26 depict an exemplary housing 2500 for housing the gas canister or cartridge 2300 (FIG. 24) in accordance with an embodiment of the present disclosure. The housing 2500 comprises a top portion 2501 and a bottom portion 2502 that are connected together via adhesive, tabs and slots and/or sonic welding. Protrusions or pins 2504-2507 are stacking, positioning or alignment structures or features that align the gas canister or cartridge 2300. The top portion 2501 and the bottom portion 2502 are connected around the gas canister or cartridge 2300 such that the neck 2401 and the lid 2402 of the gas canister or cartridge 2300 are exposed. Other stacking or alignment structures or features may be employed, for example screws, bolts, bands or clips.

In addition, the housing comprises a PCB 2503 including a non-transitory computer- or processor-readable storage medium connected to the gas canister or cartridge 2300, for instance around the neck 2401 of the gas cartridge 2300. The storage medium (e.g., memory) stores data or other information indicative of characteristics of the gas cartridge 2300. For example, the data or information may be indicative of the a unique identifier that uniquely identifiers the gas canister or cartridge 2300, the type of gas contained within the gas cartridge 2300, a quantity of gas and/or a pressure of the gas in the gas canister or cartridge 2300. As explained below, the gas canister or cartridge 2300 may additionally, or alternatively, include one or more data carriers, for example machine-readable symbols, RFID transponders, magnetic stripes, which store the data and other information.

In some embodiments, the PCB 2503 may further include a controller (e.g., microprocessor, programmable gate array, application specific integrated circuit) capable of executing instructions, which may also be stored on the storage medium. The instructions may implement a gas canister or cartridge program. The gas canister or cartridge program may determine the actual contents of the gas canister or cartridge 2300 at various times during use. Additionally or alternatively, the information stored in the storage medium may include a key, token or other security mechanism, which is required by the culture system to operate. Such may prevent use of unauthorized gas canister or cartridges 2300, which might damage the culture system. Additionally or alternatively, the gas canister or cartridge program interacts with the culture system to authenticate the media cartridge 2300.

Figure 27:
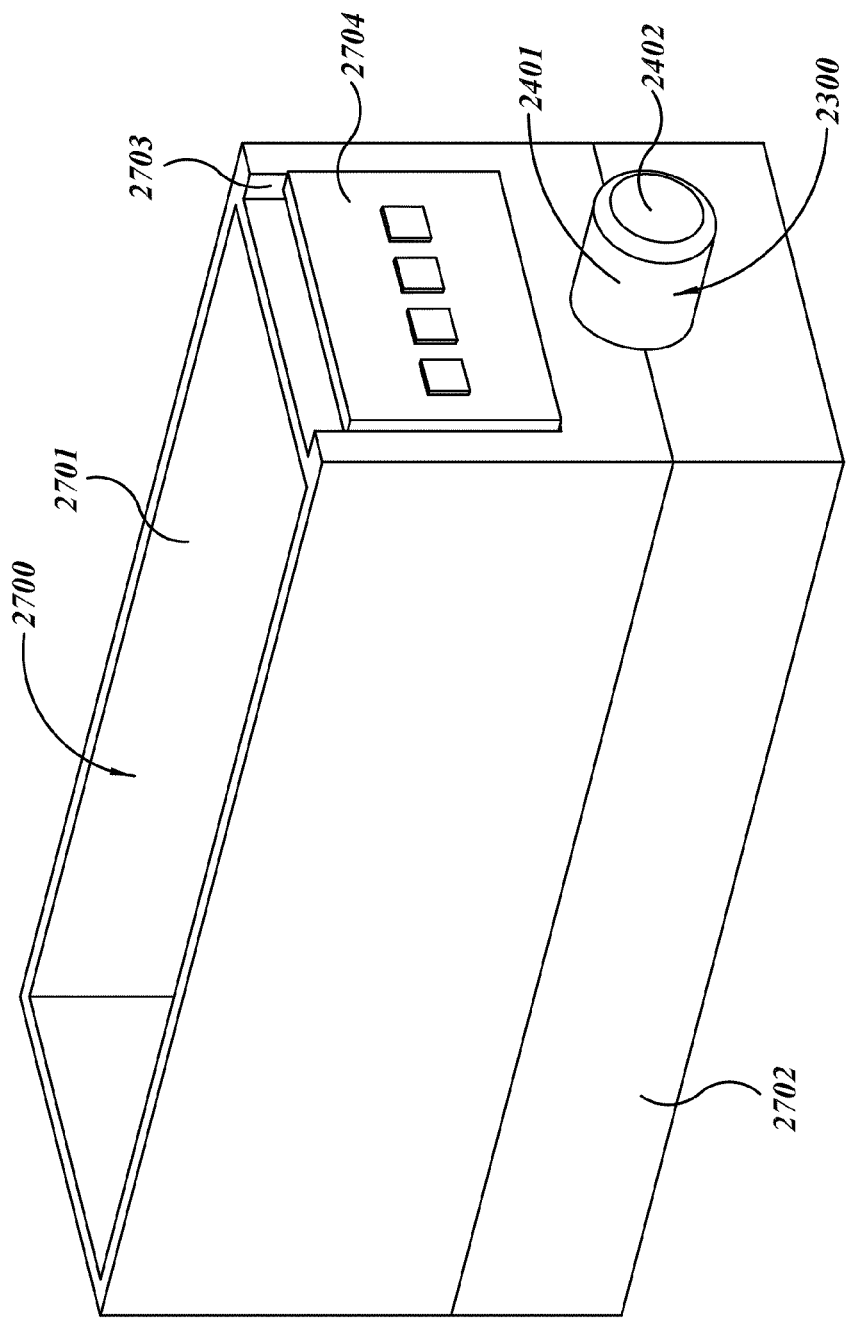
FIG. 27 is a perspective view of another exemplary housing for housing the gas cartridge depicted in FIG. 24 in accordance with an embodiment of the present disclosure.
Figure 28:
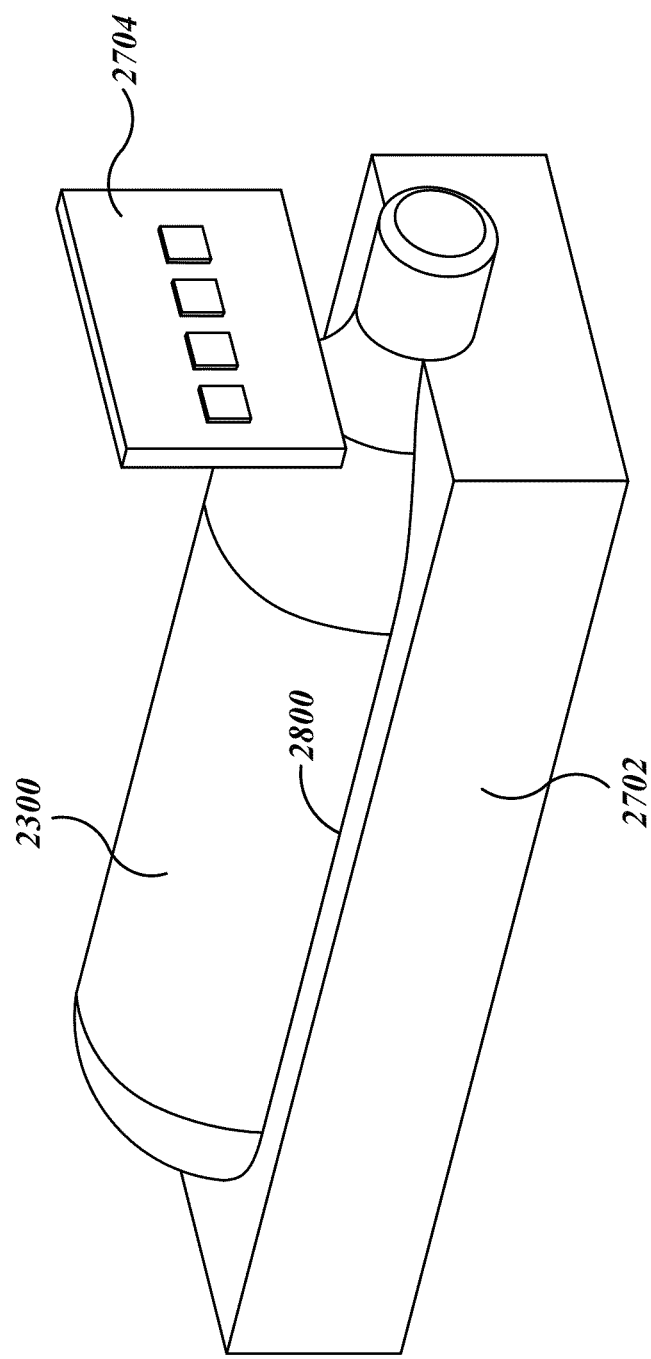
FIG. 28 is a cut away view of the housing depicted in FIG. 27.
Figure 29:
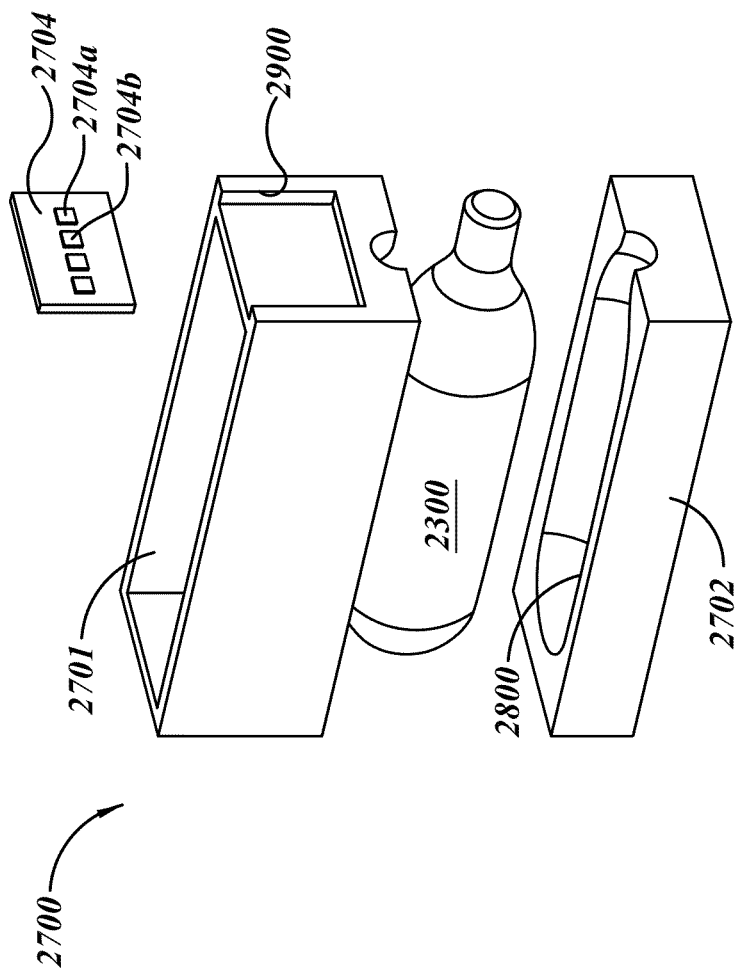
FIG. 29 is an exploded view of the housing depicted in FIG. 27.

FIGS. 27-29 depict another exemplary housing 2700 for housing the gas canister or cartridge 2300 (FIG. 24). In particular, FIG. 29 shows the upper portion 2701 and the lower portion 2702 separated. In such an embodiment, the housing 2700 comprises a top portion 2701 and a bottom portion 2702 that are fastened together around the gas canister or cartridge 2300. Only the neck 2401 and the lid 2402 of the gas canister or cartridge 2300 are exposed.

In addition, the housing 2700 comprises a PCB 2704. Such PCB 2704 comprises a non-transitory computer- or processor-readable storage medium (e.g., memory) 2704a (only called out in FIG. 27) that stores data or other information indicative of characteristics of the gas cartridge 2300, described hereinabove. The PCB 2704 may also include one or more contacts or terminals 2704b (only one called out in FIG. 27) that allow communications to be established with the controller of the cell culture system 103.

The bottom portion 2702 (FIG. 28) has an opening 2800 that is in the shape of the gas canister or cartridge 2300. Thus, the gas canister or cartridge 2300 fits within the opening 2800.

Further, the PCB 2704 fits within a slot 2900 of the upper portion 2701 of the housing 2700.

Figure 30:
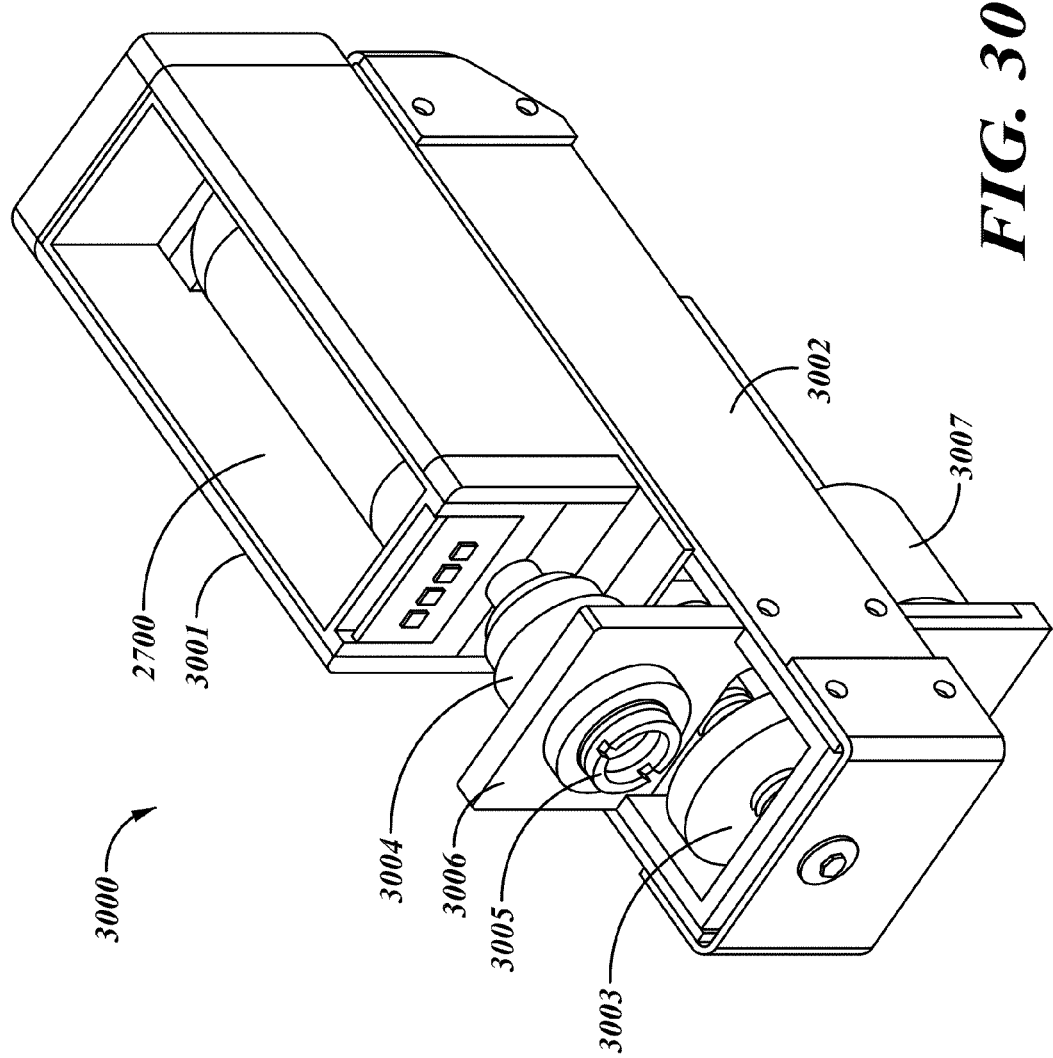
FIG. 30 is a perspective view of an exemplary gas cartridge assembly using the gas cartridge housing depicted in FIG. 27 in accordance with an embodiment of the present disclosure.

FIG. 30 depicts an assembly 3000 that holds the housing 2700 described hereinabove. In this regard, the assembly 3000 comprises a substantially hollow tray 3001 in which the housing 2700 is inserted. In addition, the assembly 3000 comprises a bottom container 3002. The bottom container 3002 houses a worm drive 3003 or other transmission (e.g., rack and pinion, bar linkage), which is shown in more detail with reference to FIG. 31. The worm drive 3003 is controlled via a motor 3007 located on the bottom of the assembly 3000.

The assembly 3000 further comprises a frame 3006 that holds a cylinder piercing mechanism 3001 and a coupler interface 3005 to for connecting to a tube (not shown), for example. In operation, the piercing mechanism 3004 pierces the lid 2402 (FIG. 24) of the gas canister or cartridge 2300 (FIG. 24), thereby establishing fluid communication between the gas canister or cartridge 2300 and the interface 3005 that is connected to a tube.

Figure 31:
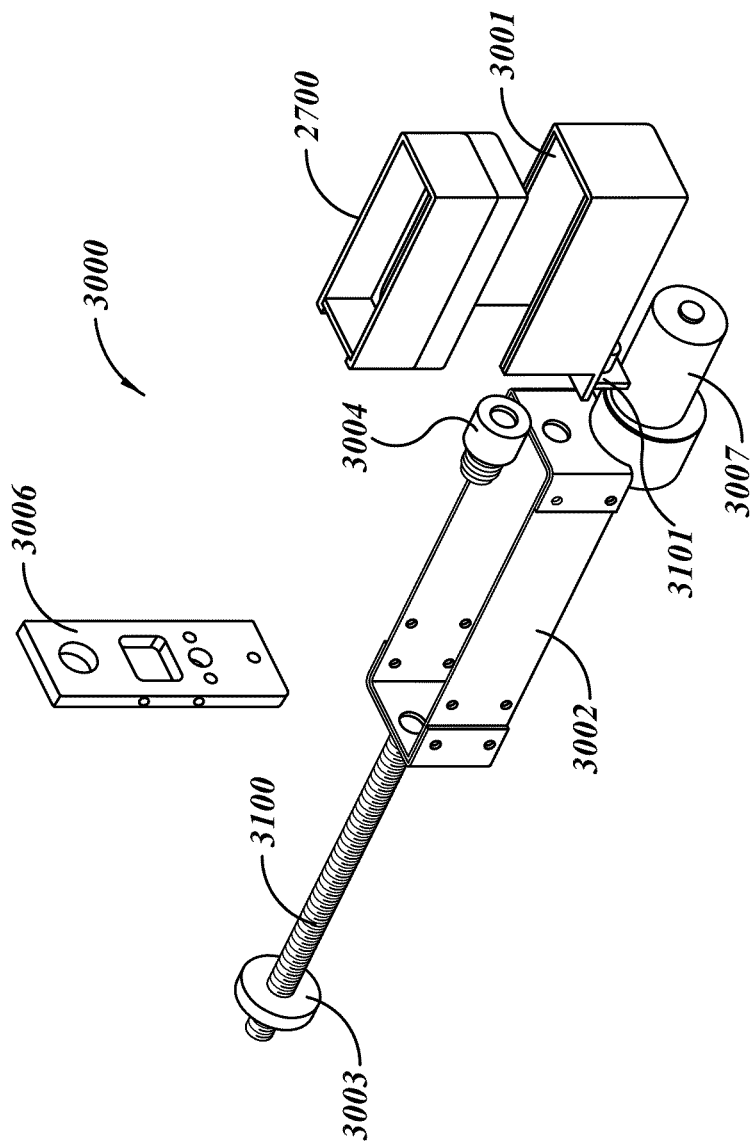
FIG. 31 is an exploded view of the gas cartridge assembly depicted in FIG. 30.

FIG. 31 is an exploded view of the assembly 3000. Notably, the substantially hollow tray 3001 holds the housing 2700 that houses the gas canister or cartridge 2300 (FIG. 28). The tray 3001 comprises a radial protrusion 3101 such as a flange that has a threaded opening (not shown) therein. A threaded extension 3100 of the worm drive 3003 fits within the opening, and when the motor 3007 operates, the worm drive 3003 pulls or retracts the tray 3001 having the housing 2700 over the top of the container 3002.

Figure 32:
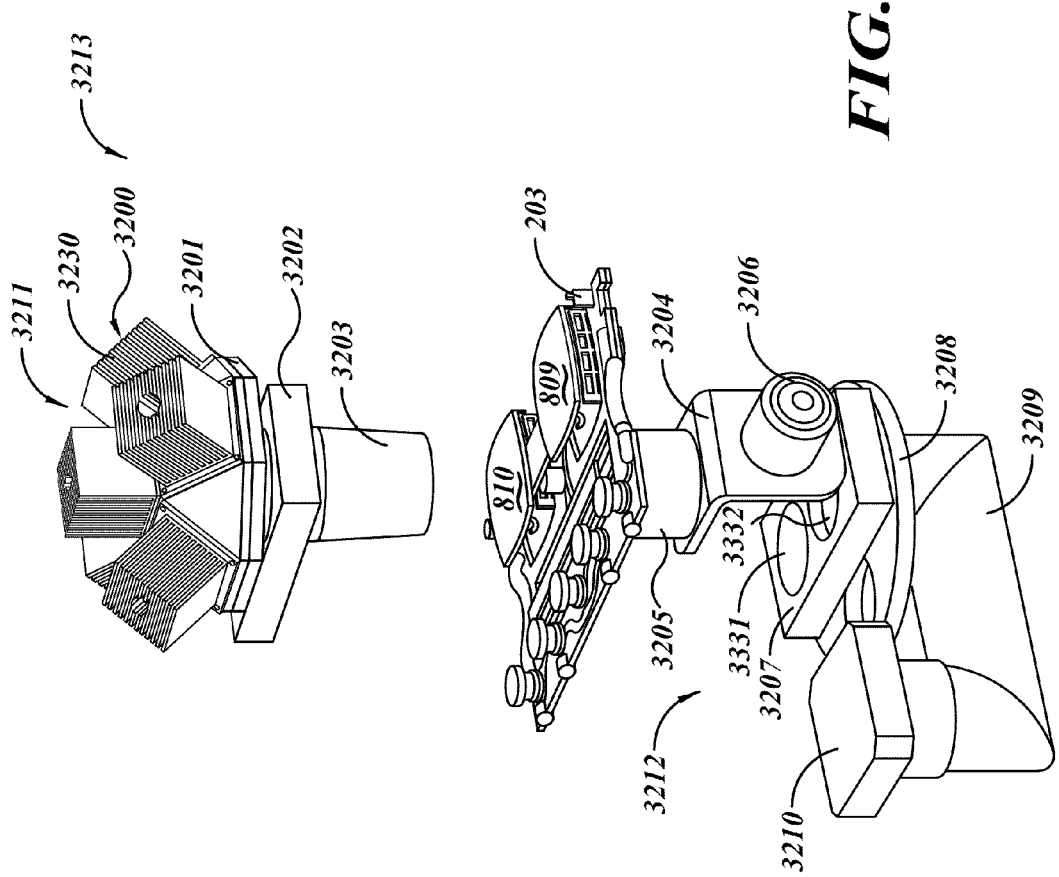
FIG. 32 is a perspective view of an exemplary microscopy subsystem used in the cell culture system of FIG. 2 in accordance with an embodiment of the present disclosure.

FIG. 32 depicts an exemplary microscopy subsystem 3213 in accordance with an embodiment of the present disclosure. The microscopy subsystem 3213 comprises an illumination assembly 3211 and an objective assembly 3212.

The illumination assembly 3211 allows illumination (e.g., visible, near-infrared, infrared, ultraviolet) of a cell or other biological material culture contained within the growth cartridge 203. The illumination assembly 3211 comprises a plurality of passively cooled light emitting diode (LED) array boards 3200 having heat sink modules 3230. In one embodiment, each board 3200 contains eight LEDs (not shown) comprising two each of wavelengths of white, 403 nanometers (nm), 465 nm, and 565 nm. Additionally or alternatively, any other wavelengths may be employed. In such an embodiment, there are five boards 3200, and each board 3200 comprises eight LEDs totaling forty LEDs.

The illumination assembly 3211 further comprises a collimator 3201. The collimator 3201 gathers the light emitted from the LEDs and directs the light toward a condenser 3203. The illumination assembly 3211 further comprises a 2-position turret 3202 that contains one empty opening (not shown) and a second opening (not shown) having a polarizer (not shown) and Nomarsky prism (not shown). The polarizer and the Nomarsky prism are used when a user desires differential interference contrast (DIC). Note that the turret 3202 can be slid, rotated or otherwise moved into a first position, where the light from the LED boards 3200 goes through the empty opening or to a second position, where the light from the LED boards 3200 travels through the polarizer and Nomarsky prism.

Light emitted from the condenser 3203 shines on one or the other of the cell cultures contained within growth cartridge 203 (FIG. 2). In this regard, the assembly 3211 is mounted to the X-Y-Z table 217 (FIG. 2), and can be moved in a direction such that the light emitting from the condenser 3203 shines through either one of the growth chambers 809, 810.

The microscopy subsystem 3213 further comprises an objective assembly 3212 for capturing images of the cell cultures contained within the growth cartridge 203. The objective assembly comprises a dual objective turret 3204. The dual objective turret 3204 may include at least one high magnification objective 3205 situated underneath the growth cartridge 203. In one embodiment, the objective 3205 is a 40× objective infinity corrected, APO PLAN and compatible with fluorescent wavelengths. The turret is moveable such that a second low magnification objective 3206 may be used instead of the high magnification objective 3205.

In addition, the objective assembly 3212 comprises a two-position turret 3207. The turret 3207 comprises an empty opening 3331 for obtaining normal images. In addition, the turret 3207 comprises an opening 3332 having a polarizer and Nomarsky prism in order to obtain DIC images. Other imaging techniques may be employed such as bright field or phase contrast imaging techniques.

In addition, the objective assembly 3212 comprises a filter turret 3208. The filter turret 3208 has numerous openings each having respective different optical filters to filter particular wavelengths while passing other wavelengths of illumination. In this regard, the turret 3208 may have an empty opening for obtaining unfiltered (e.g., white light) digital images. In addition, the turret 3208 may have an opening having a filter for each wavelength associated with fluorescence. Notably, the filter used removes undesirable wavelengths thereby allowing a digital image of fluorescence to be captured. Suitably sensitive imagers should be employed.

In addition, the objective assembly comprises an illumination tube 3209 that is in connection with a camera or imager head 3210. Illumination travels through the illumination tube 3209 to the camera or imager head 3210. The camera or imager head 3210 includes one or more imagers that are operable to capture digital images of the cell or other biological tissue cultures within the growth cartridge 203. In one embodiment, the illumination tube has a length of approximately 200 millimeters (mm). Such allows most infinity corrected optics to be used. Furthermore, the illumination tube 3209 may have two or more turns or bends to maximize space efficiency. A focusing lens (not shown) may be located, for example, 200 mm from the bottom of the objective 3205 to focus the image on the camera or imager. A second 10× ocular lens (not shown) may direct the focused image to the imager (e.g., charge-coupled device or CCD) located in the camera or imager head 3210. In one embodiment, the focusing lens could be combined with the ocular lens in order to conserve space. Additionally, one or more selectively adjustable apertures may be provided.

Note that the objective assembly 3212 is also mounted to the X-Y-Z table 217. Thus, the objective assembly 3212 can also be moved accordingly to obtain digital images of cell cultures in both the growth chambers 809 and 810.

Figure 33:
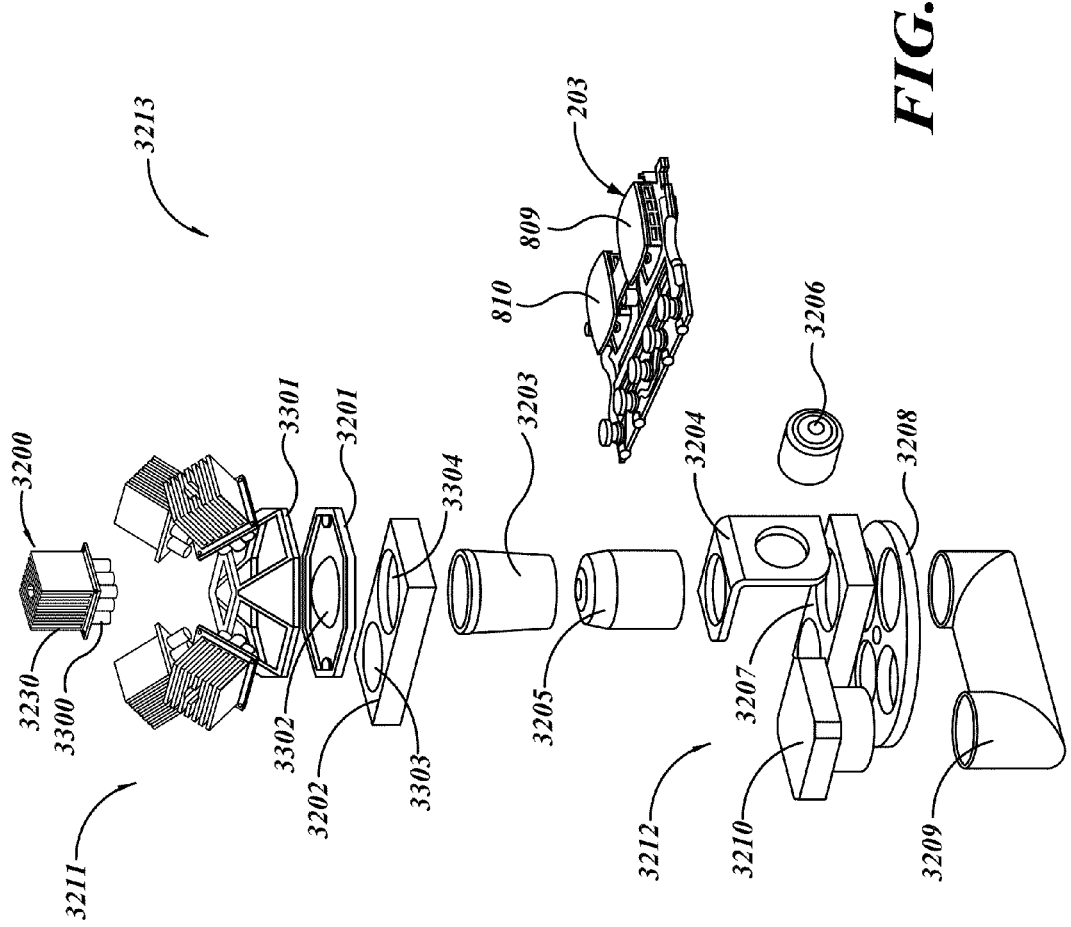
FIG. 33 is an exploded view of the microscopy subsystem of FIG. 32.

FIG. 33 is an exploded view of the microscopy subsystem 3213 shown in FIG. 32. Notably, FIG. 33 depicts the housing 3301 to which the LED boards 3200 are attached. Each of the LED boards 3200 may include, for example, eight LEDs 3300.

Further, FIG. 33 depicts the collimator 3201. The collimator 3201 attaches to the housing 3301 and comprises a lens 3302 that directs illumination (e.g., light) emitted by the LEDs 3300 through one of two openings 3303 or 3304 of the sliding polarizer 3202. As described hereinabove, one of the openings 3303 may be empty and simply passes the illumination (e.g., light) emitted from the LEDs 3300 without any filtering to the condenser 3203. The other opening 3304 may have a polarizer and Nomarsky lens mounted therein to transmit only a portion of the illumination through to the condenser, depending upon the type of image that is desired by a user (not shown).

FIG. 33 further shows the condenser 3203, which receives illumination emitted by the LEDs 3300 through the collimator 3201 and the turret 3202. The condenser 3203 directs the illumination to one or more of the growth chambers 809 or 810, depending upon the location of the illumination assembly 3211.

FIG. 33 further shows the objective turret 3204. The objective turret 3204 can have mounted to it a high magnification objective 3205 and a low magnification objective 3206. The turret can be moved such that the growth chamber 809 or 810 is alternatively in the field-of-view of the high magnification objective 3205 or in the field-of-view of the low magnification objective 3206.

FIG. 33 further shows the two-position turret 3207. One of the openings of the turret 3207 may be empty, to allow all illumination to pass through the turret unfiltered. Whereas, the second opening may have a polarizer and Nomarsky prism mounted therein through which only selected illumination passes.

The fluorescent filter turret 3208 may have four openings. One opening may be empty, to allow all illumination to pass through the turret 3208 unfiltered. Whereas, the other three openings may have respective ones of different filters mounted therein to selectively filter out particular wavelengths of illumination, i.e., one filter to pass respective ones of each of three desired wavelengths associated with fluorescence.

FIG. 33 further shows the illumination tube 3209 and the camera or imager head 3210. The illumination tube 3209 interfaces with one of the openings in the turret 3208. Illumination passes through the illumination tube 3209 to a CCD (not shown) in the camera or imager head 3210, which captures digital images of the contents of at least a portion of at least one of the wells or growth chambers 809,810, depending upon the location of the illumination assembly 3211 and the objective assembly 3212.

Figure 34:
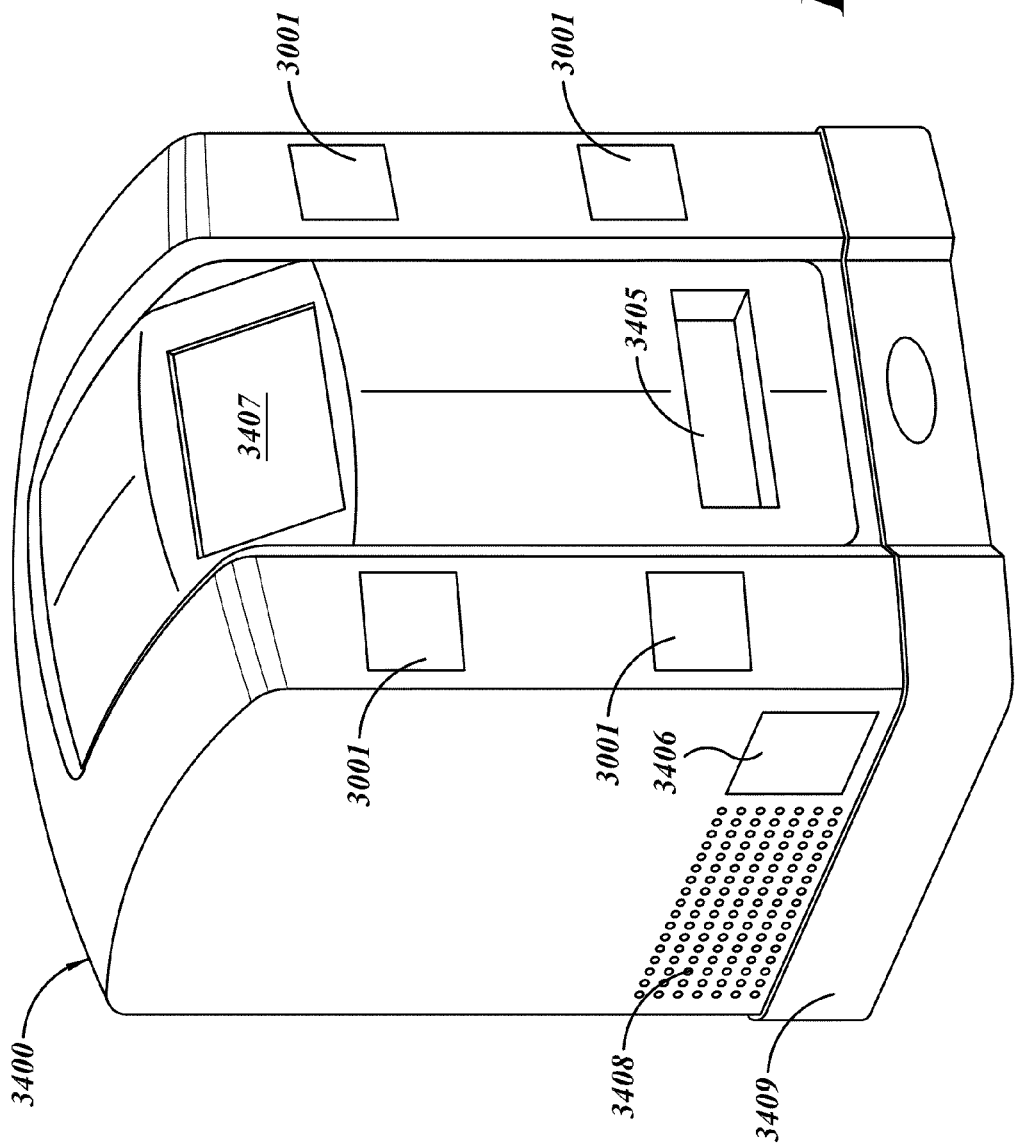
FIG. 34 is a perspective view of an exemplary casing for housing the cell culture system depicted in FIG. 2.

FIG. 34 shows a culture system 102, according to one illustrated embodiment.

The culture system 102 includes a housing 3400 and may include a touch screen display 3407 accessible by an end user from an exterior of the housing 3400. As described further herein, the touch screen display 3407 provides information to the end user (not shown). The touch screen display 3407 may also present a graphical user interface to the end user, including various user selectable icons, menus, radio buttons, dialog boxes, text and/or images which may prompt the end user and may allow the end user to enter input to control operation of the culture system 102.

The housing 3400 includes a plurality of gas canister or cartridge tray receptacles 3001, each sized and dimensioned to receive a gas canister or a media or a waste cartridge. When actuated, the gas canister or cartridge trays 3001 open and extend outwardly so that gas canister or cartridge housings 2700 (FIG. 30) may be inserted, or removed and replaced.

The housing 3400 further comprises a growth cassette receiver 3405. The growth cassette receiver is sized and dimensioned to removably receive a removable multi-well growth cassette therein.

The growth cassette or cartridge 203 (FIG. 8) can be inserted into the opening 3405, and pulled or withdrawn into position into the growth receiver by the ejector/puller components 209 (FIGS. 2) and 250 (FIG. 2).

The housing 3400 may include microscope receptacle and cover 3406. The microscope receptacle and cover 3406 allows an end user to access a microscopy system located in the housing, from an exterior thereof.

Further, the housing 3400 may has a plurality of vents or exhausts 3408. During operation such openings allow gas to vent or exhaust from the housing 3400 and/or allow atmospheric air to enter the housing. The air may be supplied to the wells and/or subwells of the growth cassette is specified by the culturing protocol being executed. Additionally, or alternatively, the vent or exhaust may allow cool air to be drawn into the housing and warm air vent therefrom, in order to cool the various components of the culture system 203 during operation. The housing 3400 may be rotatable mounted to a base 3409 for rotation about a vertical axis.

Figure 35A:
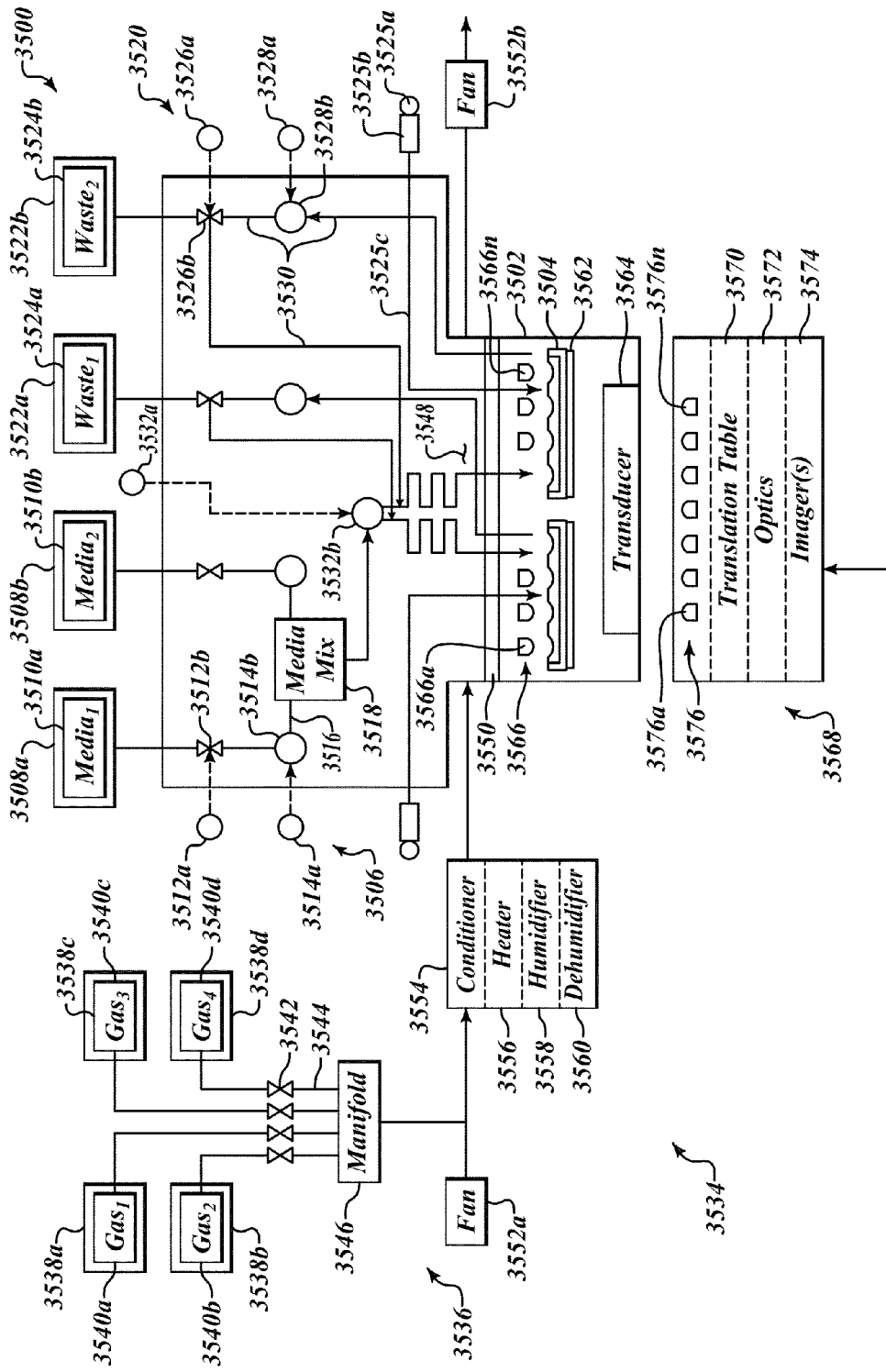
FIGS. 35A and 35B is a schematic diagram of the culture system, showing a control subsystem in detail.
Figure 35B:
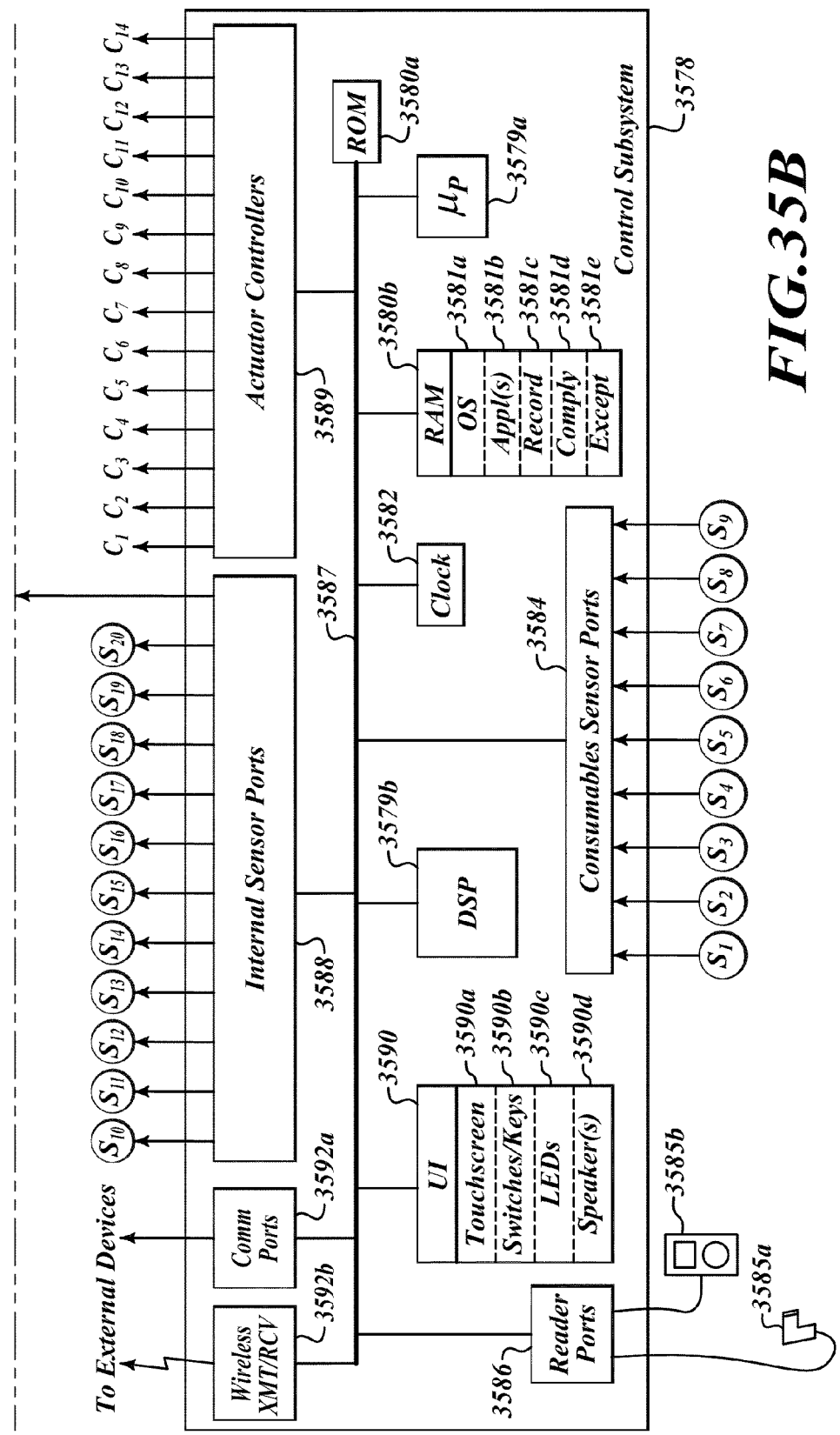

FIGS. 35A and 35B show the culture system 3500 identical or similar to that described above.

The culture system 3500 may be used to culture or incubate biological materials, for example cells, bacteria, tissue, proteins, fungi, and/or photosynthetic materials such as photosynthetic organisms, including photosynthetic macro-organisms and micro-organisms. The culture system 3500 may, for example be used to culture animal cells such as mammalian cells or cell lines, or to culture non-mammalian cells such as plant cells, yeast, and/or microbes such as viruses, bacteria or protists. Such may be employed in research or manufacturing or production. For example, the culture system 3500 may be employed in tissue or organ culturing or tissue engineering or in the production of vaccines.

As discussed in more detail elsewhere herein, the culture system 3500 is operable to precise control a large variety of conditions under which cells or other biological material are grown. As discussed in more detail elsewhere herein, the culture system 3500 may execute defined culturing protocols, automating the culturing process. As discussed in more detail elsewhere herein, the culture system 3500 is also operable to sense, measure or collect information or data regarding the culturing, including information related to the actual operational conditions of the culture system 3500, information related to the actual environmental conditions to which the biological material is subjected, over time during the culturing, and/or information related to the condition of the biological material itself, over time during the performance of the culturing protocol. As discussed in more detail elsewhere herein, the culture system 3500 may automatically sense, measure or collect this information or data as part of executing any one of a number of defined culturing protocols, further automating the culturing process and allowing reporting and verification of experimentation or manufacturing production. Also as discussed in more detail elsewhere herein, the culture system 3500 may automatically perform analysis on the culturing operation using the sensed measured or otherwise collected information or data, including analysis of digital images or micrographs of the biological material over time during the culturing performance of the culturing protocol. The culture system may use the results of the analysis to control or adjust various aspects and/or conditions of the culturing process in accord with a defined culturing protocol being executed by the culture system. Again, this may significantly automate the culturing process.

Automation may free researchers to perform more important tasks or tasks requiring the researchers' specific skills. Automation may also enhance quality or repeatability. Such can be important in the research environment, reducing the number of times that an experiment needs to be run. Such may also be important in a production or manufacturing environment where quality assurance may be required.

As described below and elsewhere herein, the culture system employs removable multi-well growth cassettes. Such may advantageously allow a large number of cultures to be preformed simultaneously. For example, the same type of biological material may be cultured simultaneously using different media while being subjected to identical culturing conditions. Comparisons may be made between various wells, or even subwells. For example, various materials may be distributed between the wells or subwells and assessed for cytotoxic effect.

As described below and elsewhere herein, the culture system may advantageously employ removable cartridges or canisters to supply various materials such as growth media, gases, reagents, and/or dyes, as well as to collect waste generated by the culturing process. The media and waste cartridges may further advantageously directly fluidly communicatively couple to the growth cassette, for example, without any intervening conduit of the culture system. Such may ensure that the various components of the culture system remain clean and uncontaminated by materials used during previous culturing operations. Additionally, the gas canisters may advantageously directly fluidly communicatively couple to the growth cassette, for example, without any intervening conduit of the culture system, or alternatively via an intervening conduit.

As described below and elsewhere herein, the culture system may advantageously employ kits which may include any two or more of: removable multi-well growth cassettes, removable media cartridges, removable waste cartridges, removable gas canisters, sets of reagents, sets of dyes or stains, and/or non-transitory computer- or processor-readable media that store processor-executable instructions which cause a culture system to perform a number of culturing operations in accordance with a defined culturing protocol. The wells and/or subwells of the removable multi-well growth cassettes may include or contain various treatments, substances or coatings specified by a particular defined culturing protocol. The removable media cartridges may each contain media or a type and quantity specified by a particular defined culturing protocol. The removable waste media cartridges may be sized to contain the quantity or amount of waste expected to be generated during performance of a particular defined culturing protocol. The removable gas canisters may each contain a gas of a type and quantity specified by a particular defined culturing protocol. The sets of reagents may each contain vials or other containers of one or more reagents of a type and quantity specified by a particular defined culturing protocol. The sets of dyes or stains may each contain vials or other containers of one or more dyes or stains of a type and quantity specified by a particular defined culturing protocol. The non-transitory computer- or processor-readable media may store processor-executable instructions in a high level language, a low level language, as source code and/or object code. The non-transitory computer- or processor-readable media may take any of a large variety of forms, including but not limited to a Flash or thumb drive, Universal Serial Bus USB) card, magnetic "floppy" disk, optical disk (e.g., compact disk or CD). The kits may advantageously supply all the materials required to perform a culturing, including the machine-executable instructions. Such may further automate the culturing process, industrializing the culturing system. The kits may also ensure that sufficient quantities of materials are supplied, without waste. Such may significantly reduce costs, and reduce the amount of waste generated.

While an embodiment employing the advantageous removable cartridges and canister carrying the consumables such as media and gas is described below, other embodiments may include a fixed source, supply or line of consumables such as media or gas. For example, media or gas may be supplied via a standalone tank or reservoir. Such may be more expensive to install, so may have limited appeal to smaller research departments. However, such an approach may be advantageous for large scale production or manufacturing facilities. In such embodiments, the supply lines may advantageously directly fluidly communicatively couple to the growth cassette, for example, without any intervening conduit of the culture system.

As shown in FIGS. 35A and 35B, the culture system 3500 includes a growth cassette receiver 3502 which is sized and dimensioned to removably receive multi-well growth cassettes 3504. The growth cassette receiver 3502 may precisely position the growth cassette 3504 in the culture system 3500. Precise positioning enables imaging of a particular area over time. Thus, a particular cell cluster may be imaged over the course of performing a defined culturing protocol.

While referred to herein and in the claims as a cassette, the growth cassettes 3504 can take any form of removable cassette, cartridge, container, canister, tray or slide. Various aspects of the growth cassette 3504 were discussed above, and further aspects are discussed below with reference to FIGS. 36A and 36B. As described therein the growth cassette includes a number of distinct wells, which may optionally be subdivided into two or more subwells. As described elsewhere herein, the growth cassette 3504 may include a number of ports which allow materials (e.g., media, gases, reagents, dyes, stains) to be introduced into the growth cassette 3504 and/or to remove or exhaust materials (e.g., waste, spent atmosphere or gases) from the growth cassette 3504. The growth cassette 3504 also has various conduits or channels providing fluid paths between the ports and the wells and/or subwells. The growth cassette 3504 may include various valves for directing flows along selected conduits or channels. Also as described elsewhere herein, the growth cassette 3504 may include mixing areas, manifolds, and gas permeable membranes. Other variations are possible, for example a growth cassette 3504 which eliminates one or more of these elements, for example eliminating a manifold 3546 of the culture system 3500.

Positioning of the growth cassette 3504 in the growth cassette receiver 3502 may advantageously protect the contents of the wells and/or subwells from incidental exposure to illumination. Alternatively, or additionally, the growth cassette 3504 may have windows that selectively allow illumination, for example only when the growth cassette 3504 in positioned in the growth cassette receiver 3502. For instance, the windows over one or more wells and/or subwells may include diaphragm (e.g., iris diaphragm) or other shutter. Physical features of the multi-well growth cassette 3504 and/or optical registration marks on the multi-well growth cassette 3504 may facilitate precise position with respect to microscopy systems, whether a microscopy system of the culture system 3500 or some external microscopy system. Such may allow precise areas or cell colonies to be imaged at various times.

The culture system 3500 may include a media delivery subsystem 3506. The media delivery subsystem 3506 includes a number of media cartridge receivers 3508a, 3508b (two illustrated, collectively referenced as 3508) which are sized and dimensioned to removably receive respective media cartridges 3510a, 3510b (collectively referenced as 3510) that contain media. The media cartridges 3510 are typically full of selected media prior to use, and are emptied as media is supplied to the wells of the growth cassette 3504 during use. The media may take a variety of forms, but typically will be in the form of a liquid, semi-liquid or gel, which is supplied to be biological material as part of a culturing protocol. The media may be suitable for cell culture or for microbiological culture, depending on the specific culturing protocol being executed, and may be non-synthetic or synthetic. Suitable media may, for example include nutrient broths or mediums or Lysogeny broth or medium. Various defined or undefined growth media may be employed depending on the specific culturing protocol being executed. The media may be a minimal medium (e.g., Eagle's minimal essential medium or EMEM), a selective medium (e.g., HIS-selective medium), a reducing medium, a differential medium (e.g., mannitol salts agar, blood agar, MacConkey agar, eosin-methylene blue agar) or an enriched medium (e.g., Thioglycollate broth).

The media delivery subsystem 3506 includes one or more valve actuators 3512a, pump actuators 3514a, and conduits 3516 (only one called out of each, for sake of clarity in illustration) which are operable to selectively provide a fluidly communicative path between the wells and/or subwells of the growth cassette 3504 and media cartridges 3510 when the growth cassette 3504 and media cartridges 3510 are located in the growth cassette receiver 3502 and media cartridge receivers 3508, respectively.

For example, a valve actuator 3512a may be responsive to at least one control signal, opening or closing a valve 3512b of the growth cassette receiver 3512b to selectively provide or close a fluid communicative path in response to same. Such may advantageously control a flow of media between the media cartridge 3510 and the growth cassette 3504.

Also for example a diverter actuator 3532a may control a diverter (e.g., three-way valve) 3532b of the growth cassette 3504. The diverter 3532 is operable to selectively divert a flow of media to selected wells and/or subwells of the growth cassette. The diverter actuator 3532a may be responsive to at least one control signal to control the diverter 3532b to direct media to the selected well and/or subwell. This may advantageously allow two or more types of media to be mixed and provided to the selected well and/or subwell.

As a further example, a pump actuator 3514a may be responsive to at least one control signal to control a pump 3514b of the growth cassette 3504 to selectively pump or not pump material (e.g., media) along a fluid communicative path in response to same. Such may advantageously cause media to flow where such would not otherwise flow, for example due to gravity, lack of pressure or head, or viscosity of the media. While peristaltic pumps (e.g., pumps 220, 221 shown in FIG. 2) have been described and illustrated generally above, alternatively or additionally, other pumps may be employed, for example gear pumps.

The growth cassette 2504 may include a media mixing chamber or volume 3548 in which different types of media, from respective media cartridges 3510, may be mixed. Alternatively, the media delivery system 3506 may optionally include a media mixing chamber 3518 or volume in which different types of media, from respective media cartridges 3510, may be mixed prior to delivery to the growth cassette 3504.

Thus, the media delivery system 3506 is operable cause delivery of selected media from the media cartridges 3508 to the wells and/or subwells of the growth cassette 3504, at desired or defined times, rates, concentrations or amounts.

The culture system 3500 may include a waste extraction subsystem 3520. The waste extraction subsystem 3520 includes a number of waste cartridge receivers 3522a, 3522b (two illustrated, collectively referenced as 3522) which are sized and dimensioned to removably receive waste cartridges 3524a, 3524b (collectively 3524). The waste cartridges 3524 are typically empty prior to use, and are selectively filled with waste extracted from the wells or subwells of the growth cassette 3504 during use. Some embodiments, may employ the same removable cartridges to both deliver media and collect waste. For instance, some cartridges may contain two distinct bladders or other structure to respectively contain media and waste. Also for instance, a culture system 3500 may deliver media from a first cartridge while using a second cartridge to collect waste. The culture system 3500 may then use the empty first cartridge to collect waste. Such may occur after completion of media deliver. Alternatively, such may occur while media is delivered from a third cartridge.

The waste extraction subsystem 3520 includes one or more valves actuators 3526a (only one called out in FIG. 35A for sake of clarity in illustration), pumps actuators 3528a (only one called out in FIG. 35A for sake of clarity in illustration), conduits 3530 (only three called out in FIG. 35A for sake of clarity in illustration) which are operable to selectively provide a fluidly communicative path between the wells of the growth cassette 3504 and waste cartridges 3524 when the growth cassette 3504 and waste cartridges 3524 are located in the growth cassette receiver 3502 and waste cartridge receivers 3522, respectively.

For example, a valve actuator 3526a may be responsive to at least one control signal, opening or closing a valve (e.g., three-way valve) 2526b of the waste cartridge 3524 to selectively provide or close a fluid communicative path in response to same. The valve 2526b may advantageously selectively fluidly couple the wells and/or subwells of the growth cassette 3504 alternatively between a waste outlet and a respective media conduit or channel 3516. Such may advantageously allow a flow of waste to be diverted from the waste cartridge and returned back to the wells and/or subwells of the growth cassette 3504. This provides an alternative path, shunting at least some waste away from the waste cartridges 3524 for reuse in the wells and/or subwells of the growth cassette 3504.

Also for example, a pump actuator 3528a may be responsive to at least one control signal to control a pump 3528b of the growth cassette 3504 to selectively pump or not pump material (e.g., waste) along a fluid communicative path in response to same.

Thus, the waste extraction subsystem 3520 is operable to deliver waste extracted from the wells and/or subwells of the growth cassette 3504 to the waste cartridges 3524 or back to the wells or subwells of the growth cassette 3504, at desired or defined times, rates, concentrations and/or amounts.

The culture system 3500 may include a number of syringe pumps 3525 (two shown, only one called out in FIG. 3500) including a syringe pump actuator 3525a and a syringe holder 3525b sized and dimensioned to removably receive syringes 4752 (FIG. 47) holding various substances. The actuators 3525a are selectively operable to cause syringes 4752 to expel or provide the contents of the syringes 4752 to one or more of the wells and/or subwells of the growth cassette 3504 via one or more conduits 3525c.

As described in more detail below, the syringes 4752 may store a variety of substances useful in performing culturing and/or analysis of culturing or cultured material, for instance analysis of cultured cells. For example, the syringes 4752 may store reagents, dyes, stains or other substances. The syringes 4752 are typically provided to the holders without any associated needle. The syringe pumps 3525 may include a coupler to fluidly communicatively couple an exit port the syringe to one or more ports of the growth cartridge 3504. For instance, the syringe pump 3525 may include a LUER® lock or other coupler.

The syringe pump actuator 3525a may take any of a variety of forms, for example electric motors, solenoids or other electromechanical devices. The syringe pump actuator 3525a may be responsive to at least one control signal to control the syringe to selectively pump or not pump material (e.g., reagents, dye, stain) into the growth cassette 3504. Thus, the syringe pump 3525 is selectively operable to deliver substances or materials from one or more syringes to the wells and/or subwells of the growth cassette 3504, at desired or defined times, rates, concentrations and/or amounts.

The culture system 102 may include an environmental control subsystem 3534. The environmental control subsystem 3534 is operable to selective control an environment to which the biological material in the wells and/or subwells of the growth cassettes 3504 are exposed during a culturing or incubation cycle.

The environmental control subsystem 3534 includes an atmosphere supply subsystem 3536. The atmosphere supply subsystem includes a number of gas canister receivers 3538a-3538d (four illustrated, collectively referenced as 3538) which are sized and dimensioned to removably receive gas canisters 3540a-3540d (collectively 3540) that contain gases of various gas types. While referred to herein and in the claims as canisters, the gas canisters 3540 can take any form of removable canister, cassette, cartridge, or other container. The gas canisters 3540 are typically full of selected gas prior to use, and are emptied as gas is supplied to the wells of the growth cassette during use. The gas may take a variety of forms, but typically will include carbon dioxide, oxygen, and/or nitrogen. The gas supply subsystem 3536 includes one or more valves actuators 3542a and conduits 3544 which are operable to selectively provide a fluidly communicative path between the wells and/or subwells of the growth cassette 3504 and gas canisters 3540 when the growth cassette 3504 and gas canisters 3540 are located in the growth cassette receiver 3502 and gas canister receivers 3538, respectively.

For example, a valve actuator 3542a may be responsive to at least one control signal, opening or closing a valve 3542b of the growth cassette 3504 to selectively provide or close a fluid communicative path in response to same. The gas supply subsystem 3536 may include a port or vent 3408 (FIG. 34) to allow ambient atmospheric air to be used, in place of, or in addition to, specific gas(es) contained in the gas canisters 3540. While the gas supply system 3536 may rely on pressurized gas in the gas canisters 3540, optionally the gas supply system 3536 may include pumps or compressors (not shown) to provide pressure to the gas(es).

The gas supply system 3536 and/or growth cassette 3504 may optionally include a manifold 3546. Additionally, or alternatively, the mixing or residency chamber 3548 of the growth cassette 3504 in which different types of gases, from respective gas canisters 3540, may be mixed may serve as a manifold. For example, the growth cassette may include two or more gas inlet ports fluidly coupled to the mixing or residency chamber 3548 via one or more conduits. The gases may be delivered, for example diffused or "bubbled" via a gas permeable membrane 3550 of the growth cassette 3504. The gas permeable membrane 3550 may be positioned to cover the mixing or residency chamber 3548. The gas permeable membrane 3550 may allow gases to diffuse in one direction, toward the growth cassette 3504.

Thus, the media delivery system is operable to deliver selected an atmosphere of a desired or defined composition from the gas canisters 3540 to the wells and/or subwells of the growth cassette 3504, at desired or defined times, rates, concentrations and/or amounts.

The environmental control subsystem 3534 and/or growth cassette 3504 may include one or more fans or blowers or fan or blower actuators 3552a, 3552b (collectively 3552). For example, the environmental control subsystem 3534 may optionally include one or more inlet fans or fan actuators 3552a positioned and operable to direct gas(es) into the growth cassette receiver 3502 to expose the contents of the wells and/or subwells of the growth cassette 3504 to an atmosphere of a desired or defined composition. Alternatively, the culture system 102 may omit the inlet fan or fan actuator 3552a, for example relying on a pressurized state of the gases in the gas canisters 3540 to move the atmosphere toward the growth cassette receiver 3502. Also for example, the environmental control subsystem 3534 may include one or more exhaust fans or fan actuators 3552b positioned and operable to exhaust the atmosphere from the growth cassette receiver 3502, for example via the exhaust port or vent 3408 (FIG. 34). The exhaust fan(s) 3552b may ensure adequate dispersal of an atmosphere from the volume of the growth cassette receiver 3502 to which the contents of the wells and/or subwells of the growth cassette 3504 is exposed. For example, an atmosphere of a first composition may be exhausted prior to provision of an atmosphere of a second composition. The fans or blowers or actuators 3552 may be part of the culture system 3500 or may reside on growth cassette 3504, or may have portions residing on both the culture system 3500 and the growth cassette 3504. In some embodiments, the fans may include impellers, blades or other structures which are part of the growth cassette 3504, and the actuators may take the form of electric motors, solenoids or other actuators which are part of the culture system 3500. The actuators may be drivingly coupled to impellers, blades or other air pushers via a physical coupler such as gears, belt, or via a magnetic coupler.

The environmental control subsystem 3534 and/or growth cassette 3504 may include a conditioning subsystem 3554 operable to condition the atmosphere provided to the growth cassette receiver 3502 and growth cassette 3504. Conditioning of atmosphere may allow precise control over the culturing or incubation following various protocols. The conditioning subsystem 3554 may include one or more distinct conditioning elements.

For example, the conditioning subsystem 3554 may include an atmosphere or gas heater 3556 selectively operable in response to control signals to heat the gas or atmosphere. The atmosphere heater 3556 may take a variety of forms, for example a resistive element or coil which produces radiant and/or convective heat when a current is passed therethrough. The atmosphere heater 3556 may reside on growth cassette 3504, or may be part of the culture system 3500, or may have portions residing on both the culture system 3500 and the growth cassette 3504. One or more temperature sensors $S_{15}$ may be located in the flow path and or in the growth cassette receiver 3502, proximate the growth cassette 3504 or part of the growth cassette 3504. Signals indicative of temperature produced by the temperature sensors $S_{15}$ may be used to control the atmosphere heater 3556. For example, a feedback system may operate the heater 3556 based on the signals to maintain a desired or defined temperature for a desired or defined amount of time, or may vary the temperature over time according to some defined pattern. Complimentary electrical or optical contacts or couplers may be provided on the growth cassette 3504 and, for example on the growth cassette receiver 3502, to provide communications with the temperature sensors $S_{15}$.

Also for example, conditioning subsystem 3554 may alternatively or additionally include a humidifier 3558 selectively operable to the humidify atmosphere supplied to the growth cassette receiver 3502 and growth cassette 3504. The humidifier 3558 may be part of the culture system 3500 or may reside on growth cassette 3504, or may have portions residing on both the culture system 3500 and the growth cassette 3504. The humidifier 3558 may be fluidly coupled to receive a fluid, such as water, from a fluid reservoir (not shown), for example via a valve (not shown) and conduit (not shown). The fluid in the fluid reservoir or supplied therefrom may undergo conditioning, such as being filtered, demineralized and/or subjected to UV light. One or more relative humidity sensors $S_{16}$ may be located in the flow path and or in the growth cassette receiver or proximate the growth cassette. Signals indicative of a relative humidity produced by the relative humidity sensors $S_{16}$ may be used to control the humidifier 3558. For example, a feedback system may operate the humidifier 3558 based on the signals to maintain a desired or defined relative humidity for a desired or defined amount of time, or may vary the relative humidity over time according to some defined pattern. Complimentary electrical or optical contacts or couplers may be provided on the growth cassette 3504 and, for example on the growth cassette receiver 3502, to provide communications with the relative humidity sensors $S_{16}$.

Also for example, the conditioning subsystem 3554 may alternatively or additionally include a dehumidifier 3560 selectively operable to dehumidify atmosphere supplied to the growth cassette receiver 3502 and growth cassette 3504. The dehumidifier 3560 may be part of the culture system 3500 or may reside on growth cassette 3504, or may have portions residing on both the culture system 3500 and the growth cassette 3504. The dehumidifier 3560 may, for example include a condensation element (e.g., condenser coil, not shown), which carries a thermal transfer medium (e.g., refrigerant or coolant, not shown), and a compressor (not shown) coupled to adjust a pressure of the thermal transfer medium. The dehumidifier 3560 may be fluidly communicatively coupled to provide condensed fluid to the fluid reservoir (not shown), for example via a conduit (not shown). The dehumidifier 3560 may be used to dehumidify the atmosphere supplied to the growth cassette receiver 3502 and growth cassette 3504. The dehumidifier 3560 may be used to achieve a desired relative humidity in the atmosphere supplied to which the contents of the wells and/or subwells of the growth cassette 3504 is exposed. One or more relative humidity sensors $S_{16}$ may be located in the flow path and or in the growth cassette receiver 3502 or proximate the growth cassette 3504. Signals indicative of a relative humidity produced by the relative humidity sensors $S_{16}$ may be used to control the dehumidifier 3560. For example, a feedback system may operate the dehumidifier 3560 based on the signals to maintain a desired or defined relative humidity for a desired or defined amount of time, or may vary the relative humidity over time according to some defined pattern.

The environmental control subsystem 3534 and/or growth cassette 3504 may include suitable filters (not shown in FIGS. 35A and 35B) for filtering the gases and/or atmosphere, positioned at various locations throughout the flow paths of the culture system 3500. Filters may take a variety of forms, for example activated carbon filters beds of Zeolite. Additionally, or alternatively, the environmental control subsystem 3534 and/or growth cassette 3504 may include one or more reducing agents (not shown), electrostatic treatment subsystem (not shown) and/or UV treatment subsystems (not shown).

The culture system 3500 and/or growth cassette 3504 may include one or more growth cassette heaters 3562 selectively operable to transfer heat to the biological material in the wells and/or subwells of the growth cassette 3504. The growth cassette heaters 3562 may be thermally coupled directly to the growth cassette 3504 to conductively transfer heat thereto, or may transfer heat through a radiative heat transfer mechanism. The growth cassette heaters 3562 may take a variety of forms, for example one or more strip line heating elements. The strip line heating element may be carried by the growth cassette 3504 (i.e., attached or otherwise coupled to the growth cassette 3504 and selectively removed from the growth cassette receiver 3502 therewith). Individual strip line heating elements may be associated with individual wells or subwells, or with groups of sets of wells or subwells of the growth cassette 3504. Such may allow different heating conditions to be applied at various locations across the growth cassettes 3504. The culture system 3500 may include one or more current or voltage sources to supply current to the growth cassette heater(s) 3562. One or more temperature sensors $S_{15}$ may provide signals indicative of temperature, and used to control the current or voltage sources. Complimentary electrical or optical contacts or couplers may be provided on the growth cassette 3504 and, for example on the growth cassette receiver 3502, to provide electrical communication to supply the current to the growth cassette heater(s) 3562. Complimentary electrical or optical contacts or couplers may be provided on the growth cassette 3504 and, for example on the growth cassette receiver 3502, to provide communications with the temperature sensors $S_{15}$.

The culture system 3500 and/or growth cassette 3504 may include one or more stimulus transducers 3564 selectively operable to impart a stimulus to the biological material in the wells and/or subwells of the growth cassette 3504. The stimulus transducers 3564 may be part of the culture system 3500 or may reside on growth cassette 3504, or may have portions residing on both the culture system 3500 and the growth cassette 3504. The stimulus may be an oscillatory stimulus, for example, a mechanical oscillatory motion, ultrasonic pressure wave oscillations, oscillating magnetic field, or pulsed jet of a fluid (e.g., air). The stimulus transducers 3564 may take a variety of forms. For example, the stimulus transducers 3564 may take the form of a vibration table associated with one or more motors and/or one or more transmissions. For example, the stimulus transducers 3564 may take the form of one or more piezoelectric transducers coupled to vibrate the growth cassette 3504. As a further example, the stimulus transducers 3564 may take the form of oscillating or vibrating magnets. As an even further example, the stimulus transducers 3564 may take the form of one or more jets and source of a compressed fluid to drive the jets. As yet a further example, the stimulus transducers 3564 may take the form of a Helmholtz coil and circuitry operable to produce an oscillating magnetic field. The stimulus transducers 3564 may vibrate or oscillate or produce vibration or oscillation at one or more desired or defined frequencies. For example the stimulus transducers 3564 may vibrate at one or more ultrasonic frequencies to obtain a desired effect or mimic a particular naturally occurring condition. The defined frequency or frequencies may be specifically selected for the particular protocol, for example based on empirical studies.

The culture system 3500 and/or growth cassette 3504 may include an illumination exposure control subsystem 3566 including one or more illumination sources 3566a-3566n (only two called out in FIGS. 35A and 35B) selectively operable to provide illumination (e.g., visible, near-infrared, infrared, ultraviolet) to the biological material in the wells and/or subwells of the growth cassette 3504. Such may be used to subject biological material to cycles of illumination, for instance mimicking illumination patterns found in natural environments (e.g., circadian cycle). The illumination sources 3566a-3566n may be part of the culture system 3500 or may reside on growth cassette 3504, or may have portions residing on both the culture system 3500 and the growth cassette 3504. For example, illumination sources 3566a-3566n may be carried by the growth cassette 3504, while a current or voltage source may be part of the culture system 3500. Complimentary electrical or optical contacts or couplers may be provided on the growth cassette 3504 and, for example on the growth cassette receiver 3502, to provide electrical communication to supply the current to the illumination sources 3566a-3566n.

The illumination sources 3566a-3566n may take any of a variety of forms including incandescent sources, gas discharge sources, and/or light emitting diode sources. The illumination exposure control subsystem 3566 may include a collection of illumination sources 3566a-3566n which emit illumination in respective wavelengths, and/or may include illumination sources 3566a-3566n which each selectively emit illumination at a variety of wavelength in response to some controllable parameter or condition (e.g., applied current or voltage, or temperature). Individual illumination sources 3566a-3566n or groups of illumination sources 3566a-3566n may be focused on respective individual wells or subwells, or the illumination sources 3566a-3566n may be capable of illuminating all wells or subwells. Illumination may be diffuse or focused. As noted, above, such may allow the biological materials to be subjected to natural, or even unnatural, patterns or cycles of illumination, at various locations across the growth cassettes.

The culture system 3500 may include a microscopy subsystem 3568. The microscopy subsystem 3568 may be positioned and operable to inspect the contents of the wells and/or subwells of the growth cassette 3504 when the growth cassette 3504 is positioned in the growth cassette receiver 3502. Advantageously, the inspection may be performed without withdrawing the growth cassette 3504, and thus without interrupting a culturing protocol being executed or performed by the culture system 3500. Such may, for example assure that the biological material is subjected to a particular temperature, atmospheric composition and/or specific pattern of illumination specified by the culturing protocol, without interruption. Further, the growth cassettes 3504 may have apertures to allow imaging, or may be generally transparent or at least translucent at desired wavelengths of electromagnetic radiation (e.g., visible).

The below description of the microscopy subsystem 3568 is in terms of general components, to allow explanation of the interaction of the microscopy system 3568 with the various other elements of the culture system 3500, including the sensors, actuators and controllers. A more detail description of the specific elements of the microscopy subsystem 3568 appears above.

The microscopy subsystem 3568 may include a translation table 3570. The translation table 3570 may selective move in an X- and/or Y-dimension in a plane of the growth cassette 3504 when positioned in the growth cassette receiver 3502 and/or in a Z-dimension extending perpendicular from the plane of the growth cassette 3504 when positioned in the growth cassette receiver 3502. Such may permit selective focusing in the Z-direction, as well as in selective focusing on selected portions of the wells or subwell in the X- and/or Y-dimensions. Movement of the translation table 3570 may be achieve via various actuators (e.g., electric motors, solenoids) and transmissions (e.g., gears, linkages, belts, pulls, cams, followers, racks, pinions) that couple the actuators to the translation table. Some embodiments, may omit a distinct stimulus transducers 3564, employing the translation table to apply the desired oscillatory motion or other mechanical stimulus to the growth cassette 3504.

The microscopy subsystem 3568 may include one or more optical components 3572, for example optical lenses, optical filters, gratings, mirrors or other reflectors, including dichroic mirrors. Some, all or none of these optical components 3572 may be movable with respect to the growth cassette 3504 positioned in the growth cassette receiver 3502 and/or with respect to one another. Such movement may, for example, facilitate focusing in a Z-dimension extending perpendicular from a plane of the growth cassette 3504 when positioned in the growth cassette receiver 3502 and/or focusing in an X- and/or Y-dimension in the plane of the growth cassette 3504 when positioned in the growth cassette receiver 3502. Various actuators (e.g., electric motors, solenoids) and transmissions (e.g., gears, linkages, belts, pulls, cams, followers, racks, pinions) may couple the actuators to the optical components 3572.

The microscopy subsystem 3568 may include one or more imagers 3574 positioned and operable to capture digital images of the wells or subwells of the growth cassette 3504 positioned in the growth cassette receiver 3502. The imagers 3574 may take a variety of forms, for example arrays of charged coupled devices (CCD) or CMOS image sensors. The imagers 3574 may capture digital still images and/or moving images such as video images, using any variety of formats or image protocols (e.g., JPEG, MPEG-2, NTCS, PAL, SECAM, S-VHS, VHS-C, S-video). The imagers 3574 act as transducers, converting images or illumination (e.g., visible light, non-visible light) into digital signals. Imagers 3574 may be responsive at a variety of wavelengths, for example visible wavelengths and non-visible wavelengths (e.g., near-infrared, infrared, ultraviolet). Two or more imagers 3574 with different sensitivities may be employed to cover a variety of wavelengths. Two or more imagers 3574 with different fields of view may be employed to cover a variety of areas. Two or more imagers 3574 with different sensitivities may be employed to cover a variety of resolutions.

The microscopy subsystem may optionally include a microscopy illumination subsystem 3576 including one or more illumination sources 3576a-3576n selectively operable to provide illumination (e.g., visible, near-infrared, infrared, ultraviolet) to the biological material in the wells of the growth cassette 3504 to allow imaging of the wells or subwells. The microscopy illumination subsystem 3576 may be separate and distinct from the illumination exposure subsystem 3566. The illumination sources 3576a-3576n may take any of a variety of forms including incandescent sources, gas discharge sources, and/or advantageously light emitting diode sources. Different ones of the illumination sources 3576a-3576n may emit illumination in respective wavelengths. Alternatively, or additionally, illumination sources 3576a-3576n may each selectively emit illumination at a variety of wavelength in response to some controllable parameter or condition (e.g., applied current or voltage, or temperature). Individual illumination sources 3576a-3576n or groups of illumination sources 3576a-3576n may be focused on respective individual wells or subwells, or the illumination sources 3576a-3576n may be capable of illuminating all wells or subwells. Illumination may be diffuse or focused. As noted, above, such may allow the biological materials to be subjected different wavelengths of illumination for micrographic imaging. In other embodiments, the illumination exposure subsystem 3576 may be employed to illuminate the wells and/or subwells for micrographic imaging. Such may advantageously reduce costs and redundancy.

The culture system 102 may include a control subsystem 3578. While an exemplary control subsystem 3578 is illustrated and described, one or ordinary skill in the art will appreciate that other control subsystem architectures and elements may be employed.

The control subsystem 3578 includes one or more controllers, for example a microprocessor 3579a, digital signal processor 3579b, programmable gate array (PGA) or application specific integrated circuit (ASIC) (collectively 3579). The control subsystem 3578 includes one or more non-transitory storage mediums, for example read only memory (ROM) 3580a, random access memory (RAM) 3580b, Flash memory (not shown), or other physical computer or processor-readable storage media (collectively 3580). The various components of the control subsystem 3578 may be communicatively coupled by one or more buses or other communicative structures 3587 (only one illustrated for the sake of drawing clarity), for example power buses, data buses, and/or instructions buses. The non-transitory storage mediums 3580 may store instructions and/or data used by the controller 3579, for example an operating system (OS) 3581a and/or applications 3581b. The applications may include instructions or logic to automatically control the various components of the culture system 3500 to perform or execute a culturing or incubation protocol, for example a predefined culturing or incubation protocol selected or identified by an end user or a culturing or incubation protocol defined by the end user. The instructions as executed by the controller 3579 may additionally implement a recording module 3581c to record various operational parameters, culturing or incubation parameters, and other captured data and information, including images. The instructions as executed by the controller 3579 may also implement a reporting module 3581d to produce reports regarding culturing cycles, based on and/or including the operational parameters, culturing parameters and/or other captured information. The instructions as executed by the controller 3579 may additionally implement an exception reporting module 3581e to handle exceptions (e.g., failures, out of compliance issues or variations from expected operation or thresholds). Exception reporting may, for example, include identifying exceptions, reporting exceptions in real time and/or periodically, automatically resolving exceptions, suggesting remedial actions which an end user may perform to resolve exceptions.

The control subsystem 3578 may also include one or more clocks 3582, which may allow determination of real world dates and time. Such may be useful for operating or synchronizing with a schedule set out in a protocol. Such may additionally, or alternatively, be useful turning the culture system 3500 OFF or entering a low energy consumption sleep mode after a defined period to reduce power consumption.

The control subsystem 3578 and/or growth cassettes 3504 may include one or more consumables sensors, represented in FIG. 2 as circles with respective identifiers $S_1$-$S_9$, positioned, configured and operable to sense various operation characteristics of the various elements or components of the disinfection system 100. The consumables sensors $S_1$-$S_9$ are communicatively coupled via one or more consumables sensor ports 2584 to provide signals indicative of such to at least one of the controller 3579. The communicative coupling may be wired (e.g., electrical, optical fiber) or wireless (e.g., radio in the radio or microwave wavelengths, light including infrared). For clarity of illustration, the consumables sensors $S_1$-$S_9$ are all grouped together proximate the other elements of the control subsystem 3578. In practice, these consumables sensors $S_1$-$S_9$ will typically be located in the culture system 3500, proximate areas which the consumables sensors $S_1$-$S_9$ are monitoring. The denomination "consumables" is used to indicate that the sensors $S_1$-$S_9$ are associated with consumables components (e.g., growth cassette 3504, media cartridges 3510, waste cartridges 3524, gas canisters 3540).

The consumables sensors may, for example, include one or more growth cassette sensors $S_1$. The growth cassette sensor(s) $S_1$ may sense or otherwise determine the presence and/or absence of a growth cassette 3504 in the growth cassette receiver 3502. For example, the growth cassette sensor $S_1$ may sense a communicative coupling (e.g., electrical contacts or optical couplers) between the control subsystem 3578 and a non-transitory storage medium (not shown in FIGS. 35A and 35B) carried by the growth cassette or cartridge 3504. Also for example, the growth cassette sensor(s) $S_1$ may take the form of a portion of an optical transceiver pair or a Hall effect sensor that detects a growth cassette 3504 being received in the growth cassette receiver 3502 and/or being correctly positioned in the culture system 3500. The other portion of an optical transceiver pair or a magnetic for the Hall effect sensor may, for example, be carried by the growth cassette.

The growth cassette sensor(s) $S_1$ may additionally, or alternatively, sense or otherwise determine information regarding the particular growth cassette 3504 received in the growth cassette receiver 3502. For example, the growth cassette sensor(s) $S_1$ may sense or otherwise determine an identity of the growth cassette 3504 and/or contents of the growth cassette 3504. For instance, the growth cassette sensor(s) $S_1$ may read or otherwise sense an identifier associated with the growth cassette 3504. Association may include being stored on or attached to the growth cassette 3504 or being carried by packaging which carried the growth cassette 3504. For instance, the growth cassette sensor $S_1$ may read information (i.e., identifier, contents of well, history of use) stored in a non-transitory storage medium (not shown in FIGS. 35A and 35B) carried by the growth cassette 3504, for example over an electrical or optical path. Alternatively or additionally, the growth cassette sensor $S_1$ (e.g., machine-readable symbol scanner or imager) may optically read or otherwise sense information stored in a machine-readable symbol (not shown in FIGS. 35A and 35B) carried by the growth cassette 3504. Alternatively or additionally the growth cassette sensor $S_1$ (e.g., RFID interrogator) may wirelessly read or otherwise sense information stored in an RFID transponder carried by the growth cassette 3504. The read or sensed information may simply specify an identifier that identifies the growth cassette 3504 either uniquely or by type, or may specify the contents of the wells of the growth cassette 3504 and/or a history of use of the growth cassette 3504. The control subsystem 3578 may use the identifier to determine additional information (e.g., contents of wells, history of use) and/or to record or store information (e.g., temperatures, times, atmospheric compositions, media types and amounts, waste production) related to the culturing of the contents of the wells and/or subwells. In some embodiments, the growth cassette sensor(s) $S_1$ may communicate with a growth cassette program executing on a controller (e.g., microprocessor, programmable gate array, application specific integrated circuit, not shown in FIGS. 35A and 35B) carried by the growth cassette 3504. The growth cassette program may track various parameters related to usage of the growth cassette 3504.

The consumables sensors may, for example, include one or more media cartridge sensors $S_2$-$S_3$ (two illustrated). The media cartridge sensors $S_2$-$S_3$ may sense or otherwise determine the presence and/or absence of a media cartridge 3510 in the media cartridge receiver 3508. For example, the media cartridge sensors $S_2$-$S_3$ may sense a communicative coupling (e.g., electrical contacts or optical couplers) between the control subsystem 3578 and a non-transitory storage medium (not shown in FIGS. 35A and 35B) carried by the media cartridge 3510. Also for example, the media cartridge sensors $S_2$-$S_3$ may take the form of a portion of an optical transceiver pair or a Hall effect sensor that detects a media cartridge 3510 being received in the media cartridge receiver 3508 and/or being correctly positioned in the culture system 3500.

The media cartridge sensors $S_2$-$S_3$ may additionally, or alternatively, sense or otherwise determine information regarding the particular media cartridge 3510 received in the media cartridge receiver 3508. For example, the media cartridge sensors $S_2$-$S_3$ may sense or otherwise determine an identity of the media cartridge 3510 and/or contents of the media cartridge 3510. For instance, the media cartridge sensors $S_2$-$S_3$ may read or otherwise sense an identifier associated with the media cartridge 3510. Association may include being stored on or attached to the media cartridge 3510 or being carried by packaging which carried the media cartridge 3510. For instance, the media cartridge sensors $S_2$-$S_3$ may read information (i.e., identifier, contents type and/or amount, history of use) stored in a non-transitory storage medium (not shown in FIGS. 35A and 35B) carried by the media cartridge 3510, for example over an electrical or optical path. Alternatively or additionally, the media cartridge sensor $S_2$-$S_3$ (e.g., machine-readable symbol scanner or imager) may optically read or otherwise sense information stored in a machine-readable symbol (not shown in FIGS. 35A and 35B) carried by the media cartridge 3510. Alternatively or additionally the media cartridge sensor $S_2$-$S_3$ (e.g., RFID interrogator) may wirelessly read or otherwise sense information stored in an RFID transponder (not shown in FIGS. 35A and 35B) carried by the media cartridge 3510. The read or sensed information may simply specify an identifier that identifies the media cartridge 3510 either uniquely or by type, or may specify the contents of the media cartridge 3510 and/or a history of use of the media cartridge 3510. The contents may include the type of media and amount of media. The control subsystem 3578 may use the identifier to determine additional information (e.g., contents, history of use) and/or to record or store information (e.g., times, amounts) related to the culturing operations. In some embodiments, the media cartridge sensors $S_2$-$S_3$ may communicate with a media cartridge program executing on a controller (e.g., microprocessor, programmable gate array, application specific integrated circuit, not shown in FIGS. 35A and 35B) carried by the media cartridge 3510. The media cartridge program may track media usage, for instance amounts of media remaining at a given time.

The consumables sensors may, for example, include one or more waste cartridge sensors $S_4$-$S_5$ (two illustrated). The waste cartridge sensors $S_4$-$S_5$ may sense or otherwise determine the presence and/or absence of a waste cartridge 3524 in the waste cartridge receiver 3522. For example, the waste cartridge sensors $S_4$-$S_5$ may sense a communicative coupling (e.g., electrical contacts or optical couplers) between the control subsystem 3578 and a non-transitory storage medium (not shown in FIGS. 35A and 35B) carried by the waste cartridge 3524. Also for example, the waste cartridge sensors $S_4$-$S_5$ may take the form of a portion of an optical transceiver pair or a Hall effect sensor that detects a waste cartridge 3524 being received in the waste cartridge receiver 3522 and/or being correctly positioned in the culture system 3500.

The waste cartridge sensors $S_4$-$S_5$ may additionally, or alternatively, sense or otherwise determine information regarding the particular waste cartridge 3524 received in the waste cartridge receiver 3522. For example, the waste cartridge sensors $S_4$-$S_5$ may sense or otherwise determine an identity of the waste cartridge 3524. For instance, the waste cartridge sensors $S_4$-$S_5$ may read or otherwise sense an identifier associated with the waste cartridge 3524. Association may include being stored on or attached to the waste cartridge 3524 or being carried by packaging which carried the waste cartridge 3524. For instance, the waste cartridge sensors $S_4$-$S_5$ may read information (i.e., identifier, history of use) stored in a non-transitory storage medium (not shown in FIGS. 35A and 35B) carried by the waste cartridge 3524, for example over an electrical or optical path. Alternatively or additionally, the waste cartridge sensor $S_4$-$S_5$ (e.g., machine-readable symbol scanner or imager) may optically read or otherwise sense information stored in a machine-readable symbol (not shown in FIGS. 35A and 35B) carried by the waste cartridge 3524. Alternatively or additionally the waste cartridge sensor $S_4$-$S_5$ (e.g., RFID interrogator) may wirelessly read or otherwise sense information stored in an RFID transponder (not shown in FIGS. 35A and 35B) carried by the waste cartridge 3524. The read or sensed information may simply specify an identifier that identifies the waste cartridge 3524 either uniquely or by type. The control subsystem 3578 may use the identifier to determine additional information (e.g., contents, history of use) and/or to record or store information (e.g., times, amounts) related to the culturing operations. In some embodiments, the waste cartridge sensors $S_4$-$S_5$ may communicate with a waste cartridge program executing on a controller (e.g., microprocessor, programmable gate array, application specific integrated circuit, not shown in FIGS. 35A and 35B) carried by the waste cartridge 3524. The waste cartridge program may track waste usage, for instance amounts of waste collected or remaining capacity a given time.

The consumables sensors may, for example, include one or more gas canister sensors $S_6$-$S_9$ (two illustrated). The gas canister sensors $S_6$-$S_9$ may sense or otherwise determine the presence and/or absence of a gas canister 3540 coupled to the gas canister receiver 3538. For example, the gas canister sensors $S_6$-$S_9$ may sense a communicative coupling (e.g., electrical contacts or optical couplers) between the control subsystem 3578 and a non-transitory storage medium (not shown in FIGS. 35A and 35B) carried by the gas canister 3540. Also for example, the gas canister sensors $S_6$-$S_9$ may take the form of a portion of an optical transceiver pair or a Hall effect sensor that detects a gas canister 3540 being coupled to the gas canister receiver 3538 and/or being correctly positioned in the culture system 3500.

The gas canister sensors $S_6$-$S_9$ may additionally, or alternatively, sense or otherwise determine information regarding the particular gas canister 3540 received in the gas canister receiver 3538. For example, the gas canister sensors $S_6$-$S_9$ may sense or otherwise determine an identity of the gas canister 3540 and/or contents of the gas canister 3540. For instance, the gas canister sensors $S_6$-$S_9$ may read or otherwise sense an identifier associated with the gas canister 3540. Association may include being stored on or attached to the gas canister 3540 or being carried by packaging which carried the gas canister 3540. For instance, the gas canister sensors $S_6$-$S_9$ may read information (i.e., identifier, contents type and/or amount, history of use) stored in a non-transitory storage medium (not shown in FIGS. 35A and 35B) carried by the gas canister 3540, for example over an electrical or optical path. Alternatively or additionally, the gas canister sensor $S_6$-$S_9$ (e.g., machine-readable symbol scanner or imager) may optically read or otherwise sense information stored in a machine-readable symbol (not shown in FIGS. 35A and 35B) carried by the gas canister 3540. Alternatively or additionally the gas canister sensor $S_6$-$S_9$ (e.g., RFID interrogator) may wirelessly read or otherwise sense information stored in an RFID transponder (not shown in FIGS. 35A and 35B) carried by the gas canister 3540. The read or sensed information may simply specify an identifier that identifies the gas canister 3540 either uniquely or by type, or may specify the contents of the gas canister 3540 and/or a history of use of the gas canister 3540. The contents may include the type of gas and amount of gas. The control subsystem 3578 may use the identifier to determine additional information (e.g., contents, history of use) and/or to record or store information (e.g., times, amounts) related to the culturing operations. In some embodiments, the gas canister sensors $S_6$-$S_9$ may communicate with a gas canister program executing on a controller (e.g., microprocessor, programmable gate array, application specific integrated circuit, not shown in FIGS. 35A and 35B) carried by the gas canister 3540. The gas canister program may track gas usage, for instance amounts of gas used and/or amount of gas remaining at a given time, and/or pressure within the gas canister 3540.

The control subsystem 3578 may include additional consumables sensors and/or may omit some of the consumables sensors discussed above. Additionally, or alternatively, standalone automatic data collection devices may be employed to sense or read data from data carriers (e.g., machine-readable symbols, RFID transponders, magnetic stripes, touch or optical memory devices). Such may, for example, include machine-readable symbol readers 3585a and/or RFID readers or interrogators 3585b (collectively 3585). Various suitable standalone readers 3585 are commercially available from Intermec Technologies. The machine-readable symbol readers 3585a and/or RFID readers or interrogators 3585b may be communicatively coupled to the control subsystem 3578 by conventional wired communications ports (e.g., USB port, Ethernet port, RJ-11 port) or wireless communications ports (e.g., Bluetooth, WI-FI) collectively 3586. As discussed below, various readings, measurements or determinations by the consumable sensors $S_1$-$S_9$ may be employed in controlling operation of the culture system 3500, recording information regarding performance of a protocol by the culture system 3500, reporting on the same and/or exception reporting.

The control subsystem 3578 and/or growth cassette 3504 may include one or more internal sensors, represented in FIG. 35B as circles with respective identifiers ($S_{10}$-$S_{20}$), positioned, configured and operable to sense various operation characteristics of the various elements or components of the culture system 3500 or environmental conditions therein or in the growth cassette 3504. The internal sensors $S_{10}$-$S_{20}$ are communicatively coupled via one or more internal sensor ports 3588 to provide signals indicative of operation characteristics to a controller 3579 (e.g., microprocessor, DSP). For clarity of illustration, the internal sensors $S_{10}$-$S_{20}$ are all grouped together proximate the other elements of the control subsystem 3578. In practice, these internal sensors $S_{10}$-$S_{20}$ will typically be located proximate the various elements or components of the culturing system 3500 and/or growth cassettes 3504 which the internal sensors $S_{10}$-$S_{20}$ are monitoring. The denomination "internal" is used to indicate that the sensors $S_{10}$-$S_{20}$ monitor or sense operational characteristics or environmental conditions of the culture system 3500 and/or growth cassettes 3504, and to distinguish such from consumables sensors $S_1$-$S_9$, discussed above. Where certain internal sensors $S_{10}$-$S_{20}$ may be carried by the growth cassettes 3504, complimentary electrical or optical contacts or couplers may be provided on the growth cassette 3504 and, for example on the growth cassette receiver 3502, to provide communications between the internal sensors $S_{10}$-$S_{20}$ and the control subsystem 3578.

The internal sensors may, for example, include one or more motor sensors $S_{10}$ (only one illustrated) positioned to sense or measure operational characteristics of an electric motor. Motor sensors $S_{10}$ may be positioned to sense characteristic of one or more of the various electric motors in the culture system 3500, including electric motors associated with the growth cassette receiver 3502, the stimulus transducer 3564, and microscopy subsystem 3568 including the X-Y-Z translation table 3570 and other electric motors such as those associate with optical components 3572 of the microscopy subsystem 3568. The motor sensors $S_{10}$ may determine whether an electrical motor is operating, a speed or frequency of the electrical motor or other transducer, and/or a rotational position or orientation of a shaft of the electric motor. The motor sensors $S_{10}$ may take a variety of forms, for example an optical encoder or a Hall effect sensor. Information encoded in a signal produced by the motor sensor $S_{10}$ may used to control operation of the culture system 3500, including performing a self test and to identifying exceptions (e.g., out of compliance conditions).

The internal sensors may, for example, include one or more valve sensors $S_{11}$ (only one illustrated) positioned to sense or measure operational characteristics of a valve. Valve sensors $S_{11}$ may be positioned to sense characteristic of one or more of the various valves in the culture system 3500, including valves 3512 associated with the media subsystem 3506, valves 3526 associated with the waste subsystem 3520 and valves 3542 associated with the gas supply subsystem 3536, to name a few. The valve sensor $S_{11}$ may determine whether a valve is operating and/or determine a position or condition (e.g., open. closed) of the valve. The valve sensor $S_{11}$ may take a variety of forms, for example an optical encoder, a Hall effect sensor, and/or pair of electrical contacts. Information encoded in a signal produced by the valve sensor $S_{11}$ may used to control operation of the culture system 3500, including performing a self test and to identifying exceptions.

The internal sensors may, for example, include one or more pump sensors $S_{12}$ (only one illustrated) positioned to sense or measure operational characteristics of a pump. Pump sensors $S_{12}$ may be positioned to sense characteristic of one or more of the various pumps in the culture system 3500, including pumps 3514 associated with the media subsystem 3506, pumps 3528 associated with the waste subsystem 2520 and/or pumps (not shown) associated with the gas supply subsystem 2526, to name a few. The pump sensor $S_{12}$ may determine whether a pump is operating and/or a speed or rate of pumping, flow rate of pumped materials and/or other operational conditions of the pump. The pump sensor $S_{12}$ may take a variety of forms, for example an optical encoder, a Hall effect sensor, and/or a flow rate sensor or anemometer. Information encoded in a signal produced by the pump sensor $S_{12}$ may used to control operation of the culture system 102, including performing a self test and to identifying exceptions.

The internal sensors may, for example, include one or more fan sensors $S_{13}$ (only one illustrated) positioned to sense or measure operational characteristics of a fan. Fan sensors $S_{13}$ may be positioned to sense characteristic of one or more of the various fans in the culture system 3500, including fans 3552 associated with the environmental control subsystem 3534. The fan sensor $S_{13}$ may determine whether a fan 3552 is operating and/or a fan speed, flow rate of fan stream, and/or other operational conditions of the fan 3552. The fan sensors $S_{13}$ may take a variety of forms, for example an optical encoder, a Hall effect sensor, and/or a flow rate sensor or anemometer. Information encoded in a signal produced by the fan sensor $S_{13}$ may used to control operation of the culture system 3500, including performing a self test and to identifying exceptions.

The internal sensors may, for example, include one or more illumination sensors $S_{14}$ positioned to sense or measure illumination at one or more wavelengths being provided to the wells or subwells of the growth cassette 3504. The illumination sensors $S_{14}$ may take any of a large variety of forms including positive-intrinsic-negative (pin) photodiodes, phototransistors, charge coupled devices (CCD), and Vidicons to name a few. Information encoded in a signal produced by the illumination sensor $S_{14}$ may used to control operation of the culture system 3500, including performing a self test and to identifying exceptions. In some embodiments, the imager 3574 may be employed to sense illumination of the wells or subwells of the growth cassette 3504.

The internal sensors may, for example, include one or more environmental characteristic sensors positioned to sense environmental conditions in the culture system 3500, and particularly in or proximate the growth cassette receiver 3502 and the wells and/or subwells of the growth cassette 3504. Such may allow feedback control of the illumination sources 3566 and/or assure that actual illumination patterns follow nominal illumination patterns set out in a defined protocol, within some threshold. Such may also allow actual illumination characteristics to be recorded.

For example, one or more temperature sensors $S_{15}$ may be positioned to sense or monitor temperature at one or more locations. For instance, temperature sensors $S_{15}$ may be positioned to sense or monitor temperature of the atmosphere or gas heater 3556 or proximate to the growth cassette heaters 3562. Also for instance, temperature sensors $S_{15}$ may be positioned to sense or monitor temperature of the atmosphere being provided to the growth cassette receiver upstream of the growth cassette receiver 3502 or the atmosphere proximate the wells and/or subwells of the growth cassette 3504. Such may allow feedback control of the atmosphere or gas heater 3556 and/or growth cassette heaters 3562 and/or assure that an actual temperature follow nominal temperatures set out in a defined protocol, within some threshold. Such may also allow actual temperatures to be recorded.

Also for example, one or more relative humidity sensors $S_{16}$ may be positioned to sense or monitor a relative humidity in the atmosphere being provided to the growth cassette receiver 3502 or proximate the wells and/or subwells of the growth cassette 3504. The relative humidity sensors $S_{16}$ may take a variety of forms, for instance capacitive relative humidity sensors, organic semiconductor copper phthalocyanine (CuPc) relative humidity and illumination sensors. Such may allow feedback control of the humidifier 3558 and/or dehumidifier 3560 and/or assure that relative humidity follows nominal relative humidity set out in a defined protocol, within some threshold. Such may also allow actual relative humidity to be recorded.

As a further example, one or more atmosphere composition sensors $S_{17}$ may positioned to sense or monitor an amount, density, concentration or partial pressure of different gases which constitute the atmosphere being provided to the growth cassette receiver 3502 upstream of the growth cassette receiver 3502 or proximate the wells and/or subwells of the growth cassette 3504. Atmosphere composition sensors $S_{17}$ may take a large variety for forms, for example capacitor-type gas sensors, semiconducting metal oxide gas sensors, nano-structured gas sensors, and/or a sensor array for a variety of gases to name a few. Such may allow feedback control of the various elements or components of the gas supply system 3536 of the culture system 3500 and/or assure that the composition of the atmosphere follows nominal composition set out in a defined protocol, within some threshold. Such may also allow actual atmospheric composition to be recorded.

As yet a further example, one or more pH sensors $S_{18}$ may be positioned to sense or monitor a pH in one or more wells and/or subwells of the growth cassette 3504. The pH sensors $S_{18}$ may take a large variety for forms, for example an Ag—AgCl combination electrode pH sensor or a calomel electrode pH sensor, or any other of the large number of commercially available pH sensors. Such may allow feedback control of the various elements or components of the culture system 3500 and/or assure that the actual pH in the wells and/or subwells follows nominal pH or pattern of pH set out in a defined protocol, within some threshold. Such may also allow actual pH to be recorded.

As yet even a further example, one or more dissolved gas sensors $S_{19}$ may positioned to sense or monitor dissolved gas(es) in one or more wells and/or subwells of the growth cassette 3504. The dissolved gas $S_{19}$ may take a large variety for forms, for example membrane based dissolved gas sensors, optically based dissolved gas sensors, or any other of the large number of commercially available dissolved gas sensors. Such may allow feedback control of the various elements or components of the culture system 3500 and/or assure that the actual dissolved gas(es) in the wells and/or subwells follows nominal dissolved gas(es) or pattern of dissolved gas(es) set out in a defined protocol, within some threshold. Such may also allow actual dissolved gas(es) to be recorded.

As yet even a further example, one or more nutrient sensors $S_{20}$ may be positioned to sense or monitor nutrient level(s) in one or more wells and/or subwells of the growth cassette 3504. Nutrients may, for example, include macronutrients and/or micronutrients, for instance certain minerals, amino acids, sugars, and vitamins, simpler chemical elements, such as carbon, hydrogen, nitrogen, phosphorus, and sulfur. The nutrient sensors $S_{20}$ may take a large variety for forms, for example liquid crystal based chemical sensors, or any other of the large number of commercially available chemical sensors. Such may allow feedback control of the various elements or components of the culture system 3500 and/or assure that the actual nutrient level(s) in the wells and/or subwells follows nominal nutrient level(s) or a pattern of nutrient level(s) set out in a defined protocol, within some threshold. Such may also allow actual nutrients level(s) to be recorded.

While, not illustrated, one or more conductivity sensors may positioned to sense or monitor electrical conductivity or resistivity in one or more wells and/or subwells of the growth cassette 3504. The conductivity sensors may take a large variety for forms, for instance two-electrode conductivity sensors, four electrode conductivity sensors, toroidal conductivity sensors, or any other of the large number of commercially available conductivity sensors. Such may allow feedback control of the various elements or components of the culture system 3500 and/or assure that the actual conductivity level(s) in the wells and/or subwells follows nominal conductivity level(s) or a pattern of conductivity level(s) set out in a defined protocol, within some threshold. Such may also allow actual conductivity level(s) to be recorded.

Thus, the internal sensors $S_{10}$-$S_{20}$ may allow precise environmental control and perfusion of one well or a set of subwells with an array of coating matrixes. This may provide better and more reproducible cell growth conditions than microplates. There are many variables of interest in primary cell culture, for example pH, temperature, nutrient concentrations, presence or absence of growth factor, surface chemistries, initial plating density, vibration, exposure to light, contamination (mycoplasma) etc. The internal sensors $S_{10}$-$S_{20}$ may allow precise monitoring of such variables and control of the environmental conditions to which the contents of the wells and/or subwells are exposed.

In addition to the other sensors, the imager(s) 3574 of the microscopy subsystem 3568 is communicatively coupled to the control subsystem 3578. The imager(s) 3574 may communicatively coupled via one or more buses, networks of other connections. Thus, the control subsystem 3578 may process image information representing digital images of part or all of the contents of the wells or sub wells of the growth cassette 3504. Typically, such processing would be performed by a dedicated digital signal processor 3579b, although other components may be employed (e.g., microprocessor 3579a). Processing or analysis may include spectral analysis which may occur for one or more wavelengths. The spectral or other analysis of the captured images or image information may be performed in conjunction with analysis of other measured, sensed or determined variables or characteristics, for example operational conditions, environmental conditions and/or conditions of the contents of the wells and/or subwells. Conditions may, for example, include temperatures, pH, electrical conductivity, chemical analysis, etc. Such may allow feedback control of the various elements or components of the culture system 3500 and/or assure that the culturing is progressing within some threshold as compared to some nominal expectations set out in a defined protocol. Processing or analysis may, for example, include characterization and/or evaluation of cell morphology (e.g., movement, division, differentiation, death), including indicia or one or more of colony characteristics including: size, type of margin, colony elevation, colony texture, light transmission, and/or pigmentation. For example, digital images captured at two or more times, or even continuously (e.g., 30 frames per second) may be analyzed to determine when cells reach confluence, at which point the culturing protocol may indicate or specify a particular action or sets of actions, or an adjustment to certain environmental conditions. Each time an image is taken; the various variables can be recorded and plotted alongside the time lapsed representation of the experiment. Since the culture system instrument incorporates multiple wells, it is easy to compare two or more different assay conditions. For example, each well, and the subwells therein, may be subjected to a respective set of environmental conditions, which differ from well to well. For example, a temperature and atmosphere supplied to a first well may differ from that supplied to a second well. Thus, analysis may occur in real- or almost real time, allowing analytical feedback control over operation of the culture system 3500.

The control subsystem 3578 may include additional internal sensors $S_{10}$-$S_{20}$ and/or may omit some of the internal sensors $S_{10}$-$S_{20}$ discussed above. As discussed below, various readings, measurements or determinations by the internal sensors $S_{10}$-$S_{20}$ may be employed in controlling operation of the culture system 3500, recording information regarding performance of a protocol by the culture system 3500, reporting on the same and/or exception reporting.

The control subsystem 3578 may include one or more actuator controllers 3589 (only one shown for clarity of illustration) communicatively coupled to control one or more elements of the culture system 3500. The actuator controller(s) 3589 may operate in conjunction with a controller 3579, such as a microprocessor 3579a and/or 3579b, typically based on sensed conditions and programmed logic, to provide control signals $C_1$-$C_{12}$ to control motors, solenoids, valves, pumps, fans, blowers, diverters, heaters, compressors, illuminators, and/or other actuators or components of the culture system 3500. For clarity of illustration, the actuator control signals $C_1$-$C_{12}$ all grouped together proximate the other elements of the control subsystem 3578. In practice, these signals are coupled to motors, solenoids, pumps, valves and other actuators typically located throughout the culture system 3500 and typically housed therein.

For example, the actuator controller(s) 3589 may provide control signals $C_1$ to control the electric motor(s) which retract and extend the growth cassette 3504. For example, the control signals $C_1$ may cause the electric motors to turn in a first rotational direction to retract the growth cassette 3504 into the culture system 3500 and operate in a second rotational direction to extend or eject the growth cassette 3504 from the culture system 3500.

The actuator controller(s) 3589 may provide control signals $C_2$ (only one shown for clarity of illustration) to control one or more valves. Such may, for example, control valves 3512 which regulate flow from the media cartridges 3510 to the growth cassette receiver 3502, valves 3526 which regulate flow from the gas canisters 3540 to the growth cassette receiver 3502, valves 3542 which regulate flow from the growth cassette receiver 3502 to the waste cartridges 3524, and/or other valves which control flow of various fluids (i.e., liquids, gases) within the culturing system 3500 (e.g., diverter, flow of fluid such as water between fluid reservoir (not shown) and humidifier 3558 or dehumidifier 3560). In most instances, separate sets of control signals $C_2$ are supplied to respective electric motors, solenoids or other actuators coupled to operate respective ones of the valves.

The actuator controller(s) 3589 may provide control signals $C_3$ (only one shown for clarity of illustration) to control one or more pumps. Such may, for example, control pumps 3514 which pump media from the media cartridges 3510 to the growth cassette receiver 3502 and/or pumps 3528 which pump waste to the waste cartridges 3524 from the growth cassette receiver 3502. In most instances, separate sets of control signals $C_3$ are supplied to respective electric motors, solenoids or other actuators coupled to operate respective ones of the pumps.

The actuator controller(s) 3589 may provide control signals $C_4$ to control operation of one or more manifolds 3546. Such may, for example, control the supply of different types of gases to the growth cassette receiver 3502. In most instances, the control signals $C_4$ are supplied to an electric motor, solenoid or other actuator coupled to operate the manifold 3546.

The actuator controller(s) 3589 may provide control signals $C_5$ (only one shown for clarity of illustration) to control one or more fans. Such may, for example, control a state (e.g., ON/OFF) and/or speed the fans, for instance a atmosphere or gas supply fan 3552a to supply an atmosphere to the growth cassette receiver 3502 or an extraction or exhaust fan 3552b to extract or withdraw the atmosphere from the growth cassette receiver 3502. In some embodiments, a single 3552 fan may be employed to draw an atmosphere into the growth cassette receiver 3502 and well as exhaust the atmosphere therefrom. In such embodiments, the control signals $C_5$ may cause the fan 3552 to operate (e.g., rotate) in a first direction (e.g., clockwise) when drawing the atmosphere into the growth cassette receiver 3502, and operate in a second, opposite direction (e.g., counterclockwise) when extracting or expelling the atmosphere from the growth cassette receiver 3502. In most instances, separate sets of control signals $C_5$ are supplied to respective electric motors, solenoids or other actuators coupled to operate respective ones of the fans 3552.

The actuator controller(s) 3589 may provide control signals $C_6$ (only one shown for clarity of illustration) to control one or more heaters, for instance to control an atmosphere or gas heater 3556 or growth cassette heaters 3562. Such may, for example, control a state (e.g., ON/OFF) and/or thermal output (e.g., magnitude) of the heater(s) 3556, 3562. For instance, the control signals $C_6$ may cause the atmosphere or gas heater 3556 to adjust a temperature of air or other gases being delivered to the growth cassette receiver to a desired or defined temperature. Also for instance, the control signals $C_6$ may cause the growth cassette heaters 3562 to adjust a temperature of the growth cassette and/or contents of the wells and/or subwells of the growth cassette 3504 to a desired or defined temperature. Such may operate in a feedback loop with one or more temperature sensors $S_{15}$. In most instances, separate sets of control signals $C_6$ are supplied to respective current or voltage sources coupled to supply current to respective ones of the heaters 3556, 3562.

The actuator controller(s) 3589 may provide control signals $C_7$ to control the humidifier 3558. Such may, for example, control a state (e.g., ON/OFF) and/or output (e.g., magnitude) of the humidifier 3558. For instance, the control signals $C_7$ may cause the humidifier 3558 to adjust a relative humidity of air or other gases being delivered to the growth cassette receiver 3502 to a desired or defined relative humidity. Such may operate in a feedback loop with one or more relative humidity sensors $S_{16}$. In most instances, control signals $C_7$ are supplied to respective current or voltage sources coupled to supply current to respective heaters, fans or compressors of the humidifier 3558.

The actuator controller(s) 3589 may provide control signals $C_8$ to control the dehumidifier 3560. Such may, for example, control a state (e.g., ON/OFF) and/or output (e.g., magnitude) of the dehumidifier 3560. For instance, the control signals $C_8$ may cause the dehumidifier 3560 to adjust a relative humidity of air or other gases being delivered to the growth cassette receiver 3502 to a desired or defined relative humidity. Such may operate in a feedback loop with one or more relative humidity sensors $S_{16}$. In most instances, control signals $C_8$ are supplied to respective current or voltage sources coupled to supply current to respective fans or compressors of the dehumidifier 3560.

The actuator controller(s) 3589 may provide control signals $C_9$ to control the illumination sources 3566a-3566n of the illumination exposure subsystem 3566. Such may, for example, control a state (e.g., ON/OFF) and/or output (e.g., magnitude) of the illumination, as well as wavelength of illumination. For instance, the control signals $C_9$ may adjust an intensity of illumination delivered to the growth cassette receiver 3502 to a desired or defined intensity. Also for instance, the control signals $C_9$ may adjust a wavelength of illumination delivered to the growth cassette receiver 3502 to a desired or defined wavelength or sets of wavelengths. Such may be achieved by selectively actuating illumination sources 3566a-3566n which emit respective wavelengths of illumination. Such may additionally or alternatively be achieved by selectively actuating illumination sources 3566a-3566n which are capable of emitting a different wavelengths, for example in response to different levels of applied current or voltage. The illumination may operate in a feedback loop with one or more illumination sensors $S_{14}$ to produce illumination or cycles of illumination at desired intensities and/or wavelengths in the visible and non-visible (e.g., infrared, near-infrared, ultraviolet) portions of the electromagnetic spectrum. In most instances, control signals $C_9$ are supplied to respective current or voltage sources coupled to supply current to respective illumination sources 3566a-3566n (e.g., LEDs).

The actuator controller(s) 3589 may provide control signals $C_{10}$ to control one or more stimulus transducers 3564, to impart a stimulus to the biological material in the wells and/or subwells of the growth cassette 3504. As explained above, the stimulus may be an oscillatory stimulus, for example, a mechanical oscillatory motion, ultrasonic pressure wave oscillations, oscillating magnetic field, or pulsed jet of a fluid (e.g., air). Thus, the control signals $C_{10}$ may, for instance control a state (e.g., ON/OFF) or frequency (e.g., oscillation or vibration) of the stimulus transducers 3564. The control signals $C_4$ may be a relatively simple sinusoidal fluctuating voltage or current signals, or may be more complex mixtures. For example the control signals $C_{10}$ may employ multiple complex wave forms. The control signals $C_{10}$ may take the form of analog signals or digital signals. The control signals $C_{10}$ may take the form of pulse width modulated signals. The control signals $C_{10}$ may be applied to an electric motor, solenoid, piezoelectric device or other actuator to cause the stimulus transducers 3564 to vibrate or oscillate at a number of respective frequencies, specifically selected to achieve a desired or defined oscillatory pattern set out or specified in a particular culturing protocol being executed or performed by the culture system. Alternatively, control signals $C_{10}$ may cause the stimulus transducers 3564 to produce some other form of stimulus. For example, the control signals $C_{10}$ may be applied to a current or voltage source to cause a set of Helmholtz coils to emit a varying magnetic field at a desired or defined frequency. Also for example, the control signals $C_{10}$ may be applied to a valve or compressor to cause a jet to emit a varying or pulsed jet of fluid (e.g., air) at a desired or defined frequency.

Also for example, the actuator controller(s) 3589 may provide control signals $C_{11}$ to control the electric motor(s), solenoid(s) or other actuator(s) which translate the translation table 3570 of the microscopy subsystem 3568 and/or which move optical components 3572 (e.g., lens, filters) of the microscopy subsystem 3568.

Also for example, the actuator controller(s) 3589 may provide control signals $C_{12}$ to control the imager(s) 3574 of the microscopy subsystem. For example, the control signals $C_{12}$ may control a state (ON/OFF) or condition, frequency of image capture, field-of-view, depth-of-field, focal point, resolution, aperture, f-stop and/or format or protocol of image capture of the imagers 3574.

The actuator controller(s) 3589 may provide control signals $C_{13}$ to control the microscopy illumination subsystem 3576. Such may, for example, control a state (e.g., ON/OFF) and/or output (e.g., magnitude) of the illumination. For instance, the control signals $C_8$ may cause the microscopy illumination subsystem 3576 to adjust an intensity of illumination delivered to the growth cassette receiver 3502, and hence to the growth cassette 3504, to a desired or defined intensity. Such may operate in a feedback loop with one or more illumination sensors S14 or the imager(s) 3574. In most instances, control signals $C_8$ are supplied to respective current or voltage sources coupled to supply current to respective illumination sources 3576a-3576n (e.g., LEDs).

The actuator controller(s) 3589 may provide control signals $C_{14}$ (only one shown for clarity of illustration) to control one or more syringe pump actuators 3525a of a one or more syringe pumps 3525. Such may, for example, control syringe pumps 3525 which pump materials or substances from the removable syringes 4752 (FIG. 47) to the wells and/or subwells of the growth cassette receiver 3502. In most instances, separate sets of control signals $C_{14}$ are supplied to respective electric motors, solenoids or other actuators coupled to operate respective ones of the syringe pumps 3525.

The control subsystem 3578 may include additional actuator controller and/or control and/or may omit some of the actuator controllers 3589 and/or control signals $C_1$-$C_{13}$ discussed above. As discussed below, various readings, measurements or determinations by the consumable sensors, $S_1$-$S_9$, internal sensors $S_{10}$-$S_{20}$ may be employed in controlling operation of the culture system 3500 via the control signals $C_1$-$C_{13}$, recording information regarding performance of a protocol by the culture system 3500, reporting on the same and/or exception reporting.

As previously noted, the control subsystem 3578 may include, implement or interface with a user interface 3590, for example including a touch screen display 3590a, switches or keys 3590b, visual indicators (e.g., LEDs) 3590c and/or speaker(s) 3590d.

The control subsystem 3578 may include a number of communications ports to provide wired (e.g., electrical or optical fiber) or wireless (e.g., radio including radio and microwave frequencies, light including visible or infrared) communications. For example, the control subsystem 3678 may include one or more wired ports 3592a to provide wired communications with external devices such as computers, server computers, networks, and/or other disinfection systems. Such wired ports 3592a may conform to any of a large variety of existing specifications and protocols (e.g., RJ-11, USB, FIREWIRE®, Ethernet). The control subsystem 3578 may include one or more wireless ports 3592b including transmitters, receivers or transceivers and/or antennas. Such wireless ports 3792b may conform to any of a large variety of existing specifications and protocols (e.g., 802.11, BLUETOOTH®, WI-FI, MI-FI). Such may allow uni- or bi-directional communications, for instance uni-cast, multi-cast or broadcast communications.

The control subsystem 236 may include one or more reader ports 3586 to communicatively couple with one or more automatic data collection readers 3585. The automatic data collection readers 3585 are dedicated to reading and/or writing data to one or more data carriers such as machine-readable symbols (not shown in FIGS. 35A and 35B) and RFID transponders or tags (not shown in FIGS. 35A and 35B). The automatic data collection readers 3585 may, for example, take the form of, or include, a machine-readable symbol reader 3585a, for instance a scanner or imager capability of optically reading machine-readable symbols (e.g., barcode, area or matrix code or stacked code symbols).

Also for example, the automatic data collection readers 3585 may take the form of, or include, an RFID reader 3585b, for instance an RFID interrogator capability of wirelessly reading information from an RFID data carrier such as an RFID transponder or tag. The automatic data collection readers 3585 may combine machine-readable symbol and RFID reading capabilities. Suitable dedicated automatic data collection readers 3585 may be commercially available from Intermec Technologies or Symbol Technologies. Additionally, or alternatively, the dedicated automatic data collection readers 3585 may be capable of reading or writing to other data carriers such as optical memories, touch memories (e.g., available from Dallas Semiconductor), magnetic stripes, etc.

The data carriers may take a large variety of forms, including but not limited to labels or tags that carry machine-readable symbols or that otherwise encode machine-readable information (e.g., RFID, optical memories, touch memories, magnetic stripes). The data carrier may advantageously encode information in two or more forms, for example an RFID transponder that carries or bears a machine-readable symbol.

The automatic data collection readers 3585 may include one or more processors and/or memory (not illustrated). The automatic data collection readers 3585 may be configured to process or pre-process information read from the data carrier. For example, the automatic data collection readers 3585 may be configured to automatically recognize symbols from various symbologies and decode the same. The automatic data collection readers 3585 may be configured to write data to a data carrier. For example, the dedicated automatic data collection reader 3585b may be configured to automatically write information to an RFID data carrier.

The automatic data collection readers 3585 may be employed to read information from data carriers physically associated with a growth cassette, media or waste cartridge, gas canister. The automatic data collection readers 3585 may be employed to read information from data carriers which encode a culturing protocol or culturing protocol identifier that identifies a specific culturing protocol, to automatically configure a culture system 3500 to perform or execute a defined culturing protocol. Such can be integrated with other automatically collected information, such as information indicative of a condition of one or more components of the culture system 3500 and operation thereof, as well as sensed parameters or information including the digital images collected by the imager 3574 of the biological material being subjected to the culturing protocol.

Information read from a data carrier may, for example include an identifier, such as a unique identifier that uniquely identifies the RFID transponder or tag, disinfection system, end user or room. A database stored on a non-transitory computer-readable storage medium (e.g., ROM 3580a, RAM 3580b) may associate the identifier with information that identifies the object to which the RFID transponder or tag is attached, as well as information about the object. The information may include identity of the object (growth cassette 3504, media cartridge 3510, waste cartridge 3524, gas canister 3540) such as manufacturer, model, type, classification, lot number and/or date of manufacture of the type of media or gas, amounts, quantities, pressures. The information may include a history of the use of the culturing system 3500, for instance compliance with a specific protocol.

Figure 36A:
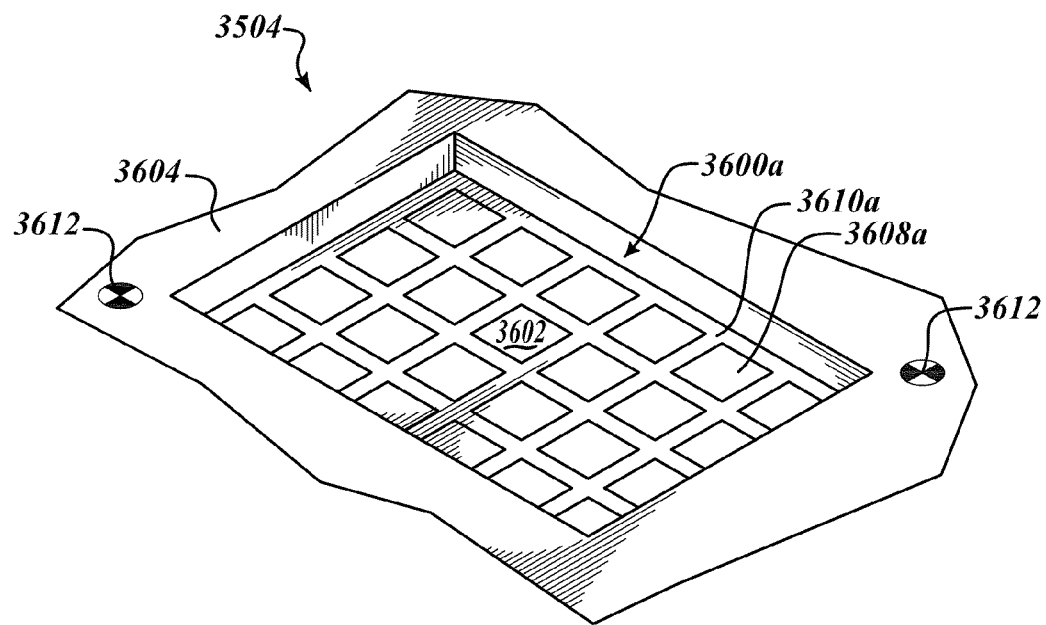
FIG. 36A is a partial isometric view of a portion of a removable multi-well growth cassette showing one well subdivided into a plurality of subwells according to one illustrated embodiment.
Figure 36B:
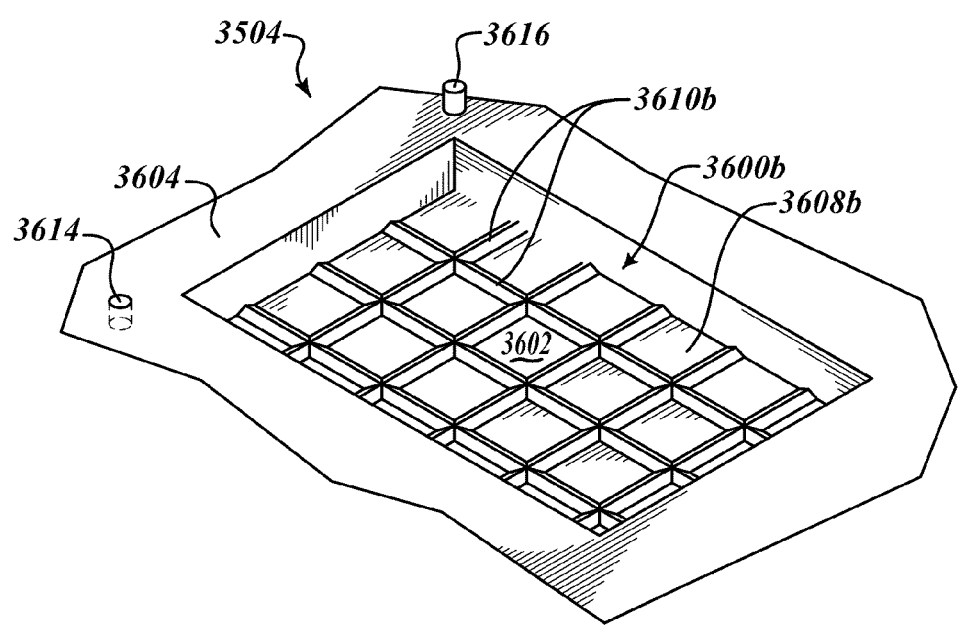
FIG. 36B is a partial isometric view of a portion of a removable multi-well growth cassette showing one well subdivided into a plurality of subwells according to another illustrated embodiment.

FIGS. 36A and 36B show the growth cassette 3504 according to two respective embodiments.

The wells 3600a, 3600b (collectively 3600) of the growth cassette may take the form of distinct recesses formed in the growth cassette 3504, and may include a floor or bottom surface 3602 and one or more peripheral walls 3604 which separate each respective well from other wells and form an exterior of the growth cassette 3504. Preferable the bottom surface 3602 is very flat, for example to facilitate image capture. The bottom surface 3602 may, for example, be formed of a polystyrene, which may be plasma treated to clean and functionalize the polystyrene by making the polystyrene hydrophilic. Once the bottom surface 3602 is functionalized various coatings may be applied. For example, different proteins (e.g., fibronectin, collagen, keratin) may be coated on an entire well, or distributed across subdivided areas of a well (i.e., subwells). Such may enhance cell growth and/or attachment. Other coatings may include a hydrogel, which may enable cell growth, and may be particularly useful in stem cell related applications. Also for example, a layer of silicon dioxide may be coated or deposited providing a glass-like texture or covering. Such may be used to implement selective cell adhesion or for applied surface chemistries that are available for silicon surfaces, or for specific detection systems. Various coatings may be applied by a manufacturer of the multi-well growth cassette 3500 and/or by an end user or purchaser.

One or more of the wells 3600 may be subdivided into two or more subwells 3608a, 3608b (only one called out in each of FIGS. 36A and 36B, collectively 3608), for example portioned into 24 distinct sections. Alternatively, there may be any other number of subwells 3608k for example 96 or 256 subwells 3608. The subwells 3608 may, for instance, be organized in an ordered fashion, for example as a linear or one-dimensional array or as a two-dimensional array.

In particular, the subwells 3608 may be subdivided by a physical barrier. As illustrated in FIG. 36A, the physical barrier may take the form of distinct surfaces 3610a or portions of surfaces with specific surface characteristics, for example a specific chemical, physical or electrical characteristic. For instance, the barrier may take the form of a hydrophobic surface 3610a, while the surface of the subwells 3608a may be a hydrophilic surface. Such characteristic may be integral to the substrate of the growth cassette 3504, for example achieved through doping or some other treatment. Alternatively, the characteristic may be achieved via a coating adhered or otherwise coupled to the substrate of the growth cassette 3504. For example, each well or each subwell may have a respective one of a variety of coatings, which may accelerate and optimize assay development, allowing comparison of various compounds or materials across the multi-well growth cassette 3504. Where integral to the bottom surface 3602, the wells 3600 may include optical indicia to indicate the boundaries of the various subwells 3608. For example, grid lines may be carried by the bottom surface 3602, which may, for instance, be silk screened onto the bottom surface 3602.

Alternatively, or additionally, as illustrated in FIG. 36B, the physical barrier may take the form of a wall or walls 3610b (two called out in FIG. 36B). Alternatively, or additionally, the physical barrier may take the form of one or more trenches or recesses formed in the floor or bottom 3602 of the well 3600.

As discussed above, the wells and/or subwells 3608 may be coated with or may contain a variety of substances and via a variety of techniques (e.g., plasma deposition). For example, the wells or subwells 3608 may include a gel coating, such as a hydrogel, Also for example, the wells or subwells 3608 may include glass or glass like coating, for example a silicon dioxide coating or treatment. Also for example, the wells or subwells 3608 may include specific proteins. For instance, each subwell 3608 may have a respective protein selected from a variety of different proteins. Also for example, the wells or subwells 3608 may include hydrophilic and/or hydrophobic coatings. Also for example, the wells or subwells 3608 may include specific nutritive coatings. Also for example, the wells or subwells 3608 may include agar or agar-like coatings. Also for example, the wells or subwells 3608 may include gradient coatings. Also for example, the wells or subwells 3608 may include specific active pharmaceutical ingredient (API) coatings. Also for example, the wells or subwells 3608 may include specialize sensor coatings, that is coatings that are responsive to particular conditions to generate a detectable signal or response.

Additionally, or alternatively, the wells or subwells 3608 may include various inserts. Also for example, the wells or subwells 3608 may include migration assay inserts or matrix inserts.

The growth cassettes 3504 may, for example, including a number of optical registration indicia 3612 (two called out in FIG. 36A) which provides registration in at least two planar dimensions and about at least one rotational axis. Such may facilitate imaging, analysis and/or handling. Alternatively, or additionally, the growth cassettes 3504 may, for example, include a number of mechanical registration features (e.g., recess 3614, pin 3616) which provides registration in at least two planar dimensions and about at least one rotational axis. Again such may facilitate imaging, analysis and/or handling.

Figure 37:
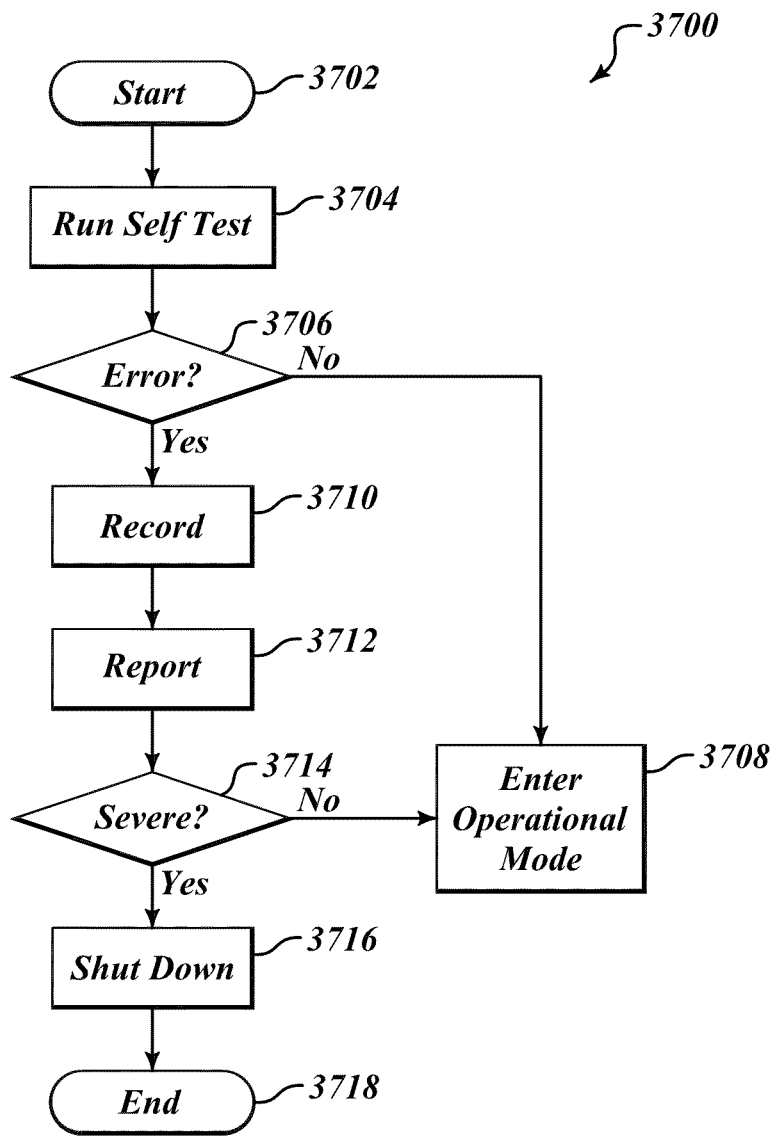
FIG. 37 is a flow chart of a high level method of operating a culture system, according to one illustrated embodiment.

FIG. 37 shows a high level method 3700 of operating a culture system, according to one illustrated embodiment.

The method 3700 starts at 3702. For example, the method 3700 may start in response to powering up of the culture system 102, 3500, turning on the culture system 102, 3500, or a user entry by an end user to start or run the culture system 102, 3500. At 3704, the culture system 102, 3500 or control subsystem 3578 thereof, performs a self-test. The self-test may include confirming that the various systems, subsystems, and components of the culture system 102, 3500 are operational. For example, the self-test may include determining that various components of the control subsystem 3578 are operational. At 3706, the culture system 102, 3500 or control subsystem 3578 determines whether there is an error resulting from the self-test.

If an error has not occurred, the culture system 102, 3500 or control subsystem 3578 enters an operational mode at 3708. If an error has occurred, the culture system 102, 3500 or control subsystem 3578 records information regarding the error at 3710, for example in an error log. The information may indicate a particular component that is out of compliance and/or other error or exception condition. At 3712, the culture system 102, 3500 or control subsystem 3578 reports the error. For example, the culture system 102, 3500 or control subsystem 3578 may provide one or more indications to an end user via a user interface. For instance, a red LED and/or audible warning signal may be provided. Also for example, the culture system 102, 3500 or control subsystem 3578 may transmit a notification remotely from the culture system 102, 3500. For instance, the culture system 102, 3500 or control subsystem 3578 may transmit an email, place a page, send a text message, leave a voicemail or print a paper report.

At 3714, the culture system 102, 3500 or control subsystem 3578 determines whether the error is severe. If the error is not severe, in some instances the culture system 102, 3500 or control subsystem 3578 may enter the operational mode at 3708. Alternatively, if the error is severe, the culture system and/or control subsystem shuts down at 3716. The method 3700 terminates at 3718.

Figure 38:
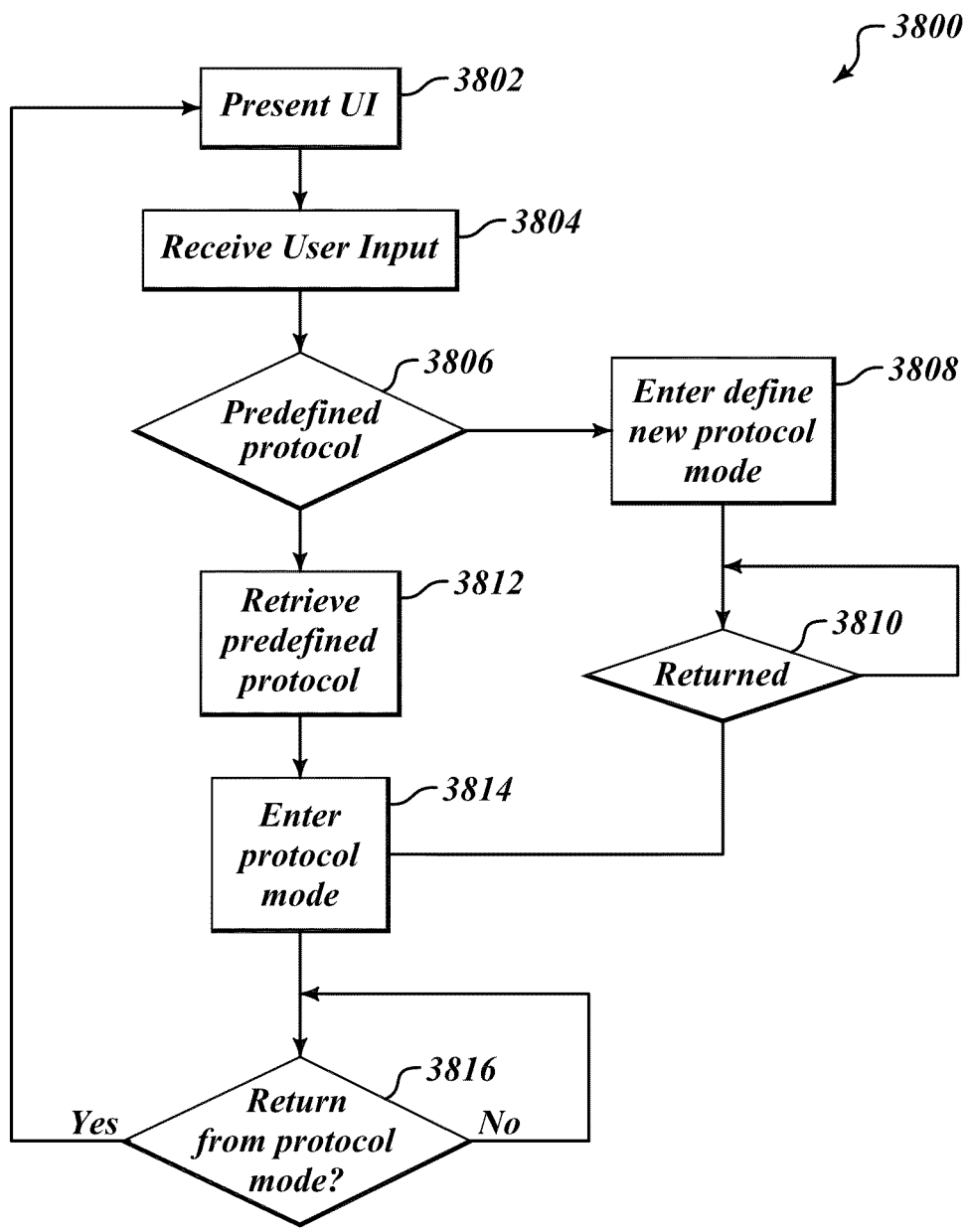
FIG. 38 is a flow chart of an intermediate level method of operating a culture system in an operational mode, according to one illustrated embodiment, the method.

FIG. 38 shows an intermediate level method 3800 of operating a culture system in an operational mode, according to one illustrated embodiment.

At 3802, the culture system 102, 3500 or control subsystem 3578 presents a user interface. For example, the culture system 102, 3500 or control subsystem 3578 may present a graphical user interface on a touch screen display. Alternatively, the graphical user interface may be provided remotely from the culture system 102, 3500, for example via a network such as a local area network, wide area network (e.g., Internet or Worldwide Web), an extranet, an intranet or a telecommunications network such as a cellular network, POTS (plain old telephone service) and/or other telephony network. The graphical user interface may include one or more user-selectable elements and/or icons. For example, the user interface may include one or more graphical icons, text, pull down menus, radio buttons, dialogue boxes, text or graphics.

At 3806, the culture system 102, 3500 or control subsystem 3578 receives user input. The user input may take the form of selections of various user-selectable icons and/or selections or activations of various switches, buttons, and/or keys. The user input may also take the form of signals received remotely from an end user control device. The end user control device can take any of a variety of forms, including desktop computers, workstations, laptop computers, handheld devices such as personal digital assistants, netbook computers, tablet devices, personal digital assistants, and/or cellular phones.

At 3806, the culture system 102, 3500 or control subsystem 3578 determines whether the user input identified a previously defined (i.e., predefined) culturing protocol to be executed. A number of predefined culturing protocols may be stored in one or more nontransitory storage mediums such as one or more databases. The predefined culturing protocols may set out specific acts, steps, parameters, values to be executed in performing a particular culturing protocol.

If the received user input indicates that the end user intends to define a new culturing protocol, the culture system 102, 3500 or control subsystem 3578 enters a define new protocol mode at 3808. The method 3800 then executes a wait loop until a return occurs at 3810 from the enter define new protocol mode 3808.

If the user input indicated selection of a predefined protocol, then the culture system 102, 3500 or control subsystem 3578 retrieves the predefined protocol at 3812. Retrieving the predefined protocol may include retrieving instructions from a computer- or processor-readable non-transitory storage medium which may be local or remotely located with respect to the culture system.

At 3814, the culture system 102, 3500 or control subsystem 3578 enters a protocol mode. As described in detail below, the culture system 102, 3500 executes or performs a defined protocol in the protocol mode.

The culture system and/or control subsystem executes a wait loop until a return from the protocol mode occurs at 3816. The method 3800 may return control to presenting a user interface at 3802.

Figure 39:
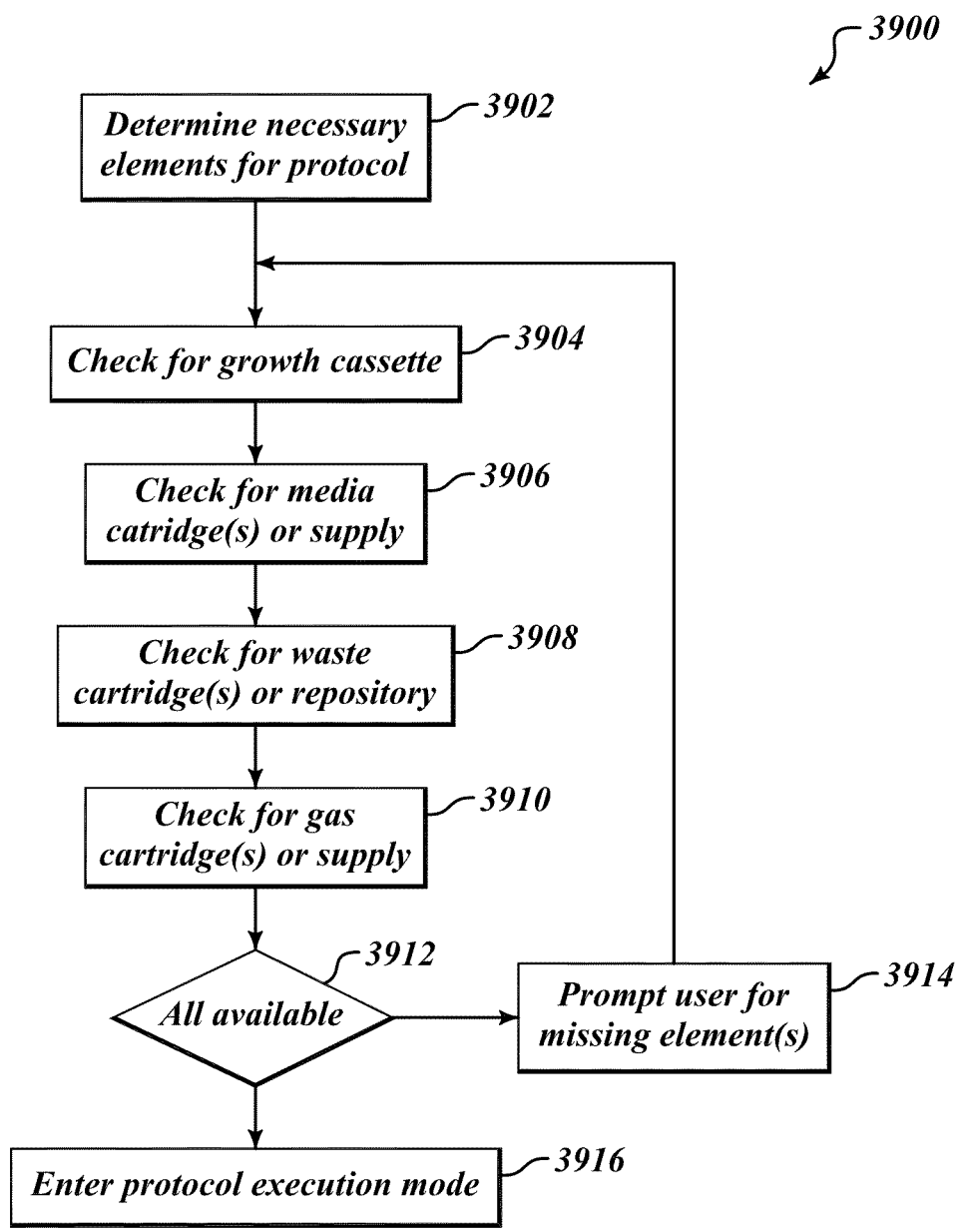
FIG. 39 is a flow chart of an intermediate level method of operating a culture system in a protocol mode, according to one illustrated embodiment.

FIG. 39 shows an intermediate level method 3900 of operating a culture system in a protocol mode, according to one illustrated embodiment.

At 3902, the culture system 102, 3500 or control subsystem 3578 determines which elements are necessary or required for performing the defined culturing protocol. Such may include determining which particular materials (e.g., media, gases, reagents, stains, dyes) and/or components are necessary for performing the culturing protocol. For example, such may include determining specific types and quantities of media and/or gases required, and/or estimating an amount of waste that will be generated or produced in performing the selected defined culturing protocol. Such may also include determining specific contents of wells and/or subwells of a multi-well growth cassette.

At 3904, the culture system 102, 3500 or control subsystem 3578 checks to determine that a multi-well growth cassette is in the growth receiver. Such may not only determine the presence or absence of a multi-well growth cassette, but may also confirm an identity of the multi-well growth cassette, thereby assuring that the wells and/or subwells have the correct contents.

At 3906, the culture system 102, 3500 or control subsystem 3578 checks for one or more media cartridges installed in the respective cartridge receivers. Such may not only determine the presence or absence of a media cartridge, but may also confirm an identity of the media cartridge, thereby assuring that the correct type and/or quantity of media is available. Alternatively, the culture system and/or control subsystem may determine whether there is a continuous or other supply of media available, for example from a large standalone reservoir.

At 3908, the culture system 102, 3500 or control subsystem 3578 checks for one or more waste cartridges installed at the waste cartridge receptacles. Such may not only determine the presence or absence of a waste cartridge, but may also confirm an identity of the waste cartridge, thereby assuring that there is sufficient volume available to store waste expected to be generated when performing the selected defined culturing protocol. Alternatively, the culture system 102, 3500 or control subsystem 3578 may determine whether there is a standalone reservoir or waste feed system to handle the waste to be generated when performing the selected defined culturing protocol.

At 3910, the culture system 102, 3500 or control subsystem 3578 checks for one or more gas canisters installed at the gas canister receivers. Such may not only determine the presence or absence of a gas canister, but may also confirm an identity of the gas canisters, thereby assuring that the correct type and/or quantity of gas at the correct pressure is available. For example, the culture system and/or control subsystem may determine that two or more gas canisters are present, that the gas canisters contain the gases specified by the selected defined culturing protocol, and that suitable amounts and/or pressures of gas are present in each canister.

At 3912, the culture system 102, 3500 or control subsystem 3578 confirms whether all the necessary elements are available. If the culture system 102, 3500 or control subsystem 3578 determines that one or more elements is not present, a user prompt is generated at 3914 for the missing elements. The user prompt may identify specific elements missing. The user prompt may be displayed on a display of the culture system 102, 3500, an aural alert may be provided and/or a notification may be sent remotely. If all necessary elements are determined to be available, the culture system 102, 3500 or control subsystem 3578 enters a protocol execution mode at 3916.

Figure 40:
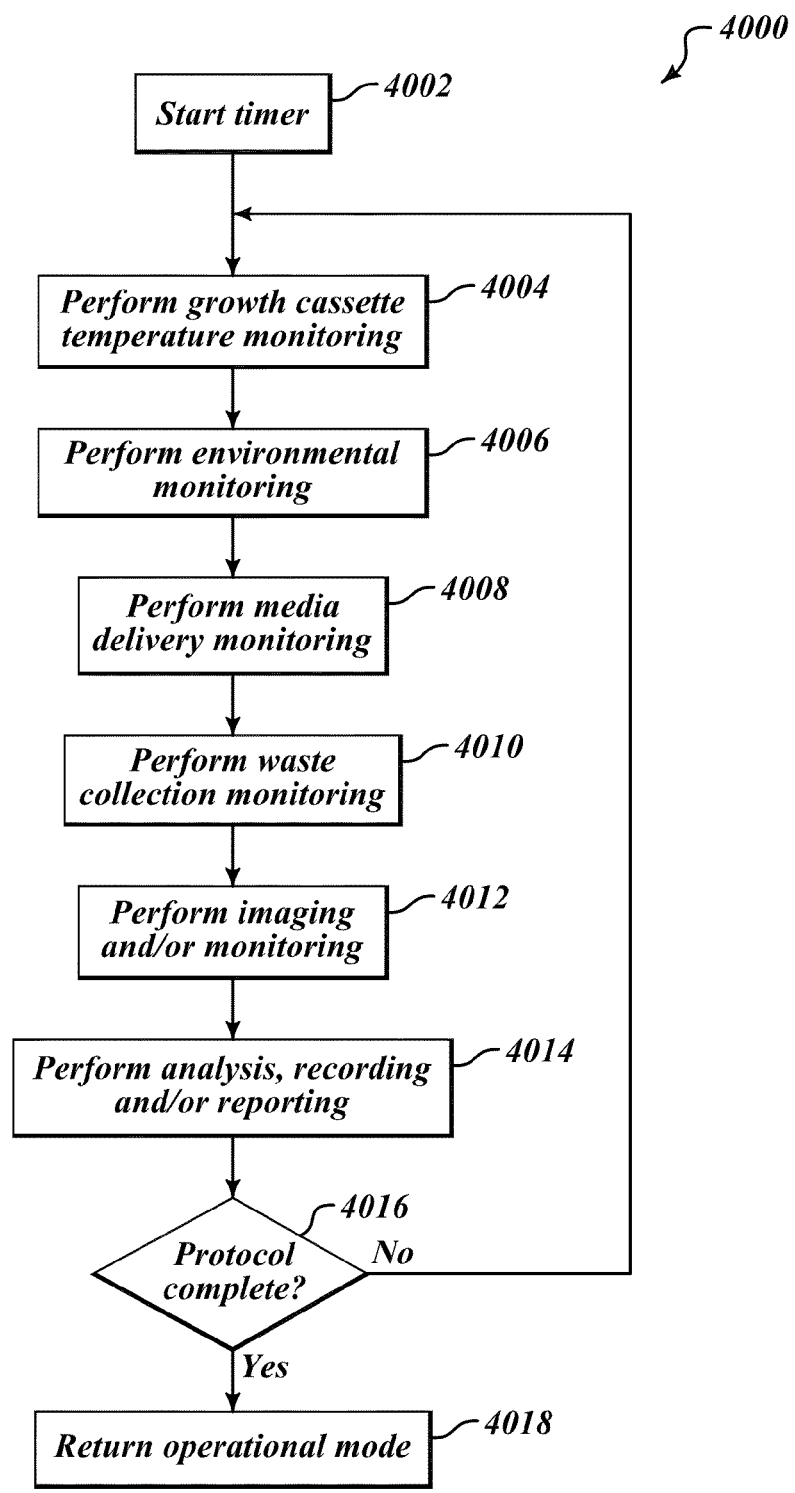
FIG. 40 is a flow chart of an intermediate level method of operating a culture system in a protocol execution mode, according to one illustrated embodiment.

FIG. 40 shows an intermediate level method 4000 of operating a culture system in a protocol execution mode, according to one illustrated embodiment. The method 4000 may be employed in performing the protocol execution mode 3916 (FIG. 39) of the method of 3900.

At 4002, the culture system 102, 3500 or control subsystem 3578 starts a timer. The timer may be used to time various operations or acts specified by a culturing protocol. Alternatively, or additionally, various operations may be synchronized with the flow of operations set out in the selected defined culturing protocol.

At 4004, the culture system 102, 3500 or control subsystem 3578 performs growth cassette temperature monitoring. For example, one or more temperature sensors proximate the growth cassette receiver 3502 and/or the growth cassette 3504 may sense the temperature and provide a corresponding signal to the control subsystem 3578.

At 4006, the culture system 102, 3500 or control subsystem 3578 performs environmental monitoring. For example, the culture system 102, 3500 or control subsystem 3578 may monitor relative humidity, atmospheric temperature, illumination, pressure, pH, conductivity, gas composition, partial pressures, pressure, or other environmental conditions via various environmental sensors located throughout the culture system 102, 3500.

At 4008, the culture system 102, 3500 or control subsystem 3578 performs media delivery monitoring. For example, the culture system 102, 3500 or control subsystem 3578 may monitor a flow rate of media from one or more media cartridges 3510. Additionally, or alternatively, the culture system 102, 3500 or control subsystem 3578 may monitor an amount of media remaining in one or more medial cartridges 3510.

At 4010, the culture system 102, 3500 or control subsystem 3578 performs waste collection monitoring. For example, the culture system 102, 3500 or control subsystem 3578 may monitor a flow rate or amounts of waste delivered to one or more waste cartridges 3524. Additionally or alternatively, the culture system 102, 3500 or control subsystem 3578 may monitor an available volume in one or more waste cartridges 3524.

At 4012, the culture system 102, 3500 or control subsystem 3578 performs imaging and/or monitoring. For example, the culture system 102, 3500 or control subsystem 3578 may control one or more imagers to periodically, aperiodically, or continuously capture images of at least portions of one or more wells and/or subwells of the multi-well growth cassette 3504. Also for example, the culture system 102, 3500 or control subsystem 3578 may cause the wells and/or subwells to be illuminated and/or adjust optical components of a microscopy system 3568.

At 4014, the culture system 102, 3500 or control subsystem 3578 performs analysis, recording, and/or reporting. Such may include analysis using various sensed operational conditions, environmental conditions, and/or digital images.

For example, analysis may include scoring cell phenotypes in images for unusual or rare morphologies, using fluorescence. Screening hundred of cells and comparing quantitative features automatically is a major step towards industrializing primary cell culture and analysis. The culture system 102, 3500 has the requisite hardware and dye perfusion capabilities to automatically implement morphological screening. To accomplish phenotype screening, the image analysis data is analyzed using a machine learning software package.

Also for example, unlike other instruments which require the operator to move plates from incubators to the microscopy instrument, the culture system 102, 3500 provides an all-in-one approach. In particular, the culture system 102, 3500 has the ability to track colony formation over time without any operator involvement.

Analysis may be used to control further operations of the culture system 102, 3500 while executing the selected defined culturing protocol. Analysis may also be used to prepare reports with respect to the selected defined culturing protocol. Reports may take any variety of forms, and may advantageously fully document the performance of the selected defined culturing protocol.

At 4016, the culture system 102, 3500 or control subsystem 3578 determines whether the selected defined culturing protocol is complete. If the selected defined culturing protocol is not complete, control returns to 4004 and the various operations are repeated. If the selected defined culturing protocol is complete, the culture system and/or control subsystem returns to the operational mode at 4018.

Figure 41:
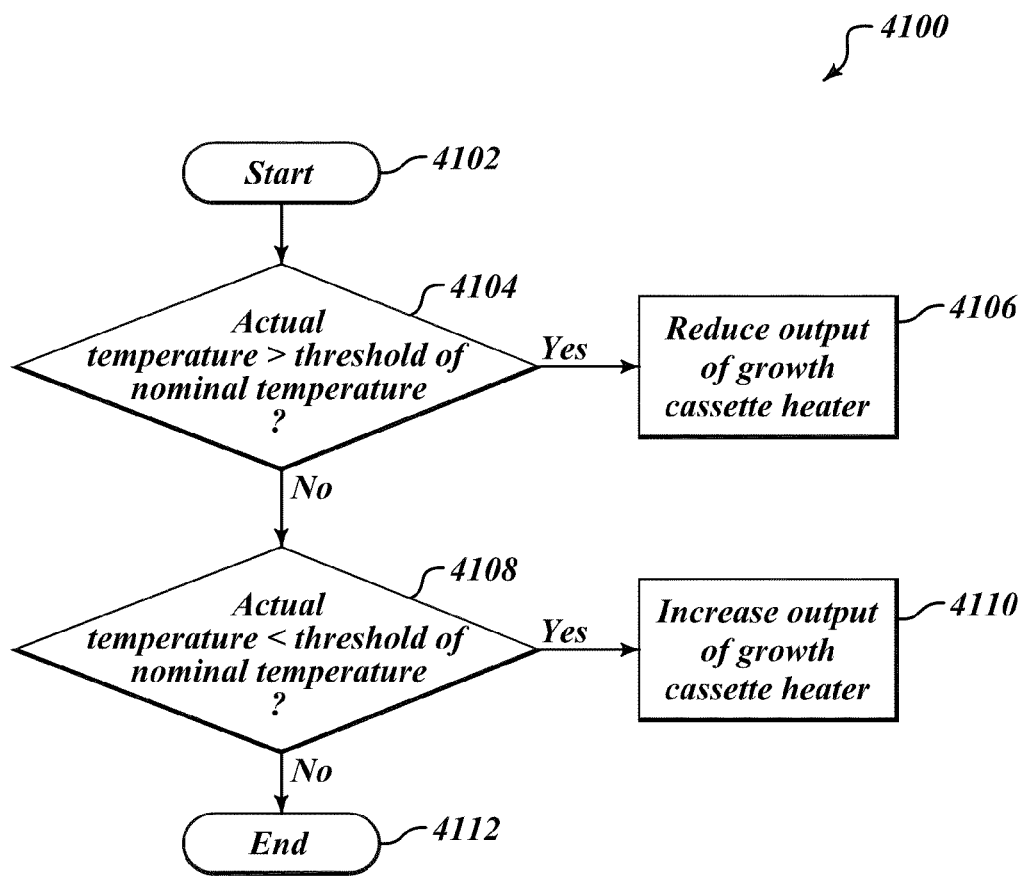
FIG. 41 is a flow chart of a low level method of operating a culture system to monitor and/or adjust temperature of a removable multi-well growth cassette, according to one illustrated embodiment.

FIG. 41 shows a low level method 4100 of operating a culture system to monitoring and/or adjust a temperature of a removable multi-well growth cassette 3504, according to one illustrated embodiment. The method 4100 may be executed in performing the growth cassette temperature monitoring 4004 (FIG. 40) of the method 4000.

The method 4100 starts at 4102. For example, the method 4100 may start in response to a call from the method 4000.

At 4104, the culture system 102, 3500 or control subsystem 3578 determines whether the actual temperature as measured or sensed at least proximate the multi-well growth cassette 3504 is greater than some threshold of a nominal growth cassette temperature set out in the selected defined specific culturing protocol being executed. If the actual temperature exceeds the threshold, the culture system 102, 3500 or control subsystem 3578 reduces an output of the growth cassette heater 3562 at 4106.

At 4108, the culture system 102, 3500 or control subsystem 3578 determines whether the actual temperature as measured or sensed at least proximate the multi-well growth cassette 3504 is less than a threshold of a nominal growth cassette temperature set out in the selected defined culturing protocol being executed. If the actual temperature is less than the threshold, the culture system 102, 3500 or control subsystem 3578 increases the output of the growth cassette heater 3562 at 4110.

If neither condition is met, the output of the growth cassette heater 3562 remains constant. The method 4100 ends at 4112.

Figure 42A:
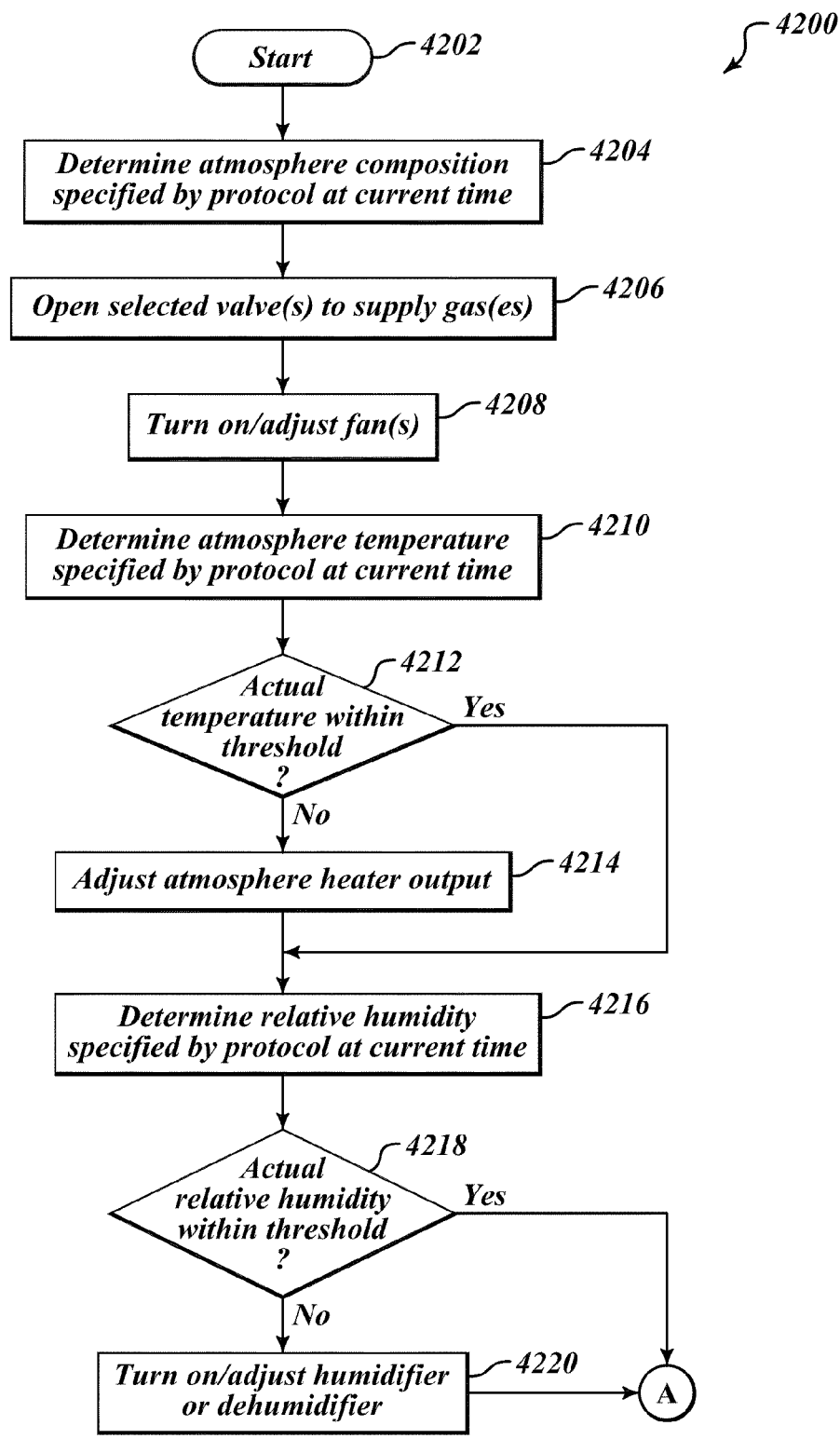
FIGS. 42A-42B is a flow chart of a low level method of operating an environmental control subsystem of the culture system to monitor and/or adjust environmental conditions at least proximate the removable multi-well growth cassette, according to one illustrated embodiment.
Figure 42B:
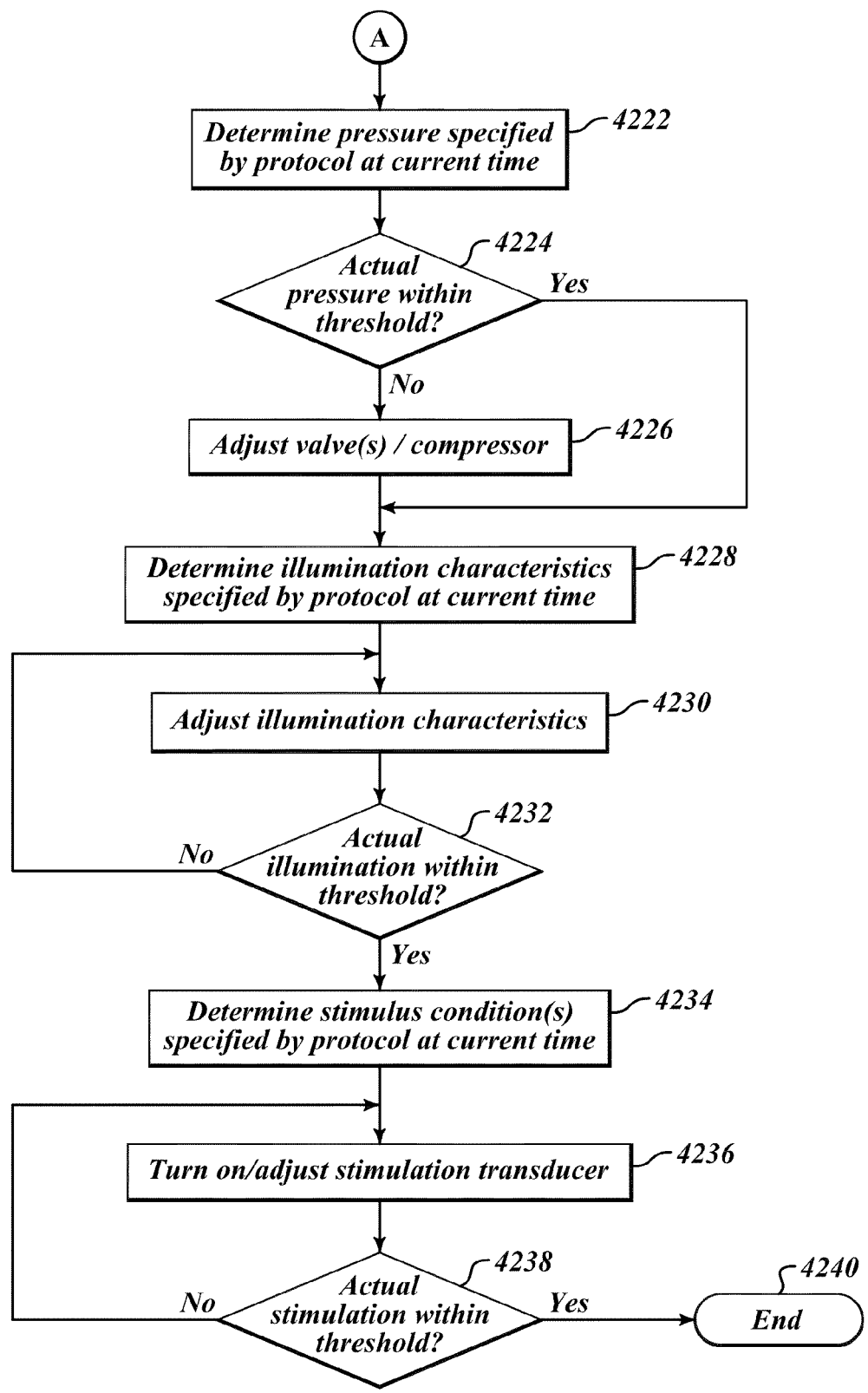

FIGS. 42A-42B show a low level method of operating an environmental control subsystem of a culture system, according to one illustrated embodiment. The method 4200 may be performed in executing the environmental monitoring 4006 (FIG. 40) of the method 4000.

The method 4200 starts at 4202. For example, the method 4200 may start in response to a call from the method 4000.

At 4204, the culture system 102, 3500 or control subsystem 3578 determines a nominal composition of an atmosphere that is specified by the selected defined culturing protocol at the current time or point of execution in the culturing protocol. For example, a defined culturing protocol may set out different atmospheric compositions which the contents of the wells and/or subwells are to be exposed to during different portions of the culturing protocol. For instance, at a first time or period, the culturing protocol may specify an atmosphere containing or consisting essentially of nitrogen, while at a second time or period the culturing protocol may specify an atmosphere containing of consisting essentially of carbon dioxide.

At 4206, the culture system 102, 3500 or control subsystem 3578 opens selected valves 3542 to supply gases to the wells and/or subwells of the multi-well growth cassette 3503 as specified by the selected defined culturing protocol being executed. Optionally, at 4208, the culture system 102, 3500 or control subsystem 3578 may turn on or adjust one or more fans 3552. For example, the culture system 102, 3500 or control subsystem 3578 may turn or adjust the speed of a fan to deliver a selected atmosphere to the wells and/or subwells of the multi-well growth cassette 3504, and/or to exhaust a selected atmosphere from proximate the wells and/or subwells of the multi-well growth cassette 3504.

At 4210, the culture system 102, 3500 or control subsystem 3578 determines a nominal atmospheric temperature specified by the selected defined culturing protocol being executed for the current time or portion of the defined culturing protocol. At 4212, the culture system 102, 3500 or control subsystem 3578 determines whether an actual atmosphere temperature measured or sensed is within a threshold of the nominal atmosphere temperature specified by the defined culturing protocol. If the actual atmosphere temperature is not within the threshold of the nominal atmospheric temperature, the culture system 102, 3500 or control subsystem 3578 adjusts an atmosphere heater 3556 output at 4214. For example, current supplied to the atmosphere heater 3556 may be increased or decreased to adjust the output. Control then passes to 4216. If the actual atmosphere temperature measured or sensed is within the threshold of the nominal atmosphere temperature, control passes directly to 4216.

At 4216, the culture system 102, 3500 or control subsystem 3578 determines a nominal relative humidity specified by the selected defined culturing protocol being executed, for the current time or portion of the protocol. At 4218, the culture system 102, 3500 or control subsystem 3578 determines whether an actual relative humidity measured or sensed is within a threshold of the nominal relative humidity. If the actual relative humidity is not within the threshold of the nominal relative humidity, the culture system 102, 3500 or control subsystem 3578 turns on and/or adjusts a humidifier 2558 or dehumidifier 3560 at 4220. For example, the culture system 102, 3500 or control subsystem 3578 may adjust the speed of a compressor that compresses a thermal transfer medium flowing through a coolant loop.

At 4222, the culture system 102, 3500 or control subsystem 3578 determines a nominal pressure specified by the selected defined culturing protocol being executed, for the current time or portion of the defined culturing protocol. At 4224, the culture system 102, 3500 or control subsystem 3578 determines whether an actual pressure measured or sensed is within a threshold of the nominal pressure. If the actual measured pressure is not within the threshold of the nominal pressure, the culture system 102, 3500 or control subsystem 3578 adjusts one or more valves 3542 or a compressor (not shown) at 4226. For example, the culture system 102, 3500 or control subsystem 3578 may adjust a valve 3542 to increase or decrease a gas flow from a gas canister 3540. Also for example, the culture system 102, 3500 or control subsystem 3578 may adjust a valve to vent or exhaust atmosphere from the growth cassette receiver 3502. Control then passes to 4228. If the actual pressure measured or sensed is within the threshold of the nominal pressure, control passes directly to 4228.

At 4228, the culture system 102, 3500 or control subsystem 3578 determines one or more nominal illumination characteristics specified by the selected defined culturing protocol, for the current time or portion of the defined culturing protocol. At 4230, the culture system 102, 3500 or control subsystem 3578 adjusts illumination characteristics accordingly. At 4232, the culture system 102, 3500 or control subsystem 3578 may determine whether the actual illumination characteristics measured or sensed are within a threshold of the nominal illumination characteristics specified by the defined culturing protocol. If the actual illumination characteristics measured or sensed are not within the threshold of the nominal illumination characteristics, control may return to 4230, where illumination characteristics are adjusted.

At 4234, the culture system 102, 3500 or control subsystem 3578 determines nominal stimulus conditions specified by the selected defined culturing protocol, for the current time or portion of the protocol. At 4236, the culture system 102, 3500 or control subsystem 3578 turns on or adjusts a stimulation transducer 3564. For example, the culture system 102, 3500 or control subsystem 3578 may apply a current and/or voltage to a stimulation transducer 3564 at one or more frequencies. At 4238, the culture system 102, 3500 or control subsystem 3578 may determine whether an actual stimulation characteristic measured or sensed is within a threshold of the nominal stimulation characteristic specified by the defined culturing protocol being executed. If the actual stimulation characteristics measured or sensed are not within the threshold of the nominal stimulation characteristics, control may return to 4236, where stimulation characteristics are adjusted. Otherwise control passes to 4240 where the method 4200 ends.

Figure 43:
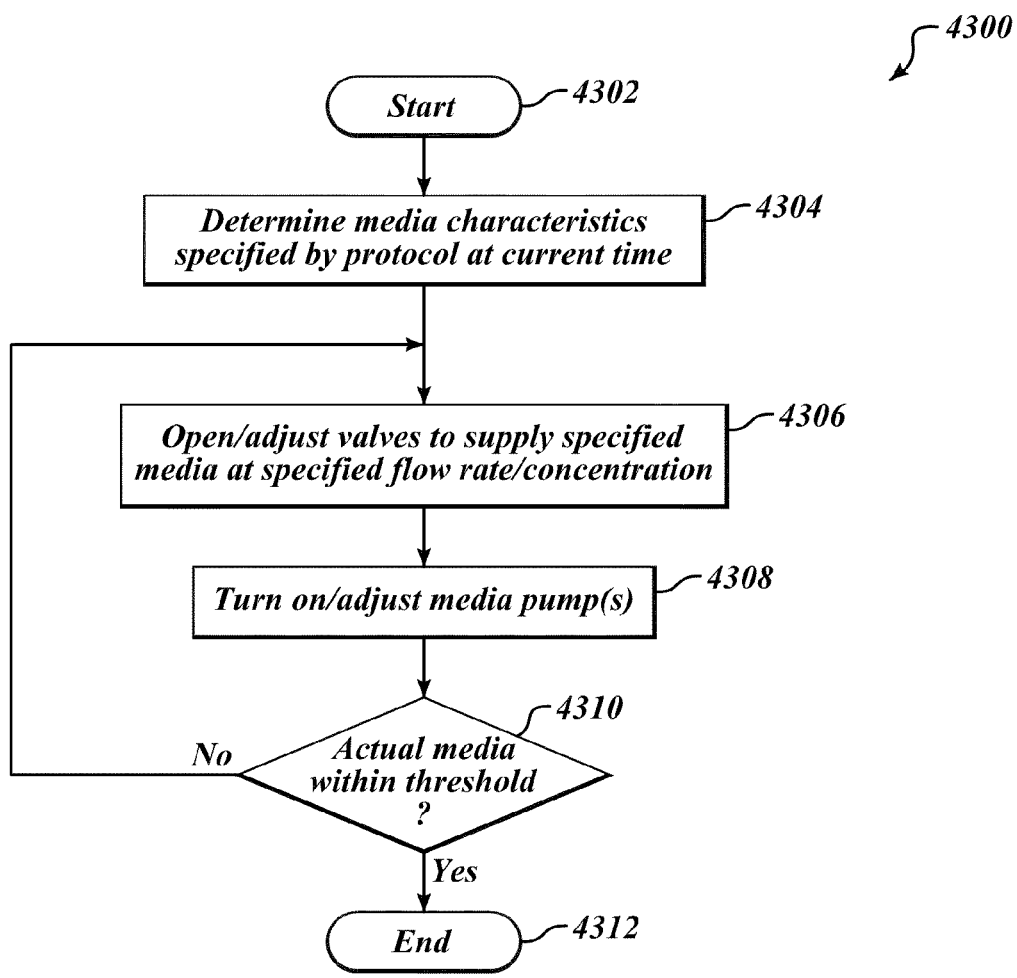
FIG. 43 is a flow chart of a low level method of operating a media supply system of the culture system to selectively supply media to the wells or the removable multi-well growth cassette, according to one illustrated embodiment.

FIG. 43 shows a low level method 4300 of operating a media supply subsystem of a culture system to selectively supply or deliver media to one or more wells and/or subwells of a removable multi-well growth cassette, according to one illustrated embodiment. The method 4300 may be used in performing the media delivery monitoring 4008 (FIG. 40) of the method 4000.

The method 4300 may start at 4302. For example, the method 4300 may start in response to a call from the method 4000.

At 4304, the culture system 102, 3500 or control subsystem 3578 determines nominal media characteristics specified by the selected defined culturing protocol being executed, for the current time or portion of the defined culturing protocol. For example, a culturing protocol may specify a first type of media to be supplied to one or more wells and/or subwells of the growth cassette 3504 at a first time or period, while specifying a second media type to be supplied at a second time or period. Such may also specify specific flow rates of media at different times or portions of the culturing protocol.

At 4306, the culture system 102, 3500 or control subsystem 3578 opens or adjusts one or more valves 3512 to supply specified media to the wells and/or subwells of the growth cassette 3504 at the nominal flow rate specified by the culturing protocol being executed. Again, the specific media types and/or flow rates or concentrations may vary at different times and/or portions of the culturing protocol. Optionally at 4308, the culture system 102, 3500 or control subsystem 3578 optionally turns on and/or adjusts one or more media pumps 3514. Such may facilitate controlling flow rate from the media cartridges 3510.

At 4310, the culture system 102, 3500 or control subsystem 3578 determines whether an actual media characteristic measured or sensed is within a threshold of the nominal media characteristic specified by the culturing protocol being executed for the particular time or portion of the protocol. If the actual media characteristics are not within the threshold of the nominal media characteristics, control returns to 4308 where the valves 3512 are adjusted. Otherwise control may pass to 4312 where the method 4300 may terminate.

Figure 44:
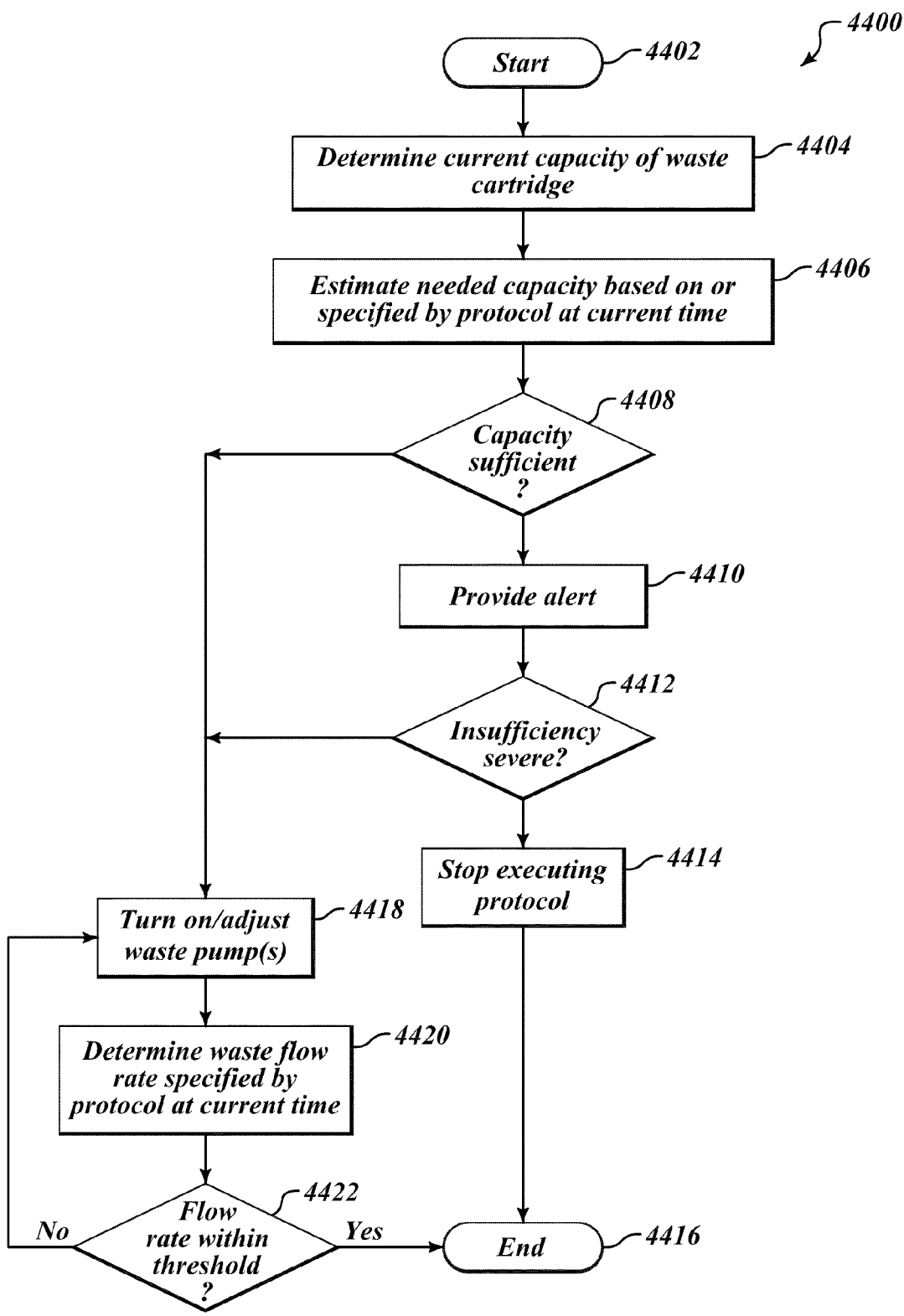
FIG. 44 is a flow chart of a low level method of operating a waste control subsystem of the culture system to collect and direct waste generated by the culturing, according to one illustrated embodiment.

FIG. 44 shows a low level method 4400 operating a waste control subsystem 3520 of the culture system 102, 3500 to collect and direct waste generated by the culturing, according to one illustrated embodiment. The method 4400 may be executed in performing the waste collection monitoring 4010 (FIG. 40) of the method 4000.

The method 4400 may start at 4402. For example, the method 4400 may start in response to a call from the method 4000.

At 4404, the culture system 102, 3500 or control subsystem 3578 may determine a current capacity of one or more waste cartridges received by or mounted in the culture system. The current capacity may be measured, sensed, calculated or otherwise determined. At 4406, the culture system 102, 3500 or control subsystem 3578 may estimate or otherwise determine a needed waste capacity, based on or specified by the selected defined culturing protocol.

At 4408, the culture system 102, 3500 or control subsystem 3578 determines whether the available capacity is sufficient to meet the estimated need. If the available capacity is not sufficient to meet the estimated need, the culture system 102, 3500 or control subsystem 3578 provides an alert to the user if the capacity is not sufficient 4410. The alert may take any of a variety of forms. For example, the alert may include a warning indication (e.g., red LED flashing) and/or an audible alert. Also for example, the alert may take the form of an email message, text message, page, or printed alert.

At 4412, the culture system 102, 3500 or control subsystem 3578 determines whether the insufficiency is severe. If the insufficiency is severe, the culture system 102, 3500 or control subsystem 3578 stops executing the selected defined culturing protocol at 4414. The method 4400 may then terminate at 4416.

If either the determined available capacity is sufficient or the insufficiency is not severe, the culture system 102, 3500 or control subsystem 3578 may turn on or adjusts waste pumps 3528a at 4418.

At 4420, the culture system 102, 3500 or control subsystem 3578 determines a nominal waste flow rate specified by the selected defined culturing protocol being executed, for the current time or portion of the protocol. At 4422, the culture system 102, 3500 or control subsystem 3578 determines whether the actual flow rate measured, sensed or otherwise determined is within a threshold of the nominal flow rate specified by the selected defined culturing protocol. If the actual flow rate is not within the threshold of the nominal flow rate, the culture system 102, 3500 or control subsystem 3578 adjusts the waste pumps 3528a at 4418. Otherwise, the method 4400 may terminate at 4416.

Figure 45:
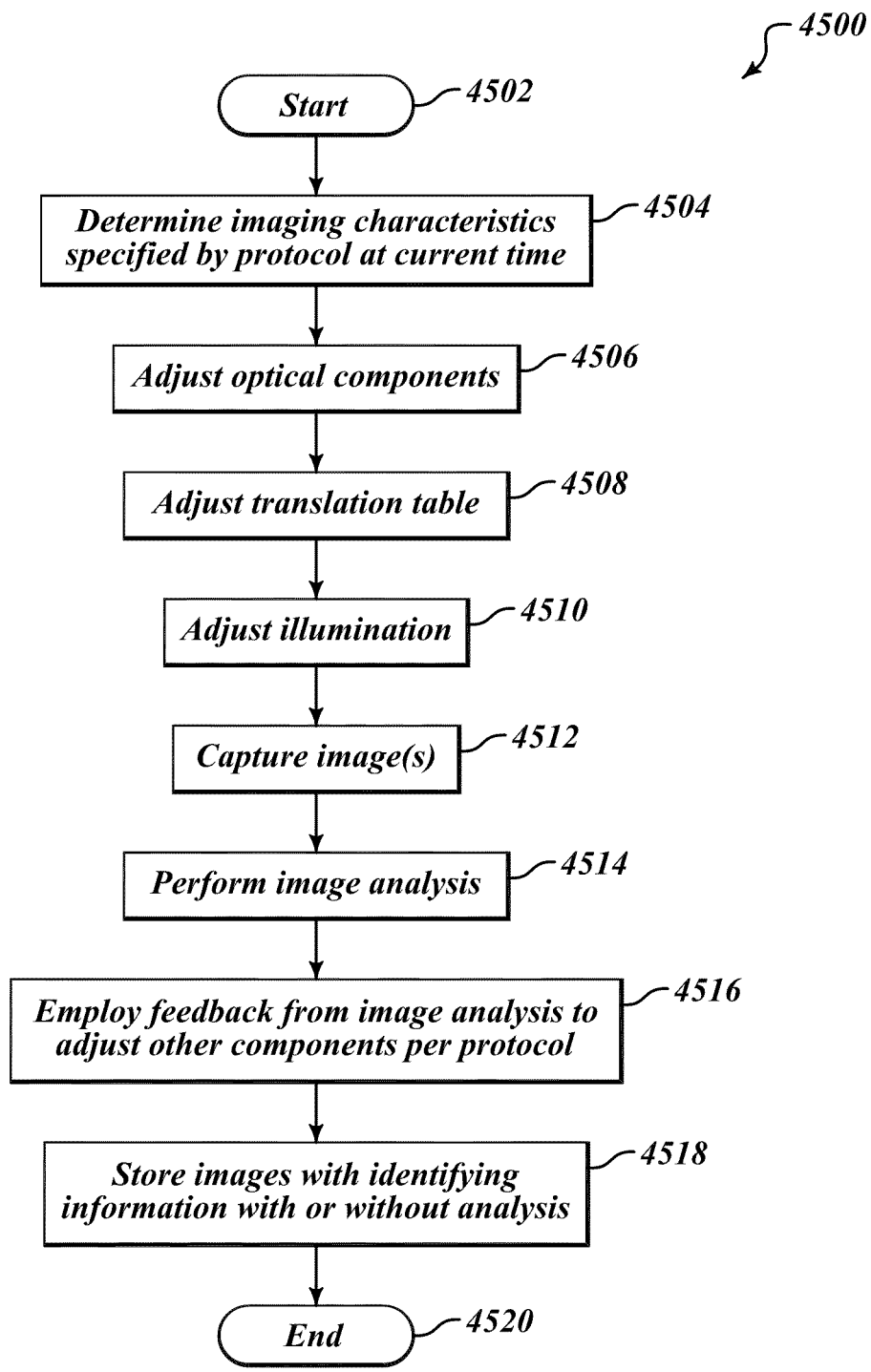
FIG. 45 is a flow chart of a low level method of operating a microscopy subsystem of the culture system to magnify and image at least portions of the wells of the removable multi-well growth cassette, according to one illustrated embodiment.

FIG. 45 shows a low level method 4500 of operating a microscopy subsystem of the culture system to magnify and image at least portions of the wells of the removable multi-well growth cassette, according to one illustrated embodiment. The method 4500 may be employed in performing the imaging and/or or monitoring 4012 (FIG. 40) of the method 4000.

The method 4500 may start at 4502. For example, the method 4500 may start in response to a call from the method 4000.

At 4504, the culture system 102, 3500 or control subsystem 3578 determines one or more nominal imaging characteristics specified by the selected defined culturing protocol being executed, for a current time or portion of the protocol. At 4506, the culture system 102, 3500 or control subsystem 3578 adjusts one or more optical components 3572 of a microscopy system 3568. For example, the culture system 102, 3500 or control subsystem 3578 may move optical elements 3572 such as lenses and/or optical filters with respect to one another and/or with respect to the wells and/or subwells of the multi-well growth cassette 3504. Such may allow focusing or use of selective filters. At 4508, the culture system 102, 3500 or control subsystem 3578 may adjust a position of a translation table 3570. For example, the translation table 3570 may be linearly adjustable in three dimensions. Such may allow focusing in a Z dimension perpendicular or generally perpendicular to a plane of the multi-well growth cassette 3504. Such may also allow focusing in an X dimension and/or Y dimension parallel or generally parallel to the plane of the multi-well growth cassette 3504.

At 4510, the culture system 102, 3500 or control subsystem 3578 adjusts illumination provide by the microscopy illumination subsystem 3576. The illumination may be adjusted according to one or more nominal characteristics specified by the selected defined culturing protocol being executed, for the current time or point in the defined culturing protocol. The illumination may facilitate imaging. The illumination may be in one or more wavelengths, for example, visible wavelengths, near infrared wave lengths, infrared wavelengths, and/or ultraviolet wavelengths, to name a few.

At 4512, the culture system 102, 3500 or control subsystem 3578 captures one or more images of at least a portion of one or more wells and/or subwells of the multi-well growth cassette 3504. As generally set out above, the microscopy system 3568 may include one or more imagers 3574 which may take a variety of types or formats. The imagers 3574 convert electromagnetic radiation (e.g., visible light) into digital signals that are representative of an image of the portion of the wells and/or subwells.

At 4514, the culture system 102, 3500 or control subsystem 3578 performs image analysis. For example, a digital signal processor 3579b may execute one or more image analysis routines on the captured digital images. Such may, for example, compare digital images captured at different times to identify differences. Such may, for example, identify cell growth and/or clustering of cells.

At 4516, the culture system 102, 3500 or control subsystem 3578 may optionally employ feedback from the image analysis to adjust one or more components of the culture system 102, 3500 in accordance with the selected defined culturing protocol being executed.

At 4518, the culture system 102, 3500 or control subsystem 3578 may store digital images with or without identifying information and with or without analysis to one or more nontransitory computer or processor readable storage mediums. For example, information may be stored to one or more databases, either locally to the culture system 102, 3500 or remotely therefrom.

The method 4500 may terminate at 4520.

Figure 46A:
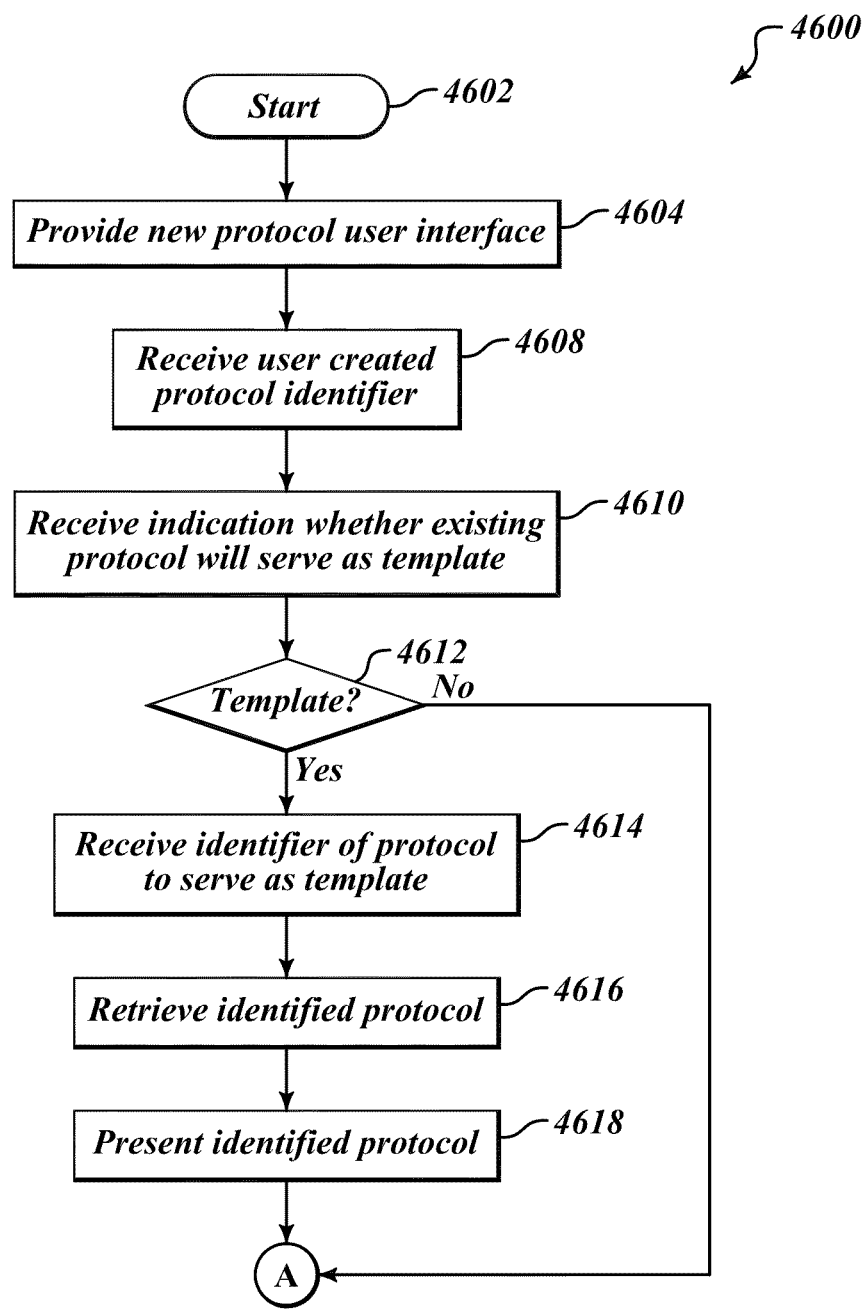
FIGS. 46A-46C is a flow chart of an intermediate level method of operating the culture system or some local or remote computer or processor based device to define a new culturing protocol for execution by a culture system, according to one illustrated embodiment.
Figure 46B:
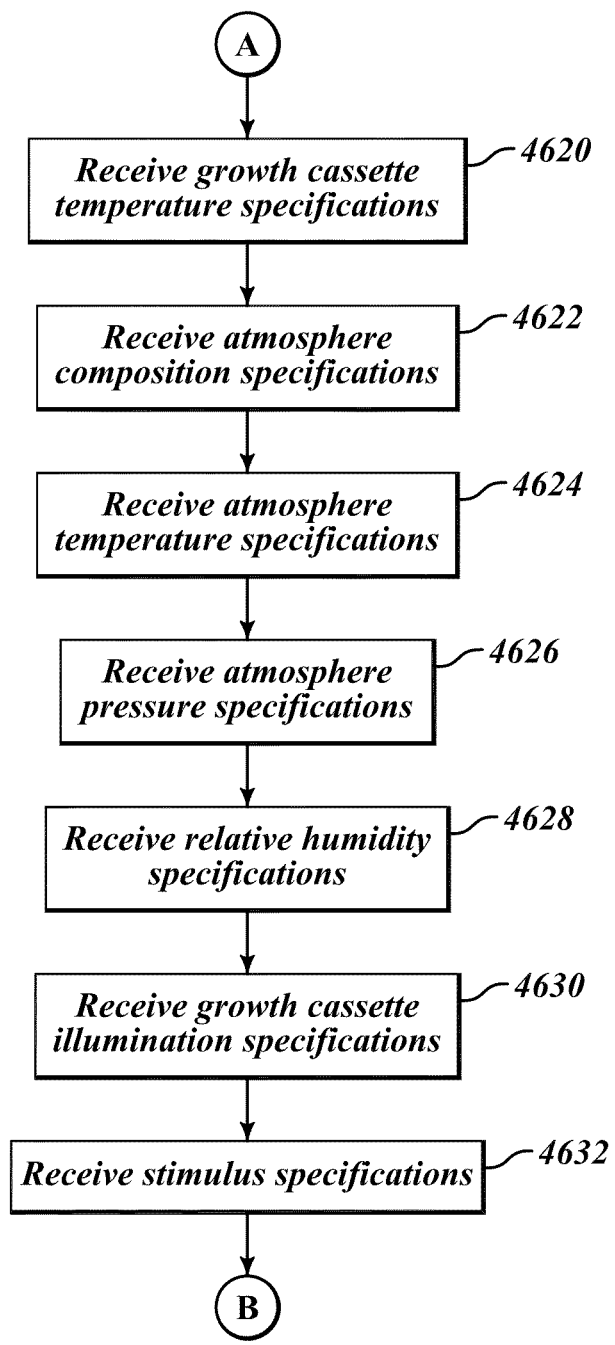
Figure 46C:
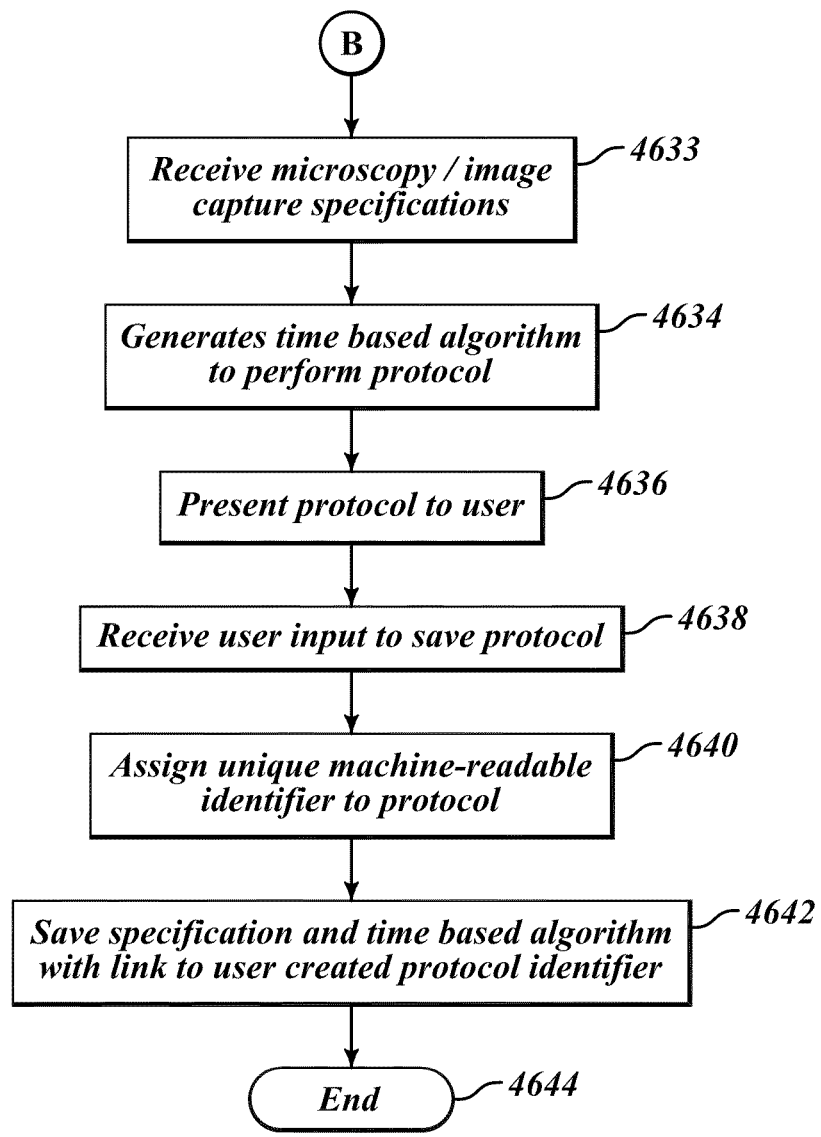

FIGS. 46A-46C show an intermediate level method 4600 of operating the culture system or some local or remote computer or processor based device to define a new culturing protocol for execution by a culture system, according to one illustrated embodiment. The method 4600 may be employed in executing the define new protocol mode 3808 (FIG. 38) of method 3800.

The method 4600 may start at 4602. For example, the method 4600 may start in response to a call from method 3800.

At 4604, the culture system 102, 3500 or control subsystem 3578 provides a new protocol user interface. For example, the culture system 102, 3500 or control subsystem 3578 may provide a graphical user interface via one or more screens or touch screen displays. The graphical user interface may include one or more user selectable icons, text, images, pull down menus, radio buttons, and/or dialogue boxes that allow an end user to specify a new culturing protocol.

At 4608, the culture system 102, 3500 or control subsystem 3578 receives a user created protocol identifier. The user created protocol identifier may be an identifier that is easy for a human to understand and relate to. This contrasts from machine assigned identifiers which may not be generally understandable to users. This provides a short-hand way for an end user to refer to a specific defined culturing protocol.

At 4610, the culture system 102, 3500 or control subsystem 3578 receives an indication from the user whether an existing protocol will serve as a template. For example, the end user may be attempting to define a new protocol that is very similar to an existing culturing protocol. At 4612, the culture system 102, 3500 or control subsystem 3578 determines whether a template was requested.

If a template was requested, the culture system 102, 3500 or control subsystem 3578 receives an identifier of the selected previously defined culturing protocol that is to serve as the template. At 4616, the culture system 102, 3500 or control subsystem 3578 retrieves the identified culturing protocol. For example, the culture system 102, 3500 or control subsystem 3578 may convert a human-recognizable culturing protocol identifier to a machine-recognizable culturing protocol identifier. The culture system 102, 3500 or control subsystem 3578 may then retrieve the specified previously defined culturing protocol from a nontransitory computer- or processor-readable storage medium. At 4618, the culture system 102, 3500 or control subsystem 3578 presents the identified previously defined protocol to the end user. The identified previously defined culturing protocol may serve as a template to allow the end user to modify certain operations and/or parameters to define the new culturing protocol. Control then passes to 4620. If a template is not selected, control passes directly to 4620.

At 4620, the culture system 102, 3500 or control subsystem 3578 receives nominal growth cassette temperature specifications. Such may specify nominal temperatures for the growth cassette 3502 or multi-well growth cassette 3504 at various times and/or points during the new culturing protocol being defined.

At 4622, the culture system 102, 3500 or control subsystem 3578 receives nominal atmospheric composition specifications. Such may specify nominal values for the composition of the atmosphere to which the contents of the wells and/or subwells of the multi-well growth cassette 3504 will be exposed, at various times or points during the culturing protocol being defined.

At 4624, the culture system 102, 3500 or control subsystem 3578 receives nominal atmospheric temperature specifications. The nominal atmosphere temperature specifications may specify specific temperatures for the atmosphere to which the contents of the wells and/or subwells of the multi-well growth cassette 3504 will be exposed, at various times or points during the culturing protocol being defined.

At 4626, the culture system 102, 3500 or control subsystem 3578 receives nominal atmosphere pressure specifications. The nominal atmosphere pressure specifications may define specific pressures for the atmosphere to which the contents of the wells and/or subwells of the multi-well growth cassette 3504 will be exposed, at different times and/or points during the culturing protocol being defined.

At 4628, the culture system 102, 3500 or control subsystem 3578 receives nominal relative humidity specifications.

The nominal relative humidity specifications may specify specific relative humidity levels for the atmosphere to which the contents of the wells and/or subwells of the multi-well growth cassette 3504 will be exposed, during various times and/or portions of the culturing protocol being defined.

At 4630, the culture system 102, 3500 or control subsystem 3578 receives nominal growth cassette illumination specifications. The nominal growth cassette illumination specifications may specify various illumination characteristics to which the contents of the wells and/or subwells of the multi-well growth cassette 3504 will be subjected to, during various times and/or portions of the culturing protocol being defined.

At 4632, the culture system 102, 3500 or control subsystem 3578 receives nominal stimulus characteristic specifications. The nominal stimulus characteristic specifications may specify various types, frequencies, or other aspects of one or more stimuli which may be applied to the contents and/or directly to the wells and/or subwells of the multi-well growth cassette 3504 during one or more times or portions of the culturing protocol being defined.

At 4633, the culture system 102, 3500 or control subsystem 3578 may receive nominal microscopy and/or imaging characteristic specifications. The nominal microscopy and/or imaging characteristic specifications may specify various times and/or rates of image capture, magnifications, focal points, filters or filtering, illumination wavelengths and magnitudes or levels, positions of the XYZ translation table 3570 to illuminate, magnify and/or image at least portions of the wells and/or subwells of the multi-well growth cassette 3504 during one or more times or portions of the culturing protocol being defined.

At 4634, the culture system 102, 3500 or control subsystem 3578 may generate a time-based algorithm to perform the new culturing protocol being defined. For example, the culture system 102, 3500 or control subsystem 3578 may define a set of operations and/or operational parameters. Such may be in the form of a high level programming language. Such may additionally, or alternatively, be in the form of a low level language such as Object Code or Assembler Code.

At 4636, the culture system 102, 3500 or control subsystem 3578 presents the newly defined culturing protocol to the user for evaluation. For example, the culture system 102, 3500 or control subsystem 3578 may present the newly defined culturing protocol as a series of operations with specific conditions or parameters specified for each operation. Such may be set out in a timeline type fashion.

At 4638, the culture system 102, 3500 or control subsystem 3578 receives user input to save the newly defined culturing protocol. At 4640, the culture system 102, 3500 or control subsystem 3578 assigns a unique machine-understandable identifier to the newly defined culturing protocol. The machine-understandable identifier may make it easier for various culture systems to employ defined culturing protocols.

At 4642, the culture system 102, 3500 or control subsystem 3578 saves the nominal specifications and/or the time-based algorithm. Such is saved with a link or other logical connection to the user-created protocol identifier. Such may allow end users to conveniently refer to various culturing protocols by easy-to-recognize names.

The method 4600 may terminate at 4644.

Figure 47:
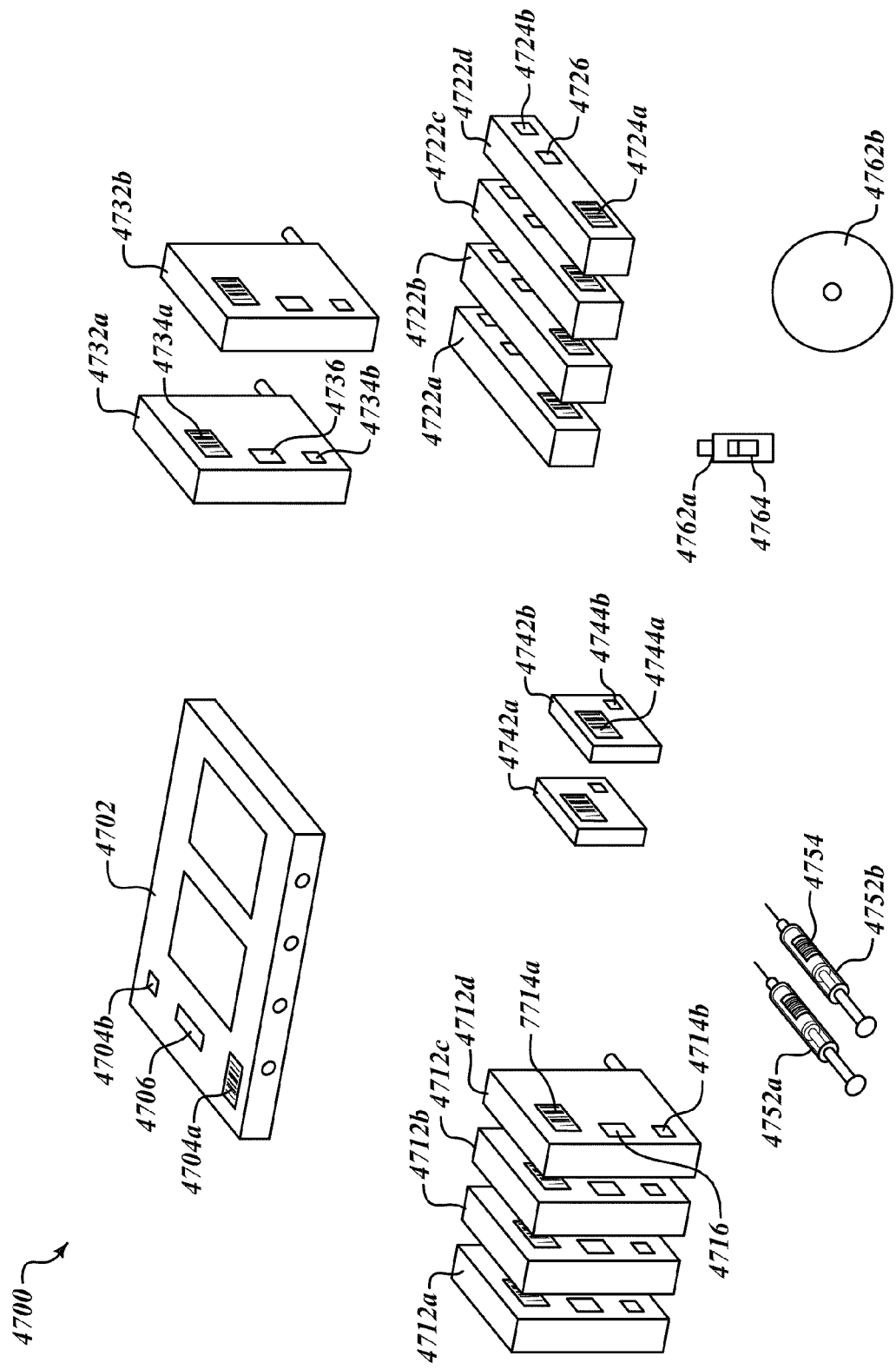
FIG. 47 is an isometric view of a kit for use with a culture system, according to one illustrated embodiment.
Figure 48:
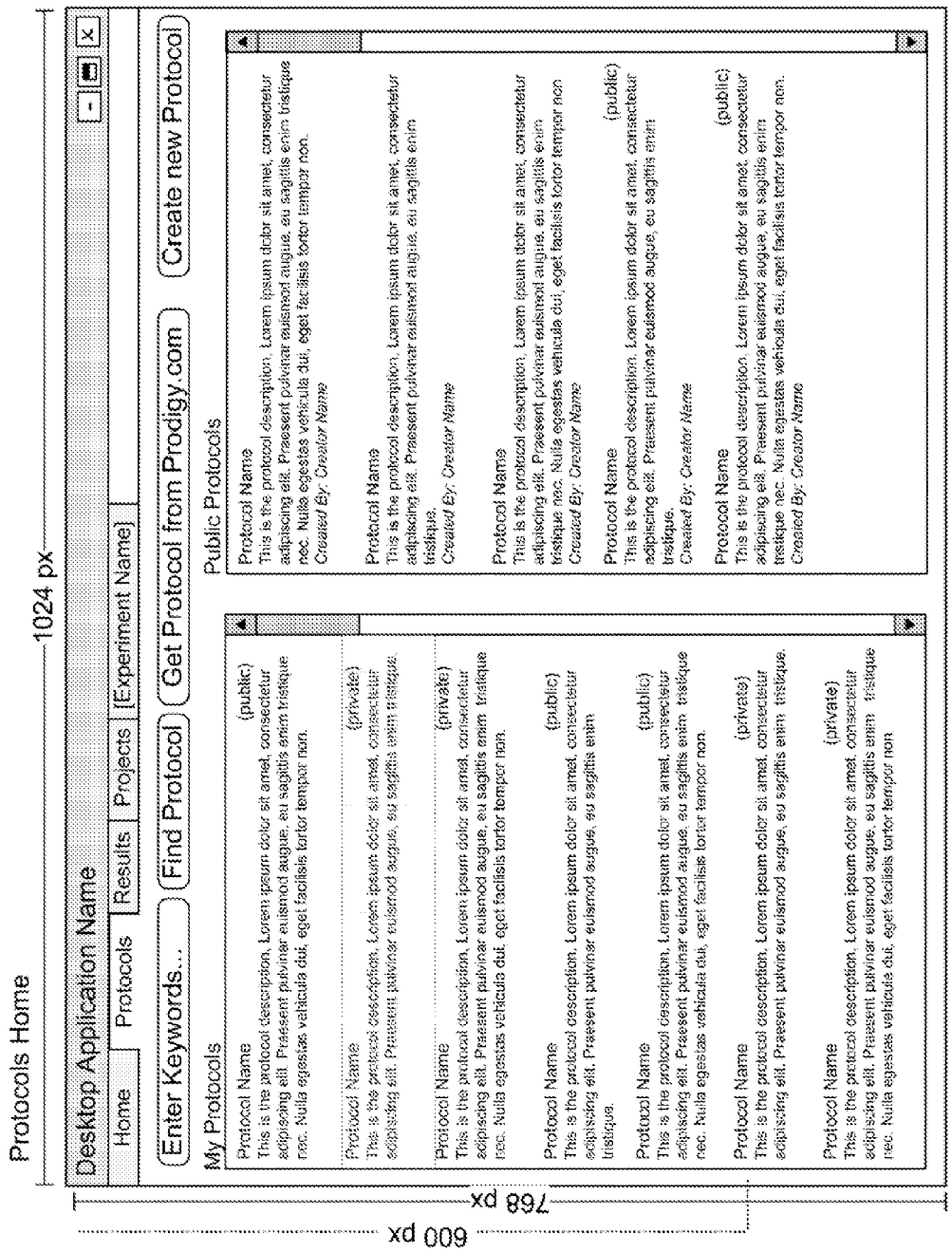
Figure 49:
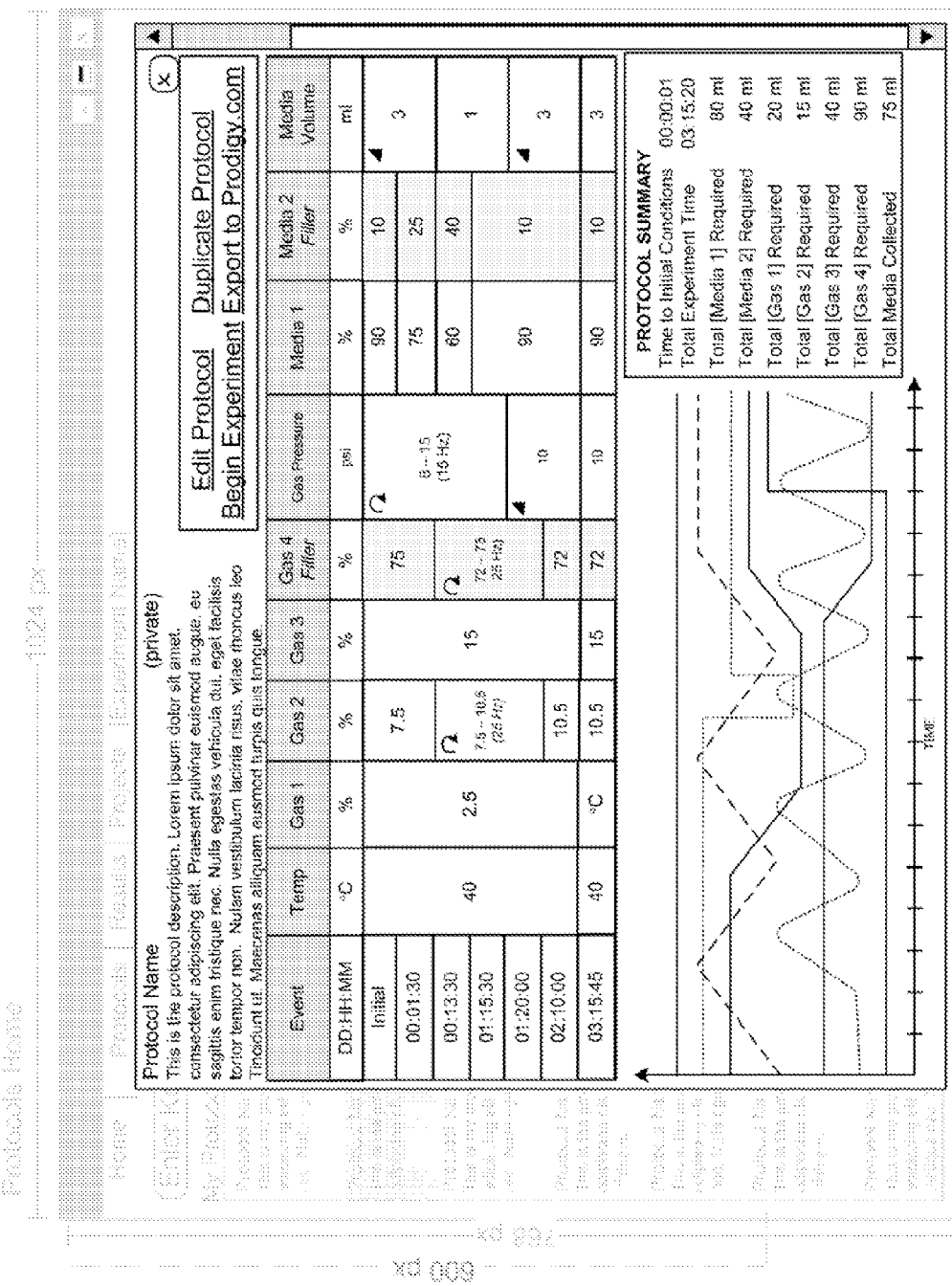
Figure 50:
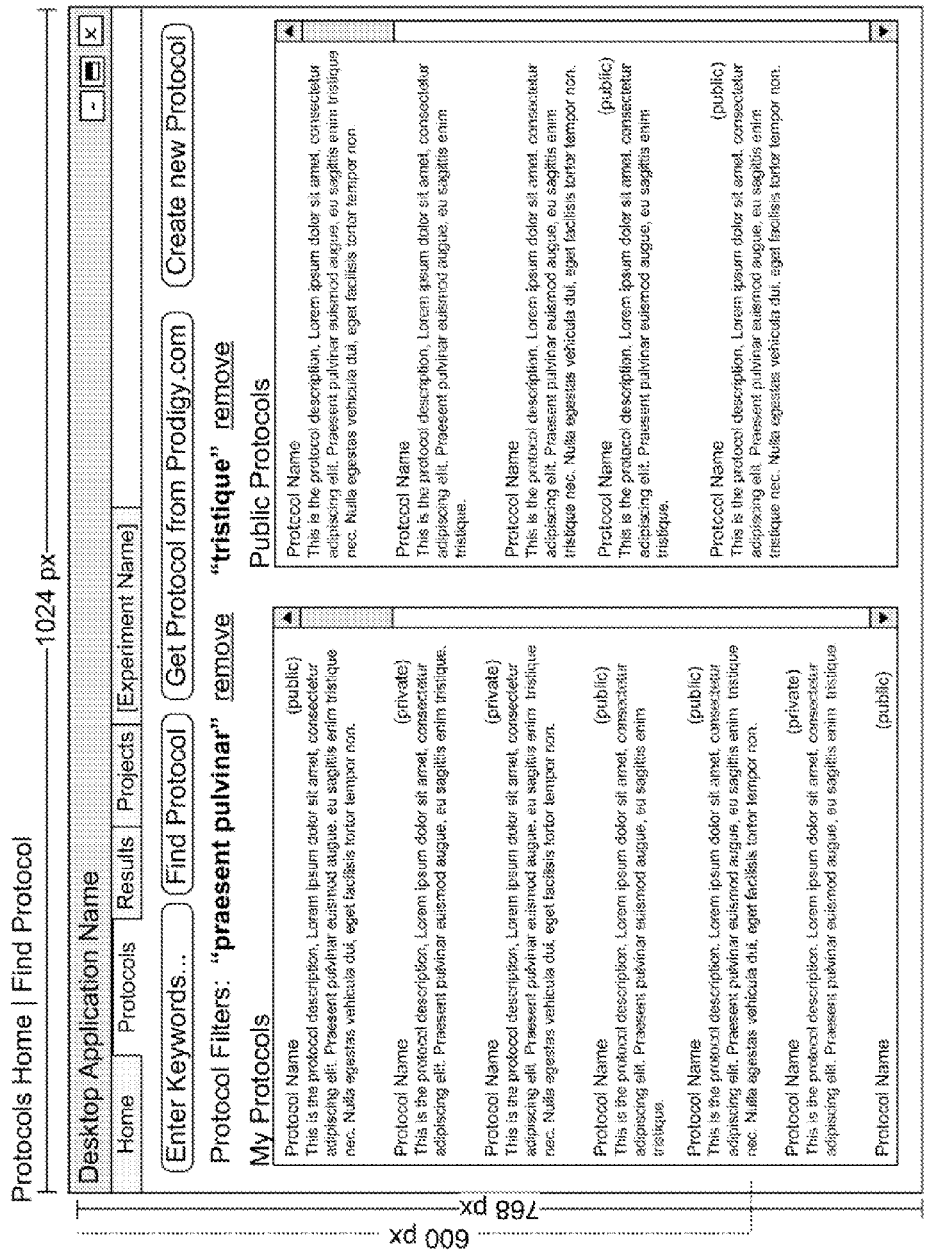
Figure 52:
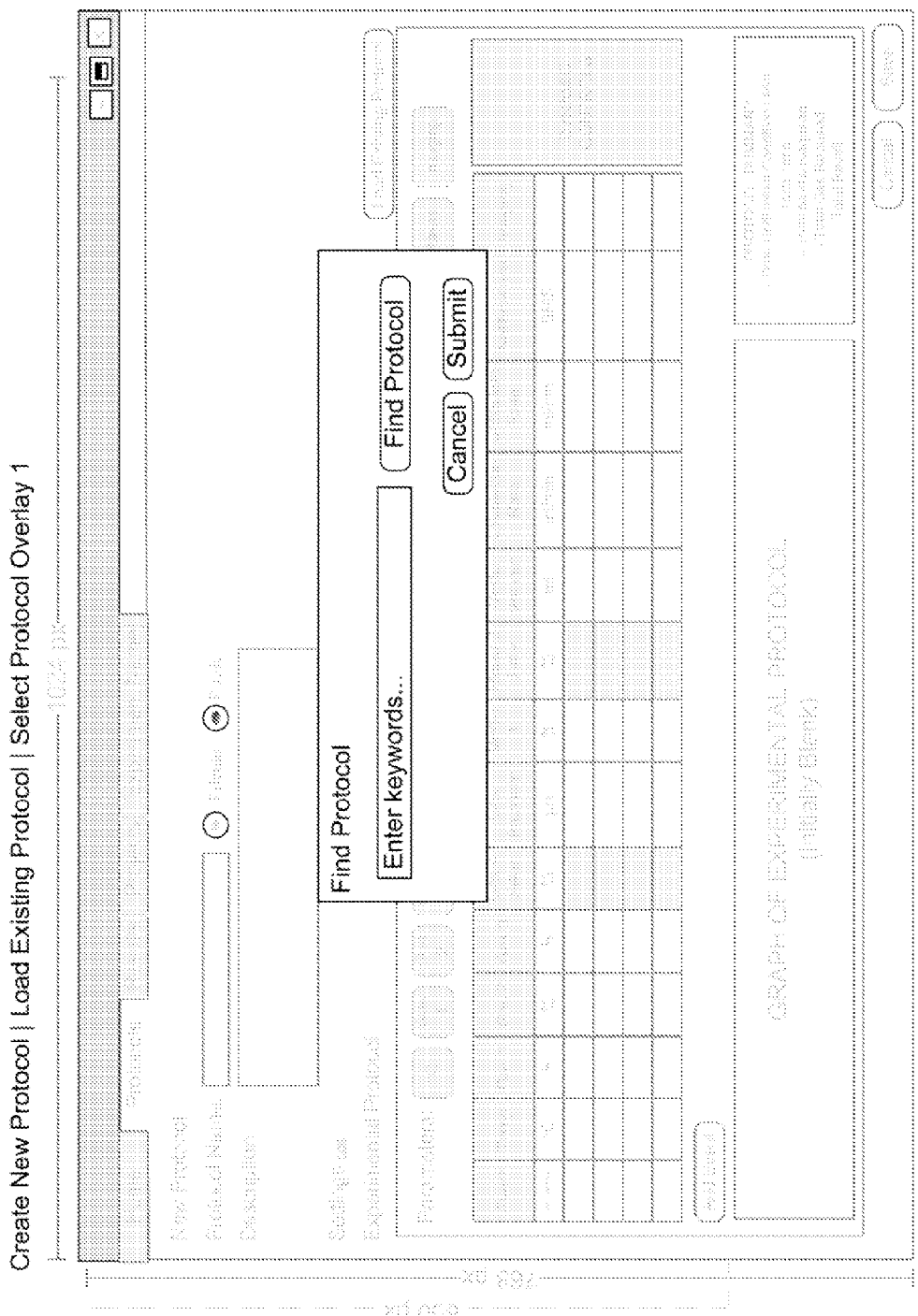
Figure 53:
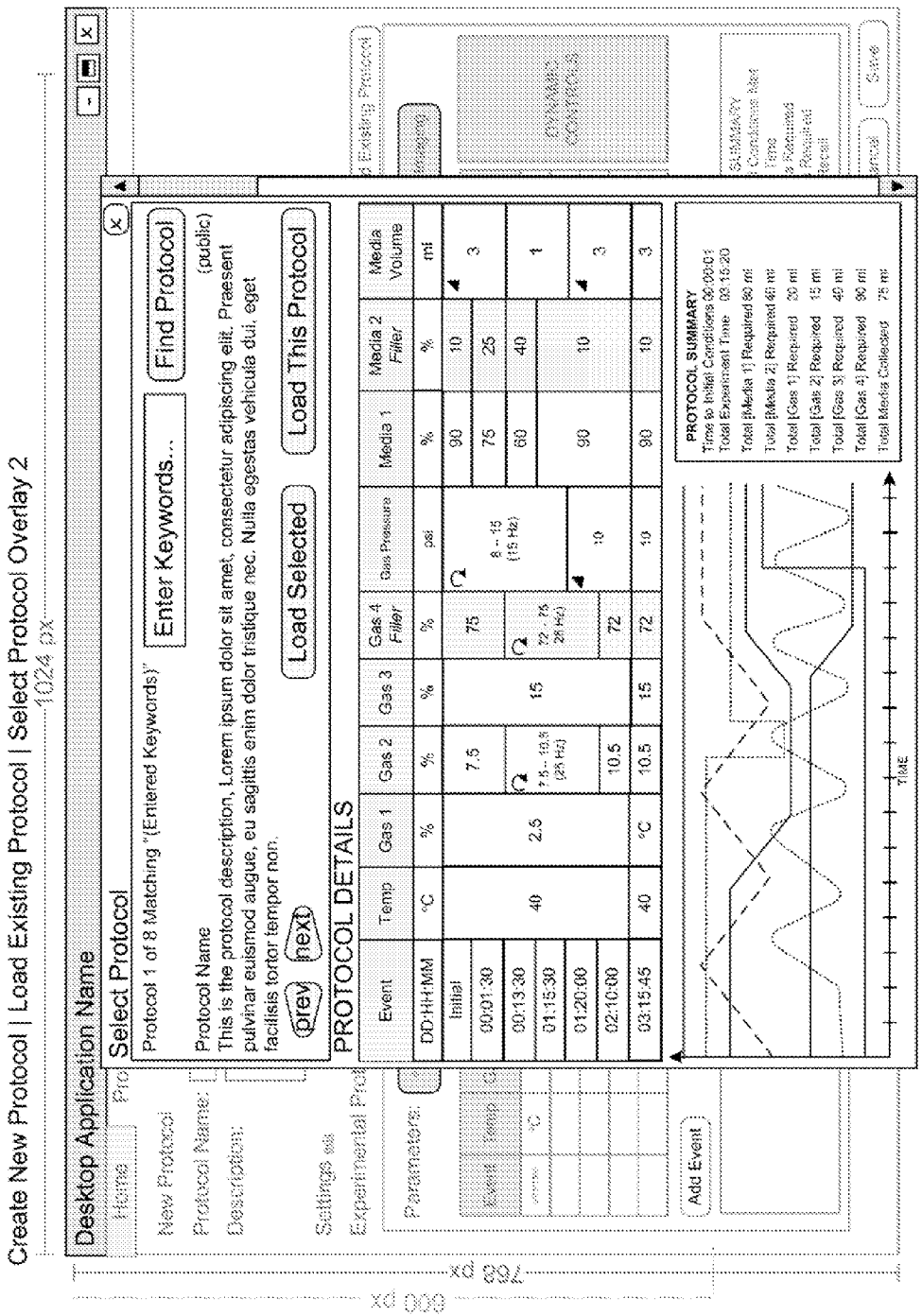
Figure 54:
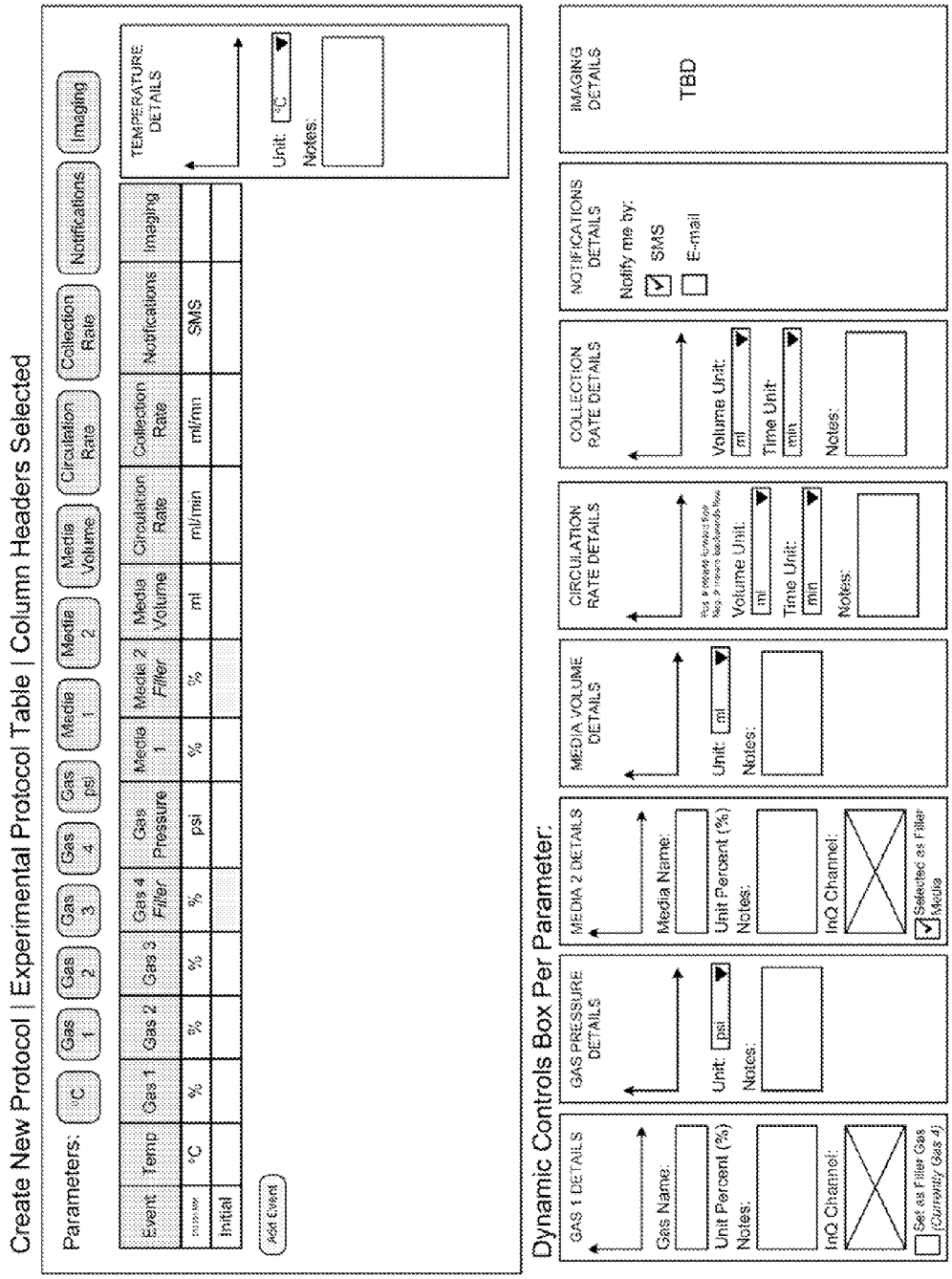
Figure 59:
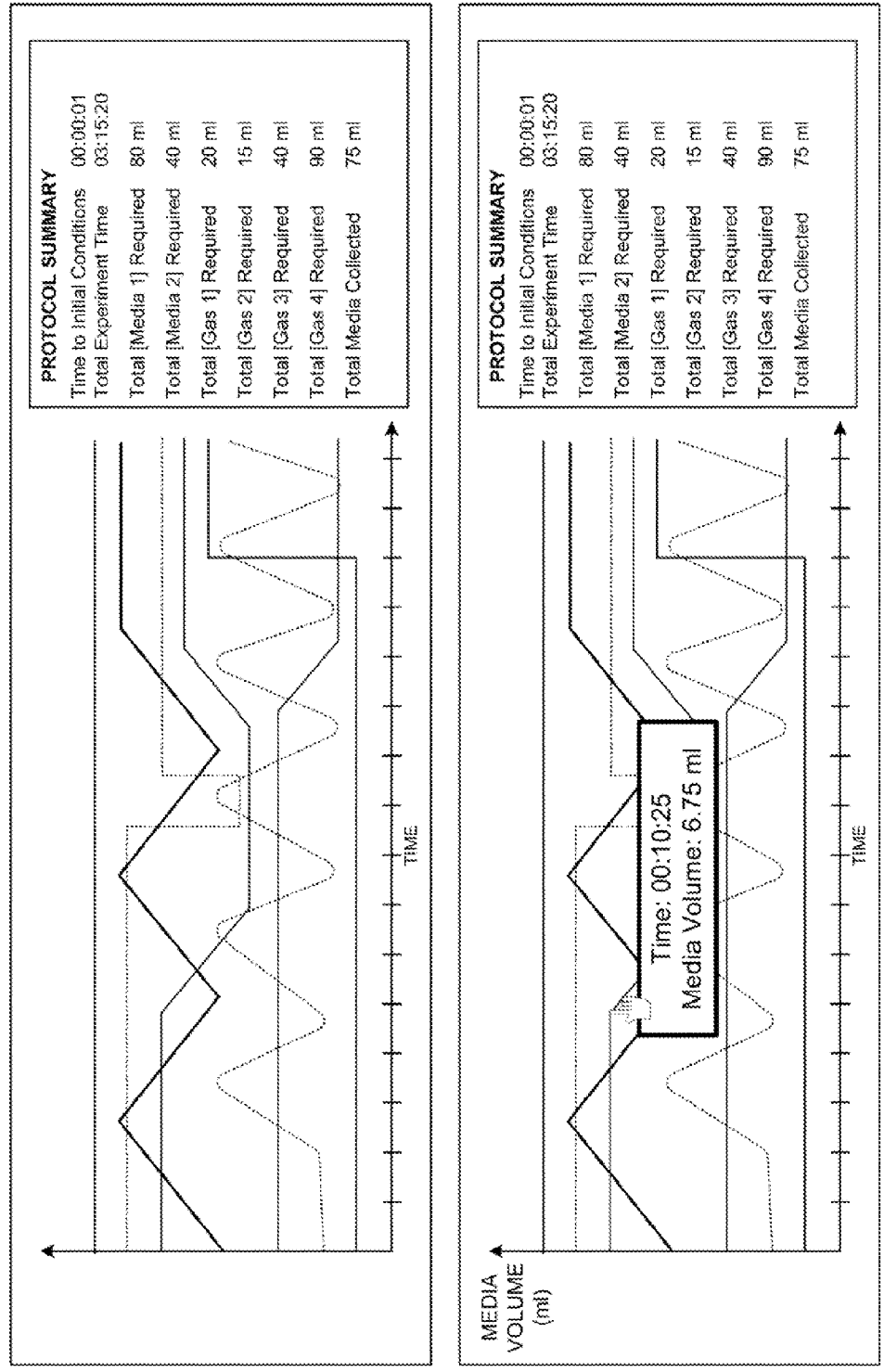
Figure 60:
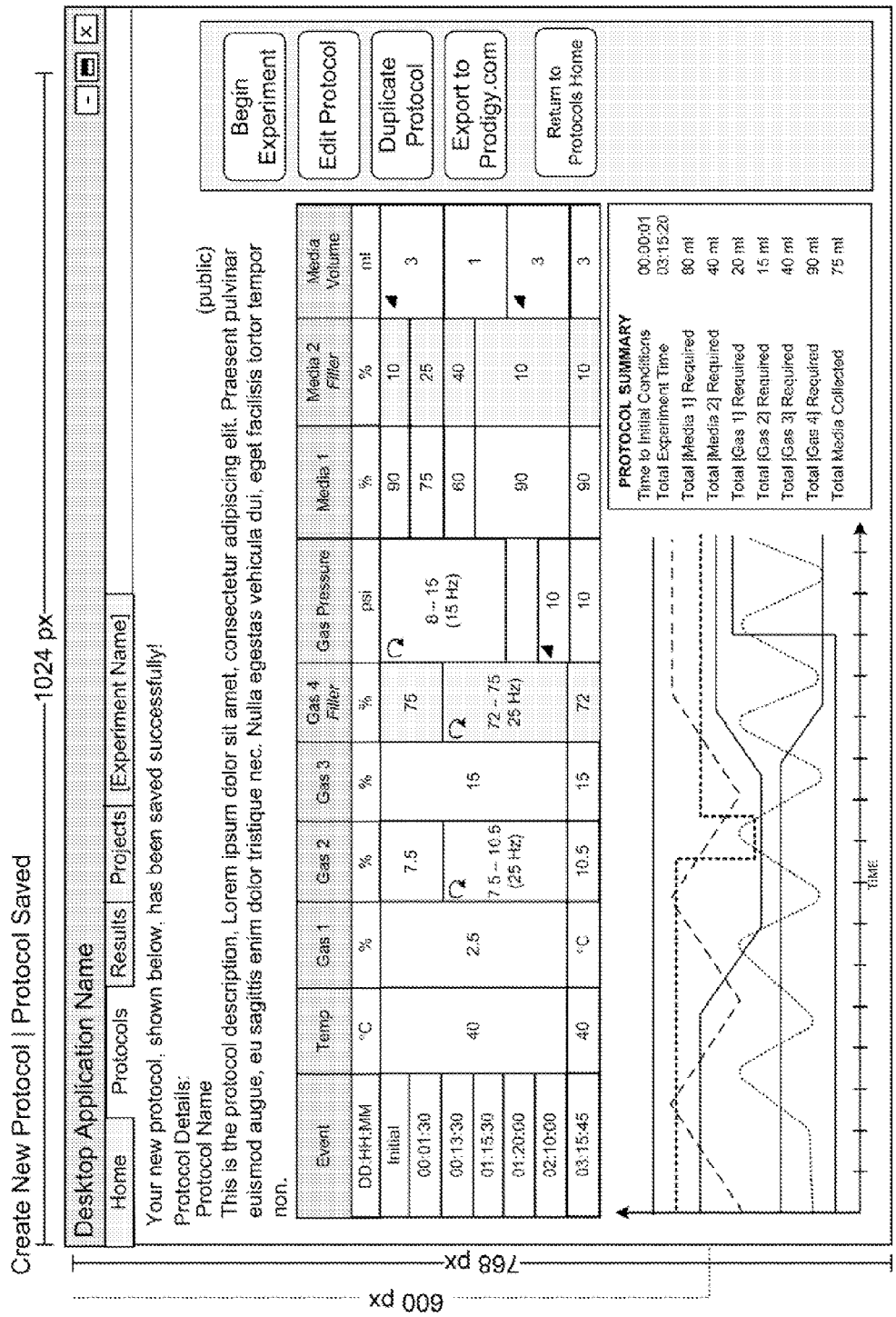
Figure 61:
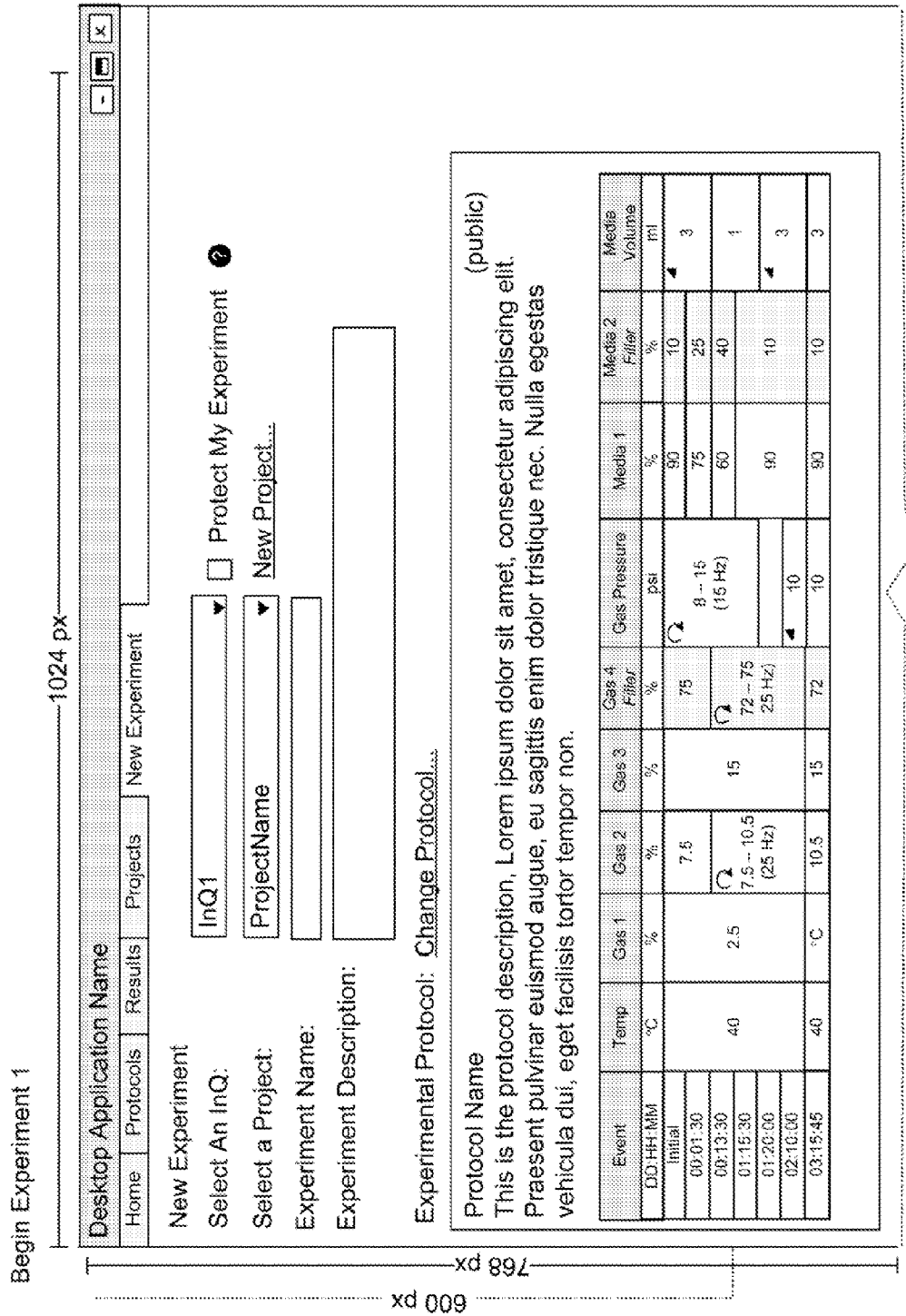
FIGS. 61-72 are screenshots of a protocol execution portion of a user interface used to interact with a culture system, according to one illustrated embodiment.
Figure 62:
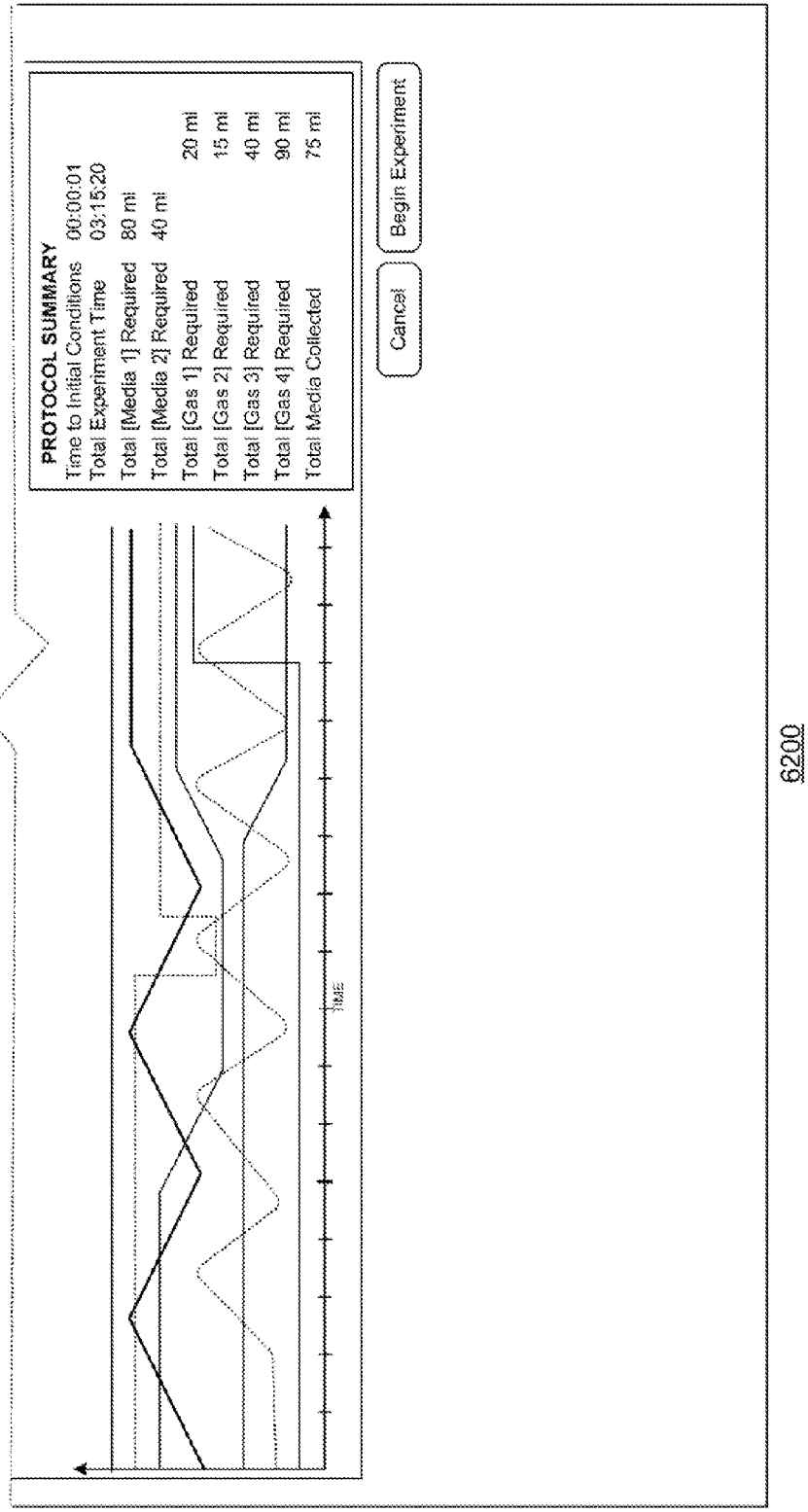
Figure 63:
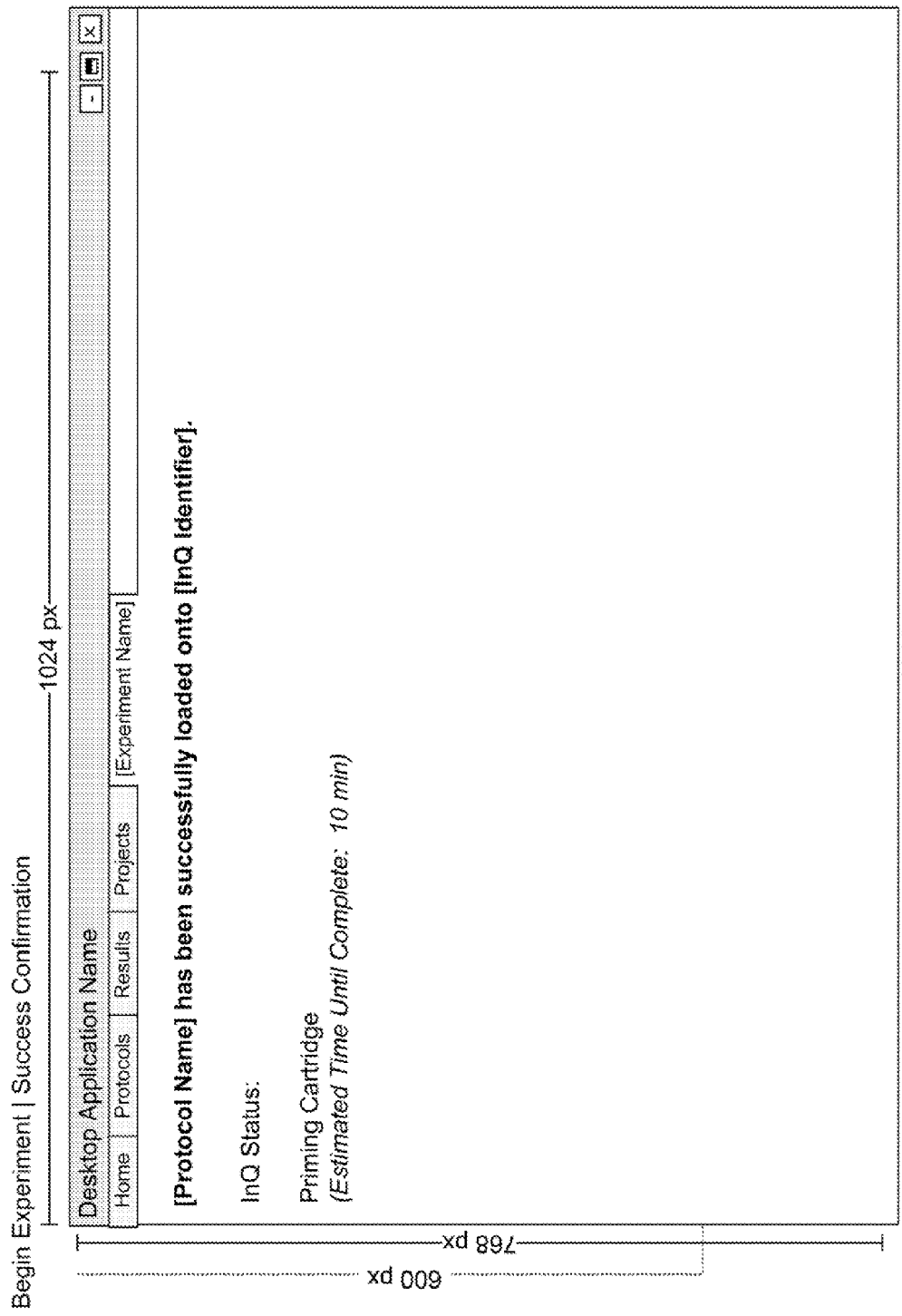
Figure 64:
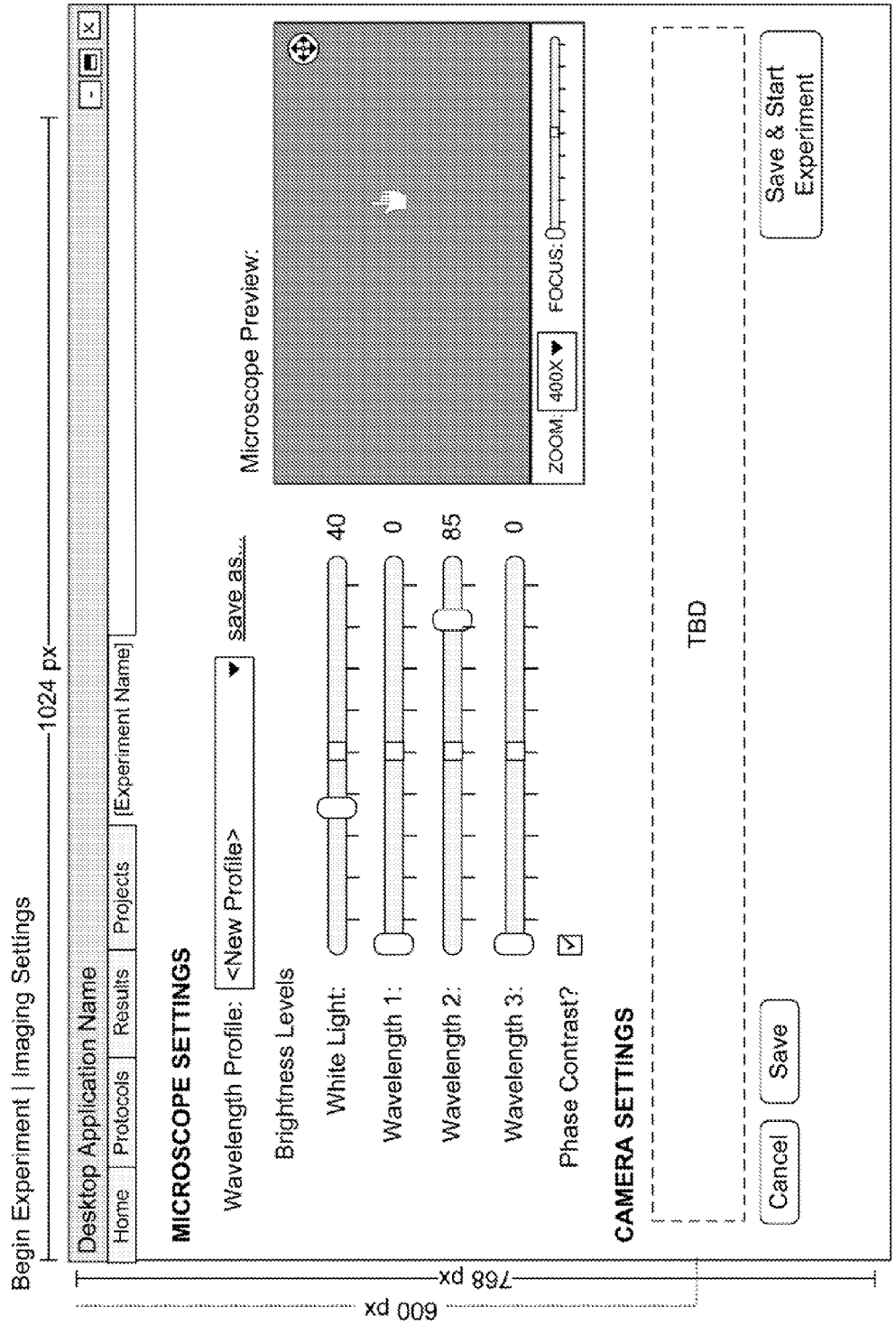
Figure 65:
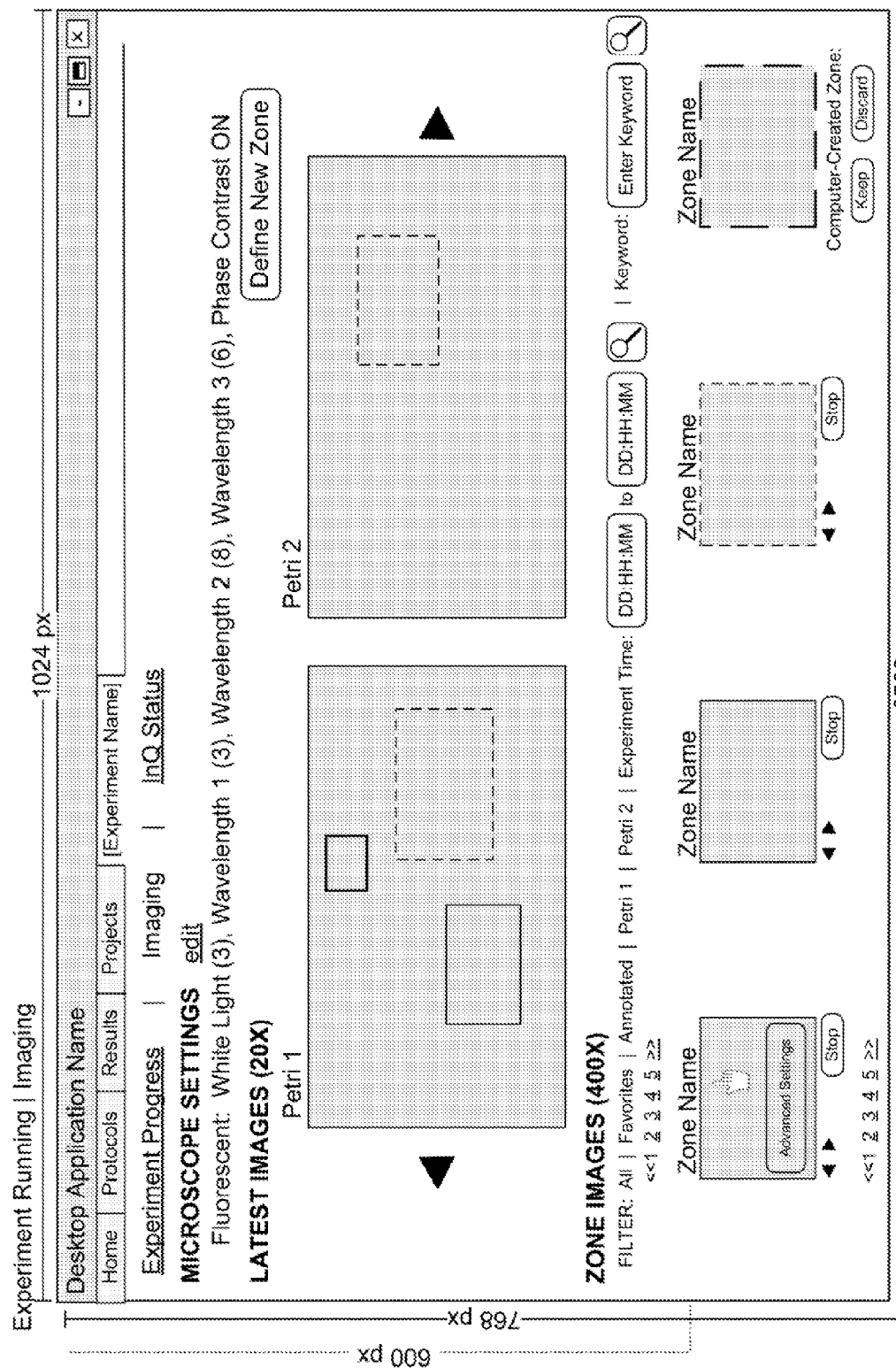
Figure 66:
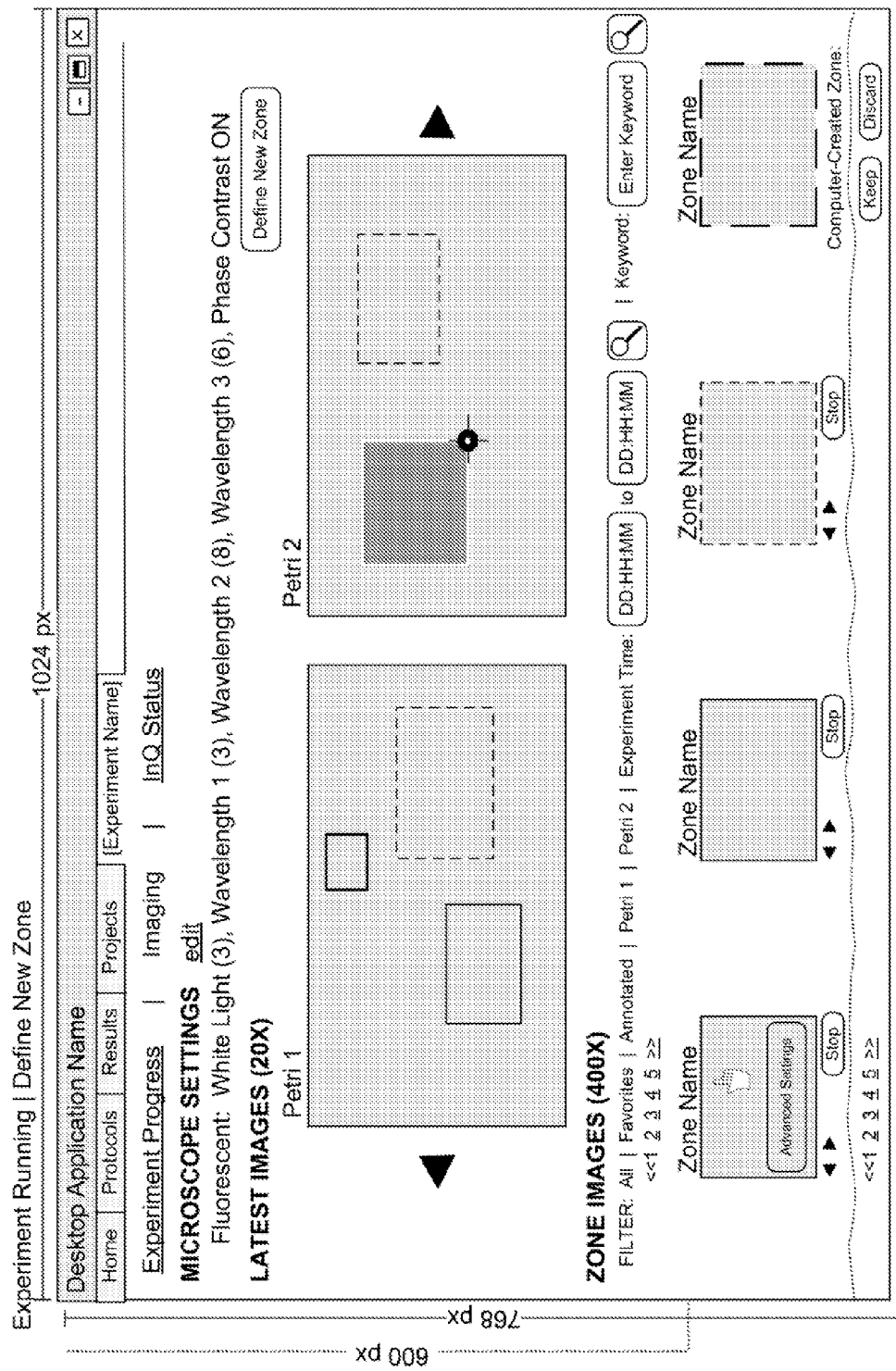
Figure 67:
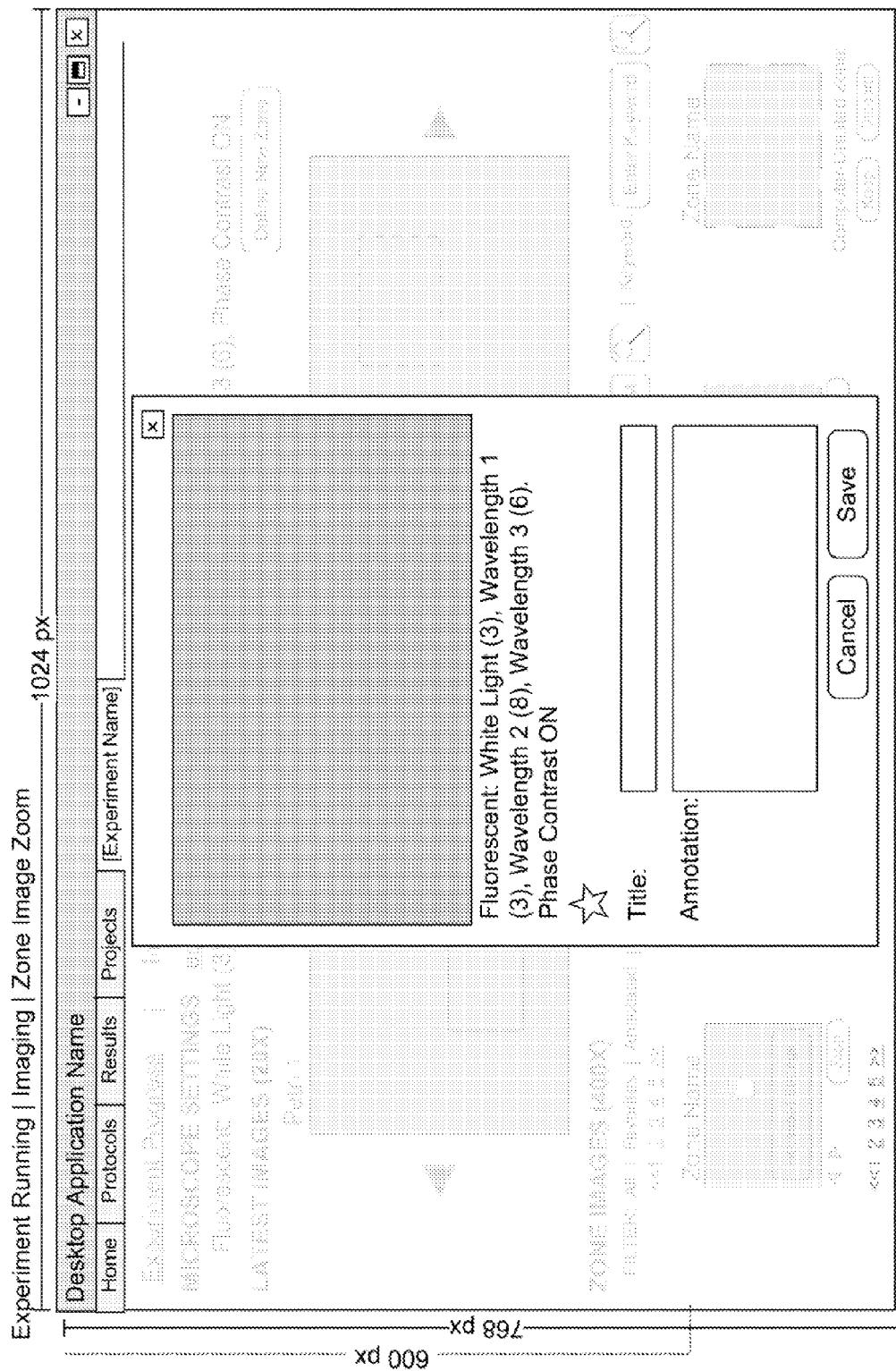
Figure 68:
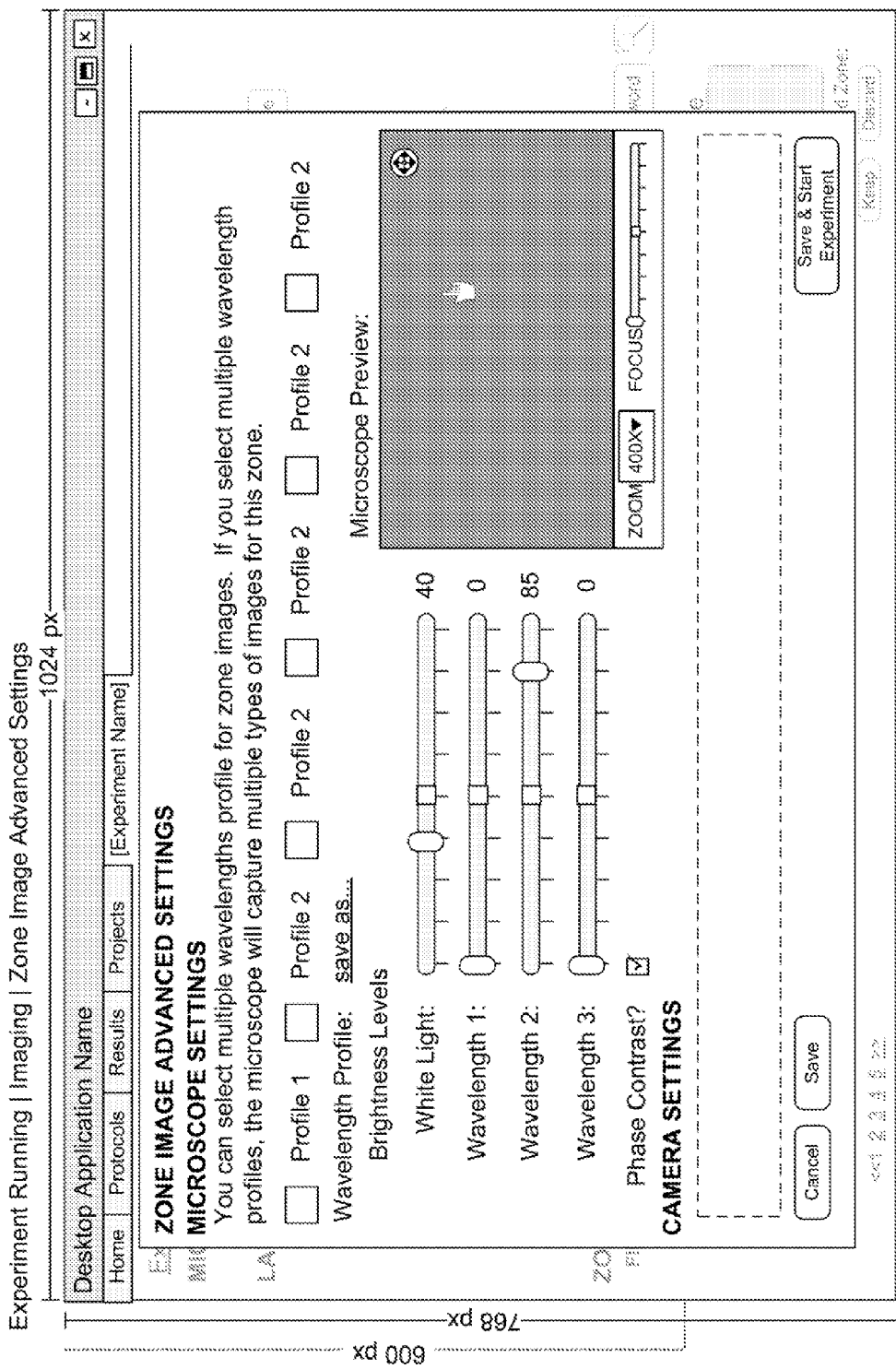
Figure 69:
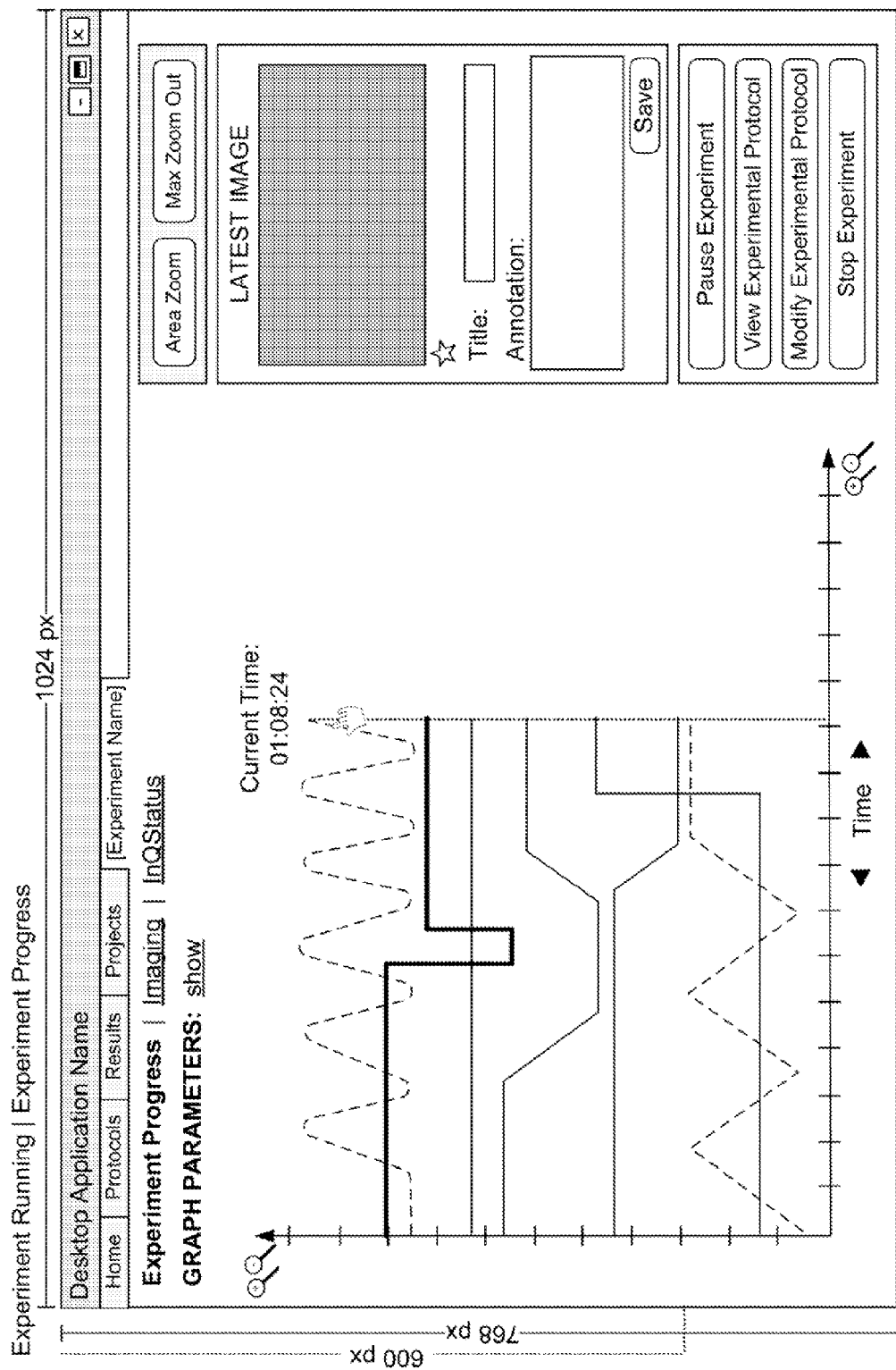
Figure 70:
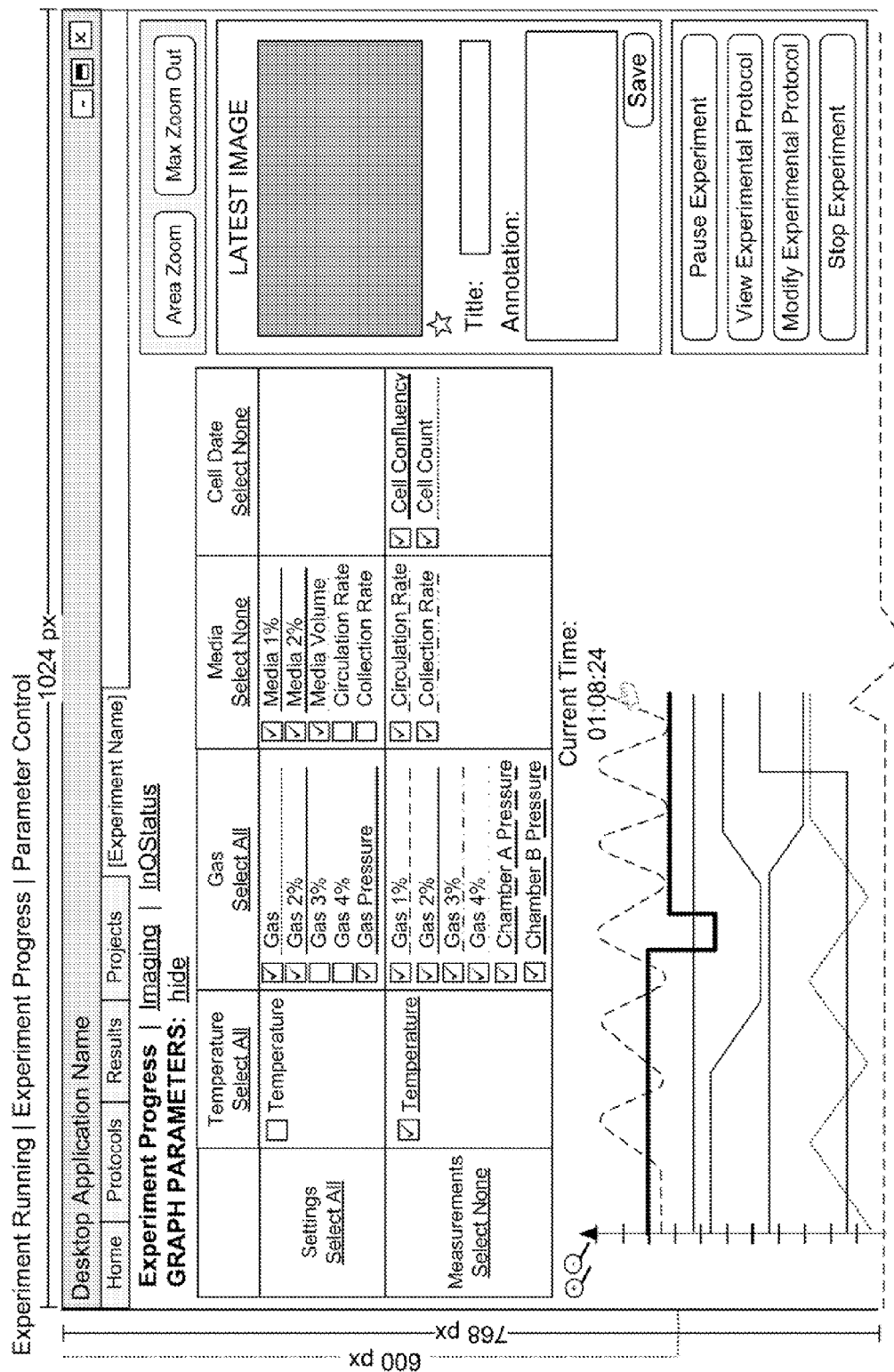
Figure 71:
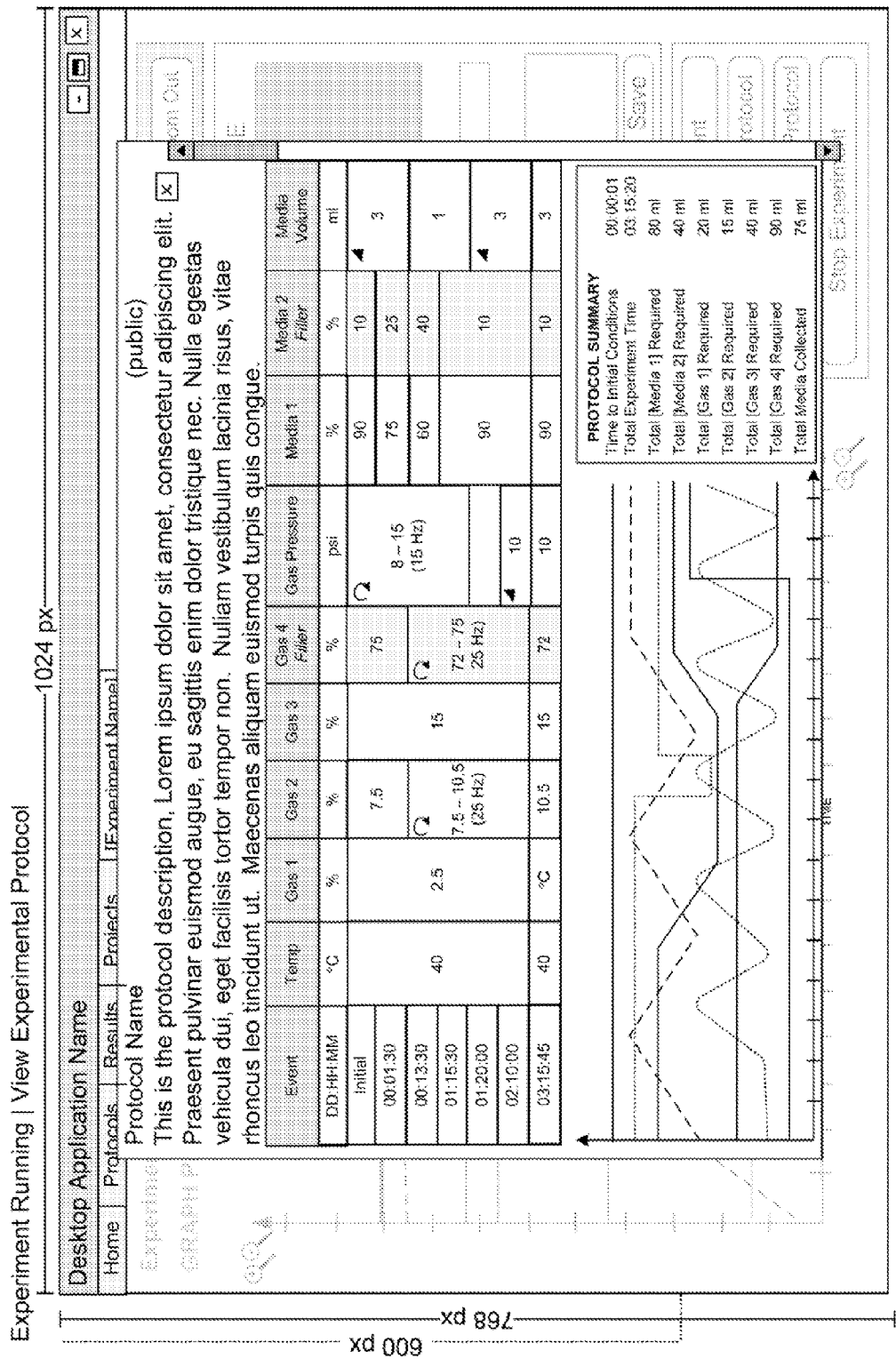
Figure 72:
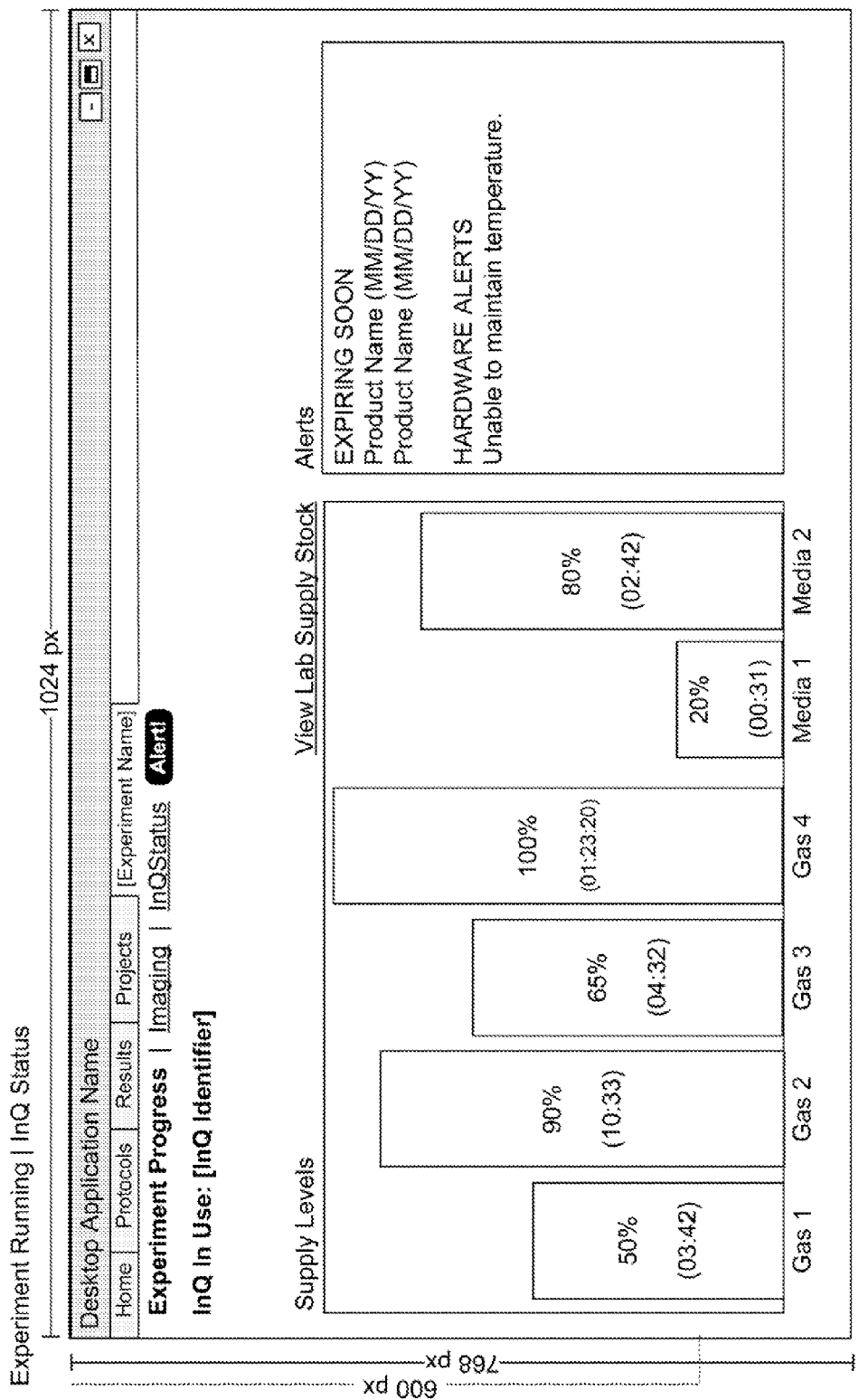
Figure 73:
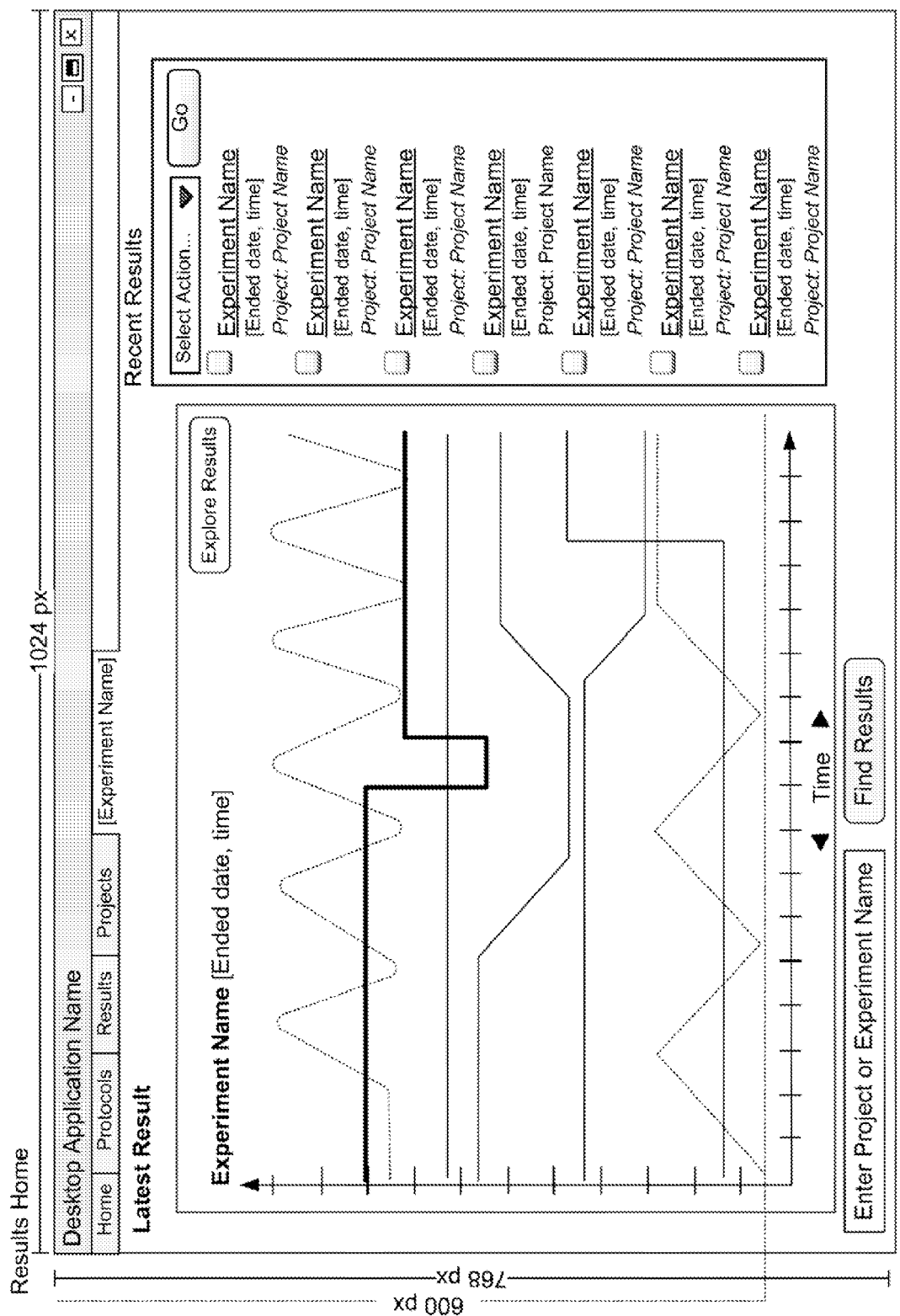
Figure 76:
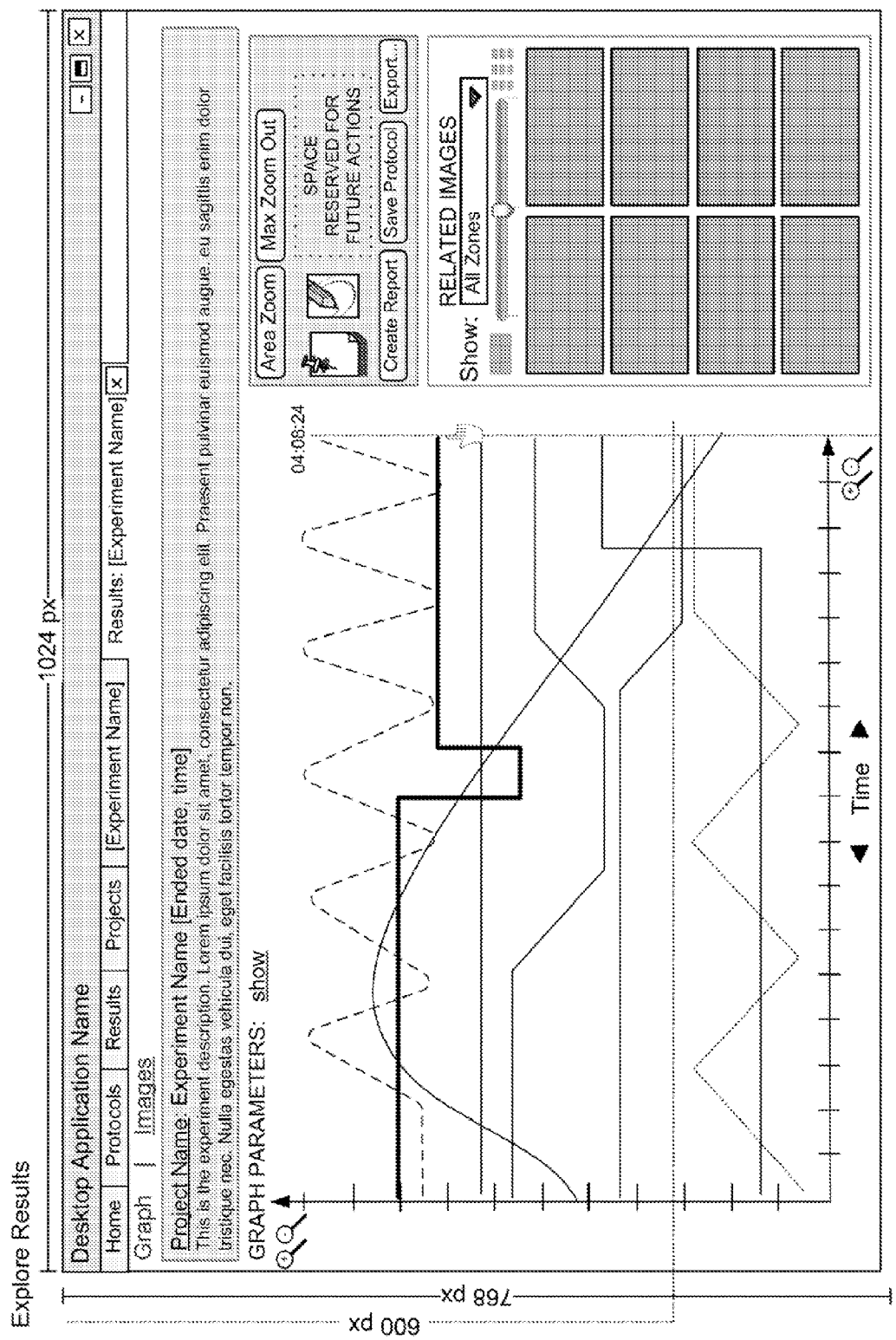
Figure 77:
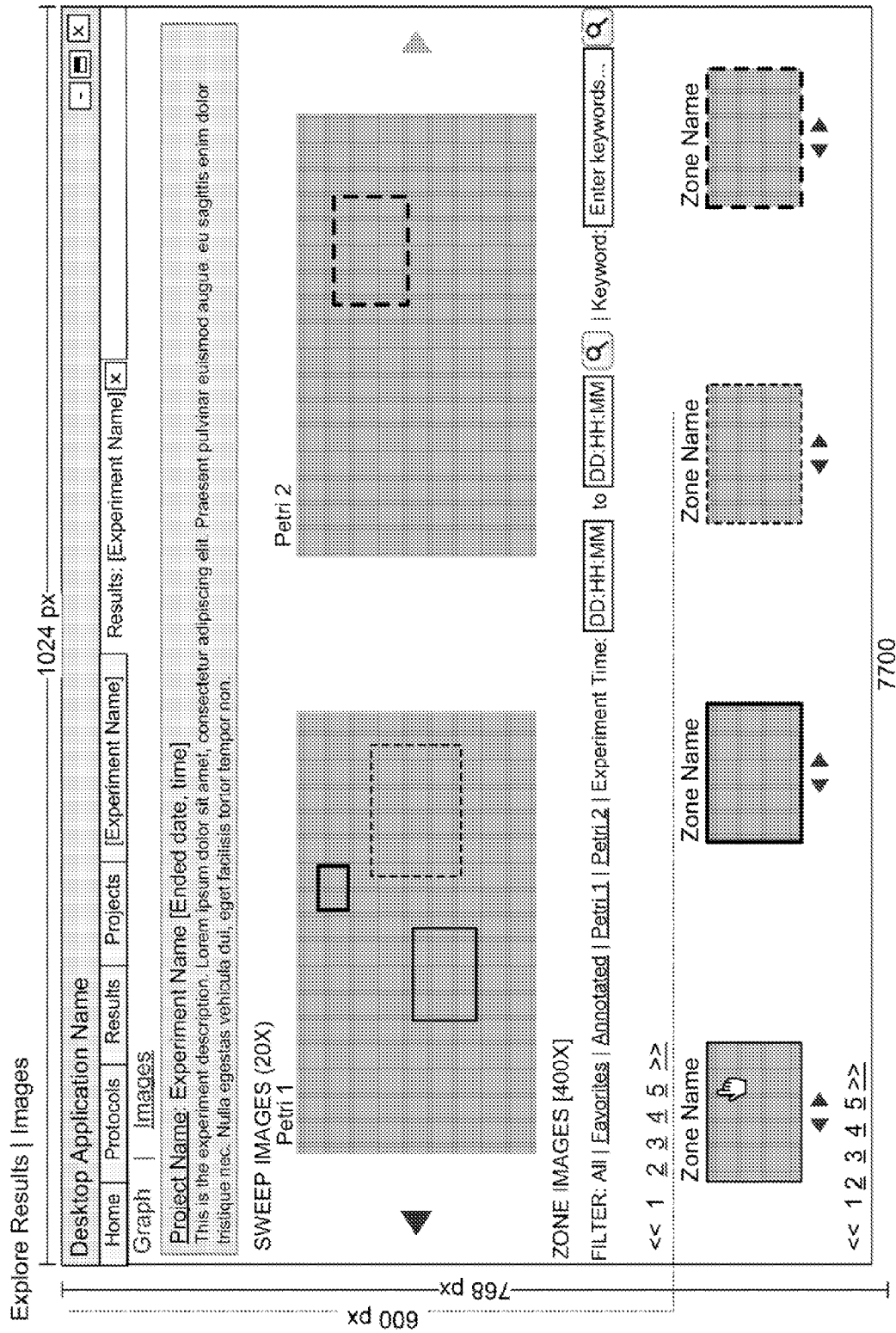
Figure 78:
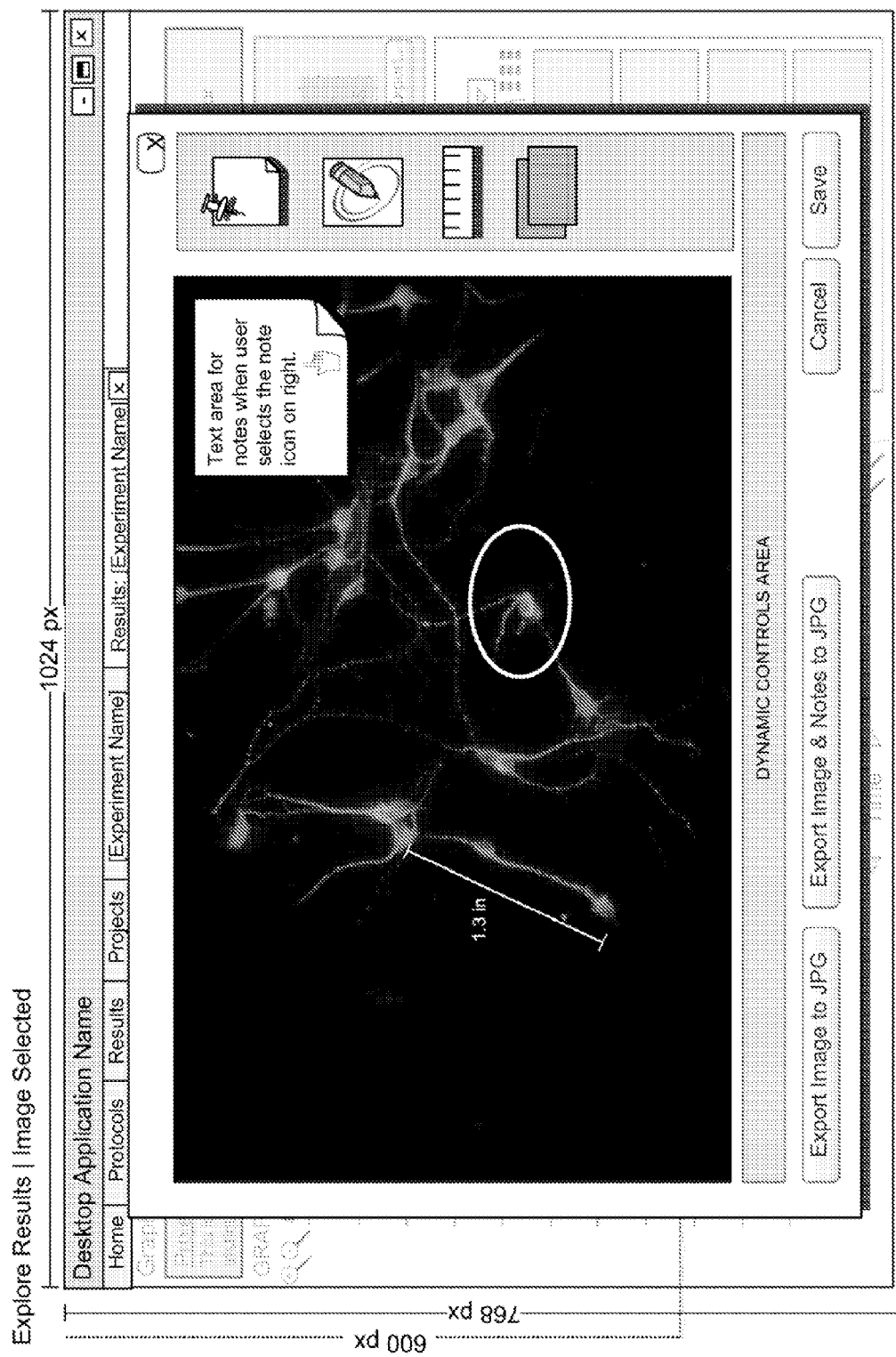
Figure 79:
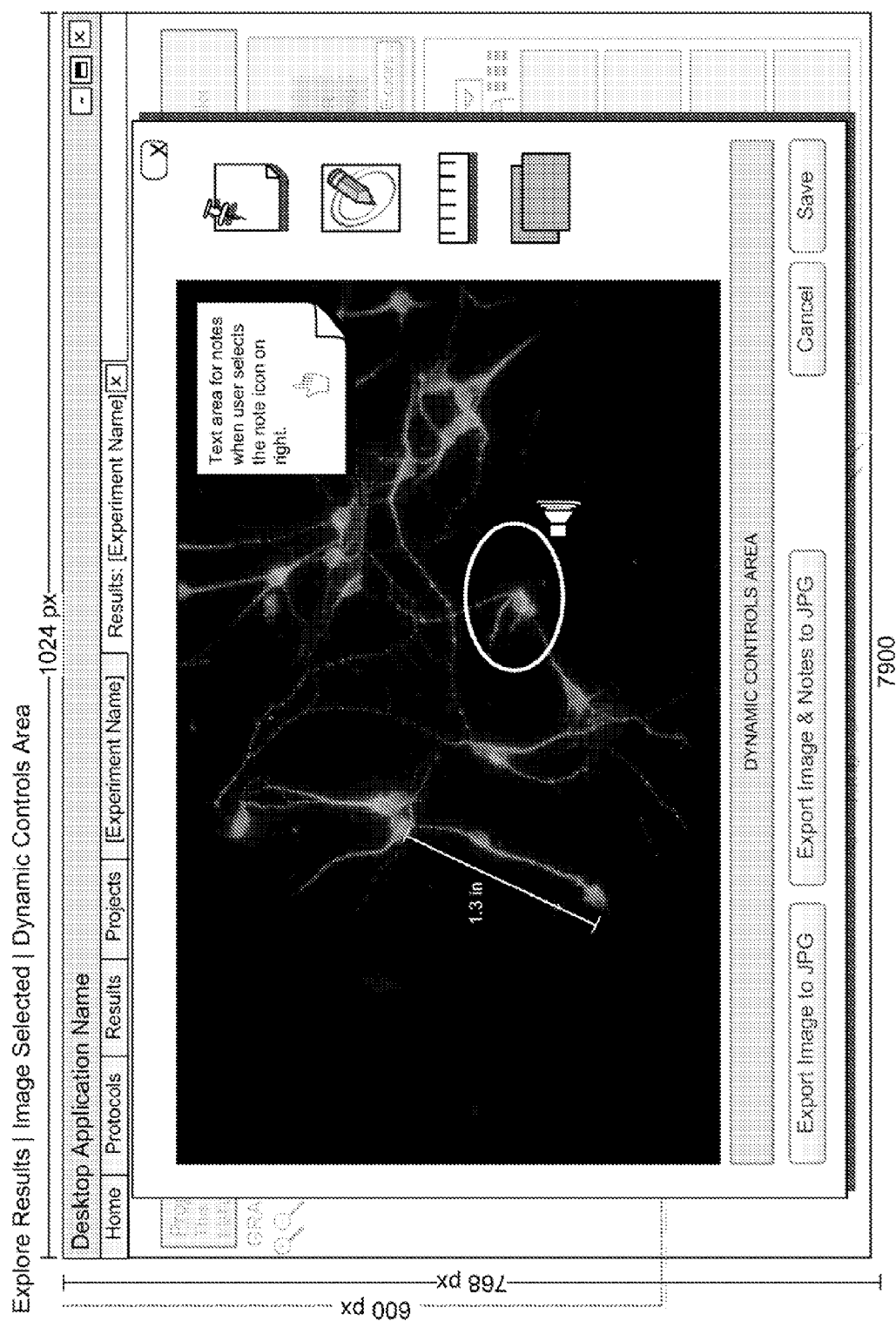
Figure 80:
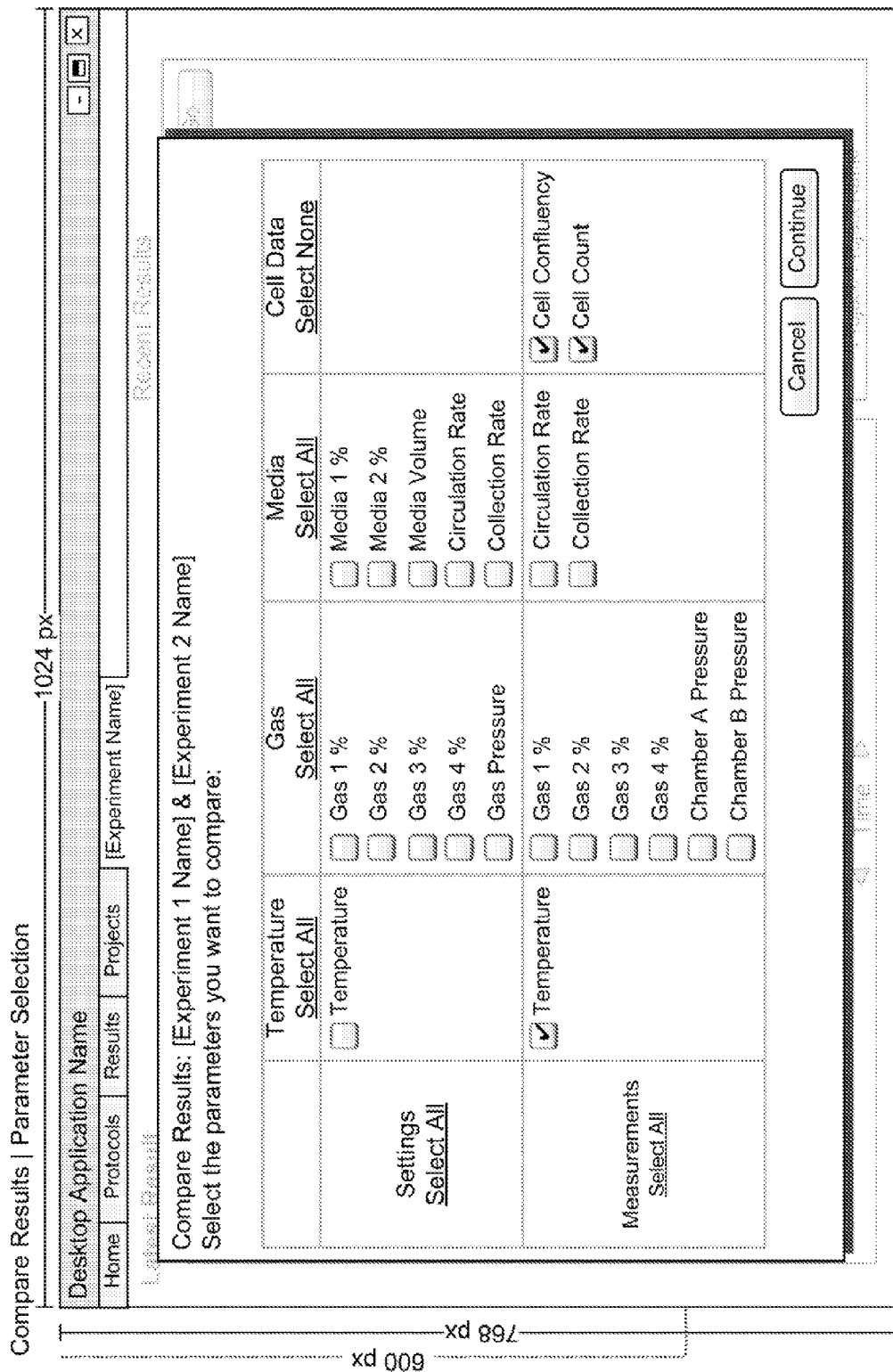
Figure 81:
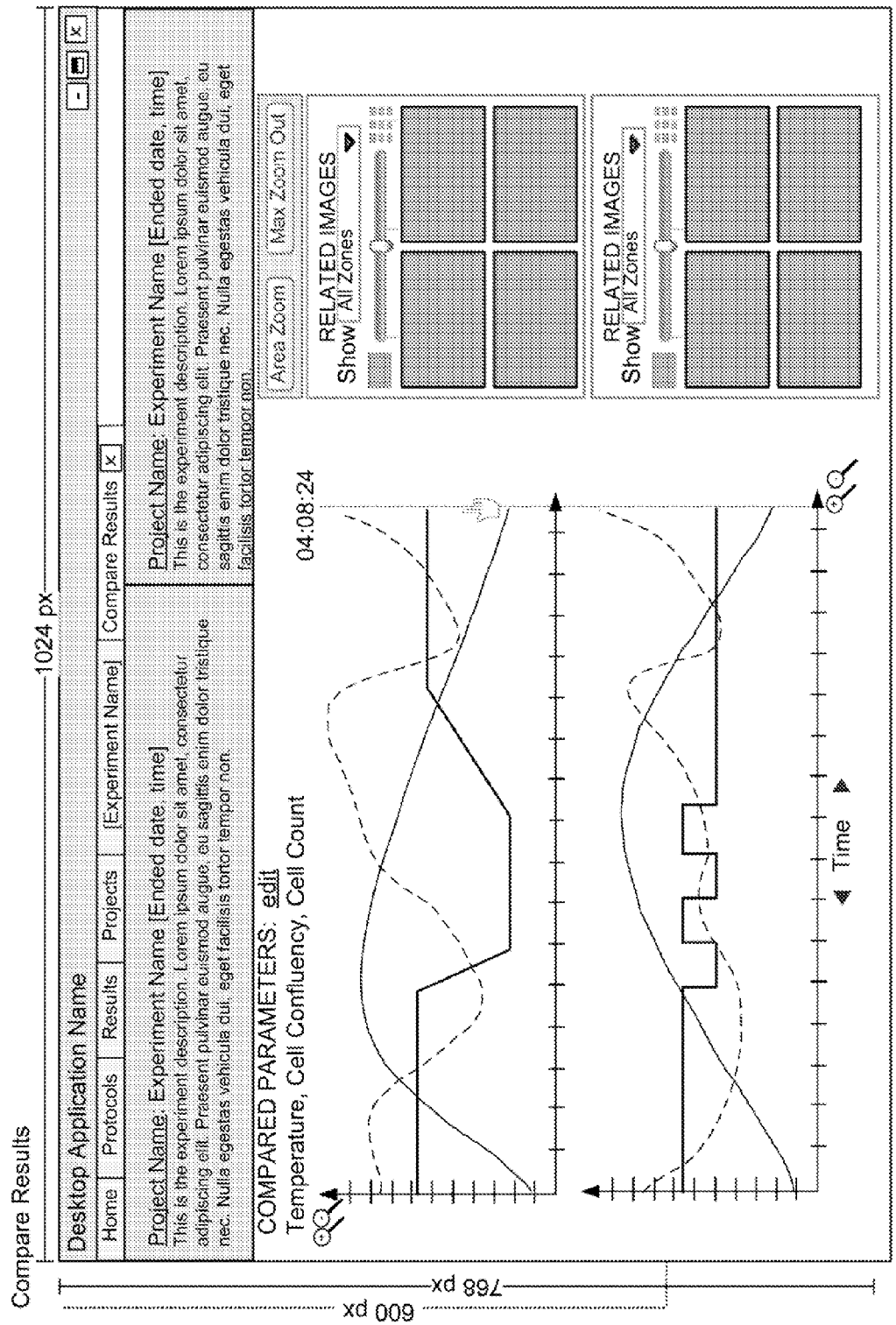

FIG. 47 shows a kit 4700 for use with a culture system 102, 3500, according to one illustrated embodiment.

A kit may be provided for performing defined culturing protocols using the culture system 102, 3500. The kit may provide all needed materials, or at least some of the material required to perform the defined culturing protocol. The materials may be packaged together, to conveniently allow an end user to obtain the necessary materials in the required quantities, preferably without significant waste. In addition to being convenient, such may reduce costs associated with performing culturing protocols. Such may additionally, or alternatively reduce waste associated with performing protocols since only the required amounts of materials are provided.

The kit 4700 may include one or more removable multi-well growth cassettes 4702 sized and dimensioned to be received by a growth cassette receiver of the culture system 102, 3500. The growth cassette 4702 may include a plurality of wells and/or subwells. The wells and/or subwells may include or hold various coatings or materials. The coatings or material may be specific to a given defined culturing protocol or may be generic to a large number of different culturing protocols. The coatings or material may be preloaded or deposited into the wells and/or subwells prior to sale of the kit 4700, for example being loaded by a manufacturer or distributor of the kit 4700.

The multi-well growth cassette 4702 may include one or more data carriers (collectively 4704) that store or encode data or other information. For example, the multi-well growth cassette 4702 may include one or more machine-readable symbols 4704a and/or RFID transponders 4704b. The data carriers 4704 may, for example, encode a unique identifier that uniquely identifies the multi-media growth cassette 4702. The unique identifier may be used to obtain additional information about the multi-well growth cassette via a database, for example contents type and/or quantity, manufacturer, sale or manufacturing date, history of use. Additionally, or alternatively, the data carriers 4704 may encode data or other information indicative of the contents of the multi-well growth cassette 4702 and/or a history of use of same. Additionally, or alternatively, the data carriers 4704 may encode data or other information to authenticate the growth cassette 4702 to the culture system 102, 3500, for example a key, token or other security mechanism. The multi-well growth cassette 4702 may optionally include one or more controllers 4706 (e.g., microprocessor, programmable gate array, application specific integrated circuit) capable of executing instructions. The controller 4706 may perform some growth cassette monitoring operations and/or may interoperate with the culture system 102, 3500 to authenticate or otherwise verify or authorized use of the multi-well growth cassette 4702 with the culture system 102, 3500.

The kit 4700 may include one or more removable media cartridges 4712a-4712d (four illustrated, collectively 4712) sized and dimensioned to be received by a media cartridge receivers of the culture system 102, 3500. The media cartridges 4712 may include a reservoir (e.g., bag, bladder, container) to hold media. The types and/or quantities of media may be specific to a given defined culturing protocol or may be generic to a large number of different culturing protocols. The media may be preloaded or deposited into the media cartridges 4712 prior to sale of the kit 4700, for example being loaded by a manufacturer or distributor of the kit 4700.

The media cartridges 4712 may include one or more data carriers (collectively 4714) that store or encode data or other information. For example, the media cartridges 4712 may include one or more machine-readable symbols 4714a and/or RFID transponders 4714b. The data carriers 4714 may, for example, encode a unique identifier that uniquely identifies the media cartridges 4712. The unique identifier may be used to obtain additional information about the media cartridge 4712 via a database, for example contents type and/or quantity, manufacturer, sale or manufacturing date, history of use and reuse. Additionally, or alternatively, the data carriers 4714 may encode data or other information indicative of the contents of the media cartridges 4712 and/or a history of use of same. Additionally, or alternatively, the data carriers 4714 may encode data or other information to authenticate the media cartridge 4712 to the culture system 102, 3500, for example a key, token or other security mechanism. The media cartridges 4712 may optionally include one or more controllers 4716 (e.g., microprocessor, programmable gate array, application specific integrated circuit) capable of executing instructions. The controller 4716 may perform some media cartridge monitoring operations such as monitoring the current contents thereof, and/or may interoperate with the culture system 102, 3500 to authenticate or otherwise verify or authorized use of the media cartridges 4712 with the culture system 102, 3500.

The kit 4700 may include one or more removable gas canisters 4722a-4712d (four illustrated, collectively 4722) sized and dimensioned to be received by gas canister receivers of the culture system 102, 3500. The gas canisters 4722 may include a reservoir (e.g., container) to hold gas. The types and/or quantities of gas may be specific to a given defined culturing protocol or may be generic to a large number of different culturing protocols. The gas may be preloaded or deposited into the gas canisters 4722 prior to sale of the kit 4700, for example being loaded by a manufacturer or distributor of the kit 4700.

The gas canisters 4722 may include one or more data carriers (collectively 4724) that store or encode data or other information. For example, the gas canisters 4722 may include one or more machine-readable symbols 4724a and/or RFID transponders 4724b. The data carriers 4724 may, for example, encode a unique identifier that uniquely identifies the gas canister 4722. The unique identifier may be used to obtain additional information about the gas canister 4722 via a database, for example contents type and/or quantity, starting pressure, manufacturer, sale or manufacturing date, history of use and reuse. Additionally, or alternatively, the data carriers 4724 may encode data or other information indicative of the contents of the gas canisters 4722 and/or a history of use or reuse of same. Additionally, or alternatively, the data carriers 4724 may encode data or other information to authenticate the gas canister 4722 to the culture system 102, 3500, for example a key, token or other security mechanism. The gas canisters 4722 may optionally include one or more controllers 4726 (e.g., microprocessor, programmable gate array, application specific integrated circuit) capable of executing instructions. The controller 4726 may perform some gas canister monitoring operations such as monitoring the current contents thereof, and/or may interoperate with the culture system 102, 3500 to authenticate or otherwise verify or authorized use of the gas canisters 4722 with the culture system 102, 3500.

The kit 4700 may include one or more removable waste cartridges 4732a, 4712b (two illustrated, collectively 4722) sized and dimensioned to be received by waste cartridge receivers of the culture system 102, 3500. The waste cartridges 4732 may include a reservoir (e.g., bag, bladder, container) to hold waste. The quantities of waste to be held or accumulated may be specific to a given defined culturing protocol or may be generic to a large number of different culturing protocols. The waste cartridges typically start out empty, and waste is collected or accumulated during performance of a culturing protocol by the culture system 102, 3500.

The waste cartridges 4732 may include one or more data carriers (collectively 4734) that store or encode data or other information. For example, the waste cartridges 4732 may include one or more machine-readable symbols 4734a and/or RFID transponders 4734b. The data carriers 4734 may, for example, encode a unique identifier that uniquely identifies the waste cartridges 4732. The unique identifier may be used to obtain additional information about the waste cartridge 4732 via a database, for example size, manufacturer, sale or manufacturing date, history of use and/or reuse. Additionally, or alternatively, the data carriers 4734 may encode data or other information indicative of the size of the waste cartridge 4732 and/or a history of use or reuse of same. Additionally, or alternatively, the data carriers 4714 may encode data or other information to authenticate the waste cartridge 4732 to the culture system 102, 3500, for example a key, token or other security mechanism. The waste cartridges 4732 may optionally include one or more controllers 4736 (e.g., microprocessor, programmable gate array, application specific integrated circuit) capable of executing instructions. The controller 4736 may perform some waste cartridge monitoring operations such as monitoring the current level or quantity of contents thereof, the remaining capacity thereof, and/or may interoperate with the culture system 102, 3500 to authenticate or otherwise verify or authorized use of the waste cartridges 4732 with the culture system 102, 3500.

The kit 4700 may include one or more dye or stain containers 4742a, 4742b (two illustrated, collectively 4742). The dye or stain containers 4742 may hold dye or stain. The types and/or quantities of dye or stain may be specific to a given defined culturing protocol or may be generic to a large number of different culturing protocols. The dye or stain may be preloaded or deposited into the dye or stain containers 4742 prior to sale of the kit 4700, for example being loaded by a manufacturer or distributor of the kit 4700.

The dye or stain containers 4742 may include one or more data carriers (collectively 4744) that store or encode data or other information. For example, the dye or stain containers 4742 may include one or more machine-readable symbols 4744a and/or RFID transponders 4744b. The data carriers 4744 may, for example, encode a unique identifier that uniquely identifies the dye or stain container 4742. The unique identifier may be used to obtain additional information about the dye or stain container 4742 via a database, for example contents type and/or quantity, manufacturer, sale or manufacturing date, history of use and reuse. Additionally, or alternatively, the data carriers 4744 may encode data or other information indicative of the contents of the dye or stain containers 4742 and/or a history of use or reuse of same. Additionally, or alternatively, the data carriers 4744 may encode data or other information to authenticate the dye or stain container 4742 to the culture system 102, 3500, for example a key, token or other security mechanism. The dye or stain containers 4742 may optionally include one or more controllers (not shown).

The kit 4700 may include one or more reagent containers 4752a, 4752b (two illustrated, collectively 4752), illustrated in form of syringes and needles. The reagent containers 4752 may hold reagent. The types and/or quantities of reagent may be specific to a given defined culturing protocol or may be generic to a large number of different culturing protocols. The reagent may be preloaded or deposited into the reagent containers 4752 prior to sale of the kit 4700, for example being loaded by a manufacturer or distributor of the kit 4700.

The reagent containers 4752 may include one or more data carriers 4754 (only one shown) that store or encode data or other information. For example, the reagent containers 4752 may include one or more machine-readable symbols and/or RFID transponders. The data carriers 4754 may, for example, encode a unique identifier that uniquely identifies the reagent container 4752. The unique identifier may be used to obtain additional information about the reagent container 4752 via a database, for example contents type and/or quantity, manufacturer, sale or manufacturing date, history of use and reuse. Additionally, or alternatively, the data carriers 4754 may encode data or other information indicative of the contents of the reagent containers 4752 and/or a history of use or reuse of same. Additionally, or alternatively, the data carriers 4754 may encode data or other information to authenticate the reagent container 4752 to the culture system 102, 3500, for example a key, token or other security mechanism. The reagent containers 4752 may optionally include one or more controllers (not shown).

The kit 4700 may include one or more non-transitory computer- or processor-readable storage mediums 4762a, 4762b (two illustrated, collectively 4762), illustrated in form of a Flash, USB or thumbnail drive 4762a and a CD-Rom 4762b. The non-transitory computer- or processor-readable storage mediums 4762 may store instructions and/or data or other information which when executed by a control subsystem causes a culturing system 102, 3500 to perform a particular defied culturing protocol. The types and/or quantities of materials supplied as part of the kit 470 may be sufficient to perform the particular defined culturing protocol without excessive waste. The instructions and/or data or other information may be stored on the non-transitory computer- or processor-readable storage mediums 4762 prior to sale of the kit 4700, for example being loaded by a manufacturer or distributor of the kit 4700.

The non-transitory computer- or processor-readable storage media 4762 may include one or more data carriers 4764 (only one shown) that store or encode data or other information. For example, the non-transitory computer- or processor-readable storage media 4762a may include one or more machine-readable symbols and/or RFID transponders. The data carriers 4764 may, for example, encode a unique identifier that uniquely identifies the non-transitory computer- or processor-readable storage media 4762. The unique identifier may be used to obtain additional information about the non-transitory computer- or processor-readable storage media 4762 via a database, for example a specification of the culturing protocol stored therein. Additionally, or alternatively, the data carriers 4764 may encode data or other information indicative of the contents of the non-transitory computer- or processor-readable storage mediums 4762 and/or a history of use or reuse of same. Additionally, or alternatively, the data carriers 4764 may encode data or other information to authenticate the non-transitory computer- or processor-readable storage media 4762 to the culture system 102, 3500, for example a key, token or other security mechanism. The non-transitory computer- or processor-readable storage mediums 4762 may optionally include one or more controllers (not shown).

The information stored on the non-transitory computer- or processor-readable storage mediums 4762 may be encrypted and secured by various other technological mechanisms such as keys, tokens, passwords, etc. Such may ensure that culturing systems will only execute authenticate or authorized culturing protocols. Such may also ensure that the instructions stored on the particular non-transitory computer- or processor-readable storage mediums 4762 will one operate or function with the materials packaged therewith. Such authentication, verification or security functions may be implement by the culturing system and/or by processors associated with the various consumables cassettes, cartridges, canisters or other containers included with the kit 4700.

The kit 4700 may include additional materials. For example, while not illustrated, the kit 4700 may include tissue scaffold material to provide a frame for tissue growth.

Kits 4700 may come in a variety of forms, for different applications. For example, a stem cell optimization kit may, for instance include: a multi-well growth cassette with 24 sections each pre-coated with protein (n=3) at different concentrations (n=8); two media cartridges (with or without cell culture media), a waste cartridge, additional growth media and growth factors, fluorescent dyes, and a first defined culturing protocol stored on a non-transitory computer- or processor-readable storage medium.

Also for example, a stem cell experiment kit may, for instance include: a multi-well growth cassette with wells pre-coating based on results from a previous optimization experiment, two media cartridges (with or without cell culture media), a waste cartridge, additional growth media, cell dissociation reagents, fluorescent dyes, and a second defined culturing protocol stored on a non-transitory computer- or processor-readable storage medium.

Thus, the kit 4700 may, for example, provide all of the necessary components for a 14 day experiment. Which identifies which pre-coating condition is optimal for that cell line. Such makes a complicated experiment simple.

EXAMPLE

In phase 1, the culture system 102, 3500 is programmed to plate feeder cells until attachment is complete. The culture system 102, 3500 can determine the optimal media and coating surface for feeder cells to attach. The culture system 102, 3500 can detect the end point by image analysis, rather than using a fixed time.

In phase 2, once the feeder cells are attached, the highly valuable and rare embryonic stem cell mix culture can be added to the wells and/or subwells. Again, the culture system 102, 3500 can measure and precisely control the environment for cell propagation. The environment settings and growth media can easily be changed between phases 1 and 2 by pre-set programs and switching media cartridges and/or gas canisters. Furthermore, the microscopy system can raster scan image the well and identify stem cell colony formation.

In phase 3, once an embryonic stem cell colony is identified by image scanning, an alert can be sent to the operator or user and the embryonic stem cell colony can be immediately sub-cultured for further growth separate from the feeder cells. Such may, for example, occur in a second multi-well growth cassette.

Since there are three distinct phases: feeder cell attachment, stem cell propagation and stem cell sub-culture growth, each phase may require distinct media, gases and distinct growth factors.

FIGS. 48-60 are screenshots of a protocol definition portion of a user interface 4800 used to interact with a culture system, according to one illustrated embodiment.

The user interface 4800 includes a plurality of screens or displays identified by reference numbers 4800, 4900, 5000,

5100, 5200, 5300, 5400, 5500, 5600, 5700, 5800, 5900, 6000, respectively, with various user selectable icons or controls, entry fields, as well as displays of data, information, text and/or images.

FIGS. 61-72 are screenshots of a protocol execution portion of a user interface 4800 used to interact with a culture system, according to one illustrated embodiment.

The user interface 4800 includes a plurality of screens or displays identified by reference numbers 6100, 6200, 6300, 6400, 6500, 6600, 6700, 6800, 6900, 7000, 7100, 7200, respectively, with various user selectable icons or controls, entry fields, as well as displays of data, information, text and/or images.

FIGS. 73-81 are screenshots of a results portion of a user interface 4800 used to interact with a culture system, according to one illustrated embodiment.

The user interface 4800 includes a plurality of screens or displays identified by reference numbers 7300, 7400, 7500, 7600, 7700, 7800, 7900, 8000, 8100, respectively, with various user selectable icons or controls, entry fields, as well as displays of data, information, text and/or images.

Figure 82:
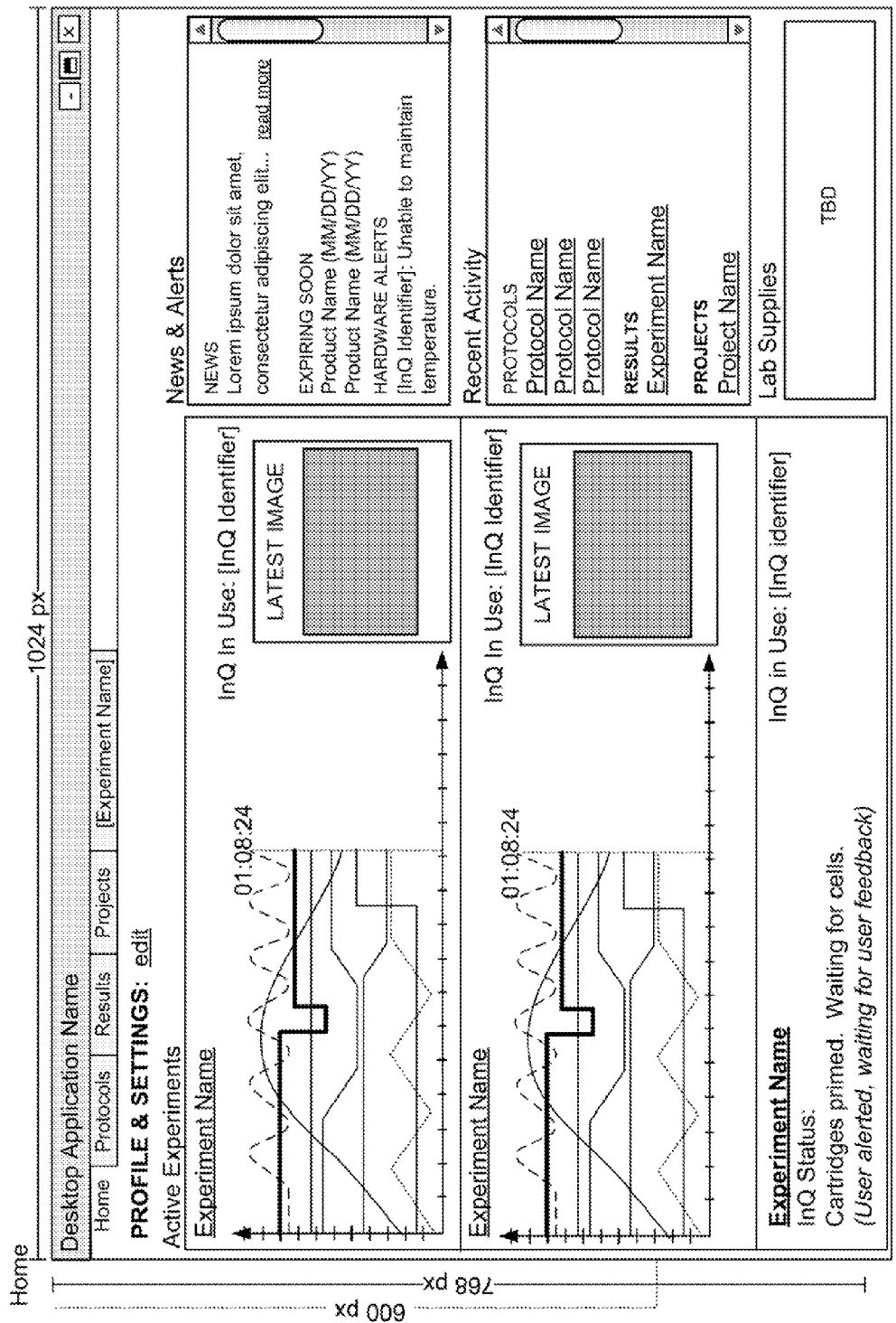
FIGS. 82-83 are screenshots of a home or main menu portion of a user interface used to interact with a culture system, according to one illustrated embodiment.
Figure 83:
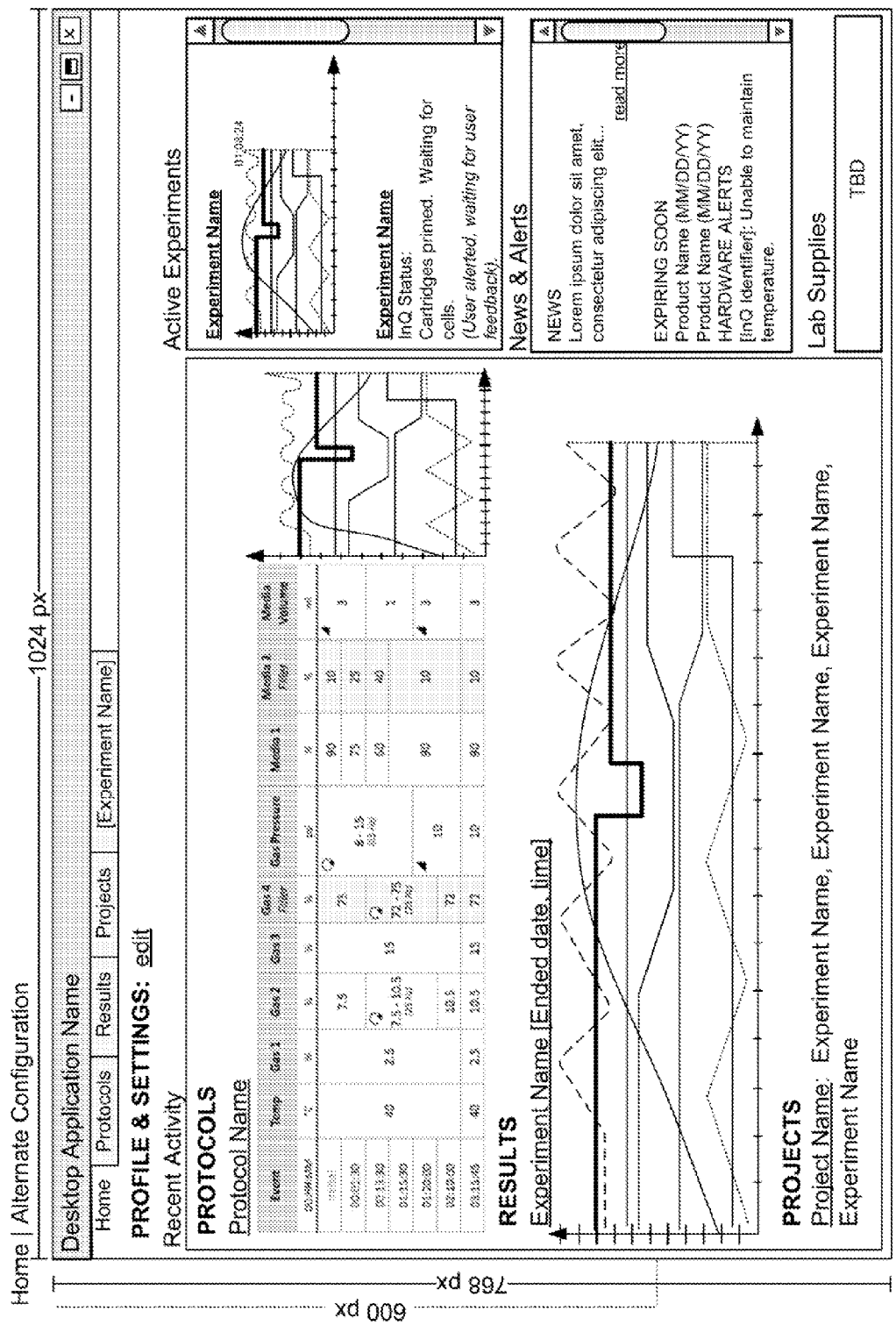

FIGS. 82-83 are screenshots of a home or main menu portion of a user interface used to interact with a culture system, according to one illustrated embodiment.

The user interface 4800 includes a plurality of screens or displays identified by reference numbers 8200, 8300, respectively, with various user selectable icons or controls, entry fields, as well as displays of data, information, text and/or images.

Figure 84:
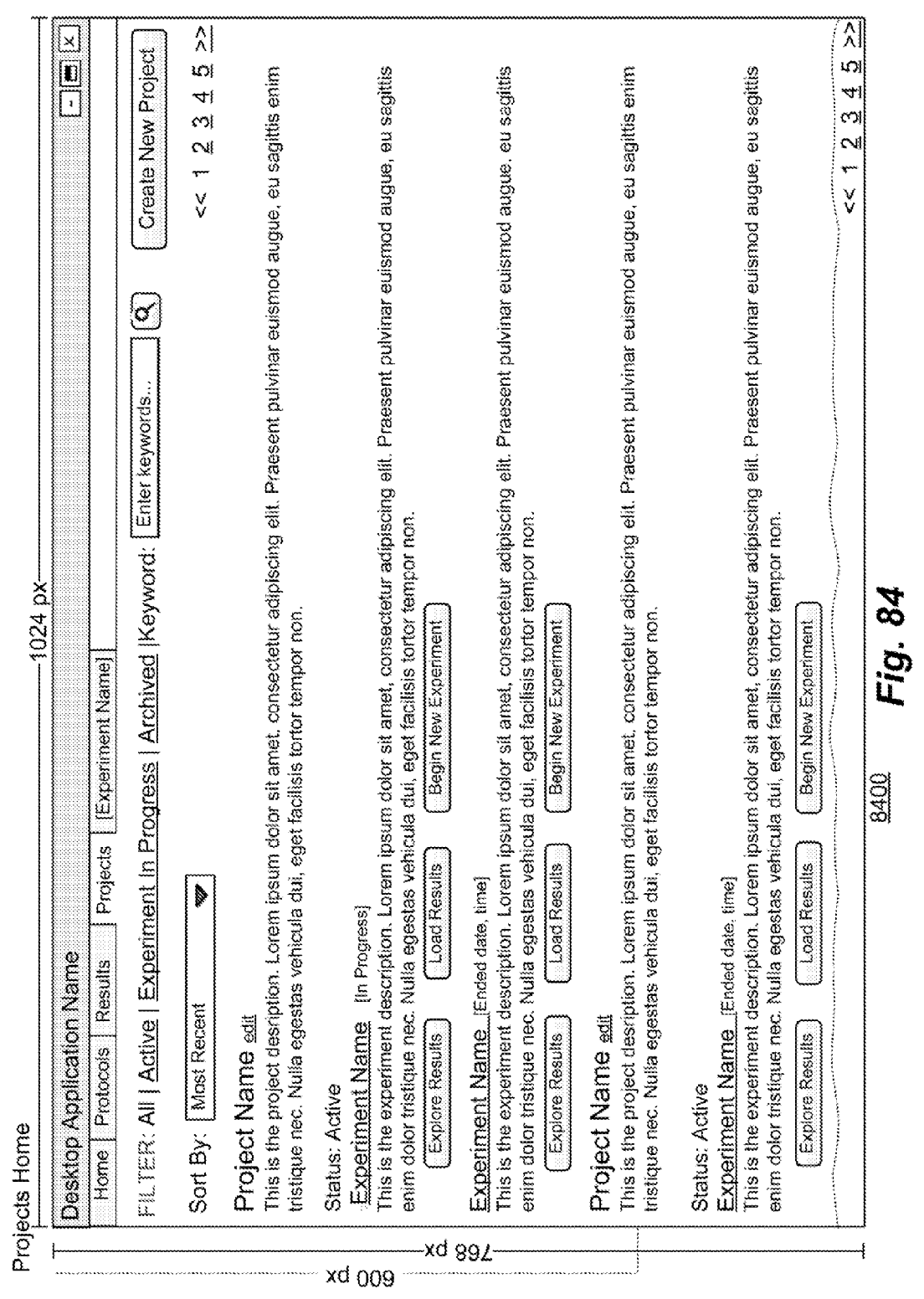
Figure 85:
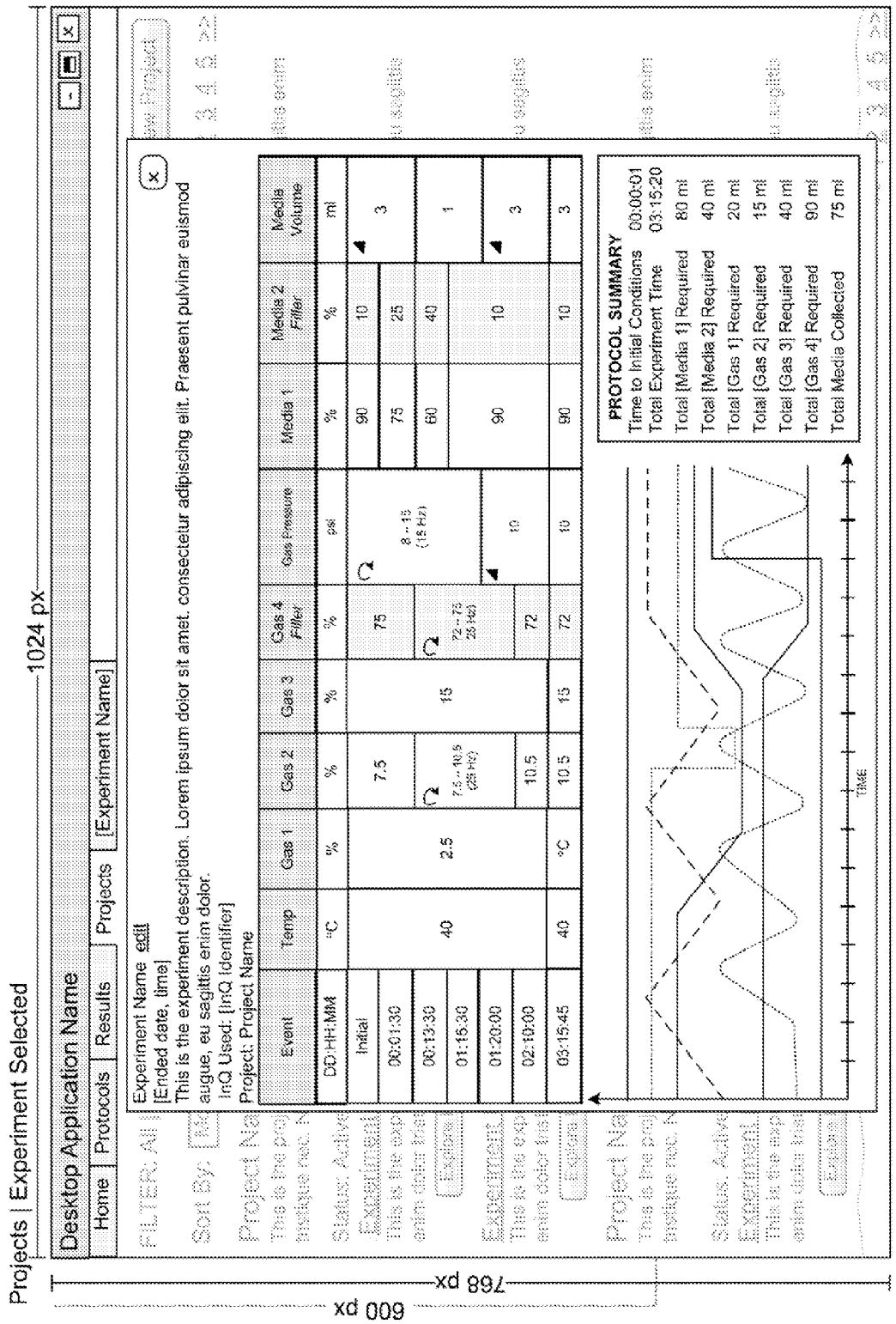

FIGS. 84-85 are screenshots of a project portion of a user interface 4800 used to interact with a culture system, according to one illustrated embodiment.

The user interface 4800 includes a plurality of screens or displays identified by reference numbers 8400, 8500, respectively, with various user selectable icons or controls, entry fields, as well as displays of data, information, text and/or images.

Figure 86:
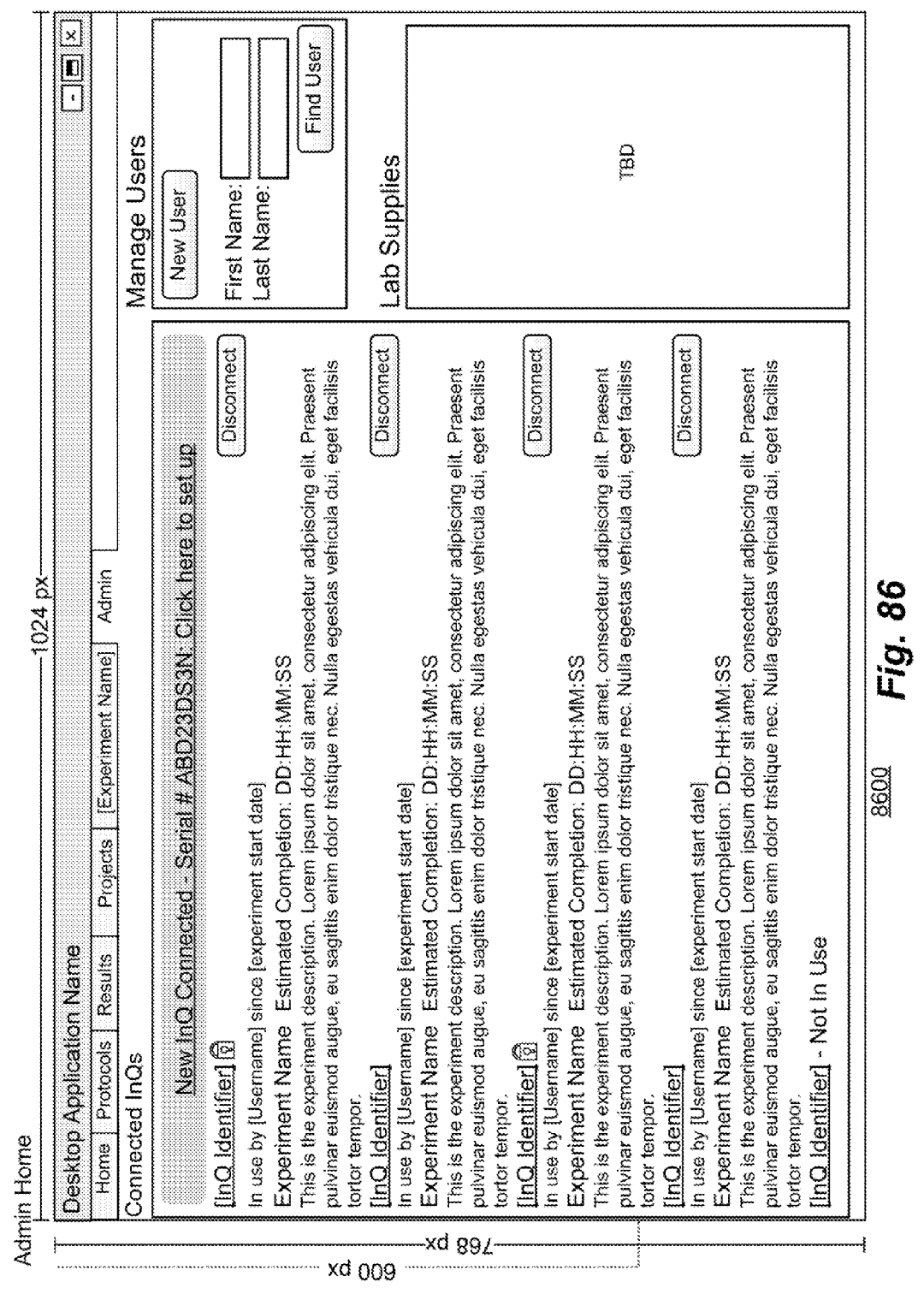
Figure 87:
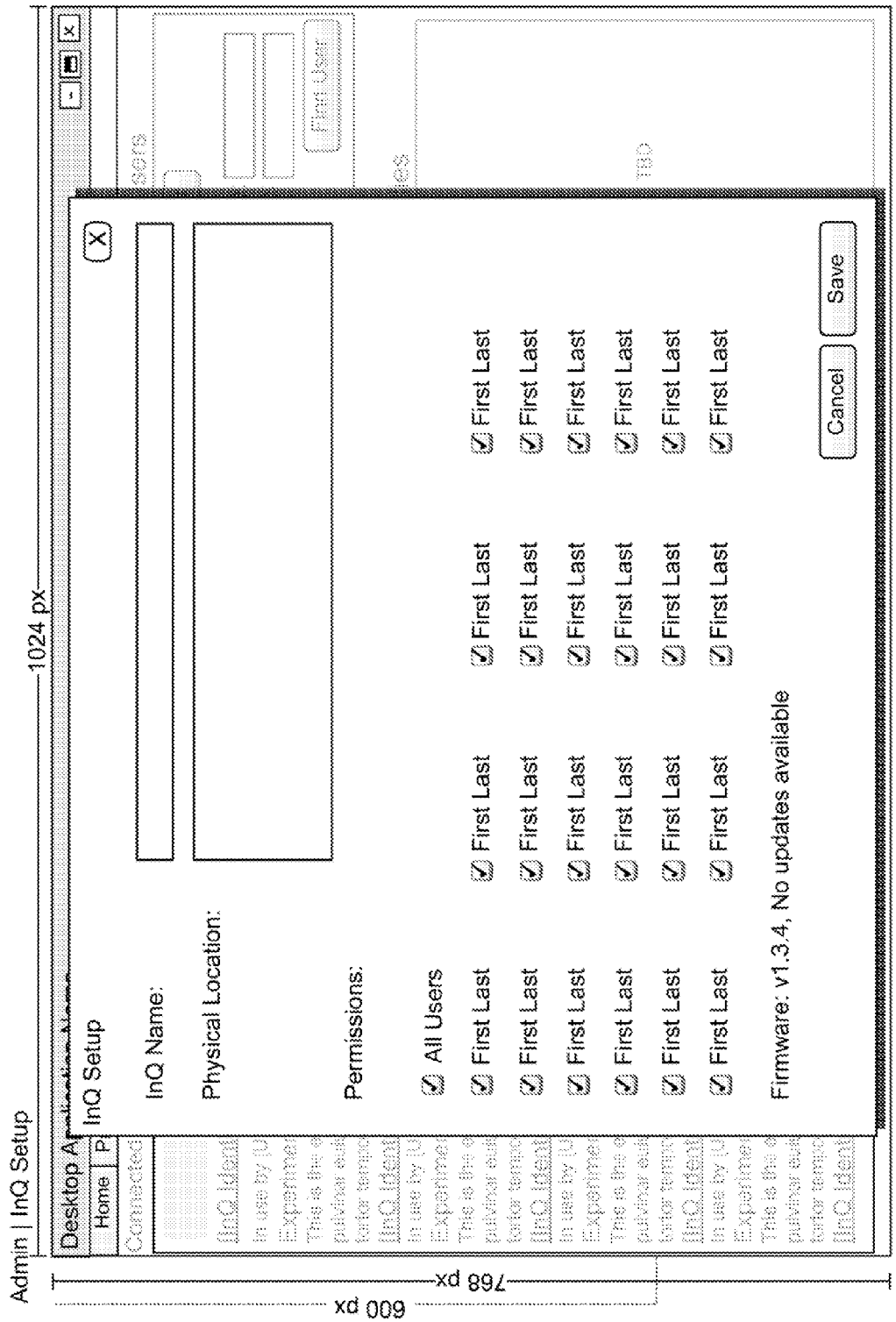
Figure 88:
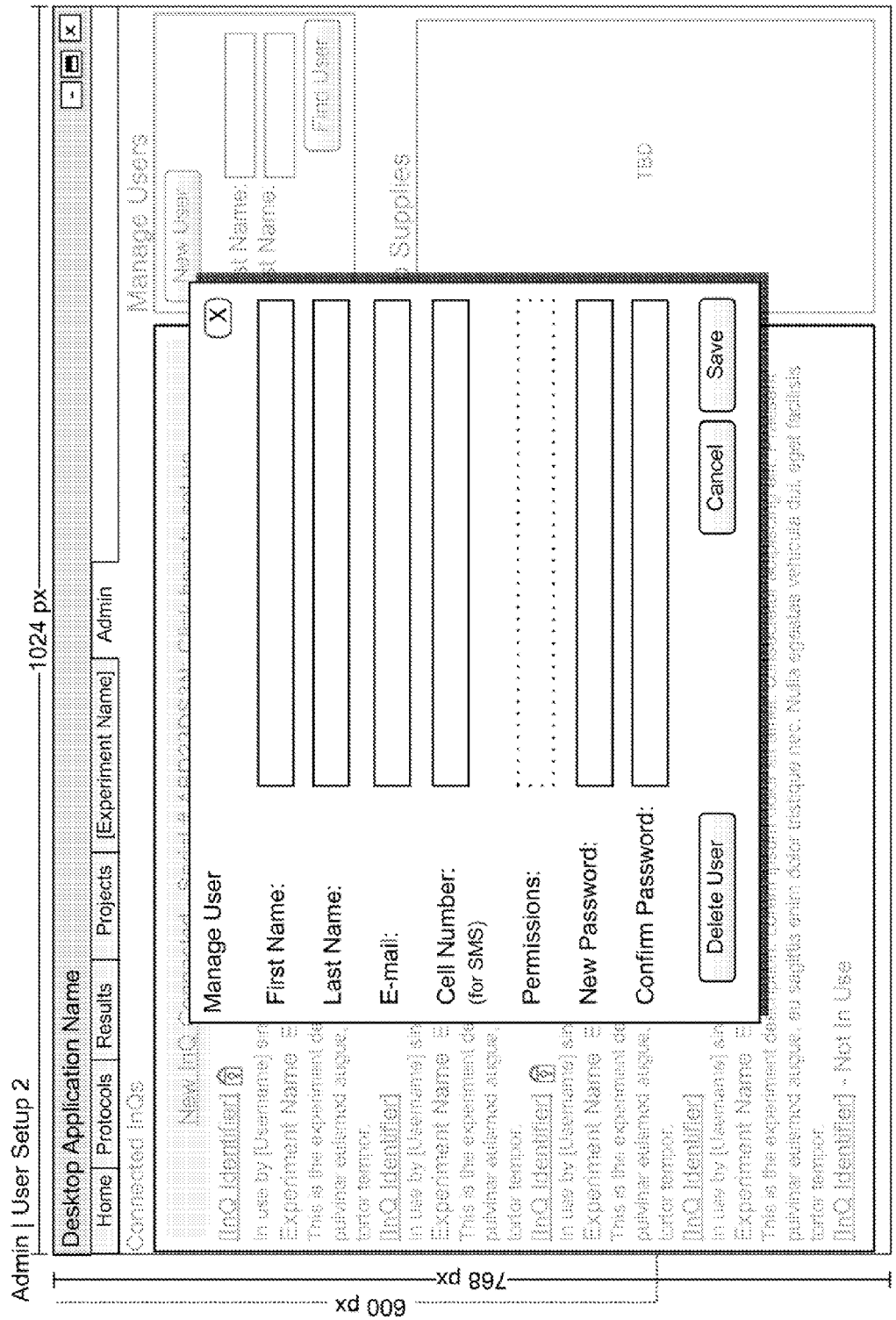

FIGS. 86-88 are screenshots of an administration portion of a user interface 4800 used to interact with a culture system, according to one illustrated embodiment.

The user interface 4800 includes a plurality of screens or displays identified by reference numbers 8600, 8700, 8800, respectively, with various user selectable icons or controls, entry fields, as well as displays of data, information, text and/or images.

Figure 89:
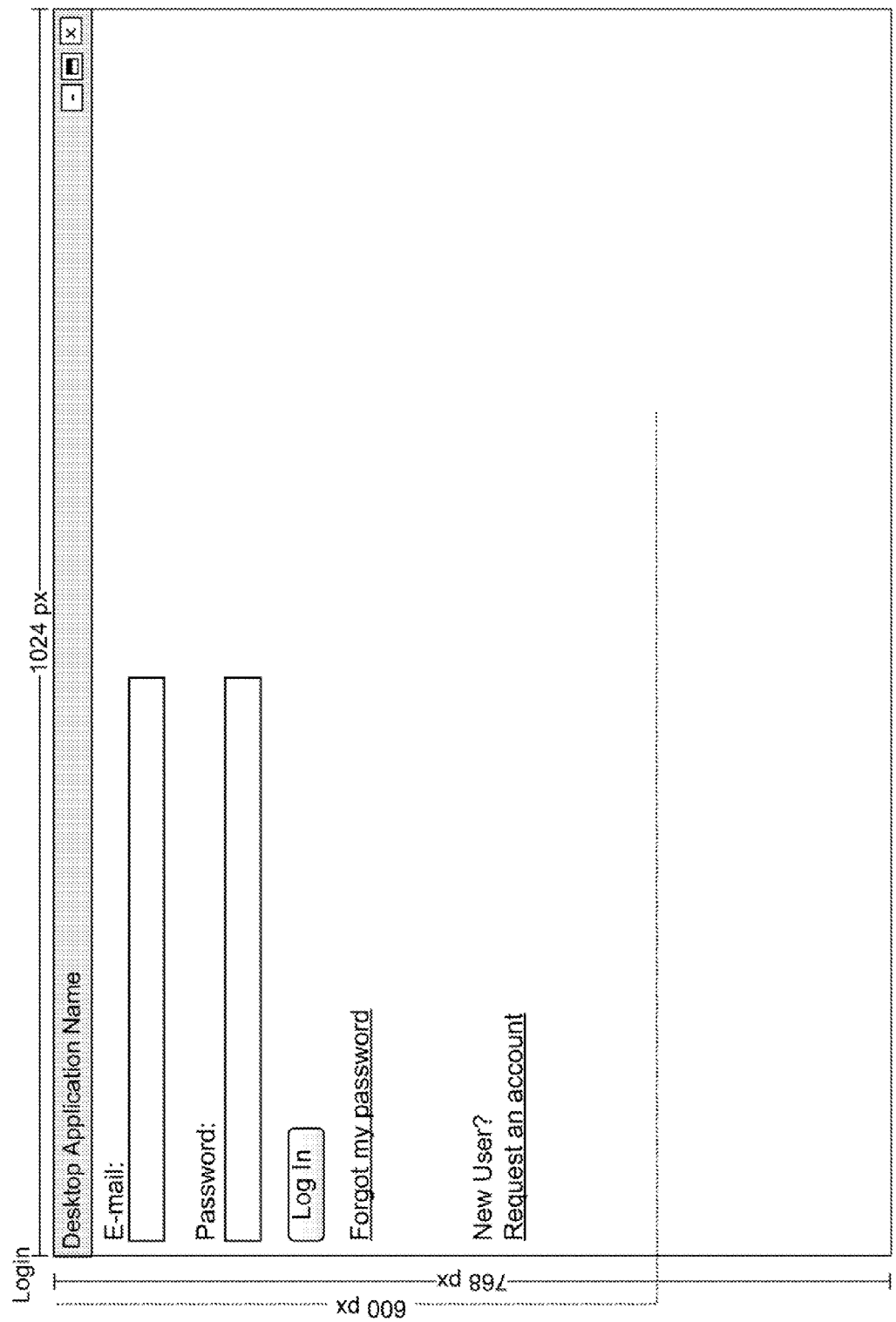
FIG. 89 is a screenshot of a login portion of a user interface used to interact with a culture system, according to one illustrated embodiment.

FIG. 89 is a screenshot of a login portion of a user interface 4800 used to interact with a culture system, according to one illustrated embodiment.

The user interface 4800 includes a plurality of screens or displays identified by reference number 8900, with various user selectable icons or controls, entry fields, as well as displays of data, information, text and/or images.

Figure 90:
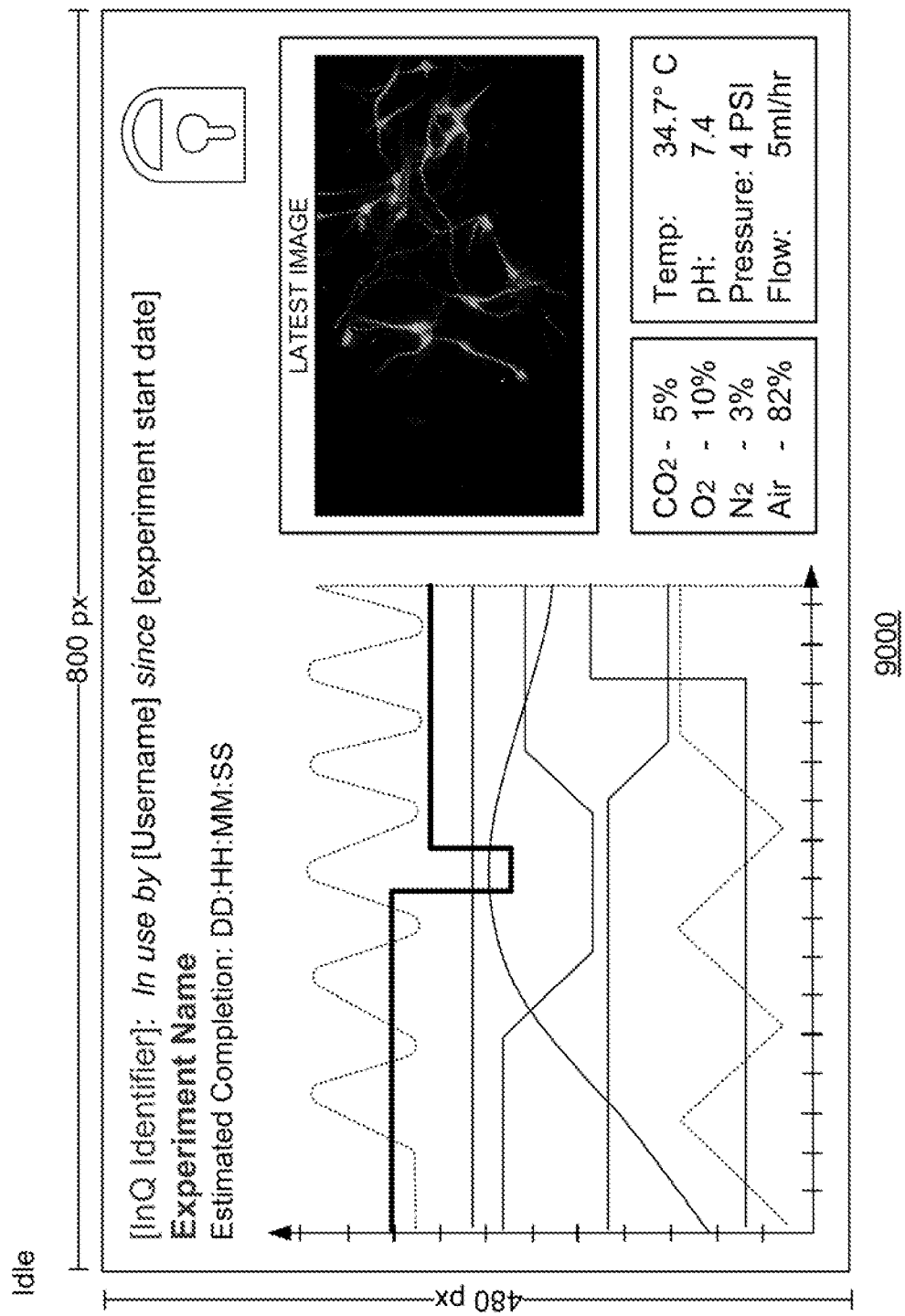
FIGS. 90-92 are screenshots of an idle portion of a user interface used to interact with a culture system, according to one illustrated embodiment, the idle portion may occur during a protocol execution portion.
Figure 91:
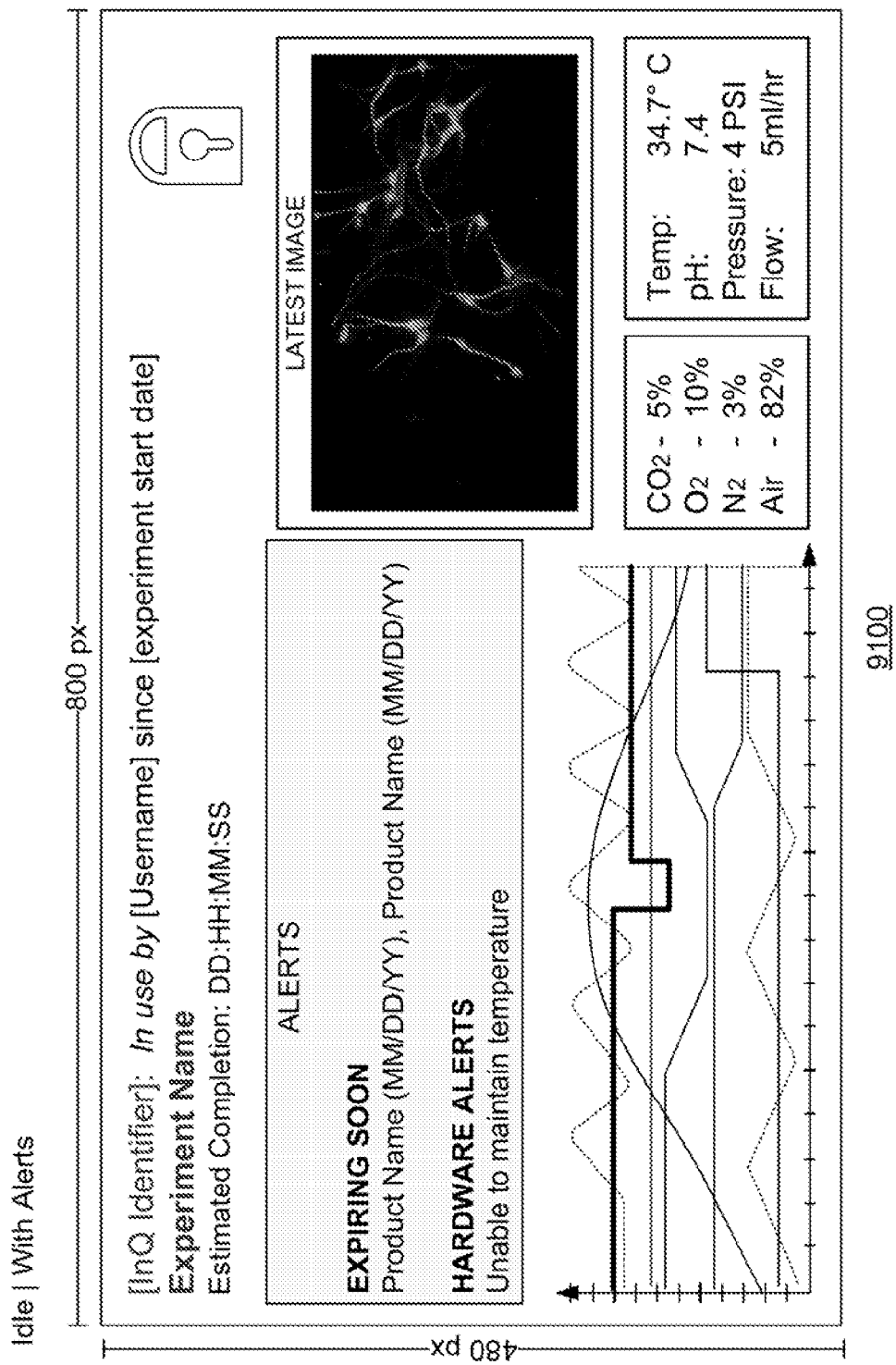
Figure 92:
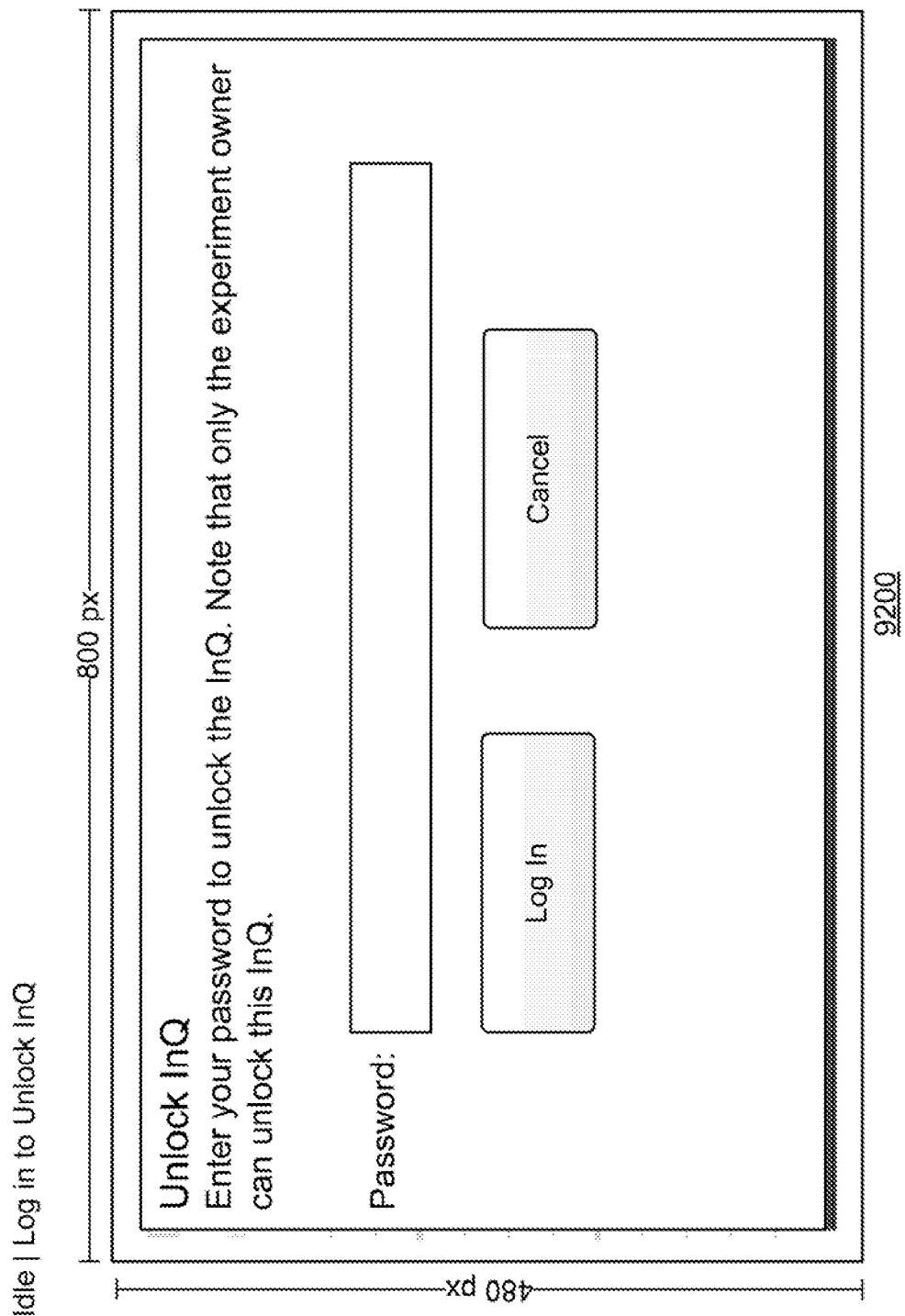
Figure 93:
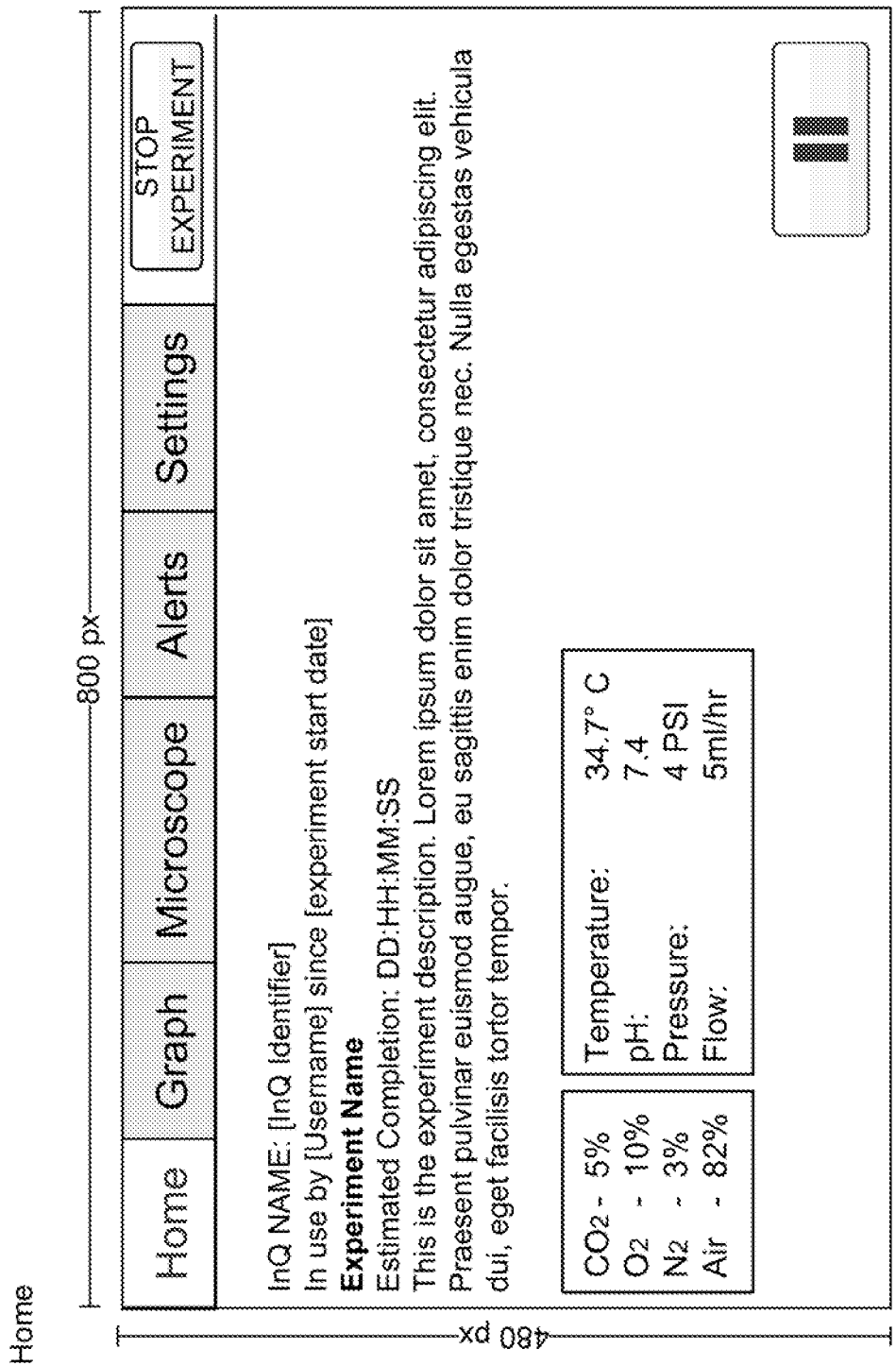
FIGS. 93-96 are screenshots of a pause culturing protocol portion of a user interface used to interact with a culture system, according to one illustrated embodiment, which may be used to pauses execution of a culturing protocol.
Figure 94:
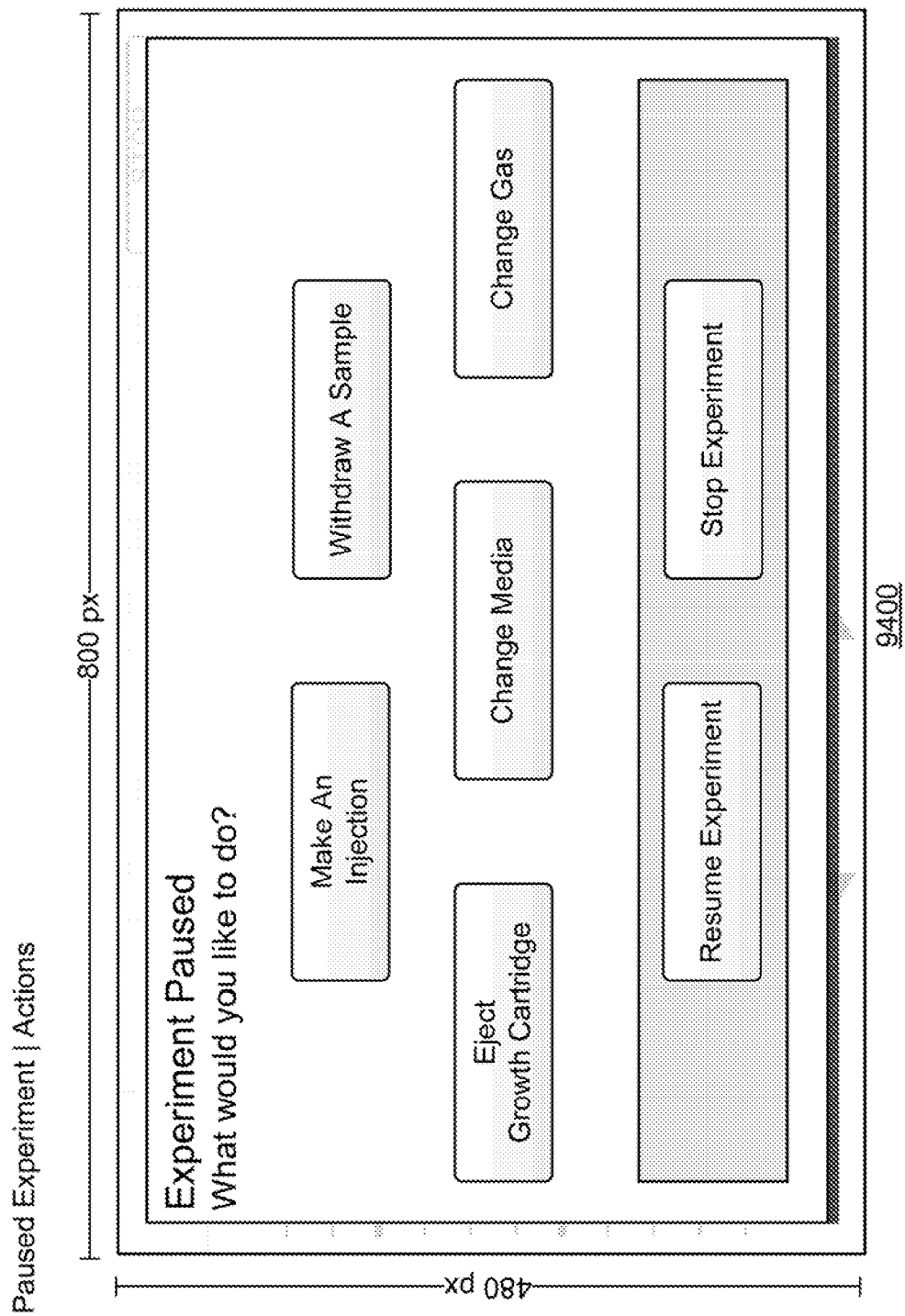
Figure 95:
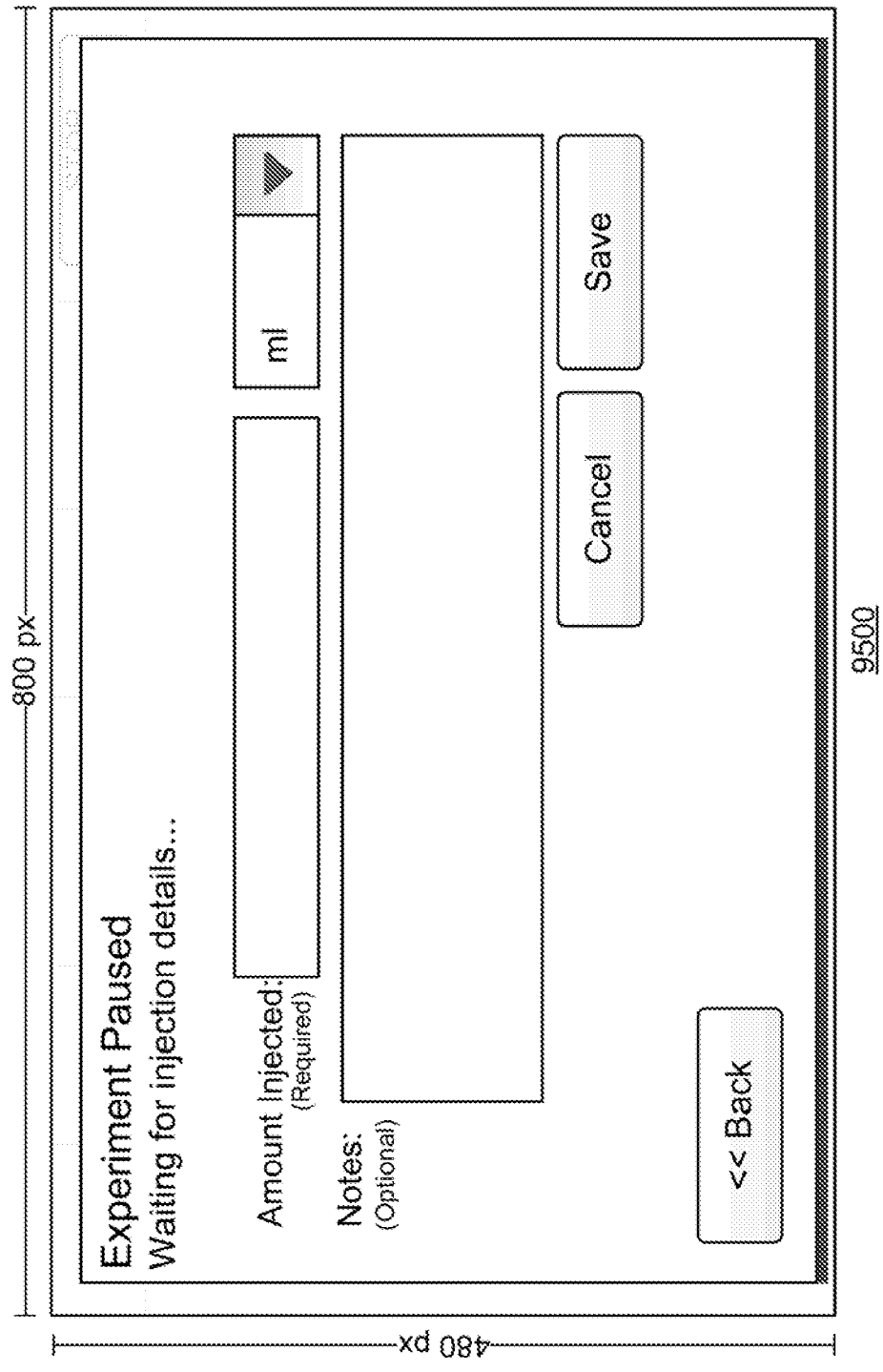
Figure 96:
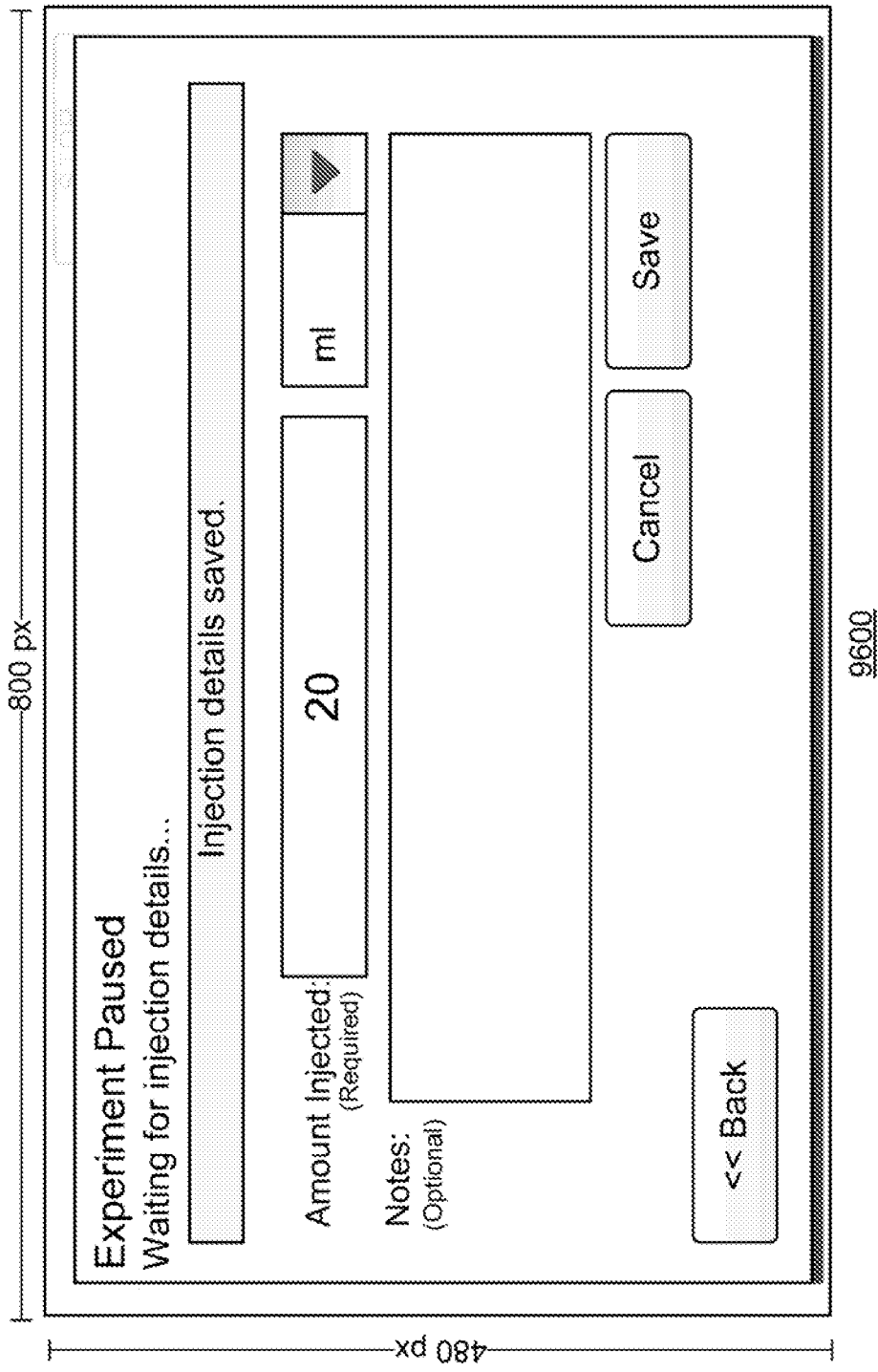

FIGS. 90-92 are screenshots of an idle portion of a user interface 4800 used to interact with a culture system, according to one illustrated embodiment, the idle portion may occur during a protocol execution portion.

The user interface 4800 includes a plurality of screens or displays identified by reference numbers 9000, 9100, 9200, respectively, with various user selectable icons or controls, entry fields, as well as displays of data, information, text and/or images.

FIGS. 93-96 are screenshots of a pause culturing protocol portion of a user interface 4800 used to interact with a culture system, according to one illustrated embodiment, which may be used to pauses execution of a culturing protocol.

The user interface 4800 includes a plurality of screens or displays identified by reference numbers 9300, 9400, 9500, 9600, respectively, with various user selectable icons or controls, entry fields, as well as displays of data, information, text and/or images.

Figure 97:
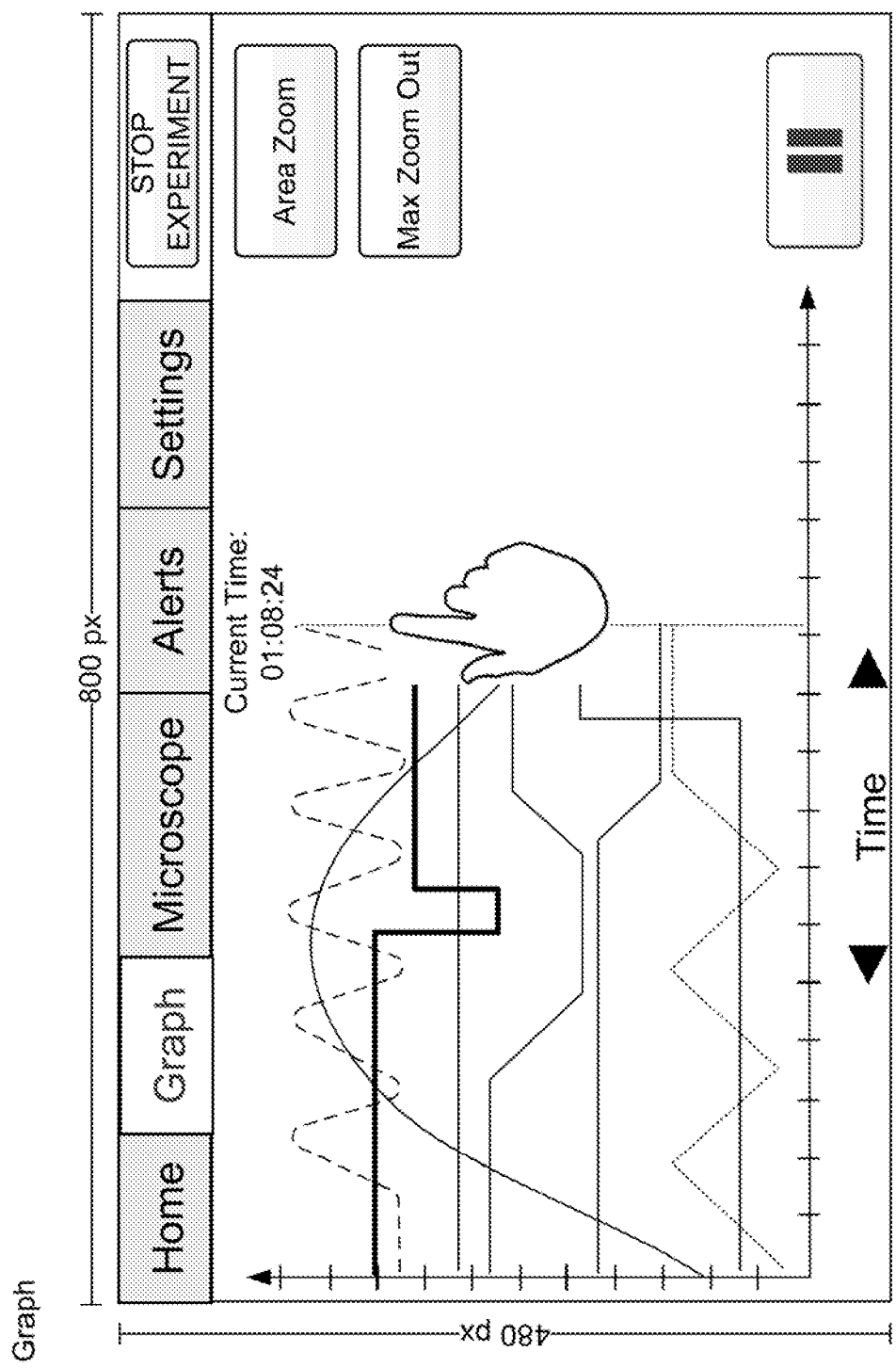
FIG. 97 is a screenshot of a graphing portion of a user interface used to interact with a culture system, according to one illustrated embodiment, showing a graph of various parameters as a function of time with respect to a flow of time of the protocol.

FIG. 97 is a screenshot of a graphing portion of a user interface 4800 used to interact with a culture system, according to one illustrated embodiment, showing a graph of various parameters as a function of time with respect to a flow of time of the protocol.

The user interface 4800 includes a plurality of screens or displays identified by reference number 9700, with various user selectable icons or controls, entry fields, as well as displays of data, information, text and/or images.

Figure 98:
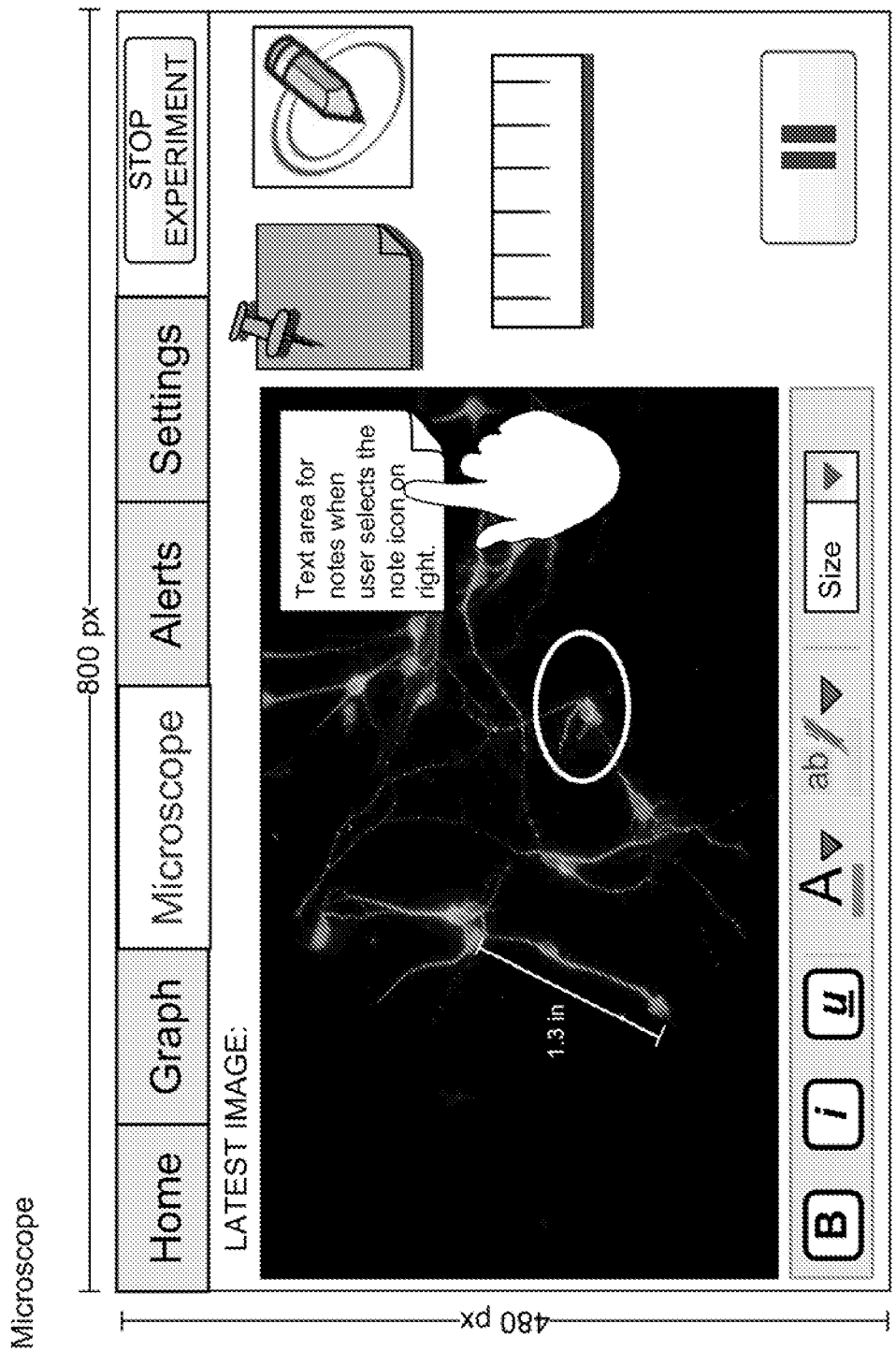
FIG. 98 is a screenshot of a microscope portion of a user interface used to interact with a culture system, according to one illustrated embodiment, which may be used to review and examiner digital images captured by the microscopy subsystem.

FIG. 98 is a screenshot of a microscope portion of a user interface 4800 used to interact with a culture system, according to one illustrated embodiment, which may be used to review and examiner digital images captured by the microscopy subsystem.

The user interface 4800 includes a plurality of screens or displays identified by reference number 9800, with various user selectable icons or controls, entry fields, as well as displays of data, information, text and/or images.

Figure 99:
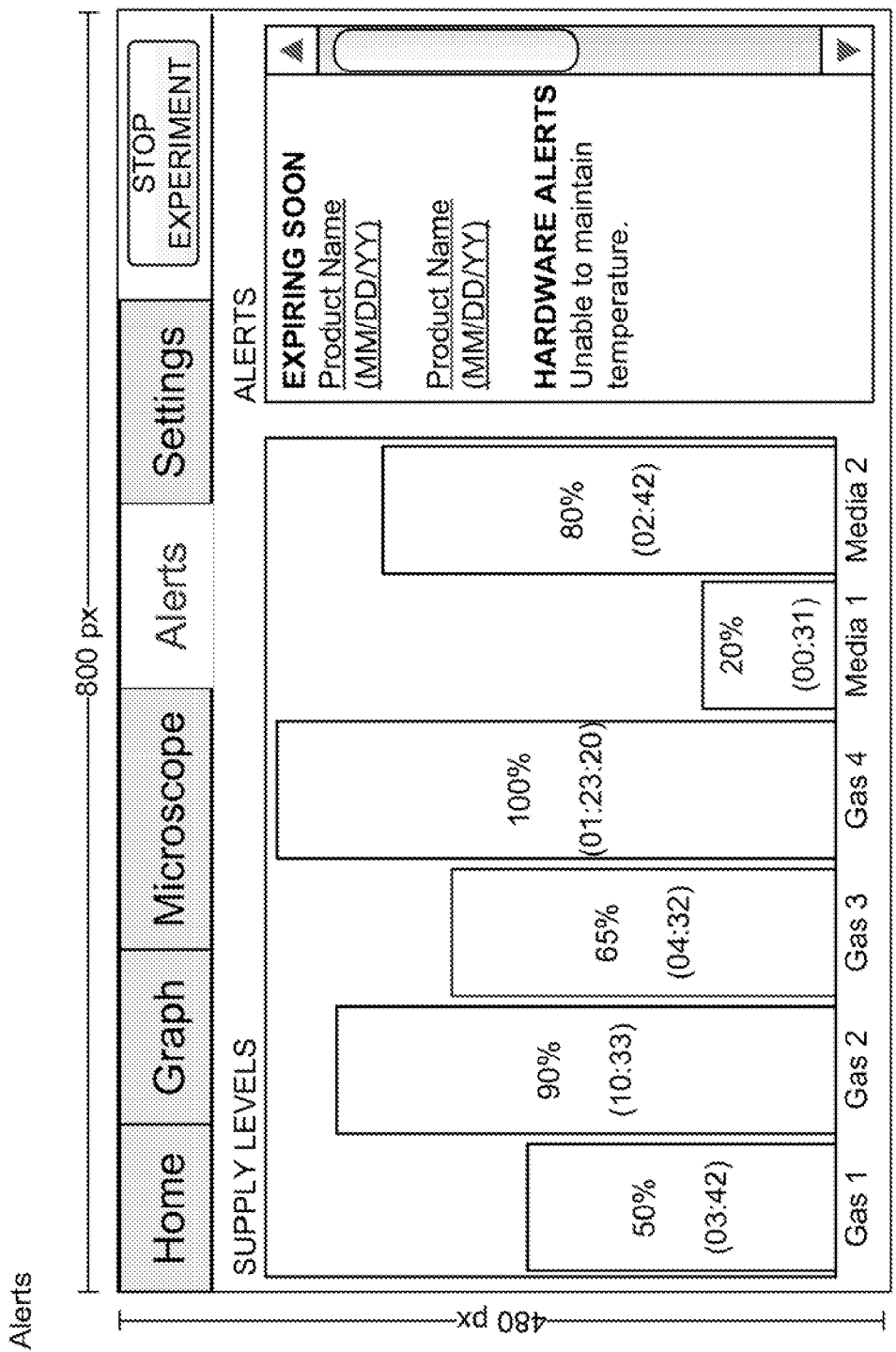
FIGS. 99-100 is a screenshot of an alert portion of a user interface used to interact with a culture system, according to one illustrated embodiment, which may display supply levels for media, gas or other material, various alerts or exceptions and/or licensing information.
Figure 100:
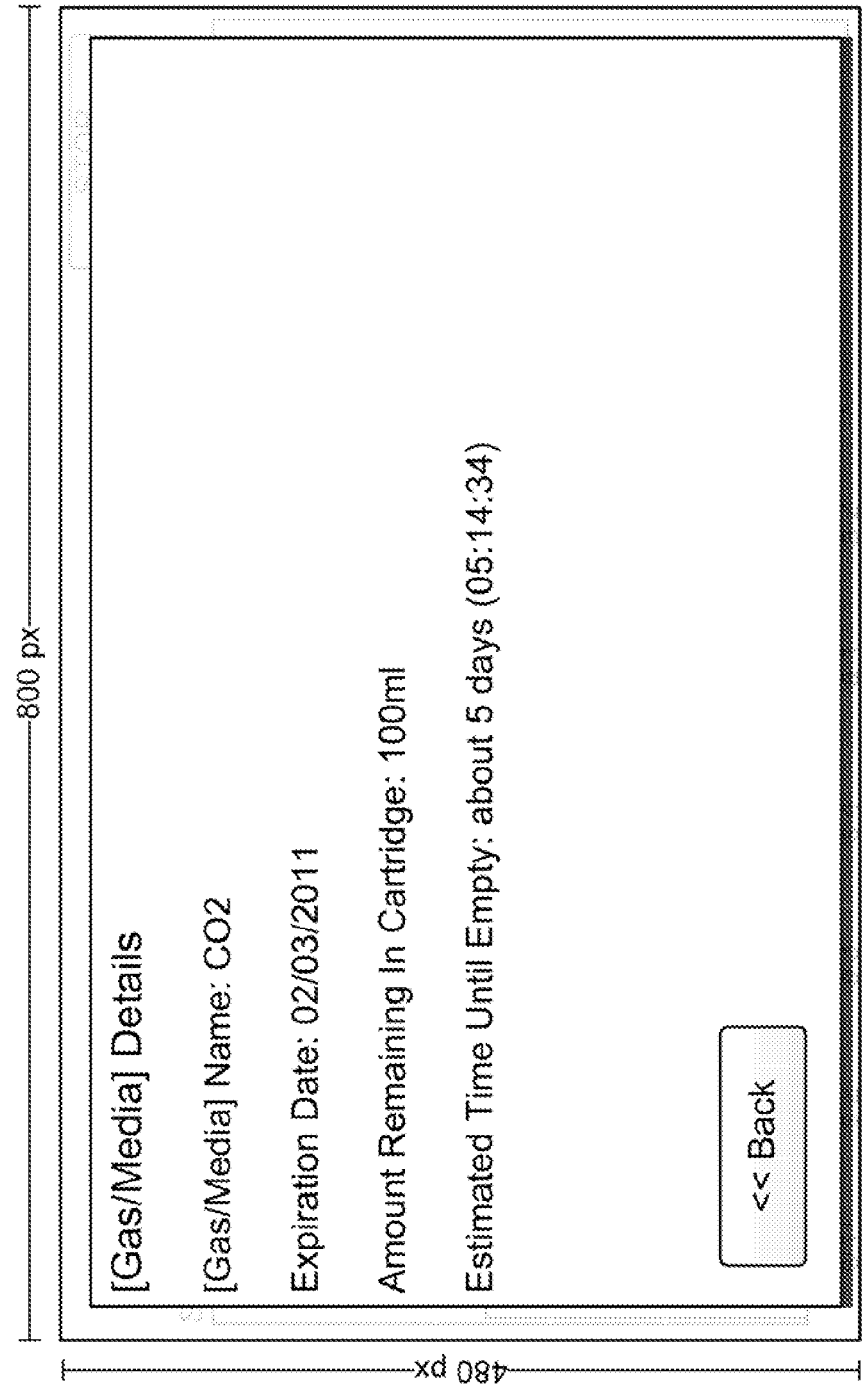

FIGS. 99-100 is a screenshot of an alert portion of a user interface 4800 used to interact with a culture system, according to one illustrated embodiment, which may display supply levels for media, gas or other material, various alerts or exceptions and/or licensing information.

The user interface 4800 includes a plurality of screens or displays identified by reference numbers 9900, 10000, respectively, with various user selectable icons or controls, entry fields, as well as displays of data, information, text and/or images.

Figure 101:
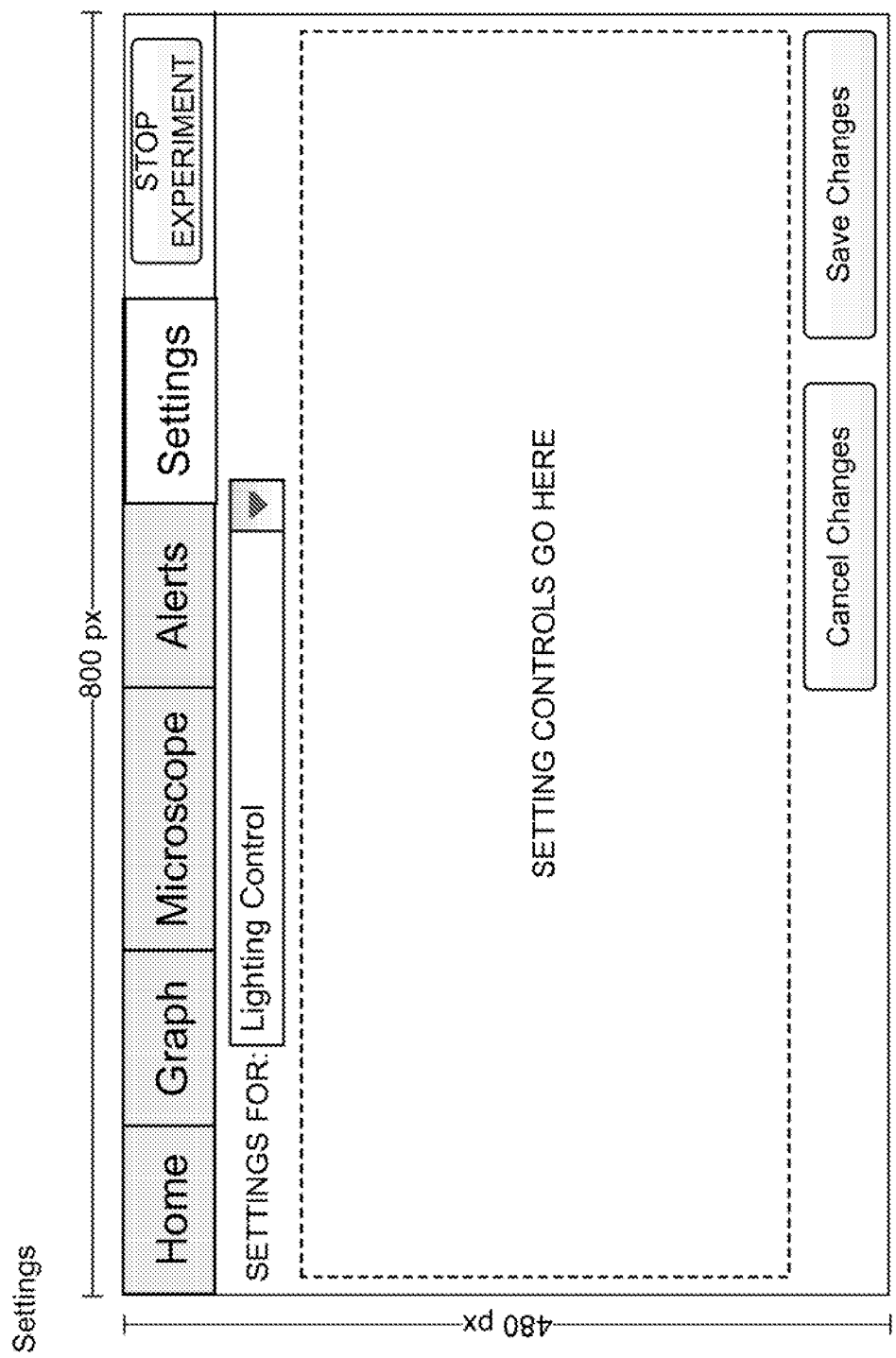
FIG. 101 is a screenshot of a settings portion of a user interface used to interact with a culture system, according to one illustrated embodiment, which may allow the user to set or control settings for various components of the culturing system.

FIG. 101 is a screenshot of a settings portion of a user interface 4800 used to interact with a culture system, according to one illustrated embodiment, which may allow the user to set or control settings for various components of the culturing system.

The user interface 4800 includes a plurality of screens or displays identified by reference number 10100, with various user selectable icons or controls, entry fields, as well as displays of data, information, text and/or images.

CONCLUSION

The culturing systems described herein provide a platform that is comprised of multiple integrated subsystems. These systems include: cell growth chamber, media conditioning and environmental support, control, sensor, analytical feedback system, and software and web architecture.

A cell growth chamber is supported by a media conditioning system that controls the growth environment. The media conditioning system supplies and mixes media; supplies, mixes, and delivers gas to the media; controls media perfusion and disposal; controls the temperature of media throughout the system; and controls media flow throughout the device.

A control and feedback subsystem provides sensors throughout the system, both internal and peripheral; these sensors can either be for control purposes or to provide data from the cell growth samples. The data from all of the sensors can be analyzed in real time to adjust conditions in the experiment. Analytical sensors can consist of a variety of microscope systems, imaging systems, spectral analysis systems, or other systems designed to directly analyze the culture. This data can be processed down and used to provide complex data feedback from the experiment.

The software and Web architecture integrates control of the subsystems and experimental analysis into one or more software applications. These applications can reside in the firmware, in an onboard computer, in a networked computer, in an Internet application, or an Internet-capable or enabled device.

The cell growth chamber (e.g., wells and/or subwells) is a volume specified for the growth of cell cultures. There may, for example, be two distinct growth chambers that are separate channels, each with the ability to run separate environmental conditions. The growth chamber is currently located on a growth cassette that contains manifolds for the conditioning of media, but it doesn't necessarily have to be packaged that way. The growth chamber can be made of various materials, it can have different coatings, inserts, and can be set up in different channel and multi-well configurations.

The growth chamber and/or wells or subwells of the growth cassette may be formed from polystyrene. The growth chamber and/or wells or subwells of the growth cassette may include a hydrophilic coating. The growth chamber and/or wells or subwells of the growth cassette may be flat to facilitate optical imaging. The growth chamber and/or wells or subwells of the growth cassette may include selectively removable lids that provide access to an interior thereof. The lids may, for example be hinged, and may snap into place. Alternatively, the lids include a thread and may screw into place. One or more septa may provide access, for example via a needle, pipette or other tool. The portions of the growth cassette may from a media and/or gas manifold for selectively mixing or providing media from two or more media sources, and/or gases from two or more gas sources to the growth chamber and/or wells or subwells of the growth cassette.

The growth chamber and/or wells or subwells of the growth cassette may receive multi-well inserts into single channel thereof. A single media and gas mix may be provided concurrently to all wells or growth chamber. The growth chamber and/or growth cassette may include any number of wells and/or sub-wells.

The growth chamber and/or wells or subwells of the growth cassette may include hydrophilic or hydrophobic coatings, employing various functional groups. The growth chamber and/or wells or subwells of the growth cassette may include protein coatings and/or nutritive coatings.

The growth chamber and/or wells or subwells of the growth cassette may receive migration assay inserts or matrix inserts. The growth chamber and/or wells or subwells of the growth cassette may include various gradient coatings. The growth chamber and/or wells or subwells of the growth cassette may include various active pharmaceutical ingredients (API) coatings or agar or agar-like coatings. The growth chamber and/or wells or subwells of the growth cassette may include specialized sensor coatings.

The growth chamber and/or wells or subwells of the growth cassette may have a glass bottom or glass-like bottom or coating (e.g., $SiO_2$). The growth chamber and/or wells or subwells of the growth cassette may include an ELIZA-type shield isolator device embedding.

The growth chamber and/or wells or subwells of the growth cassette may be separate from all media handling. The growth chamber and/or wells or subwells of the growth cassette may, alternatively, be part of all-in-one media handling, media reservoir, device. The growth chamber and/or wells or subwells of the growth cassette may be a permanently, non-removable, part of culture system. For example, the growth cassette may provide gas and/or media manifold separate from the growth chambers or wells.

The growth chamber and/or wells or subwells of the growth cassette may be selectively pressurized. The growth chamber and/or wells or subwells of the growth cassette may have variable volumes. For example, different growth cassettes may be supplied to the culture system depending on the specific volume of the wells or growth chambers desired.

The growth chamber and/or wells or subwells of the growth cassette may be provide in a carousel design, as an endless array of multi-growth chambers or wells on single cassette or table. The culture system may include a suitable turntable and/or motor and/or transmission for rotating the carousel.

The growth chamber and/or wells or subwells of the growth cassette may be may provide other access ports or full-time access ports and/or manifolds. The growth cassette may employ aseptic quick connections other than those illustrated and described herein. The growth cassette may employ pumps other than those illustrated and described herein, for example employing needle primes. The growth cassette may employ valves other than those illustrated and described herein, for example employing needle valve actuators. Further, the growth cassette may a single media channel approach or may employ more than the two illustrated media channels. The growth cassette may couple to a single gas supply or multiple gas supplies.

The media conditioning and environmental support system encompasses all mechanisms used to supply, condition, heat the gas and media, as well as to direct flow of gas and media. The media may be supplied by removable media cartridges. The media cartridges may include one or more reservoir bags, bladders or other containers positioned at least partially inside a functional housing. In some embodiments, the housing may contain one or more bags, bladders or other containers to hold media, and may contain one or more separate bags, bladders or other containers to hold waste. In some embodiment the media cartridges may omit the housing. The media cartridges may be pre-filled with media by a manufacturer, or may be filled or refilled by an end user. The media cartridges may include a volume sensor to sense, measure or otherwise determine a volume in the bags, bladders or other containers. The media cartridges, waste cartridges and/or gas canisters may employ quick connection mechanisms other than those illustrated and described herein. Alternatively, media may be supplied from an external source such as a standalone media tank or media reservoir. As a further alternative, media may be stored in media reservoirs built into the growth cassettes.

Gas may be supplied in small canisters or cartridges. The gas canisters may, for example, be disposable. The gas and media may be aseptically connected to the growth cassette, where a manifold ensures mixing of media channels (e.g., dual channels), introduces gas, heats the media and delivers the media to the growth chamber (e.g., wells and/or subwell). After delivery, the manifold also exhausts gas, and collects waste, for example via waste collection cartridges. Other configurations could collect or dispose of the media and gas in bulk containers, fraction collectors, analyzers, refreshers, or other subsystems or devices. Alternatively, gas may be supplied from an external source such as a standalone gas tank or gas reservoir. Gas may also be supplied via a gas generator or gas or air pump or compressor.

Other configurations of these systems and subsystems are possible. Many of the pumps, valves and/or other mechanisms can be replaced by other pumps, valves or other mechanisms which achieve similar functions. Media may be delivered to the growth cassette via tubing or micro-channels.

The media cartridge may include a gear drive rack built therein, an optional an identification chip or non-transitory storage medium that stores an identifier.

The media cartridge may, for example, include a housing that stores a single bag or bladder. The media cartridge may include a septa addition port. The septa may allow addition of various materials to the media. Alternatively, the septa may allow venting of the bag, bladder, chamber or other container of the media cartridge. Further, the media cartridge may include a sterile, quick connect interface, for example using the septa and a piercer. Such may provide a direct fluidly communicative connection to a port of the growth cassette.

The media cartridge may include one or more level viewing ports to allow inspect of the level of media contained therein. The media cartridge may include a valve, for example a pinch valve. The media cartridge may include a pump or portion thereof, for example a peristaltic pump drive.

The gas canister may include a disposable cylinder and a custom housing. The gas canister may optionally include an identification chip or non-transitory storage medium that stores an identifier.

The growth cassette may include an integrated growth chamber and gas/media manifold. The growth cassette may a septa connection to provide fluid communicatively coupling via a septa. The growth cassette may include one or more filters for dispersed flow. The growth cassette may include one or more heating channels. The growth cassette may include one or more peristaltic pumps or portions thereof. The growth cassette may include an identification chip that stores identifying information or data. The growth cassette may include a boot connection to allow gas introduction. The growth cassette may include one or more gas permeable membranes to allow gas introduction via diffusion or bubbling. The growth cassette may include gas dissolved in the media. The growth cassette may include a dual channel/dual growth chamber or well design. The growth cassette may include a valve body and valve interface to various external actuators. The growth cassette may include a recirculation valve, allow media or "waste" collected from the growth chamber of wells to be re-circulated back to the growth chamber or wells or to other growth chambers or wells.

The gas mixing system or atmosphere supply subsystem may rely on a gas mixing algorithm and method. The gas mixing system or atmosphere supply subsystem may include a gas mixer. The gas mixing system or atmosphere supply subsystem may include multiple channels and small reservoirs. The gas mixing system or atmosphere supply subsystem may include vents and be configured to perform controlled venting to an exterior of the culture system. The gas mixing system or atmosphere supply subsystem may include one or more couplers that allow gas communicative coupling to an analyzer. Such may, for example, allow analysis to be performed on vented or exhausted gas. The analysis may be used in controlling operation of the culturing system.

A media condition subsystem may employ multiple media cartridges. The media condition subsystem may perform temperature control via ambient and direct heating via heaters and/or cooling via exhaust fans, Peltier devices and/or compressors. The media condition subsystem may employ pumps, of any of a large variety of pump types. Volume flow sensing or measurement may be performed via one or more flow sensors or encoders associated with the pumps. A media condition subsystem may valves, of any of a large variety of valve types. The media condition subsystem may collect waste via one or more waste collection cartridges, for example via a respective waste collection cartridge for each channel. Spent media cartridges may be employed as waste collection cartridges. The media condition subsystem may monitor pumping to track media and/or waste volumes. The media condition subsystem may allow for aseptic engagement and disengagement of media and/or waste cartridges, for example via septa, puncture devices, and/or direct coupling.

The growth chambers or wells and/or subwells the growth cassette may be isolated from ambient light. An illumination exposure control subsystem may provide controlled illumination to the contents of the growth chambers or wells and/or subwells the growth cassette. For example, the illumination exposure control subsystem may provide cycle illumination to the contents of the growth chambers or wells and/or subwells the growth cassette. The illumination may be provided at one or more selected wavelengths, which may, or may not, vary over time. Additionally, or alternatively, the illumination may be provided at one or more illumination levels or intensities, which may, or may not, vary over time. Illumination may be periodic or aperiodic.

The culture system and/or growth cassette includes numerous sensors which provide data or information for implementing a feedback loop to either ensure an accurate environment or enable culturing operations that can change based on sample or environmental conditions. Many of these sensors are in-line with the gas or media flow to validate the experimental environment. Other sensors can be located in or near the growth chamber or wells to provide direct feedback on the cell growth. Using expansion ports, peripheral sensors or analytical systems can still directly analyze the environment and be interfaced into the control loop. These could be individual sensors or complete systems such as HPLCs, spectrometers, or the like. Finally, a variety of analytical systems can be used inside or in conjunction with the device. One or more specialized microscope systems may be located inside the culture system, which include imagers to capture image data which may be used in providing feedback control. The imager can take any variety of forms including those capable of using spectral, reflected light, or other non-contact analysis device.

Sensors may include various pressure sensors. Pressure sensors may be positioned to sense supply gas pressure. Pressure sensors may be positioned to sense mixture pressure. Pressure sensors may be positioned to sense pressure in the growth chamber or wells. Pressure sensors may be positioned to sense ambient or atmosphere pressure.

Sensors may include various temperature sensors. Temperature sensors may be positioned to sense temperature in the interior of the culture system, for example proximate or at the growth chamber or wells. Temperature sensors may be directly coupled to an aluminum thimble. Temperature sensors may be positioned to sense temperature in a mixing chamber.

Sensors may include gas sensors responsive to the presence of various gases. For example, sensors may include carbon dioxide sensors positioned to sense carbon dioxide at least proximate the growth chamber or wells.

Sensors may include pH sensors responsive to a pH level. For example, sensors may include pH sensors positioned to sense pH in or at least proximate the growth chamber or wells. The pH sensors may be electronic, with electrodes positioned in the growth chamber or wells. The pH sensor may include an indicator, and may implement or be communicatively coupled to a colorimetric analyzer.

Sensors may include electrical conductivity sensors responsive to an electrical conductivity. For example, sensors may include electrical conductivity sensors positioned to sense electrical conductivity of contents in the growth chamber or wells.

The sensors may include various imagers, such as imagers which are part of, or associated with, the microscopy subsystem. The imagers may capture images as digital images or digital image data. The microscopy system may include, or implement, a fluorescence/phase contrast microscope. Such may include automated control over the various features and parameters. The microscopy system may include structures to provide for various, selectable levels of magnification. The microscopy system may include a microscopy illumination subsystem operable to provide various selectable wavelengths of illumination, for example from a number of LEDs or OLEDs. The microscopy system may include a translation table or other structure to move the field-of-view of at least the imager with respect to the growth chambers or wells. The microscopy subsystem may include light microscope, confocal microscope, spectrophotometer, cell counter, or other indirect analysis device either as an integral part of the culture system, or as a peripheral to the culture system.

The culture system may be communicatively coupled to receive information or data from a variety of external sensors, for example via a USB port. External sensors may, for example, receive samples via one or more ports, for instance syringe ports. The syringe ports may, for example, take the form of Luer locks. The external sensors, may for example, include pH sensors, dissolved gas (e.g., $CO_2$, $O_2$) sensors, and/or spectrometer such as an infrared (IR) spectrometer.

The system includes instructions stored on one or more non-transitory computer- or process-readable storage mediums, for example stored as software or firmware. These instructions tie together the operation of the various subsystems of the culture system, and may implement one or more feedback loops or mechanisms. These instructions also present the end user, located either locally or remotely, with a control user interface. While the instructions may take a large variety of forms, employing a variety of software architectures, one exemplary embodiment is discussed immediately below.

A base level firmware may be responsible for directly controlling the internal mechanisms of the culture system and providing feedback from the various sensors, with consumable sensors, internal sensors or external (i.e., peripheral) sensors. Several different inter IC (I2C) buses may be used with master controllers that communicate directly with an onboard processor based control subsystem. Other types of buses or even non-bus communicative channels may be employed. Many new buses can be added later if desired to support new sensors or internal devices. The onboard processor based control subsystem executes instructions which cause the onboard processor based control subsystem to parse commands to its respective 12C master controller. The onboard processor based control subsystem is also responsible for image processing, receiving feedback from additional peripheral sensors, and providing a user interface for simple machine commands.

The culture systems include communications components (e.g., modems, Ethernet cards) to interface with external devices, whether local or remotely located from the culture system. For example, a culture system may be communicatively networked so that a standalone computer system (e.g., personal computer or PC) on the network executing a desktop application can be used to design experiments, administer the culture system, provide permissions, receive data feedback from one or more networked culture systems, organize old and new data, form reports and other multimedia data, and perform post-processing on data. The networked nature of the culture systems allows server functions such as remote backup of data, firmware and software updates, and allowing a hub of communication between the culture systems and authorized Internet capable or enabled devices (e.g., smart phones, computers, etc) from anywhere in the world. The software executing on remote computers or processor-based devices may implement simple viewers allowing viewing of culture protocol progress, images, and data. Additionally or alternatively, the software executing on remote computers or processor-based devices may implement allow provide complete user interfaces allowing control of the culturing device, including selection, execution and/or modification of defined culturing protocols, from remote locations.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other environments, not necessarily the exemplary culture system using removable cartridges or canisters of consumables generally described above. The culture system may, for example, receive or more consumables from non-removable sources, such as fixed tanks or reservoirs. Such may be particularly suitable for large scale production or manufacturing facilities or laboratories.

As explained above, the culture systems, as well as the kits, may advantageously automate the culturing or incubation process. Such may free researchers, technicians or others from the mundane tasks associated with culturing, which often requires "around the clock" attention. Such may also advantageously allow remote control or tracking of the culturing or incubation process. Again, reducing the workload on the researcher, technician or others. Also as explained above, such may reduce the cost of supplies, and reduce waste and associated costs.

Also as explained above, automated collection and/or analysis of information allows a number of feedback loops or processes to be established in the culturing protocol, further automating the culturing process. Thus, the culture system may select a given operation to perform and/or environmental condition based on analysis of operational or environmental conditions or analysis of the biological material itself (e.g., digital images, electrical conductivity).

Also as explained above, automated collection and/or analysis of information allows a reporting and/or quality control over the culturing process. Such may be useful to verify or demonstrate research results, for example for publication. Such may also be useful to demonstrate that products (e.g., cultured tissue or engineered tissue or cultured organs) comply with certain requirements. Such is useful in defending against liability claims, as well as meeting requirements imposed by insurers and/or governmental mandates. For instance, reporting may be useful in complying with regulatory requirements mandated by the U.S. Food and Drug Agency (FDA) or other regulatory agency.

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of physical non-transitory signal bearing media include, but are not limited to, the following: recordable type media such as Flash, thumb or USB drives, floppy disks, hard disk drives, optical disks or CD ROMs, digital tape, and/or computer memory.

U.S. provisional patent application Ser. No. 61/305,458 filed Feb. 17, 2010 is incorporated herein by reference in its entirety. The various embodiments described above can be combined to provide further embodiments. Aspects of the embodiments can be modified to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A growth cassette for use with culture systems, the growth cassette comprising:
 a housing having an exterior and an interior, the interior including a plurality of distinct wells, the housing sized and dimensioned to be removably received by a growth cassette receiver of a culture system;
 a first media inlet accessible from the exterior of the housing;
 a first media inlet valve selectively operable to control a media flow via the first media inlet, the first media inlet valve selectively coupleable to be driven from the exterior of the housing by a first actuator of the culture system;
 a second media inlet accessible from the exterior of the housing;
 a second media inlet valve selectively operable to control a media flow via the second media inlet, the second media inlet valve selectively coupleable to be driven from the exterior of the housing by a second actuator of the culture system;
 at least one diverter valve selectively coupleable to be driven from the exterior of the housing by a third actuator of the culture system;
 a media channel in the interior of the housing that provides fluid communication between the first media inlet valve, the second media inlet valve and the at least one diverter valve;
 a first channel in the interior of the housing that provides fluid communication between the at least one diverter valve and a first one of the wells; and
 a second channel in the interior of the housing that provides fluid communication between the at least one diverter valve and a second one of the wells,
 wherein the at least one diverter valve is operable to provide passage from the media channel, selectively to the first channel and the second channel.

2. The growth cassette of claim 1 wherein the first and the second media inlets are sized and dimensioned to respectively directly couple to a media outlet of each of a respective one of a number of media cartridges received by the culture system without any intervening conduit of the culture system.

3. The growth cassette of claim 1, further comprising:
 a first filter and flow straightening structure located in the first channel; and
 a second filter and flow straightening structure located in the second channel.

4. The growth cassette of claim 1, further comprising:
 a first rupturable membrane covering the first media inlet; and
 a second rupturable membrane covering the second media inlet.

5. The growth cassette of claim 1 wherein at least a portion of the first channel is a tortuous fluid path and at least a portion of the second channel is a tortuous fluid path.

6. The growth cassette of claim 5, further comprising:
 at least one heater element positioned along at least a portion of the tortuous fluid path of the first or the second channel and in intimate contact therewith.

7. The growth cassette of claim 1, further comprising:
 at least one septum that selectively provides access via a removable conduit to at least one of the wells from an exterior of the housing to provide a biological material thereto.

8. The growth cassette of claim 1, further comprising:
 a first waste outlet accessible from the exterior of the housing;
 a first waste outlet valve selectively operable to control a waste flow via the first waste outlet;
 a second waste outlet accessible from the exterior of the housing;
 a second waste outlet valve selectively operable to control a waste flow via the second waste outlet;
 a first waste channel in the interior of the housing that provides fluid communication between the first well and the first waste outlet valve; and
 a second waste channel in the interior of the housing that provides fluid communication between the second well and the second waste outlet valve.

9. The growth cassette of claim 8 wherein the first and the second waste outlets are sized and dimensioned to respectively directly couple to a waste inlet of each of a respective one or a number of waste cartridges received by the culture system.

10. The growth cassette of claim 8 wherein the first waste outlet valve provides passage from the first waste channel selectively to the first waste outlet or the first channel.

11. The growth cassette of claim 8 wherein
the first waste outlet valve is operable to provide passage from the first waste channel selectively to the first waste outlet or to the first channel; and
the second waste outlet valve is operable to provide passage from the second waste channel selectively to the second waste outlet or to the second channel.

12. The growth cassette of claim 8 wherein the first and the second waste outlet valves are selectively coupleable to be driven from an exterior of the housing by a number of respective actuators of the culture system.

13. The growth cassette of claim 8, further comprising:
at least one pump coupled in at least one of the first or second waste channels.

14. The growth cassette of claim 8, further comprising:
a first pump coupled in the first waste channel; and
a second pump coupled in the second waste channel.

15. The growth cassette of claim 14 wherein the first and the second pumps are selectively coupleable to be driven from an exterior of the housing by a number of respective actuators of the culture system.

16. The growth cassette of claim 8, further comprising:
a first rupturable membrane covering the first waste outlet; and
a second rupturable membrane covering the second waste outlet.

17. The growth cassette of claim 1, further comprising:
a gas permeable membrane that provides gas communication into at least one of the channels from an exterior of the housing and that substantially inhibits communication of water vapor therethrough.

18. The growth cassette of claim 1, further comprising:
at least one exhaust port that provides fluid communication between at least one of the channels and the exterior of the housing.

19. The growth cassette of claim 1, further comprising:
at least a first exhaust port that provides fluid communication between the first channel and the exterior of the housing; and
at least a second exhaust port that provides fluid communication between the second channel and the exterior of the housing.

20. The growth cassette of claim 19 wherein flow through the first and the second exhaust ports is unidirectional allowing only exhaustion of gas from the interior of the housing.

21. The growth cassette of claim 1 wherein at least one of the wells is subdivided into a plurality of sub-wells.

22. The growth cassette of claim 21 wherein the growth cassette has a floor that includes a number of boundary portions having a first characteristic and a number of sub-well portions having a second characteristic, respective ones of at least some of the boundary portions intermediate pairs of the sub-well portions to form the plurality of sub-wells and the first characteristic is at least one of a physical or a chemical characteristic that provides a relatively low adhesion of cells to the boundary portions and the second characteristic is at least one of a physical, a chemical or an electrical characteristic that provides a relatively high adhesion of cells to the sub-well portions.

23. The growth cassette of claim 1, further comprising:
at least one data carrier coupled to the housing and bearing identifying information indicative of at least one of an identity of the growth cassette, an identity of a user of the growth cassette, a date and/or time of use of the growth cassette, an environmental condition to which a content of at least one of the wells of the growth cassette was subjected, or an identity of a protocol performed using the growth cassette.

24. The growth cassette of claim 23 wherein the data carrier comprises at least one of a machine-readable symbol, a radio frequency identification transponder, a magnetic stripe, or a touch memory device.

25. The growth cassette of claim 1, further comprising:
a number of optical registration indicia which provide registration in at least two planar dimensions and about at least one rotational axis.

26. The growth cassette of claim 1, further comprising:
a number of mechanical registration features which provides registration in at least two planar dimensions and about at least one rotational axis.

27. The growth cassette of claim 1, further comprising:
a number of hinged covers selectively securable to cover respective ones of the wells of the growth cassette.

28. The growth cassette of claim 1, further comprising:
at least one pump in fluid communication at least one of the wells of the growth cassette and selectively coupleable to be driven from an exterior of the housing of the growth cassette by a respective actuator of the culture system.

29. The growth cassette of claim 28 wherein the pump is a peristaltic pump.

* * * * *